US007081564B2

(12) United States Patent
Somers et al.

(10) Patent No.: US 7,081,564 B2
(45) Date of Patent: Jul. 25, 2006

(54) PLANT FATTY ACID DESATURASES AND ALLELES THEREFOR

(75) Inventors: Daryl Somers, Winnipeg (CA);
Gerhard Rakow, Saskatoon (CA)

(73) Assignee: Her Majesty the Queen in right of Canada, as represented by the Ministry of Agriculture and Agri-Food Canada, Saskatchewan (CA)

( * ) Notice: Subject to any disclaimer, the term of this patent is extended or adjusted under 35 U.S.C. 154(b) by 190 days.

(21) Appl. No.: 10/115,571

(22) Filed: Apr. 1, 2002

(65) Prior Publication Data

US 2003/0150020 A1 Aug. 7, 2003

Related U.S. Application Data

(63) Continuation of application No. PCT/CA00/01141, filed on Sep. 29, 2000.

(51) Int. Cl.
*A01H 5/00* (2006.01)
*C12N 15/82* (2006.01)
(52) U.S. Cl. .................. 800/281; 800/298; 536/23.6
(58) Field of Classification Search ............... 800/281, 800/298; 536/23.6, 23.2
See application file for complete search history.

(56) References Cited

U.S. PATENT DOCUMENTS

| | | | |
|---|---|---|---|
| 4,554,101 A | 11/1985 | Hopp ................... | 260/112.5 R |
| 4,684,611 A | 8/1987 | Schilperoort et al. .... | 435/172.3 |
| 4,743,548 A | 5/1988 | Crossway et al. ....... | 435/172.3 |
| 4,801,540 A | 1/1989 | Hiatt et al. .............. | 435/172.3 |
| 4,940,838 A | 7/1990 | Schilperoort et al. ...... | 800/205 |
| 4,943,674 A | 7/1990 | Houck et al. .............. | 800/205 |
| 4,945,050 A | 7/1990 | Sanford et al. .......... | 435/172.1 |
| 5,015,580 A | 5/1991 | Christou et al. ......... | 435/172.3 |
| 5,149,655 A | 9/1992 | McCabe et al. ............ | 435/287 |
| 5,231,019 A | 7/1993 | Paszkowski et al. ..... | 435/172.3 |
| 5,464,763 A | 11/1995 | Schilperoort et al. .... | 435/172.3 |
| 5,466,587 A | 11/1995 | Fitzpatrick-McElligott et al. ........................ | 435/172.1 |
| 5,625,130 A | 4/1997 | Grant et al. ................ | 800/200 |
| 5,668,299 A | 9/1997 | DeBonte et al. ........... | 800/230 |
| 5,723,765 A | 3/1998 | Oliver et al. ............... | 800/205 |
| 5,767,338 A | 6/1998 | Fan ............................. | 800/200 |
| 5,777,201 A | 7/1998 | Poutre et al. ............... | 800/250 |
| 5,840,946 A | 11/1998 | Wong et al. ................ | 554/224 |
| 5,850,026 A | 12/1998 | DeBonte et al. ........... | 800/281 |

FOREIGN PATENT DOCUMENTS

| | | |
|---|---|---|
| EP | 0945 514 | 9/1999 |
| EP | 0 255 378 | 6/2002 |
| WO | WO 93/11245 | 6/1993 |
| WO | WO 94/18337 | 8/1994 |
| WO | WO 97/21340 | 6/1997 |
| WO | WO 98/56239 | 12/1998 |

OTHER PUBLICATIONS

Somers, D.,J., et al., "Identification of Molecular Markers Associated with Linoleic Acid Desaturation in Brassica Napus", *Theoretical and Applied Genetics*, DE, Springer, Berlin, vol. 96, May 1998, pp. 897-903, XP000914248, ISSN: 0040-5752.
Altschul, et al., 1990, *J. Mol. Biol.* 215:403-10.
Arondel, V., et al., "Map-based cloning of a gene controlling omega-3 fatty acid desaturation in Arabidopsis", *Science* 258 (5086), 1353-1355 (1992).
Ausubel, et al. (eds.), 1989, *Current Protocols in Molecular Biology*, vol. 1, Green Publishing Associates, Inc., and John Wiley & Sons, Inc., New York, p. 2.10.3.
Babic, et al., 1998, *Plant Cell Rep.* 17:183.
Barret, Pierre, et al., "Low Linolenic Acid Level in Rapeseed Can Be Easily Assessed Through the Detection of Two Single Base Substitution in FAD3 Genes", Abstract.
Bechtold, et al., "In planta Agrobacterium mediated gene transfer by infiltration of adult Arabidopsis thaliana plants", *C.R. Acad. Sci. Paris, Sciences de la vie/Life Sciences* 1993; 316:1194-9.
Beetham, et al., 1999, *Proc. Natl. Acad. Sci. USA* 96:8774.
Berberich, T., et al., "Two maize genes encoding omega-3 fatty acid desaturases and their differential expression to temperature", *Plant Mol. Biol.* 36 (2), 297-306 (1998).
Bhella, R.S., et al., "Nucleotide sequence of a cDNA from Limnanthes douglasii L. encoding a delta-15 linoleic acid desaturase", *Plant Physiol.* 108 (2), 861 (1995).
Binding, "Regeneration of Plants, Plant Protoplasts", CRC Press, Boca Raton, 1985.
Edwards, et al., "A simple and rapid method for the preparation of plant genomic DNA for PCR analysis", *Nucleic Acids Research*, vol. 19, No. 6, pp. 1349, 1991.
Evans, et al., "Protoplasts Isolation and Culture", *Handbook of Plant Cell Culture*, Macmillian Publishing Company, New York, 1983.

(Continued)

*Primary Examiner*—Elizabeth F. McElwain
(74) *Attorney, Agent, or Firm*—Klarquist Sparkman, LLP

(57) ABSTRACT

In one aspect, the invention provides new variants of the Fad3 enzyme, including amino acid substitutions, as well as nucleic acid sequences encoding such peptides. Other aspects of the invention include transgenic plants and plant parts. Vectors capable of transforming plant cells are provided, including the nucleic acids of the invention, including Fad3 coding sequences. Corresponding methods are provided for obtaining the transgenic plants of the invention. Methods are provided for using the plants of the invention, including selected plants and transgenic plants, to obtain plant products. Amplification primers for identifying the Fad3 alleles of the invention are provided, together with methods of obtaining plants using the Fad3 alleles of the invention as markers.

35 Claims, 25 Drawing Sheets

OTHER PUBLICATIONS

Fraley, et al., *Proc. Nat'l Acad. Sci. USA* 80:4803 (1983).
Fromm et, al., *Proc. Natl. Acad. Sci. USA* 82:5824 (1985).
Gamborg and Phillips, "Plant Cell, Tissue and Organ Culture, Fundamental Methods", Springer Berlin 1995.
Gibson, S., "Cloning of a temperature-regulated gene encoding a chloroplast omega-3 desaturase from Arabidopsis thaliana", *Plant Physiol.* 106 (4), 1615-1621 (1994).
Gordon-Kamm, et al. "The Plant Cell" 2:603 (1990).
Hamada, T., et al. "Cloning of a cDNA encoding tobacco omega-3 fatty acid desaturase", *Gene* 147 (2), 293-394 (1994).
Hamada, T., et al., "cDNA cloning of a wounding-inducible gene encoding a plastid omega-3 fatty acid desaturase from tobacco", *Plant Cell Physiol.* 37 (5), 606-611 (1996).
Harlow and Lane, 1988, *Antibodies, A Laboratory Manual*, Cold Spring Harbor Publications, New York.
Henikoff and Henikoff, 1992, *Proc. Natl. Acad. Sci. USA* 89: 10915-10919.
Horiguchi, G., et al., Developmental regulation of genes for microsome and plastid omega-3 fatty acid desaturases in wheat (Triticum aestivum L.), *Plant Cell Physiol.* 39, 540-544 (1998).
Horiguchi, G., et al., "Expression of a gene for plastid omega-3 fatty acid desaturases and changes in lipid and fatty acid compositions in light- and dark-grown wheat leaves", *Physiol. Plantarum* 96, 275-283 (1996).
Horsch, et al., *Science* 233:496 (1984).
Iba, K., "A gene encoding a chloroplast omega-3 fatty acid desaturase complements alterations in fatty acid desaturation and chloroplast copy number of the fad7 mutant of Arabidopsis thaliana", *J. Biol, Chem.* 268 (32), 24099-24105 (1993).
Jourdren, et al., 1996, *Theoretical and Applied Genetics* 93:512.
Kirsch, C., et al., "Rapid, transient, and highly localized induction of plastidial omega-3 fatty acid desaturase mRNA at fungal infection sites in Petroselinum crispum", *Proc. Natl. Acad. Sci. USA.* 94 (5), 2079-2084 (1997).
Klee, et al., *Ann. Rev. of Plant Phys.* 38:467 (1987).
Klein, et al., *Nature* 327:70 (1987).
Kodama, H., et al., "Structure, chromosomal location and expression of a rice-gene encoding the microsome omega-3 fatty acid desaturase", *Plant Mol. Biol.* 33 (3), 493-502 (1997).
Koncz and Schell, "The promoter of $T_L$-DNA gene 5 controls the tissue- specific expression of chimaeric genes carried by a novel type of *Agrobacterium* binary vector", *Mol. Gen. Genet.* (1986) 204:383-396.

Michaels, et al., 1998, "A robust method for detecting single-nucleotide changes as polymorphic markers by PCR", *The Plant Journal* 14(3): 381-385.
Moloney, et al., 1989, *Plant Cell Rep.* 8:238.
Needleman and Wunsch, 1970, *J. Mol. Biol.* 48:443.
Neff, et al., 1998, "dCAPS, a simple technique for the genetic analysis of single nucleotide polymorphisms: experimental applications in Arabidopsis thaliana genetics", *The Plant Journal* 14(3): 387-392.
Nishiuchi, T., et al., "Genomic nucleotide sequence of a gene encoding a microsomal omega-3 fatty acid desaturase from Arabidopsis thaliana", *Plant Physiol.* 105 (2), 767-768 (1994).
Paszkowski, et al., *EMBO J.* 3:2717 (1984).
Pearson and Lipman, 1988, *Proc. Natl. Acad. Sci. USA* 85:2444.
Röbbelen and Nitsch, 1975, *L.Z. PfanzenzÜchtg* 75:93.
Rogers, et al., *Methods Enzymol.* 118:627 (1986).
Sakamoto, T., et al., "Temperature-regulated mRNA accumulation and stabilization for fatty acid desaturase genes in the cyanobacterium Synechococcus sp. strain PCC 7002", *Mol. Microbiol.* 23 (6), 1281-1292 (1997).
Sakamoto, T., et al., "Cloning of omega 3 desaturase from cyanobacteria and its use in altering the degree of membrane-lipid unsaturation", *Plant Mol. Biol.* 26 (1), 249-263 (1994).
Scarth, et al., 1988, *Can J. Plant Sci.* 68:509.
Scarth, et al., 1994, *Can J. Plant Sci* 75:203.
Smith and Waterman, 1981, *Adv. Appl. Math* 2:482.
Southern, "Detection of Specific Sequences Among DNA Fragments Separated by Gel Electrophoresis", J. Mol. Biol. (1975) 98, 503-517.
Tang, F., et al., Nucleotide sequence of a cDNA clone for omega-3 fatty acid desaturase (Accession No. AF061027) from Aleurites fordii seeds (PGR99-009), *Plant Physiol.* 119, 364 (1999).
Tijssen, 1993, *Laboratory Techniques in Biochemistry and Molecular Biology—Hybridization with Nucleic Acid Probes*, Part I, Chapter 2, "Overview of principles of hybridization and the strategy of nucleic acid probe assays", Elsevier, New York.
van de Loo, F.J., "Plasmid omega-3 fatty acid desaturase cDNA from Ricinus communis", *Plant Physiol.* 105 (1), 443-444 (1994).
Yadav, N.S. et al., "Cloning of higher plant omega-3 fatty acid desaturases", *Plant Physiol.* 103 (2), 467-476 (1993).
Yamamoto, K.T. et al., *Plant Cell Physiol.* 33, 13-20 (1992).
Zhu et al., 1999, *Proc. Natl. Acad. Sci. USA* 96:8768-8773.

Figure 1
Apollo Fad3A (SEQ ID NO: 1)

```
MVVAM DQRSN VNGDS KDERF DPSAQ PPFKI GDIRA AIPKH CWVKS PLRSM   50

SYVAR DIFSV VALAV AAVYF DSWFF WPLYW AAQGT LFWAI FVLGH DCGHG  100

SFSDI PLLNT AVGHI LHSFI LVPYH GWRMS HRTHH QNHGH VENDE SWVPL  150

PEKLY KNLSH STRML RYTVP LPMLA YPLYL WYRSP GKEGS HYNPY SSLFA  200
                ↓ 213
PSERK LIATS TTAWS IMLAT LVYLS FLVGP VTVLK VYGVP YIIFV MWLDA  250
                       ↓ 275
VTYLH HHGHD DKLPW YRGKE WSYLC GGLTT IDRDY GIFNN IHHDI GTHVI  300
                                                      ↓ 347
HHLFP QIPHY HLVDA TKAAK HVLGR YYREP KTSGA IPIHL VESLV ARIKK  350

DHYVS DTGDI VFYET DPDLY VYASD KSKIN                          380
```

Figure 2

```
ApolloA (SEQ ID NO:1) 1    MVVAMDQRSNVNGDSKDERFDPSAQPPFKI 30
Consensus (SEQ ID NO:60)   MVVAMDQRSN NGD    ERFDPSAQPPFKI
L22962 (SEQ ID NO:2) 1     MVVAMDQRSNANGD---ERFDPSAQPPFKI 27

ApolloA 31   GDIRAAIPKHCWVKSPLRSMSYVARDIFSV 60
Consensus    GDIRAAIPKHCWVKSPLRSMSYVARDIF+V
L22962 28    GDIRAAIPKHCWVKSPLRSMSYVARDIFAV 57

ApolloC (SEQ ID NO:64)                             GHGSFSDIPLLNTAVGHILHSFI
ApolloA 61   VALAVAAVYFDSWFFWPLYWAAQGTLFWAIFVLGHDCGHGSFSDIPLLNTAVGHILHSFI 120
Consensus    VALAVAAVYFDSWFFWPLYWAAQGTLFWAIFVLGHDCGHGSFSDIPLLNTAVGHILHSFI
L22962 58    VALAVAAVYFDSWFFWPLYWAAQGTLFWAIFVLGHDCGHGSFSDIPLLNTAVGHILHSFI 117

ApolloC      LVPYHGWRISHRTHHQNHGHVENDESWVPLPEKLYKNLSHSTRMLRYTVPLPMLAYPLYL

ApolloA121   LVPYHGWRMSHRTHHQNHGHVENDESWVPLPEKLYKNLSHSTRMLRYTVPLPMLAYPLYL 180
Consensus    LVPYHGWR+SHRTHHQNHGHVENDESWVPLPEKLYKNLSHSTRMLRYTVPLPMLAYPLYL
L22962 118   LVPYHGWRISHRTHHQNHGHVENDESWVPLPEKLYKNLSHSTRMLRYTVPLPMLAYPLYL 177

213↓    ↓217   ↓224
ApolloC      WYRSPGKEGSHYNPYSSLFAPSERKLIATSTTCWSIVLATLVYPSFLVGPVTVLKVYGVP
ApolloA181   WYRSPGKEGSHYNPYSSLFAPSERKLIATSTTAWSIMLATLVYLSFLVGPVTVLKVYGVP 240
Consensus    WYRSPGKEGSHYNPYSSLFAPSERKLIATSTT WSIMLATLVYLSFLVGPVTVLKVYGVP
L22962 178   WYRSPGKEGSHYNPYSSLFAPSERKLIATSTTCWSIMLATLVYLSFLVGPVTVLKVYGVP 237

275↓         ↓281
ApolloC      YIIFVMWLDAVTYLHHHGHDDKLPWYRGKEWSYLRGGLTTVDRDYGIFNNIHHDIGTHVI
ApolloA241   YIIFVMWLDAVTYLHHHGHDDKLPWYRGKEWSYLCGGLTTIDRDYGIFNNIHHDIGTHVI 300
Consensus    YIIFVMWLDAVTYLHHHGHDDKLPWYRGKEWSYL GGLTTIDRDYGIFNNIHHDIGTHVI
L22962 238   YIIFVMWLDAVTYLHHHGHDDKLPWYRGKEWSYLRGGLTTIDRDYGIFNNIHHDIGTHVI 297
```

Figure 2 (continued)

```
ApolloC     HHLFPQIPHYHLVDA                                              ↓ 347
ApolloA301  HHLFPQIPHYHLVDATKAAKHVLGRYYREPKTSGAIPIHLVESLVA[R]IKKDHYVSDTGDI 360
Consensus   HHLFPQIPHYHLVDATK+AKHVLGRYYREPKTSGAIPIHLVESLVA IKKDHYVSDTGDI
L22962 298  HHLFPQIPHYHLVDATKSAKHVLGRYYREPKTSGAIPIHLVESLVA[S]IKKDHYVSDTGDI 357

Apollo  361 VFYETDPDLYVYASDKSKIN 380
Consensus   VFYETDPDLYVYASDKSKIN
L22962  358 VFYETDPDLYVYASDKSKIN 377
```

Figure 3

```
Apollo (SEQ ID NO:1)  1    MVVAMDQRSNVNGDS---KDERFDPSAQPP 27
Consensus (SEQ ID NO:69)   MVVAMDQRSNVNGDS   K+E FDPSAQPP
L01418 (SEQ ID NO:3)  1    MVVAMDQRSNVNGDSGARKEEGFDPSAQPP 30

Apollo     28  FKIGDIRAAIPKHCWVKSPLRSMSYVARDI 57
Consensus      FKIGDIRAAIPKHCWVKSPLRSMSYV RDI
L01418     31  FKIGDIRAAIPKHCWVKSPLRSMSYVTRDI 60

Apollo     58  FSVVALAVAAVYFDSWFFWPLYWAAQGTLFWAIFVLGHDCGHGSFSDIPLLNTAVGHILH 117
Consensus      F+V ALA+AAVYFDSWF WPLYW AQGTLFWAIFVLGHDCGHGSFSDIPLLN+ VGHILH
L01418     61  FAVAALAMAAVYFDSWFLWPLYWVAQGTLFWAIFVLGHDCGHGSFSDIPLLNSVVGHILH 120

Apollo    118  SFILVPYHGWRMSHRTHHQNHGHVENDESWVPLPEKLYKNLSHSTRMLRYTVPLPMLAYP 177
Consensus      SFILVPYHGWR+SHRTHHQNHGHVENDESWVPLPEKLYKNL HSTRMLRYTVPLPMLAYP
L01418    121  SFILVPYHGWRISHRTHHQNHCHVENDESWVPLPEKLYKNLPHSTRMLRYTVPLPMLAYP 180

↓ 213
Apollo    178  LYLWYRSPGKEGSHYNPYSSLFAPSERKLIATSTT[A]WSIMLATLVYLSFLVGPVTVLKVY 237
Consensus      +YLWYRSPGKEGSH+NPYSSLFAPSERKLIATSTT WSIMLATLVYLSFLV PVTVLKVY
L01418    181  IYLWYRSPGKEGSHFNPYSSLFAPSERKLIATSTT[C]WSIMLATLVYLSFLVDPVTVLKVY 240

↓ 275
Apollo    238  GVPYIIFVMWLDAVTYLHHHGHDDKLPWYRGKEWSYL[C]GGLTTIDRDYGIFNNIHHDIGT 297
Consensus      GVPYIIFVMWLDAVTYLHHHGHD+KLPWYRGKEWSYL GGLTTIDRDYGIFNNIHHDIGT
L01418    241  GVPYIIFVMWLDAVTYLHHHGHDEKLPWYRGKEWSYL[R]GGLTTIDRDYGIFNNIHHDIGT 300

↓ 347
Apollo    298  HVIHHLFPQIPHYHLVDATKAAKHVLGRYYREPKTSGAIPIHLVESLVA[R]IKKDHYVSDT 357
Consensus      HVIHHLFPQIPHYHLVDAT+AAKHVLGRYYREPKTSGAIPIHLVESLVA IKKDHYVSDT
L01418    301  HVIHHLFPQIPHYHLVDATRAAKHVLGRYYREPKTSGAIPIHLVESLVA[S]IKKDHYVSDT 360

Apollo    358  GDIVFYETDPDLYVYASDKSKIN 380
Consensus      GDIVFYETDPDLYVYASDKSKIN
L01418    361  GDIVFYETDPDLYVYASDKSKIN 383
```

Figure 4

```
Apollo (SEQ ID NO: 1)   1    MVVAMDQRSNVNGD------SKDERFDPSA 24
Consensus (SEQ ID NO:70)     MVVAMDQR+NVNGD      K+ERFDPSA
D17579 (SEQ ID NO:4)    1    MVVAMDQRTNVNGDPGAGDRKKEERFDPSA 30

Apollo     25   QPPFKIGDIRAAIPKHCWVKSPLRSMSYVA 54
Consensus       QPPFKIGDIRAAIPKHCWVKSPLRSMSYV
D17579     31   QPPFKIGDIRAAIPKHCWVKSPLRSMSYVV 60

↓ 98
Apollo     55   RDIFSVVALAVAAVYFDSWFFWPLYWAAQGTLFWAIFVLGHDCGHGSFSDIPLLNTAVGH 114
Consensus       RDI +V ALA+AAVY DSWF WPLYWAAQGTLFWAIFVLGHDCGHGSFSDIPLLN+ VGH
D17579     61   RDIIAVAALAIAAVYVDSWFLWPLYWAAQGTLFWAIFVLGHDCGHGSFSDIPLLNSVVGH 120

Apollo    115   ILHSFILVPYHGWRMSHRTHHQNHGHVENDESWVPLPEKLYKNLSHSTRMLRYTVPLPML 174
Consensus       ILHSFILVPYHGWR+SHRTHHQNHGHVENDESWVPLPE++YK L HSTRMLRYTVPLPML
D17579    121   ILHSFILVPYHGWRISHRTHHQNHGHVENDESWVPLPERVYKKLPHSTRMLRYTVPLPML 180

↓ 213
Apollo    175   AYPLYLWYRSPGKEGSHYNPYSSLFAPSERKLIATSTT[A]WSIMLATLVYLSFLVGPVTVL 234
Consensus       AYPLYL YRSPGKEGSH+NPYSSLFAPSERKLIATSTT   WSIM  +L+ LSF+ GP+ VL
D17579    181   AYPLYLCYRSPGKEGSHFNPYSSLFAPSERKLIATSTT[C]WSIMFVSLIALSFVFGPLAVL 240

↓ 275
Apollo    235   KVYGVPYIIFVMWLDAVTYLHHHGHDDKLPWYRGKEWSYL[C]GGLTTIDRDYGIFNNIHHD 294
Consensus       KVYGVPYIIFVMWLDAVTYLHHHGHD+KLPWYRGKEWSYL  GGLTTIDRDYGIFNNIHHD
D17579    241   KVYGVPYIIFVMWLDAVTYLHHHGHDEKLPWYRGKEWSYL[R]GGLTTIDRDYGIFNNIHHD 300

↓ 347
Apollo    295   IGTHVIHHLFPQIPHYHLVDATKAAKHVLGRYYREPKTSGAIPIHLVESLVA[R]IKKDHYV 354
Consensus       IGTHVIHHLFPQIPHYHLVDATKAAKHVLGRYYREPKTSGAIPIHLVESLVA IKKDHYV
D17579    301   IGTHVIHHLFPQIPHYHLVDATKAAKHVLGRYYREPKTSGAIPIHLVESLVA[S]IKKDHYV 360

Apollo    355   SDTGDIVFYETDPDLYVYASDKSKIN 380
Consensus       SDTGDIVFYETDPDLYVYASDKSKIN
D17579    361   SDTGDIVFYETDPDLYVYASDKSKIN 386
```

Figure 5

```
ApolloC  (SEQ ID NO:64)    GHGSFSDIPLLNTAVGHILHSFILVPYHGWRISHRTHH
ApolloA  (SEQ ID NO:1)     GHGSFSDIPLLNTAVGHILHSFILVPYHGWRMSHRTHH  135
Consensus (SEQ ID NO:71)   GHGSFSDIPLLNTAVGHILHSFILVPYHGWR:SHRTHH
YN90-1016 (SEQ ID NO:5)    GHGSFSDIPLLNTAVGHILHSFILVPYHGWRISHRTHH ApolloC    QNHGHVENDESWVPLPEKLYK
ApolloA    QNHGHVENDESWVPLPEKLYK  156
Consensus  QNHGHVENDESWVPLPEKLYK
YN90-1016  QNHGHVENDESWVPLPEKLYK 213↓    ↓217
ApolloC    NLSHSTRMLRYTVPLPMLAYPLYLWYRSPGKEGSHYNPYSSLFAPSERKLIATSTTCWSIV
ApolloA    NLSHSTRMLRYTVPLPMLAYPLYLWYRSPGKEGSHYNPYSSLFAPSERKLIATSTTAWSIM
Consensus  NLSHSTRMLRYTVPLPMLAYPLYLWYRSPGKEGSHYNPYSSLFAPSERKLIATSTT:WSI:
YN90-1016  NLSHSTRMLRYTVPLPMLAYPLYLWYRSPGKEGSHYNPYSSLFAPSERKLIATSTTAWSIM ↓224
ApolloC    LATLVY PSFLVGPVTVLKVYGVPYIIFVMWLDAVTYLHHHGHDDKLPWYRGKEWSY
ApolloA    LATLVYLSFLVGPVTVLKVYGVPYIIFVMWLDAVTYLHHHGHDDKLPWYRGKEWSY  273
Consensus  LATLVYLSFLVGPVTVLKVYGVPYIIFVMWLDAVTYLHHHGHDDKLPWYRGKEWSY
YN90-1016  LATLVYLSFLVGPVTVLKVYGVPYIIFVMWLDAVTYLHHHGHDDKLPWYRGKEWSY ↓ 275 ↓ 281
ApolloC    LRGGLTT VDRDYGIFNNIHHDIGTHVIHHLFPQIPHYHLVDA
ApolloA    L CGGLTTIDRDYGIFNNIHHDIGTHVIHHLFPQIPHYHLVDATKAAKHVLGRYYRE  329
Consensus  L  GGLTT DRDYGIFNNIHHDIGTHVIHHLFPQIPHYHLVDATKAAKHVLGRYYRE
YN90-1016  L RGGLTTIDRDYGIFNNIHHDIGTHVIHHLFPQIPHYHLVDATKAAKHVLGRYYRE ↓ 347
ApolloA330 PKTSGAIPIHLVESLVA RIKKDHYVSDTGDIVFYETDPDLYVYASDKSKIN  380
Consensus  PKTSGAIPIHLVESLVA IKKDHYVSDTGDIVFYETDPDLYVYASDKSKIN
YN90-1016  PKTSGAIPIHLVESLVA SIKKDHYVSDTGDIVFYETDPDLYVYASDKSKIN
```

Figure 6

```
                                                                ↓ 129
Apollo (SEQ ID NO:1) 98   GHGSFSDIPLLNTAVGHILHSFILVPYHGWR M S
Consensus (SEQ ID NO:72)  GHGSFSDIPLLNTAVGHILHSFILVPYHGWR : S
PFad3N89 (SEQ ID NO:6)    GHGSFSDIPLLNTAVGHILHSFILVPYHGWR I S Apollo       HRTHHQNHGHVENDESWVPLPEKLYK 156
Consensus    HRTHHQNHGHVENDESWVPLPEKLYK
PFad3N89     HRTHHQNHGHVENDESWVPLPEKLYK ↓ 213
Apollo       NLSHSTRMLRYTVPLPMLAYPLYLWYRSPGKEGSHYNPYSSLFAPSERKLIATSTT A WSIM
Consensus    NLSHSTRMLRYTVPLPML.YPLYLWYRSPGKEGSHYN.YSSLFAPSERKLIATSTT   WSIM
PFad3N89     NLSHSTRMLRYTVPLPMLDYPLYLWYRSPGKEGSHYNTYSSLFAPSERKLIATSTT C WSIM Apollo   218 LATLVYLSFLVGPVTVLKVYGVPYIIFVMWLDAVTYLHHHGHDDKLPWYRGKEWSY 273
Consensus    LATLVYLSFLV:PVTVLKVYGVPYIIFVMWLDAVTYLHHHGHD:KLP YRGKEWSY
PFad3N89     LATLVYLSFLVDPVTVLKVYGVPYIIFVMWLDAVTYLHHHGHDEKLP YRGKEWSY ↓ 275
Apollo   274 L C GGLTTIDRDYGIFNNIHHDIGTHVIHHLFPQIPHYHLVDA
Consensus    L   GGLTTIDRDYGIFNNIHHDIGTHVIHHLFPQIPHYHLVDA
PFad3N89     L R GGLTTIDRDYGIFNNIHHDIGTHVIHHLFPQIPHYHLVDA
```

Figure 7

```
Fad3A = SEQ ID NO:7
Fad3A ATGGTTGTCG CTATGGACCA GCGTAGCAAT GTGAACGGAG ATTCCAAGGA CGAAAGGTTT   60

Fad3A GATCCGAGCG CACAACCACC GTTTAAGATC GGAGATATAA GGGCTGCGAT TCCTAAGCAT  120

Fad3A TGTTGGGTCA AGAGTCCTTT GAGATCCATG AGCTACGTCG CGAGAGACAT TTTCTCCGTC  180

Fad3A GTGGCTCTGG CCGTCGCCGC CGTGTATTTT GATAGCTGGT TCTTCTGGCC TCTTTATTGG  240
                                                                GGACATGGG
Fad3C (SEQ ID NO:65)
Fad3A GCCGCCCAAG GGACCCTTTT CTGGGCCATC TTCGTACTCG GCCACGACTG TGGACATGGG  300

Fad3C AGTTTTTCGG ACATTCCTCT TCTGAATACT GCGGTTGGTC ATATTCTTCA TTCCTTCATT
Fad3A AGTTTCTCAG ACATTCCCCT TCTGAATACT GCGGTTGGTC ATATTCTTCA TTCCTTCATT  360

Fad3C CTCGTTCCAT ACCATGGTTG GAGAATAAGC CATCGGACAC ACCACCAGAA CCATGGCCAT
Fad3A CTCGTTCCAT ACCATGGTTG GAGAATGAGC CATCGGACAC ACCACCAGAA CCATGGCCAT  420

Fad3C GTTGAAAACG ACGAGTCTTG GGTTCCGTTG CCAGAAAAAT TATACAAGAA TTTGTCCCAC
Fad3A GTTGAAAACG ACGAGTCTTG GGTTCCGTTG CCAGAAAAAT TATACAAGAA TTTGTCCCAC  480

Fad3C AGTACACGGA TGCTCAGATA CACTGTCCCT CTCCCCATGC TCGCTTACCC TCTCTATCTG
Fad3A AGTACACGGA TGCTCAGATA CACTGTCCCT CTCCCCATGC TCGCTTACCC TCTCTATCTG  540

Fad3C TGGTACAGAA GTCCTGGTAA AGAAGGGTCA CATTATAACC CATACAGTAG TTTATTTGCC
Fad3A TGGTACAGAA GTCCTGGTAA AGAAGGGTCA CATTATAACC CATACAGTAG TTTATTTGCC  600

Fad3C CCAAGCGAGA GAAAGCTTAT TGCAACTTCA ACTACTTGCT GGTCGATCGT GTTGGCCACT
Fad3A CCAAGCGAGA GAAAGCTTAT TGCAACTTCA ACTACTGCGT GGTCGATCAT GTTGGCCACT  660

Fad3C CTTGTTTATC CATCATTCCT CGTTGGTCCG GTCACAGTTC TAAAAGTCTA TGGTGTTCCT
Fad3A CTTGTTTATC TATCATTCCT CGTTGGTCCA GTCACAGTTC TAAAAGTCTA TGGTGTTCCT  720

Fad3C TACATTATCT TTGTAATGTG GTTGGACGCT GTCACGTACT TGCATCATCA TGGTCACGAT
Fad3A TACATTATCT TTGTAATGTG GTTGGACGCT GTCACGTACT TGCATCATCA TGGTCACGAT  780

Fad3C GATAAGCTGC CTTGGTACAG AGGCAAGGAA TGCACTTATT TACGTGGAGG ATTAACAACT
Fad3A GATAAGTTGC CTTGGTACAG AGGCAAGGAA TGGAGTTATT TA[T]GTGGAGG ATTAACAACT  840

Fad3C GTTGATAGAG ATTACGGGAT CTTCAACAAC ATTCATCACG ATATTGGAAC TCACGTGATC
Fad3A ATTGATAGAG ATTACGGGAT CTTCAACAAC ATTCATCACG ATATTGGAAC TCACGTGATC  900

Fad3C CATCATCTTT TCCCACAAAT CCCTCACTAT CACTTGGTCG ATGCCA
Fad3A CATCATCTTT TCCCACAAAT CCCTCACTAT CACTTGGTCG ATGCCACGAA AGCAGCTAAA  960

Fad3A CATGTGTTGG AAGATACTA CAGAGAACCA AAGACGTCAG GAGCAATACC GATCCACTTA 1020

Fad3A GTGGAAAGTT TGGTGGCAAG GATTAAGAAA GATCATTACG TCAGTGACAC TGCTGATATT 1080

Fad3A GTCTTCTACG AGACAGATCC AGATCTCTAC GTTTATGCTT CTGACAAATC CAAATCAATT 1140

Fad3A AA                                                              1142
```

Figure 8 (SEQ ID NO: 8)

```
CATTTCACTC AGAGCCCACA CAGTTTTAGA GAGAGAGAAA CATCCCTCAA AGCTCTCTCT    60
TTCTCCGGCG ATGGTTGTCG CTATGGACCA GCGTAGCAAT GTGAACGGAG ATTCCAAGGA   120
CGAAAGGTTT GATCCGAGCG CACAACCACC GTTTAAGATC GGAGATATAA GGGCTGCGAT   180
TCCTAAGCAT TGTTGGGTCA AGAGTCCTTT GAGATCCATG AGCTACGTCG CGAGAGACAT   240
TTTCTCCGTC GTGGCTCTGG CCGTCGCCGC CGTGTATTTT GATAGCTGGT TCTTCTGGCC   300
TCTTTATTGG GCCGCCCAAG GGACCCTTTT CTGGGCCATC TTCGTACTCG GCCACGACTG   360
GTAATTTAAT TTTCAATTTA TTTTTTCTTC AACTTCTTAA TTTTGATATG TTTATATGTT   420
TTTTTCGTTT TTTGCATCGT CTTTGATTTC TTGAACGCAC GTTCGATATG AGATTTTCAC   480
TGACTTCAAG ATTTGATTCT CTTCAGGTTT ACTTTAAAAA AAAAAAAAAT TATTATGTTC   540
ACCCAAATTG GCCTATTTTA AAAGCAAAAG GGGATCTAAG ATTTTTAATT CTTCTCTTTT   600
TCAGTCGTAA CACTGCTAAC TTTTTTTTTT TGATCAAATC GTAACACTCA TAAGTCCTAA   660
CTAAACATCT TTTTCTTTCC TATAATTATT GTTGGTTCCG CATTTTATGG ATCTACGTTT   720
GAAAGTTTCA ATAAAACACA TTTTATTGTT TGAAAGTAAC AATATAATTA CTGTATATTG   780
ATTCATTTAA TTATTGTGTG TTGTTCCAAT CTACTTTCGA AATATAGTCA TGTGACACGT   840
CATATTCTAT TTTTGTTACC TTGTTGGAAC GTTTGAATTG AGTAAAGTTT AATTAACATT   900
GTGCAATAAA TGATAAACAT GTTTATGATG TAAAATTCAA TTTGAATAAT ACAGTGGACA   960
TGGGAGTTCT CAGACATTCC CTTCTGAATA CTGCGGTTGG TCATATTCTT CATTCCTTCA  1020
TTCTCGTTCC ATACCATGGT TGGTAAGTCA TTTATTTTAA CTTCTTTTTT CATGCAAATT  1080
TATTCTTGTT TTCGTATTCT TACATTTTCC TTGTCATTCT TGGTGCATGT TAGCAAACAG  1140
TAATCTGATA ACTGAAAATA TATTAATTTT TCATAGTAAA ATAATGCATG TGACTAAAAG  1200
CATCAAAATC TTTAGCATCG AAGAAAAAG AACCAAACTT TTATTTAATG CTATGGGCCT  1260
ATTTATGGTC CAATTAGCTA TTATCATATG ACATGTCCTT GAATAAATTA ATGTATAAGT  1320
TTAATATAAT ATTTATATAT TTTTGTTTTA ATGGCTTATT TTATTGTTAC ATGGATACAT  1380
CAGCTTGAAA TATCTACGAA CATGCATCAT TTTCCTAGAT ACATTTGTTT GTTGCTCAAA  1440
AAATGAATAA CGTAGTTAAA CGAGTGAGAT TCTTAGCATC TGCCTCGAAA ACGATATGTT  1500
ATTGACAATT CCAATTTCAT TTTTATGAAA ATAAATAAT AGTTTATTTT ATAATTGGGG  1560
```

Figure 8 (continued)

```
GTGGTTGCAG GAGAATGAGC CATCGGACAC ACCACCAGAA CCATGGCCAT GTTGAAAACG 1620
ACGAGTCTTG GGTTCCGGTA ATCCCCTCT  CATATTTTTT TTTTTCTTTT TTTGAAACTC 1680
TTTCATTTTA ATTTTCTTAG AATTCTATGT ATTTATTTTA ATCAATCCTT TTCCCAGTGT 1740
GAGGCTTGGA CGACCACTTG TCAGATTTGT CGTTTAGCTG TAGTAAACAA CTGATTTAAA 1800
TTGTTTATGG TACTGTAGTT AACTTTAACA ACGGGCCACT TATATTCGAG CCATTGGCAT 1860
AAAATGATTC TTCTCGAAAT TCGTTTACTT TTCTTAGTAT TTTTCAGTTT TGTAGTTTAC 1920
GTAGAACTAA TAAAAAGAAA AAAACCTATA AACACACCAC ATGCAATGAA TAAATTCGAA 1980
TATATAACCA TACTGTTAAA TATTAATTAA CATTTTAATC TTAATTTTGC ATTCCAGTTG 2040
CCAGAAAAAT TATACAAGAA TTTGTCCCAC AGTACACGGA TGCTCAGATA CACTGTCCCT 2100
CTCCCCATGC TCGCTTACCC TCTCTATCTG GTAAATCCTA ATTCCTCATT TTTCTTCCTG 2160
ATTATAATTA CAATTTTGAA TTTTTAGATT TTGAGTATTA ACTAAATATA AATTAAATTT 2220
GTTTGGGGAT GACTACAGTG GTACAGAAGT CCTGGTAAAG AAGGGTCACA TTATAACCCA 2280
TACAGTAGTT TATTTGCCCC AAGCGAGAGA AAGCTTATTG CAACTTCAAC TACTGCGTGG 2340
TCGATCATGT TGGCCACTCT TGTTTATCTA TCATTCCTCG TTGGTCCAGT CACAGTTCTA 2400
AAAGTCTATG GTGTTCCTTA CATTGTAAGT TTCATATATT TCATTATTAT ATCATTGCTA 2460
ATATAATTTG TTTTTGACAT AAAGTTTTGG AAAAATTTCA GATCTTTGTA ATGTGGTTGG 2520
ACGCTGTCAC GTACTTGCAT CATCATGGTC ACGATGATAA GTTGCCTTGG TACAGAGGCA 2580
AGGTAAGTAG ATCAACATTA ATTTATAAGA AGCAACAATG ATTAGTATTT GATTAATCTA 2640
AATTATTGAT GTTATGTGTA CAATAATAGG AATGGAGTTA TTTATGTGGA GGATTAACAA 2700
CTATTGATAG AGATTACGGG ATCTTCAACA ACATTCATCA CGATATTGGA ACTCACGTGA 2760
TCCATCATCT TTTCCCACAA ATCCCTCACT ATCACTTGGT CGATGCCACG AAAGCAGCTA 2820
AACATGTGTT GGGAAGATAC TACAGAGAAC CAAAGACGTC AGGAGCAATA CCGATCCACT 2880
TAGTGGAAAG TTTGGTGGCA AGGATTAAGA AAGATCATTA CGTCAGTGAC ACTGGTGATA 2940
TTGTCTTCTA CGAGACAGAT CCAGATCTCT ACGTTTATGC TTCTGACAAA TCCAAATCAA 3000
TTAA                                                               3004
```

Figure 9

```
SEQ
ID
NO:
 1 Apollo    1  MVVAMDQRSNVNG-----D------S---KDE---------R--FD--PSAQPPFKIGDI  33
 9 P46311    1  MVVAMDQRSNANG-----D-------------E---------R--FD--PSAQPPFKIGDI  30
10 P48624    1  MVVAMDQRSNVNG-----D------SGARKEE----------G--FD--PSAQPPFKIGDI  36
11 P48623    1  MVVAMDQRTNVNG-----DPGAGDRK---KEE----------R--FD--PSAQPPFKIGDI  39
12 3133289  45                                DS----------D--FD--PSAPPPFRLGEI  61
13 P32291   22                                              --FD--PGAPPPFKIADI  35
14 4091113  13         NGVNGFHAKEE------E---EEE---------D--FD--LSNPPPFNIGQI  42
15 P48622   79                                E---------R--FD--PGAPPPFNLADI  94
16 AAD15744 29            G-----K------R---AAD---------K--FD--PAAPPPFKIADI  49
17 P48619   84  EREEFNGIVNVDE------G---KGE----------F--FD--AGAPPPFTLADI 115
18 1754795  75  EERGSVIV-----N------G---VDE------------FD--PGAPPPFKLSDI 101
19 P48620   90                                E---------E--FD--PGAPPPFKLSDI 105
20 P46310   76  EESPLEE-----D------N---K-Q---------R--FD--PGAPPPFNLADI 101
21 BAA11475 73  EEESERTN-----N------S---GGE---------F--FD--PGAPPPFKLSDI 100
22 P48626   22                                              --FD--PSAPPPFRLAEI  35
23 4240385  64  EREEGINGVIGI-E------G---EET---------E--FD--PGAPPPFKLSDI  95
24 1786066  80                 ---EEN---------E--FD--PGAAPPFKLSDV  97
25 P48625   25                                              --FD--PSAPPPFKIAEI  38
26 P48618   37         IEE-----E-------P  KTQ---------R--FD--PGAPPPFNLADI  59
27 BAA22440 15  VEEDKRSSPLG-----E------G---DEHVAASGAAGGE--FD--PGAPPPFGLAEI  54
28 P48621   78  SVDLTNGTNG-----V------E---HEKLP-------E--FD--PGAPPPFNLADI 109
29 BAA22441 79         G-----A------A---AGG---------E--FD--PGAPPPFGLAEI  99
30 CAA07638 67  EEQTTNNG-----D------E---------------FD--PGASPPFKLSDI  90
31 699390   60  VSAPFQIASTTP-----E------E---EDEVA-------E--FD--PGSPPPFKLADI  93
32 BAA07785 24                                              --FD--PGAPPPFGLADI  37
33 BAA28358 23                                              --FD--AAKPPPFRIGDV  36
34 BAA11397 14            ------S---EDA---------RLFFD--AAKPPPFRIGDV  34
35 2197199  19                                                   PFTLKDV  25
36 S52650   21                                                   PFTLQEL  27
```

Figure 9 (continued)

```
SEQ
ID
NO:
1  Apollo   34  RAAIPKHCWVKSPLRSMSYVARD-I-FSV-VAL-A-VAAVYFD------------S---  72
9  P46311   31  RAAIPKHCWVKSPLRSMSYVARD-I-FAV-VAL-A-VAAVYFD------------S---  69
10 P48624   37  RAAIPKHCWVKSPLRSMSYVTRD-I-FAV-AAL-A-MAAVYFD------------S---  75
11 P48623   40  RAAIPKHCWVKSPLRSMSYVVRD-I-IAV-AAL-A-IAAVYVD------------S---  78
12 3133289  62  RAAIPQHCWVKSPWRSMSYVVRD-I-VVV-FAL-A-VAAFRLD------------S---  100
13 P32291   36  RAAIPKHCWEKSTLRSLSYVLRD-V-LVV-TAL-A-ASAISFN------------S---  74
14 4091113  43  RAAIPKHCWVKNPWRSLTYVFRD-V-VVV-FAL-A-AAAFYFN------------S---  81
15 P48622   95  RAAIPKHCWVKNPWMSMSYVVRD-V-AIV-FGL-A-AVAAYFN------------N---  133
16 AAD15744 50  RAAIPAHCWVKNPWRSLSYVVWD-V-AAV-FAL-L-AAAVYIN------------S---  88
17 P48619   116 RAAIPKHCWVKNPWRSMSYVLRD-V-VVV-FGL-A-AVAAYFN------------N---  154
18 1754795  102 RAAIPKHCWVKDPWRSMSYVVRD-V-VVV-FGL-A-AAAAYFN------------N---  140
19 P48620   106 REAIPKHCWVKDPWRSMGYVVRD-V-AVV-FGL-A-AVAAYFN------------N---  144
20 P46310   102 RAAIPKHCWVKNPWKSLSYVVRD-V-AIV-FAL-A-AGAAYLN------------N---  140
21 BAA11475 101 KAAIPKHCWVKNPWKSMSYVVRD-V-AIV-FGL-A-AAAAYFN------------N---  139
22 P48626   36  RNVIPKHCWVKDPLRSLSYVVRD-V-IFV-ATL-I-GIAIHLD------------S---  74
23 4240385  96  REAIPKHCWVKDPWRSMGYVVRD-V-AVV-FGL-A-AAAAYLN------------N---  134
24 1786066  98  RAAIPKHCWVKDPVRSMSYVLRD-V-LIV-FGL-A-VAASFVN------------N---  136
25 P48625   39  RASIPKHCWVKNPWRSLSYVLRD-V-LVI-AAL-V-AAAIHFD------------N---  77
26 P48618   60  RAAIPKHCWVKNPWKSMSYVRE-L-AIV-FAL-A-AAAAYLN------------N---  98
27 BAA22440 55  RAAIPKHCWVKDPWRSMAYVLRD-V-VVV-LGL-A-AAAARLD------------S---  93
28 P48621   110 RAAIPKHCWVKDPWRSMSYVVRD-V-IAV-FGL-A-AAAAYLN------------N---  148
29 BAA22441 100 RAAIPKHCWVKDPWRSMSYVLRD-V-AVV-LGL-A-AAAARLD------------S---  138
30 CAA07638 91  KAAIPKHCWVKNPWTSMSYVVRD-V-AIV-FGL-A-AAAAYFN------------N---  129
31 699390   94  RAAIPKHCWVKNQWRSMSYVVRD-V-VIV-LGL-A-AAAVAAN------------S---  132
32 BAA07785 38  RAAIPKHCWKDHWSSMGYVVRD-V-VVV-LAL-A-ATAARLD------------S---  76
33 BAA28358 37  RAAVPAHCWPQEPPASLSYVARD-V-AVV-AAL-A-AAAWRAD------------S---  75
34 BAA11397 35  RAAIPVHCWRKTPLRSLSYVARD-L-LIV-AALFA-AAASSIDL------------A---  75
37 408490   1                       MSYVVRE-L-AIV-FAL-A-AGAAYLN------------N---  23
35 2197199  26  KAAIPDYCFQPSVFRSLAYFFLD-I-GII-AGL-Y-AIAAYLD------------S---  64
36 S52650   28  RNAIPADCFEPSVVRSLGYFFLD-V-GLI-AGF-Y-ALAAYLD------------S---  66
```

Figure 9 (continued)

```
SEQ
ID
NO:
                                                His Box 1
 1 Apollo     73   ---WFF-WPL-------YWAAQGTLFWAIFVLG|HDCGH|GSFSDIPLLNTAVGHILHSFIL 121
 9 P46311     70   ---WFF-WPL-------YWAAQGTLFWAIFVLGHDCGHGSFSDIPLLNTAVGHILHSFIL 118
10 P48624     76   ---WFL-WPL-------YWVAQGTLFWAIFVLGHDCGHGSFSDIPLLNSVVGHILHSFIL 124
11 P48623     79   ---WFL-WPL-------YWAAQGTLFWAIFVLGHDCGHGSFSDIPLLNSVVGHILHSFIL 127
12 3133289   101   ---WLV-WPI-------YWAVQGTMFWAIFVLGHDCGHGSFSDSHILNSVMGHILHSSIL 149
13 P32291     75   ---WFF-WPL-------YWPAQGTMFWALFVLGHDCGHGSFSNSSKLNSFVGHILHSLIL 123
14 4091113    82   ---WLF-WPL-------YWFAQGTMFWAIFVLGHDCGHGSFSNNSSLNNVVGHLLHSSIL 130
15 P48622    134   ---WLL-WPL-------YWFAQGTMFWALFVLGHDCGHGSFSNDPRLNSVAGHLLHSSIL 182
16 AAD15744   89   ---WAF-WPV-------YWIAQGTMFWALFVLGHDCGHGSFSDNTTLNNVVGHVLHSSIL 137
17 P48619    155   ---WVA-WPL-------YWFCQGTMFWALFVLGHDCGHGSFSNNPKLNSVVGLLHSSIL 203
18 1754795   141   ---WAV-WPI-------YWFAQSTMFWALFVLGHDCGHGSFSNDPKLNSVAGHLLHSSIL 189
19 P48620    145   ---WVV-WPL-------YWFAQSTMFWALFVLGHDCGHGSFSNDPKLNSVVGHILHSSIL 193
20 P46310    141   ---WIV-WPL-------YWLAQGTMFWALFVLGHDCGHGSFSNDPKLNSVVGHLLHSSIL 189
21 BAA11475  140   ---WVV-WPL-------YWFAQSTMFWALFVLGHDCGHGSFSNNHKLNSVVGHILHSSIL 188
22 P48626     75   ---WLF-YPL-------YWAIQGTMFWAIFVLGHDCGHGSFSDSQLLNNVVGHILHSAIL 123
23 4240385   135   ---WIV-WPL-------YWAAQGTMFWALFVLGHDCGHGSFSHNPKLNSVVGHLLHSSIL 183
24 1786066   137   ---WAV-WPL-------YWLAQGTMFWALFVLGHDCGHGSFSNDAKLNSVVGHILHSSIL 185
25 P48625     78   ---WLL-WLI-------YCPIQGTMFWALFVLGHDCGHGSFSDSPLLNSLVGHILHSSIL 126
26 P48618     99   ---WLV-WPL-------YWIAQGTMFWALFVLGHDCGHGSFSNDPRLNSVVGHLLHSSIL 147
27 BAA22440   94   ---WLV-WPL-------YWAAQGTMFWALFVLGHDCGHGSFSNNPKLNSVVGHILHSSIL 142
28 P48621    149   ---WLV-WPL-------YWAAQGTMFWALFVLGHDCGHGSFSNNSKLNSVVGHLLHSSIL 197
29 BAA22441  139   ---WLV-WPL-------YWAAQGTMFWALFVLGHDCGHGSFSNNPKLNSVVGHILHSSIL 187
30 CAA07638  130   ---WLV-WPL-------YWFAQSTMFWALFVLGHDCGHGSFSNNHNLNSVAGHILHSSIL 178
31 699390    133   ---WAV-WPL-------YWVAQGTMFWALFVLGHDCGHGSFSNNHKLNSVVGHLLHSSIL 181
32 BAA07785   77   ---WLA-WPV-------YWAAQGTMFWALFVLGHDCGHGSFSNNAKLNSVVGHILHSSIL 125
33 BAA28358   76   ---WAL-WPL-------YWAVQGTMFWALFVLGHDCGHGSFSDSGTLNSVVGHLLHTFIL 124
34 BAA11397   76   ---WAWAWPL-------YWARQGTMVWALFVLGHDCGHGSFSDSAMLNNVVGHLLHSFIL 125
37 408490     24   ---WLV-WPL-------YWIAQGTMFWALFVLGHDCGHGSFSNDPRLNSVVGHLLHSSIL  72
38 BAA22439    1                                                        LHSSIL   6
39 BAA11396    1                                                NNVVGHLLHSFIL  13
35 2197199    65   ---WFF-YPI-------FWFAQGTMFWALFVVGHDCGHGSFSRSKFLNDLIGHLSHTPIL 113
40 AAD41582    1                                                              FIL   3
36 S52650     67   ---WFF-YPI-------FWLIQGTLFWSLFVVGHDCGHGSFSKSKTLNNWIGHLSHTPIL 115
```

Figure 9 (continued)

```
SEQ
ID
NO:
                        His Box 2
 1  Apollo    122 VPYHGWRMSHRTHHQNHGHVENDESWVPLPE-------K-----LYKNL-SH-----ST- 162
 9  P46311    119 VPYHGWRISHRTHHQNHGHVENDESWVPLPE-------K-----LYKNL-SH-----ST- 159
10  P48624    125 VPYHGWRISHRTHHQNHGHVENDESWVPLPE-------K-----LYKNL-PH-----ST- 165
11  P48623    128 VPYHGWRISHRTHHQNHGHVENDESWVPLPE-------R-----VYKKL-PH-----ST- 168
12  3133289   150 VPYHGWRISHKTHHSNHGHVENDESWVPLTE-------K-----TYKSL-DV-----ST- 190
13  P32291    124 VPYNGWRISHRTHHQNHGHVEKDESWVPLTE-------K-----VYKNL-DD-----MT- 164
14  4091113   131 VPYHGWRISHRTHHQNHGNVEKDESWVPLPE-------K-----IYKEM-DL-----ST- 171
15  P48622    183 VPYHGWRISHRTHHQNHGHVENDESWHPLPE-------S-----IYKNL-EK-----TT- 223
16  AAD15744  138 VPYHGWRISHRTHHQNHGHVEKDESWVPLPE-------N-----LYKKL-DF-----ST- 178
17  P48619    204 VPYHGWRISHRTHHQNHGHVENDESWHPLSE-------K-----IFKSL-DN-----VT- 244
18  1754795   190 VPYHGWRISHRTHHQNHGHVENDESWHPIPE-------K-----IYRTL-DF-----AT- 230
19  P48620    194 VPYHGWRISHRTHHQNHGHVENDESWHPLSE-------K-----IYKNL-DT-----AT- 234
20  P46310    190 VPYHGWRISHRTHHQNHGHVENDESWHPMSE-------K-----IYNTL-DK-----PT- 230
21  BAA11475  189 VPYHGWRISHRTHHQNHGHVENDESWHPIPE-------K-----IYNSL-DL-----AT- 229
22  P48626    124 VPYHGWRISHKTHHQNHGNVETDESWVPMPE-------K-----LYNKV-GY-----ST- 164
23  4240385   184 VPYHGWRISHRTHHQNHGHVENDESWQPLSE-------K-----IFRSL-DY-----MT- 224
24  1786066   186 VPYHGWRISHRTHHQNHGHVENDESWHPLSE-------K-----LFNSL-DD-----LT- 226
25  P48625    127 VPYHGWRISHKTHHQNHGHIEKDESWVPLTE-------K-----IYKNL-DS-----MT- 167
26  P48618    148 VPYHGWRISHRTHHQNHGHVENDESWHPMSE-------K-----IYKSL-DK-----PT- 188
27  BAA22440  143 VPYHGWRISHRTHHQNHGHVEKDESWHPLPE-------R-----LYKSL-DF-----MT- 183
28  P48621    198 VPYHGWRISHRTHHQHHGHAENDESWHPLPE-------K-----LFRSL-DT-----VT- 238
29  BAA22441  188 VPYHGWRISHRTHHQNHGHVEKDESWHPLPE-------R-----LYKSL-DF-----MT- 228
30  CAA07638  179 VPYHGWRISHRTHHQNHGHVENDESWHPLSE-------K-----LYNSL-DD-----IT- 219
31  699390    182 VPYHGWRIRHRTHHQNHGHVENDESWHPMSE-------K-----LFRSL-DK-----IA- 222
32  BAA07785  126 VPYNGWRISHRTHHQNHGHVENDESWHPLPE-------K-----LYRSL-DS-----ST- 166
33  BAA28358  125 VPYNGWRISHRTHHQNHGHIDRDESWHPITE-------K-----VYQKL-EP-----RT- 165
34  BAA11397  126 VPYGWRFSHRTHHQNHGHIERDESWHPITE--------K-----LYWQL-ET-----RT- 166
37  408490     73 VPYHGWRISHRTHHQNHGHVENDESWHPMSE-------K-----IYKSL-DK-----PT- 113
38  BAA22439    7 VPYHGWRISHRTHHQNHGHVEKDESWHPLPE-------R-----LYKSL-DF-----MT- 47
39  BAA11396   14 VPYHGWRFSHRTHHQNHGHIERDESWHPITE-------K-----LYWQL-ET-----RT- 54
35  2197199   114 VPFHGWRISHRTHHSNTGNIDTDESWYPIPE-------S-----KYDQM-GF-----AE- 154
40  AAD41582    4 VPYHGWRISHRTHHQNHGHVENDESWVPLPE-------K-----LYKNL-SH-----ST- 44
36  S52650    116 VPYHGWRISHRTHHANTGNIDTDESWYPVSE-------Q-----KYNQM-AW-----YE- 156
41  AAD41581    1                              LPE-------K-----LYKNL-SH-----ST- 13
42  AAD41580    1                              LPE-------K-----LYKNL-SH-----ST- 13
```

Figure 9 (continued)

```
SEQ
ID
NO:
 1 Apollo    163 -------RMLRYTVPLPM---LAYPLYLWYRSPGK---E----G--SHYNPYSSLF-APS 202
 9 P46311    160 -------RMLRYTVPLPM---LAYPLYLWYRSPGK---E----G--SHYNPYSSLF-APS 199
10 P48624    166 -------RMLRYTVPLPM---LAYPIYLWYRSPGK---E----G--SHFNPYSSLF-APS 205
11 P48623    169 -------RMLRYTVPLPM---LAYPLYLCYRSPGK---E----G--SHFNPYSSLF-APS 208
12 3133289   191 -------RLLRFTIPFPV---FAYPFYLWRSPGK---K----G--SHFNPYSDLF-APS 230
13 P32291    165 -------RMLRYSFPFPI---FAYPFYLWNRSPGK---E----G--SHFNPYSNLF-SPG 204
14 4091113   172 -------RILRYSVPLPM---FALPFYLWWRSPGK---E----G--SHFNPNSDFF-APH 211
15 P48622    224 -------QMFRFTLPFPM---LAYPFYLWNRSPGK---Q----G--SHYHPDSDLF-LPK 263
16 AAD15744  179 -------KFLRYKIPFPM---FAYPLYLWYRSPGK---T----G--SHFNPYSDLF-KPN 218
17 P48619    245 -------KTLRFSLPFPM---LAYPFYLWSRSPGK---K----G--SHFHPDSGLF-VPK 284
18 1754795   231 -------KKLRFTLPFPM---LAYPFYLWGRSPGK---K----G--SHFHPDSDLF-VPN 270
19 P48620    235 -------KKLRFTLPFPL---LAYPIYLWSRSPGK---Q----G--SHFHPDSDLF-VPN 274
20 P46310    231 -------RFFRFTLPLVM---LAYPFYLWARSPGK---K----G--SHYHPDSDLF-LPK 270
21 BAA11475  230 -------KKLRFTLPFPL---LAYPFYLWSRSPGK---K----G--SHFDPNSDLF-VPS 269
22 P48626    165 -------KFLRYKIPFPL---LAYPMYLMKRSPCK---S----G--SHFNPYSDLF-QPH 204
23 4240385   225 -------RTLRFTVPSPM---LAYPFYLWNRSPGK---T----G--SHFHPDSDLF-GPN 264
24 1786066   227 -------RKFRFTLPFPM---LAYPFYLWGRSPGK---K----G--SHYDPSSDLF-VPN 266
25 P48625    168 -------RLIRFTVPFPL---FVYPIYLFSRSPGK---E----G--SHFNPYSNLF-PPS 207
26 P48618    189 -------RFFRFTLPLVM---LAYPFYLWARSPGK---K----G--SHYHPDSDLF-LPK 228
27 BAA22440  184 -------RKLRFTMPFPL---LAFPLYLFARSPGK---S----G--SHFNPSSDLF-QPN 223
28 P48621    239 -------RMLRFTAPFPL---LAFPVYLFSRSPGK---T----G--SHFDPSSDLF-VPN 278
29 BAA22441  229 -------RKLRFTMPFPL---LAFPLYLFARSPGK---S----G--SHFNPGSDLF-QPT 268
30 CAA07638  220 -------KKFRFTLPFPL---LAYPFYLWGRSPGK---K----G--SHFDPSSDLF-VAS 259
31 699390    223 -------LTFRFKAPFPM---LAYPFYLWERSPGK---T----G--SHYHPDSDLF-VPS 262
32 BAA07785  167 -------RKLRFALPFPM---LAYPFYLWSRSPCK---S----G--SHFHPSSDLF-QPN 206
33 BAA28358  166 -------KTLRFSVPFPL---LAFPVYLWRSPGK---E----G--SHFNPSSDLF-TPK 205
34 BAA11397  167 -------KKLRFTLPFTL---LAFP---WYRSPGK---T----G--SHFLPSSDLF-SPK 203
37 408490    114 -------RFFRFTLPLVM---LAYPFYLWARSPGK---K----G--SHYHPDSDLF-LPK 153
38 BAA22439   48 -------RKLRFTMPFPL---LAFPLYLFARSPGK---S----G--SHFNPGSDLF-QPT  87
39 BAA11396   55 -------KKLRFTLPFTL---LAFP---WYRSPGK---T----G--SHFLPSSDLF-SPK  91
35 2197199   155 -------KLVRFYAPL-----IAYPIYLFKRSPGRG--P----G--SHFSPKSPLF-KPA 193
40 AAD41582   45 -------RMLRYTVPLPM---LAYPLYLWYRSPGK---E----G--SHYNPYSSLF-APS  84
36 S52650    157 -------KLLRFY--LPL---IAYPIYLFRRSPNR---Q----G--SHFMPGSPLF-RPG 194
41 AAD41581   14 -------RMLRYTVPLPM---LAYPLYLWYRSPGK---E----G--SHYNPYSSLF-APS  53
42 AAD41580   14 -------RMLRYTVPLPM---LAYPLYLWYRSPGK---E----G--SHYNPYSSLF-APS  53
```

Figure 9
(continued)

```
SEQ
ID
NO:
                       ↓ 213
 1 Apollo   203 ERKLIATSTT[A]WSIMLATLVYLSFLVGPVTVLKVYGVPYIIFVMWLDAVTYLHHHG-HD- 260
 9 P46311   200 ERKLIATSTTCWSIMLATLVYLSFLVGPVTVLKVYGVPYIIFVMWLDAVTYLHHHG-HD- 257
10 P48624   206 ERKLIATSTTCWSIMLATLVYLSFLVDPVTVLKVYGVPYIIFVMWLDAVTYLHHHG-HD- 263
11 P48623   209 ERKLIATSTTCWSIMFVSLIALSFVFGPLAVLKVYGVPYIIFVMWLDAVTYLHHHG-HD- 266
12 3133289  231 ERRDVLTSTISWSIMVALLAGLSCVFGLVPMLKLYGGPYWIFVMWLDTVTYLHHHG-HD- 288
13 P32291   205 ERKGVVTSTLCWGIVLSVLLYLSLTIGPIFMLKLYGVPYLIFVMWLDFVTYLHHHG-YT- 262
14 4091113  212 ERKAVLTSNFCFSIMALLLLYSCFVFGPVQVLKFYGIPYLVFVMWLDFVTYMHHHG-HE- 269
15 P48622   264 EKKDVLTSTACWTAMAALLVCLNFVMGPIQMLKLYGIPYWIFVMWLDFVTYLHHHG-HE- 321
16 AAD15744 219 ERGLIVTSTMCWAAMGVFLLYASTIVGPNMMFKLYGVPYLIFVMWLDTVTYLHHHG-YD- 276
17 P48619   285 ERKDIITSTACWTAMAALLVYLNFSMGPVQMLKLYGIPYWIFVMWLDFVTYLHHHG-HE- 342
18 1754795  271 ERKDVITSTVCWTAMVAILAGLSFVMGPVQLLKLYGIPYIGFVAWLDLVTYLHHHG-HD- 328
19 P48620   275 EKKDVITSTVCWTAMLALLVGLSFVIGPVQLLKLYGIPYLGNVMWLDLVTYLHHHG-HE- 332
20 P46310   271 ERKDVLTSTACWTAMAALLVCLNFTIGPIQMLKLYGIPYWINVMWLDFVTYLHHHG-HE- 328
21 BAA11475 270 EKKDVMTSTLCWTAMAALLVGLSFVMGPFQVLKLYGIPYWGFVMWLDLVTYLHHHG-HD- 327
22 P48626   205 ERKYVVTSTLCWTVMAALLLYLCTAFGSLQMFKIYGAPYLIFVMWLDFVTYLHHHG-YE- 262
23 4240385  265 ERKDVITSTVCWTAMAALLVGLSLVMGPIQLLKLYGMPYWIFVMWLDFVTYLHHHG-HE- 322
24 1786066  267 ERKDVITSTVCWTAMAALLVGLNFVMGPVKMLMLYGIPYWIFVMWLDFVTYLHHHG-HD- 324
25 P48625   208 ERKGIAISTLCWATMFSLLIYLSFITSPLLVLKLYGIPYWIFVMWLDFVTYLHHHG-HH- 265
26 P48618   229 ERNDVLTSTACWTAMAVLLVCLNFVMGPMQMLKLYVIPYWINVMWLDFVTYLHHHG-HE- 286
27 BAA22440 224 EKKDIITSTASWLAMVGVLAGLTFLMGPVAMLKLYGVPYFVFVAWLDMVTYLHHHG-HE- 281
28 P48621   279 ERKDVITSTACWAAMLGLLVGLGFVMGPIQLLKLYGVPYVIFVMWLDLVTYLHHHG-HE- 336
29 BAA22441 269 EKNDIITSTASWLAMVGVLAGLTFLMGPVPMLKLYGVPYLVFVAWLDMVTYLHHHG-HE- 326
30 CAA07638 260 EKKDVITSTVCWTAMAALLVGLSFVMGPLQVLKLYGIPYWGFVMWLDIVTYLHHHG-HE- 317
31 699390   263 EKKDVITSTICWTTMVGLLIGLSFVMGPIQILKLYVVPYWIFVMWLDFVTYLDHHG-HE- 320
32 BAA07785 207 EKKDILTSTTCWLAMAGLLAGLTVVMGPLQILKLYAVPYWIFVMWLDFVTYLHHHG-HN- 264
33 BAA28358 206 ERRDVIISTTCWFTMIALLIGMACVFGLVPVLKLYGVPYIVNVMWLDLVTYLHHHG-HQ- 263
34 BAA11397 204 EKSDVIVSTTCWCIMISLLVALACVFGPVPVLMLYGVPYLVFVMWLDLVTYLHHHG-HN- 261
37 408490   154 ERNDVLTSTACWTAMAVLLVCLNFVMGPMQMLKLYVIPYWINVMWLDFVTYLHHHG-HE- 211
38 BAA22439  88 EKNDIITSTASWLAMVGVLAGLTFLMGPVPMLKLYGVPYLVFVAWLDMVTYLHHHG-HE- 145
39 BAA11396  92 EKSDVIVSTTCWCIMISLLVALACVFGPVPVLMLYGVPYLVFVMWLDLVTYLHHHG-HN- 149
35 2197199  194 ERNDIILSTAAIIAMVGFLGWFTVQFGLLAFVKFYFVPYVIFVIWLDLVTYLHHTE-AD- 251
40 AAD41582  85 ERKLIATSTTCWSIMLATLVYLSFLVGPVTVLKVYGVPYIIFVMWLDAVTYLHHHG-HD- 142
36 S52650   195 EKAAVLTSTFALAAFVGFLGFLTWQFGWLFLLKFYVAPYLVFVVWLDLVTFLHH---TE- 250
41 AAD41581  54 ERKLIATSTTCWSIVLATLVYLSFLVGPVTVLKVYGVPYIIFVMWLDAVTYLHHHG-HD- 111
42 AAD41580  54 ERKLIATSTTCWSIVLASLVYLSFLVGPVTVLKVYGVPYIIFVMWLDAVTYLHHHG-HD- 111
```

Figure 9 (continued)

```
SEQ
ID
NO:
                              ↓ 275                    His_Box 3
 1  Apollo    261 -D-KLPWYRGKEWSYL[C]GGLTTIDRDYGIFNN-I-HHDI-G-T[HVIHH]LFPQIPHYHLVD 314
 9  P46311    258 -D-KLPWYRGKEWSYLRGGLTTIDRDYGIFNN-I-HHDI-G-THVIHHLFPQIPHYHLVD 311
10  P48624    264 -E-KLPWYRGKEWSYLRGGLTTIDRDYGIFNN-I-HHDI-G-THVIHHLFPQIPHYHLVD 317
11  P48623    267 -E-KLPWYRGKEWSYLRGGLTTIDRDYGIFNN-I-HHDI-G-THVIHHLFPQIPHYHLVD 320
12  3133289   289 -DHKLPWYRGKEWSYLRGGLTTVDRDYGLFNN-I-HHDI-G-THVIHHLFPQIPHYHLVE 343
13  P32291    263 -H-KLPWYRGQEWSYLRGGLTTVDRDYGWINN-V-HHDI-G-THVIHHLFPQIPHYHLVE 316
14  4091113   270 -E-KLPWYRGKEWSYLRGGLQTVDRDYGWINN-I-HHDI-G-THVIHHLFPQIPHYHLIE 323
15  P48622    322 -D-KLPWYRGKEWSYLRGGLTTLDRDYGWINN-I-HHDI-G-THVIHHLFPQIPHYHLVE 375
16  AAD15744  277 -K-KLPWYRSKEWSYLRGGLTTVDQDYGFFNK-I-HHDI-G-THVIHHLFPQIPHYHLVE 330
17  P48619    343 -D-KLPWYRGKAWSYLRGGLTTLDRDYGWINN-I-HHDI-G-THVIHHLFPQIPHYHLVE 396
18  1754795   329 -E-KLPWYRGKEWSYLRGGLTTLDRDYGWINN-I-HHDI-G-THVIHHLFPQIPHYHLIE 382
19  P48620    333 -D-KLPWYRGKEWSYLRGGLTTLDRDYGWINN-I-HHDI-G-THVIHHLFPQIPHYHLIE 386
20  P46310    329 -D-KLPWYRGKEWSYLRGGLTTLDRDYGLINN-I-HHDI-G-THVIHHLFPQIPHYHLVE 382
21  BAA11475  328 -D-KLPWYRGEEWSYLRGGLTTLDRDYGWINN-I-HHDI-G-THVIHHLFPQIPHYHLVE 381
22  P48626    263 -K-KLPWYRGKEWSYLRGGLTTVDRDYGLFNN-I-HHDI-G-THVIHHLFPQIPHYHLRE 316
23  4240385   323 -E-KLPWYRGNEWSYLRGGLTTLGRDYGWINN-I-HHDI-G-THVIHHFFPQIPHYHLID 376
24  1786066   325 -D-KLPWYRGKEWSYLRGGLTTLDRDYGWINN-I-HHDI-G-THVVHHLFPQIPHYHLIE 378
25  P48625    266 -Q-KLPWYRGKEWSYLRGGLTTVDRDYGWIYN-I-HHDI-G-THVIHHLFPQIPHYHLVE 319
26  P48618    287 -D-KLPWYRGKEWSYLRGGLTTLDRDYGLINN-I-HHDI-G-THVIHHLFPQIPHYHLVE 340
27  BAA22440  282 -D-KLPWYRGQEWSYLRGGLTTVDRDYGLINN-I-HHDI-G-THVIHHLFPQIPHYHLIE 335
28  P48621    337 -D-KLPWYRGKEWSYLRGGLTTVDRDYGWINN-I-HHDI-G-THVIHHLFPQIPHYHLVE 390
29  BAA22441  327 -D-KLPWYRGKEWSYLRGGLTTLDRDYGWINN-I-HHDI-G-THVIHHLFPQIPHYHLIE 380
30  CAA07638  318 -D-KVPWYRGEEWSYLRGGLTTLDRDYGWINN-I-HHDI-G-THVIHHLFPQIPHYHLVE 371
31  699390    321 -D-KLPWYRGEEWSYLRGGLTTLDRDYGLINN-I-HHDI-G-THVIHHLFPQIPHYHLVE 374
32  BAA07785  265 -D-KLPWYRGKAWSIYTGGLTTLDRDYGWLNN-I-HHDI-G-THVIHHLLPQIPHYHLVE 318
33  BAA28358  264 -D--LPWYRGEEWSYLRGGLTTVDRDYGWINN-I-HHDI-G-THVIHHLFPQIPHYHLVE 316
34  BAA11397  262 -D--LPWYRGEEWSYLRGGLTTVDRDYGWINN-I-HHDI-G-THVIHHLFPQIPHYHLVE 314
37  408490    212 -D-KLPWYRGKEWSYLRGGLTTLDRDYGLINN-I-HHDI-G-THVIHHLFPQIPHYHLVE 265
38  BAA22439  146 -D-KLPWYRGKEWSYLRGGLTTLDRDYGLINN-I-HHDI-G-THVIHHLFPQIPHYHLIE 199
39  BAA11396  150 -D--LPWYRGEEWSYLRGGLTTVDRDYGWINN-I-HHDI-G-THVIHHLFPQIPHYHLVE 202
35  2197199   252 ----IPWYRGDDWYYLKGALSTIDRDYGIFNE-I-HHNI-G-THVAHHIFHTIPHYHLKD 303
40  AAD41582  143 -D-KLPWYRGKEWSYLRGGLTTIDRDYGIFNN                             172
36  S52650    251 -D-NIPWYRGDDWYFLKGALSTIDRDYGFINP-I-HHDI-G-THVAHHIFSNMPHYKLRR 304
41  AAD41581  112 -D-KLPWYRGKEWSYLRGGLTTVDRDYGIFNN                             141
42  AAD41580  112 -D-KLPWYRGKEWSYLRGGLTTVDRDYGIFNN                             141
```

Figure 9 (continued)

```
SEQ
ID
NO:
                                     ↓ 347
 1 Apollo    315 ATKAAKHVLGRYYR---EPKTSGA-IPIHLVESLVA[R]IKKDHYV-S-DTGDIVFYETDPD 368
 9 P46311    312 ATKSAKHVLGRYYR---EPKTSGA-IPIHLVESLVASIKKDHYV-S-DTGDIVFYETDPD 365
10 P48624    318 ATRAAKHVLGRYYR---EPKTSGA-IPIHLVESLVASIKKDHYV-S-DTGDIVFYETDPD 371
11 P48623    321 ATKAAKHVLGRYYR---EPKTSGA-IPIHLVESLVASIKKDHYV-S-DTGDIVFYETDPD 374
12 3133289   344 ATRAAKPVLGKYYR---EPKRSGP-FPYHLIDNLVKSIKEDHYV-S-DTGDIVFYETDPE 397
13 P32291    317 ATKSAKSVLGKYYR---EPQKSGP-LPFHLLKYLLQSISQDHFV-S-DTGDIVYYQTDPK 370
14 4091113   324 ATKAAKPVLGKYYR---EPKKSGP-FPFHLFSNLVRSMSEDHYV-S-DIGDIVFYQTDPD 377
15 P48622    376 ATEAAKPVLGKYYR---EPKNSGP-LPLHLLGSLIKSMKQDHFV-S-DTGDVVYYEADPK 429
16 AAD15744  331 ATREAKRVLGNYYR---EPRKSGP-VPLHLIPALLKSLGRDHYV-S-DNGDIVYYQTDDE 384
17 P48619    397 ATEAAKPVMGKYYR---EPKKSGP-LPLHLLGSLVRSMSEDHYV-S-DTGDVVYYQKDPK 450
18 1754795   383 ATAAAKPVLGKYYK---EPKKSGP-FPFYLLGVLQKSMKKDHYV-S-DTGDIVYYQTDPE 436
19 P48620    387 ATEAAKPVLGKYYR---EPKKSAP-LPFHLLGDLTRSLKRDHYV-S-DVGDVVYYQTDPQ 440
20 P46310    383 ATEAAKPVLGKYYR---EPDKSGP-LPLHLLEILAKSIKEDHYV-S-DEGEVVYYKADPN 436
21 BAA11475  382 ATEAAKPVLGKYYK---EPKKSGP-LPFYLLGVLIKSMKQDHYV-S-DTGDIVYYRTDPQ 435
22 P48626    317 ATKAAKPVLGKYYR---EPKKSGP-IPFHLVKDLTRSMKQDHYV-S-DSGEIVFYQTDPH 370
23 4240385   377 ATEASKPVLGKYYR---EPDKSGP-LSFHLIGYLIRSLKKDHYV-S-DTGDVVYYQTDPQ 430
24 1786066   379 ATEAAKPVFGKYYR---EPKKSGP-VPFHLLATLWKSFKKDHFV-S-DTGDVVYYQAHPE 432
25 P48625    320 ATQAAKPVLGDYYR---EPERSAP-LPFHLIKYLIQSMRQDHFV-S-DTGDVVYYQTD   371
26 P48618    341 ATEAAKPVLGKYYR---EPDKSGP-LPLHLLGILAKSIKEDHFV-S-DEGDVVYYEADPN 394
27 BAA22440  336 ATEAAKPVLGKYYK---EPKKSGP-LPWHLFGVLAQSLKQDHYV-S-DTGDVVYYQTD   387
28 P48621    391 ATEAAKPVFGKYYR---EPKKSAAPLPFHLIGEIIRSFKTDHFV-S-DTGDVVYYQTD   443
29 BAA22441  381 ATEAAKPVLGKYYK---EPKNSGA-LPWHLFRVLAQSLKQDHYV-S-HTGDVVYYQAE   432
30 CAA07638  372 ATEAAKPVLGKYYK---EPKKSGP-LPFYLLGYLIKSMKEDHFV-S-DTGNVVYYQTDPN 425
31 699390    375 ATQAAKPIFGKYYK---EPAKSKP-LPFHLIDVLLKSLKRDHFV-P-DTGDIVYYQSDPQ 428
32 BAA07785  319 ATEAAT-VLGKYYR---EPDKSGP-FPFHLFGALARSMKSDHYV-S-DTGDIIYYQTDPK 371
33 BAA28358  317 ATKAARPVLCRYYR---EPEKSGP-LPMHLITVLLKSLRVDHFV-S-DVGDVVFYQTDPS 370
34 BAA11397  315 ATKAARPVLGRYYR---EPEKSGP-LPLHLFGVLLRTLRVDHFV-S-DVGDVVYYQTDHS 368
37 408490    266 ATEAAKPVLGKYYR---EPDKSGP-LPLHLLGILAKSIKEDHFV-S-DEGDVVYYEADPN 319
38 BAA22439  200 ATEAAKPVLGKYYK---EPKNSGA-LPWHLFRVLAQSLKQDHYV-S-HTGDVVYYQAE   251
39 BAA11396  203 ATKAARPVLGRYYR---EPEKSGP-LPLHLFGVLLRTLRVDHFV-S-DVGDVVYYQTDHS 256
35 2197199   304 ATEAIKPLLGDYYR---VSHAP-------IWRSFFRSQKACHYI-A-DQGSHLYYQ     347
36 S52650    305 ATEAIKPILGEYYRYSDEP----------IWQAFFKSYWACHFV-P-NQGSGVYYQS    349
```

Figure 9 (continued)

| SEQ ID NO: | | | | |
|---|---|---|---|---|
| 1 | Apollo | 369 | LYVYASDKSKIN | 380 |
| 9 | P46311 | 366 | LYVYASDKSKIN | 377 |
| 10 | P48624 | 372 | LYVYASDKSKIN | 383 |
| 11 | P48623 | 375 | LYVYASDKSKIN | 386 |
| 12 | 3133289 | 398 | --QFKSDPKKL | 406 |
| 13 | P32291 | 371 | LHQDSWTKSK | 380 |
| 14 | 4091113 | 378 | --IYKVDKSKLN | 387 |
| 15 | P48622 | 430 | L | 430 |
| 16 | AAD15744 | 385 | LF | 386 |
| 17 | P48619 | 451 | LSGIGGEKTE | 460 |
| 18 | 1754795 | 437 | L | 437 |
| 19 | P48620 | 441 | L | 441 |
| 20 | P46310 | 437 | LY | 438 |
| 21 | BAA11475 | 436 | L | 436 |
| 22 | P48626 | 371 | IF | 372 |
| 23 | 4240385 | 431 | L | 431 |
| 24 | 1786066 | 433 | I | 433 |
| 26 | P48618 | 395 | LY | 396 |
| 30 | CAA07638 | 426 | LY | 427 |
| 31 | 699390 | 429 | I | 429 |
| 32 | BAA07785 | 372 | L | 372 |
| 33 | BAA28358 | 371 | L | 371 |
| 34 | BAA11397 | 369 | L | 369 |
| 37 | 408490 | 320 | LY | 321 |
| 39 | BAA11396 | 257 | L | 257 |

```
         1            15 16            30 31            45 46            60 61            75 76            90
Fad3A  CATTTCACTCAGAGC CCACACAGTTTAGA GAGAGAGAAACATCC CTCAAAGCCTCTCT TTCTCCGGGGATGGT TGTCGGCTATGGACCA      90
Fad3C  --------------- -------------- --------------- -------------- --------------- ----------------       0

91          105 106          120 121          135 136          150 151          165 166          180
Fad3A  GCGTAGCAATGTGAA CGGAGATTCCAAGGA CGAAAGGTTTGATCC GAGGCACAACCACC GTTTAAGATCGGAGA TATAAGGGCTGCGAT     180
Fad3C  --------------- -------------- --------------- -------------- --------------- ----------------       0

181         195 196          210 211          225 226          240 241          255 256          270
Fad3A  TCCTAAGCATTGTTG GGTCAAGAGTCCTTT GAGATCCATGAGCTA CGTCGCGAGAGACAT TTTCTCCGTCGTGGC TCTGGCCGTCGCCGC     270
Fad3C  --------------- -------------- --------------- -------------- --------------- -GTGGACATGG-----      10

271         285 286          300 301          315 316          330 331          345 346          360
Fad3A  CGTGTATTTGATAG CTGGTTCTTCTGGCC TCTTTATTG-GGCCG CCCAAGGGACCCTTT TCTGGGCCATCTTCG TACTCGGCCACGACT     359
Fad3C  -GAGTTTTTCGG-AC ATTCCTCTTCTGAA- ---TACTGCGGTTG GTCAT---ATTCTTC ATTCCTTCATTCTCG TTCCATACCATGGTT      90

361         375 376          390 391          405 406          420 421          435 436          450
Fad3A  GGTAATTTAATTTTC AATTTATTTTTTCTT CAACTTCTTAATTTT GATATGT-TATATGT TTTTTTCGTTTTT-- TGCATCGTCTTTGAT     447
Fad3C  GGTAAGTC------- --ATTTATTTA---- -AACATCTTTTTCAT GC-AAATTAT-TCT AGTTTTCGTATTTCT TACATTTTCCTTGTC     164

451         465 466          480 481          495 496          510 511          525 526          540
Fad3A  -TTCTGAACGCACG TTCGATA--TGAGAT TT--TCACTGACTTC AAGAT-TTGATTCTC TTCAGGTTTACTTTA AAAAAAAAAAAAATT     531
Fad3C  ATTCCTGGT-GCATG TTAGCAAACTGTAAT CTGATAACTGA---A AATATATTAATTTTC --CA----TAGT--- AAATAATGCATGTG     241

541         555 556          570 571          585 586          600 601          615 616          630
Fad3A  ATTATGTTCACCCAA ATTGGCCTATTTTAA AAGCAAAAGGGGATC TAAGATTT--TTAAT TCTTCT--CTTTTTC AGTCGTAACACTGCT     617
Fad3C  ACTAAAAGCATCAAA ATCTT--TAGCATCG AAG-AAAAAAGAACC AAACTTTTATTTAAT GCTATGGCCTATT A-TGGTC-CAAT--T     324

631         645 646          660 661          675 676          690 691          705 706          720
Fad3A  AACTTTTTTTTTTG ATCAAATCGTAACAC TCATAAGTCCTAACT AAACATCTTTTTCTT TCCTATAATTATTGT TGGTTCCGCATTTTA     707
Fad3C  AGCTATTATCATATG A-CATGTCCTTGAAT AAATTAATG-TAGCT T--CATATGTGAGTT T--AATAATATTTAT ATATTTTGTTTTAA     408
```

Figure 11 Continued

```
           721         735  736         750  751         765  766         780  781         795  796         810
Fad3A  TGGATCTACGTTTGA AAGTTTCA---ATAA AACACATTTATTGT TTGAAAGTAACAAT- ATAATTACTGTATAT TGATTCATTAATTA         793
Fad3C  TGGCT-TA--TTTTA TTGTTAAATGGATAC ATCAGCTTGAAATGT CT---ACGAACATGC ATCATTTCC---TA- -GATACACTT----         482

811         825  826         840  841         855  856         870  871         885  886         900
Fad3A  TTGTGTGTGTTGTTCCA ATCTACTTTCGAAAT ATAGTCATGTGACAC GTCATATTCTCTATTT TGTTACCTTGTGTTGGA ACGTTTGAATTGAGT    883
Fad3C  --GTTTGTTGCTCAA AAATGAAT----AAC TTAGTTAAACGAGTG AGCACATGTTCTATGG- -GGT--TTCTTAGA GCATGATTATTGAG-         560

901         915  916         930  931         945  946         960  961         975  976         990
Fad3A  AAAGTT--TA-ATTA ACATTGTGCAATAAA TGATAAACATGTTTA TGATGTAAAAATTCAA TTTGAATAAATACAGT GGACATGGGAGTTCT         970
Fad3C  -AAGTTCCTAGAGTG AGGTTCTTACCGGAA T-ATAAGAATCTATC TCTT--AACTTTTAA CTAAAAAAATTAAG- ----AACCGGCTTTT         641

991         1005 1006        1020 1021        1035 1036        1050 1051        1065 1066        1080
Fad3A  CAGACATTCCCTTCT GAATACTGCGGTTGG TCATATTCTTCATTC CTTCATTCTCGTTCC ATACCATGGTTGGTA AGTCATTTATTTTAA        1060
Fad3C  AAAAC--TCGTATTT AAGAAC--CG----- ----TTTTTAGT- -TT--TTTAGTTAA AAATCAAG-----A- -GACG-------A           697

1081        1095 1096        1110 1111        1125 1126        1140 1141        1155 1156        1170
Fad3A  CTTCTCTTTTTCATGC AAATTTATTCTTGTT TTCGTA-TTCTTACA TTTTCCTTGTCATTC TTGGTGCATGTTAGC AAACAGTAATCTGAT         1149
Fad3C  GTCTTATATTCCGC TAAGA-ACTCCACCC TGAGAACTTCTCA-A TAATCATGCTC---- TTAGTGC-TCTAAG- -AAGGGTCCT----T          774

1171        1185 1186        1200 1201        1215 1216        1230 1231        1245 1246        1260
Fad3A  AACTGAAAAATATATT AATTTTTCATAGTAA AATAATGCATGTGAC TAAAAGCATCAAAAT CTTTAGCATCGAAGA AAAAAGAACCAAACT        1239
Fad3C  AAC--AAAATAT--- ------TAATAATAA GATATAGTTGGGCC CAAAA-----AAAAA CAAAAA-ACCGGTTA CAAAAGTCGCGAA--          845

1261        1275 1276        1290 1291        1305 1306        1320 1321        1335 1336        1350
Fad3A  TTTATTTAAGCTAT GGGCCTATTTATGGT CCAATTAGCTATTAT CATATGACATG-TCC TTGAATAAATTAATG TATAAGTTTAATATA         1328
Fad3C  -AGAAGGATCGATTT TGGTCTTTTTACTTGT ACTGTTTGTGGATCC CACTGGTGTGGTCC GCGATTGGTTTCTTT TTTAA-TTTAATTTA          933

1351        1365 1366        1380 1381        1395 1396        1410 1411        1425 1426        1440
Fad3A  ATATTTATATATTTT TGTTTTAAATGGCTTA TTTTATTGTTACATG GATACATCAGCTTGA AATATCTACGAACAT GCATCATTTTCCTAG        1418
Fad3C  TTTTTTTTA-ATCGG AGAAAAAA------A ATTAA--GAAACC-- AA-AAAACAGTTTTA ATCATG-------- GCCTCATGTTGGGGT        1002
```

Figure 11 Continued

```
            1441         1455 1456         1470 1471         1485 1486         1500 1501         1515 1516         1530
Fad3A  ATACATTTGTTTGTT GCTCAAAAAA---- TGAATAACGTAGTTA AACGAGTGAGATTCT TAGCATCTGCCTCGA AAACGATATGTTATT  1503
Fad3C  TGAGTTTTATATTCT GATAAGAATCCCATC TTAAAAACCCCGTTA AAC----ATGCTCT TACCATCTGCTTCGA AAATGATATGTTATT  1087

1531         1545 1546         1560 1561         1575 1576         1590 1591         1605 1606         1620
Fad3A  GACAATTCCAATTTC ATTTTTATGAAAATA AAATAATAGTTTATT TTATAATTGGGGGTG GTTGCAGGAGAATGA GCCATCGGACACACC  1593
Fad3C  GACAATTCCAATTTC ATTTTTATGAAAATA AAATTTATGAAAATA TTATAACTGAGGGTG GTTGCAGGAGAATAA GCCATCGGACACACC  1177

1621         1635 1636         1650 1651         1665 1666         1680 1681         1695 1696         1710
Fad3A  ACCAGAACCATGGCC ATGTTGAAAACGACG AGTCTTGGGTTCCGG TAATC---CCCCTC TCATATTTTTTTTT TCTTTTTTTGAAACT  1679
Fad3C  ACCAGAACCATGGCC ATGTTGAAAACGACG AGTCTTGGGTTCCGG TAATCTTTCCCTCTC TCATATTTTTTTTTC TTTTTTTTGAAATT  1267

1711         1725 1726         1740 1741         1755 1756         1770 1771         1785 1786         1800
Fad3A  CTTTCATTTTAATTT TCTTAGAATTCTATG TATTTATTTTAATCA ATCCTTTTCCCAGTG TGAGGCTTGGACGAC CACTTGTCAGATTTG  1769
Fad3C  CTTTCATTTTAATTT TCTTAGGATTCTATG TATTTATTTTAATCA ATCCTTTTCCAGTT TGAGGCTAGGACGAC CACTAGTCAGATTTG  1357

1801         1815 1816         1830 1831         1845 1846         1860 1861         1875 1876         1890
Fad3A  TCGTTTAGCTGTAGT AAACAACTGATTTAA ATTGTTTATGGTACT GTAGTTAACTTTAAC AACGGGCCACTTATA TTCGAGCCATTGGCA  1859
Fad3C  TCGTTTAGCTGTAGT TAACAACTGATTTAA ATTGTTTATAGTACT GTAGTTAACTTTAAC AACGGACCACTTATA TTCGAGCCATTGGCA  1447

1891         1905 1906         1920 1921         1935 1936         1950 1951         1965 1966         1980
Fad3A  TAAAATGATTCTTCT CGAAATTCGTTTACT TTTCTTAGTATTTTT CAGTTTTGTAGTTA CGTAGAACTAATAAA AAGAAAAAAACCTAT  1949
Fad3C  TAAAATGATTCTTCT CGAAATTCGTTTACT TTTCTTAGTATTTT CAATTTTGGAGCTTA CGTAGAACTAATAAA AAGAAAAC--CTTAT  1535

1981         1995 1996         2010 2011         2025 2026         2040 2041         2055 2056         2070
Fad3A  AAACACACCACATGC AATGAATAAATTCGA ATATATAACCATACT GTTAAATATTAATTA ACATTTTAATCTTAA TTTTGCATTCCAGTT  2039
Fad3C  AAACACACCACATGC AATGAATAAATTCGA ATATATAACCATACT GTTAAATATTAATTT ACATTTTAATCTTAA TTTTGCATTCCAGTT  1625

2071         2085 2086         2100 2101         2115 2116         2130 2131         2145 2146         2160
Fad3A  GCCAGAAAAATTATA CAAGAATTTGTCCCA CAGTACACGGATGCT CAGATACACTGTCCC TCTCCCCATGCTCGC TTACCCTCTCTATCT  2129
Fad3C  GCCAGAAAAATTATA CAAGAATTTGTCCCA CAGTACACGGATGCT CAGATACACTGTCCC TCTCCCCATGCTCGC TTACCCTCTCTATCT  1715
```

Figure 11 Continued

```
        2161       2175 2176       2190 2191       2205 2206       2220 2221       2235 2236       2250
Fad3A   GGTAAATCCTAATTC CTCATTTTTCTTCCT GATTATAATTACAAT TTTGAATTTTTAGAT TTTGAGTATTAACTA AATATAAATTAAATT   2219
Fad3C   GGTAAATCCTAATTC CTAATTTTTCTTCCT GACTATAATTACAAT TTTGAATTTTTAGAT TTTGAGTATTAACTA AATATAAATTAAATT   1805

2251       2265 2266       2280 2281       2295 2296       2310 2311       2325 2326       2340
Fad3A   TGTTTGGGGATGACT ACAGTGGTACAGAAG TCCTGGTAAAGAAGG GTCACATTATAACCC ATACAGTAGTTTATT TGCCCCAAGCGAGAG   2309
Fad3C   TGTTTGGGGATGACT ACAGTGGTACAGAAG TCCTGGTAAAGAAGG GTCACATTATAACCC ATACAGTAGTTTATT TGCCCCAAGCGAGAG   1895

2341       2355 2356       2370 2371       2385 2386       2400 2401       2415 2416       2430
Fad3A   AAAGCTTATTGCAAC TTCAACTACTGCGTG GTCGATCATGTTGGC CACTCTTGTTTATCT ATCATTCCTCGTTGG TCCAGTCACAGTTCT   2399
Fad3C   AAAGCTTATTGCAAC TTCAACTACTGCTG GTCGATCGTGTTGGC CACTCTTGTTTATCC ATCATTCCTCGTTGG TCCGGTCACAGTTCT   1985

2431       2445 2446       2460 2461       2475 2476       2490 2491       2505 2506       2520
Fad3A   AAAAGTCTATGGTGT TCCTTACATTGTAAG TTTCATATATATTCAT TATTATATCATTGCT AATATAATTGTTTT TGACATAAA-GTTTT   2488
Fad3C   AAAAGTCTATGGTGT TCCTTACATTGTAAG TTTCATATATATTCTT TATTATATCATTGCT AATATAATTGTTTT TGACATAAAAGTTTT   2075

2521       2535 2536       2550 2551       2565 2566       2580 2581       2595 2596       2610
Fad3A   GGAAAAATTTCAGAT CTTTGTAATGTGGTT GGACGCTGTCACGTA CTTGCATCATCATGG TCACGATGATAAGTT GCCTTGGTACAGAGG   2578
Fad3C   GGAAAAATTTCAGAT CTTTGTAATGTGGTT GGACGCTGTCACGTA CTTGCATCATCATGG TCACGATGATAAGCT GCCTTGGTACAGAGG   2165

2611       2625 2626       2640 2641       2655 2656       2670 2671       2685 2686       2700
Fad3A   CAAGGTAAGTAGATC AACATTAATTTATAA GAAGCAACAATGATT AGTATTTGATTAATC TAAATTATTGATGTT ATGTGTACAATAATA   2668
Fad3C   CAAGATAAGTAGATC AACATTA-TTTATAA GAAGCAATAATGATT AGTAGTTGAATAATC TGAATTTTTGATGTT -TTTGTACAATAATA   2253

2701       2715 2716       2730 2731       2745 2746       2760 2761       2775 2776       2790
Fad3A   GGAATGGAGTTATTT ATGTGGAGGATTAAC AACTATTGATAGAGA TTACGGGATCTTCAA CAACATTCATCACGA TATTGGAACTCACGT   2758
Fad3C   GGAATGGAGTTATTT ACGTGGAGGATTAAC AACTGTTGATAGAGA TTACGGGATCTTCAA CAACATTCATCACGA TATTGGAACTCACGT   2343

2791       2805 2806       2820 2821       2835 2836       2850 2851       2865 2866       2880
Fad3A   GATCCATCATCTTTT CCCACAAATCCCTCA CTATCACTTGGTCGA TGCCACGAAAGCAGC TAAACATGTGTTGGG AAGATACTACAGAGA   2848
Fad3C   GATCCATCATCTTTT CCCACAAATCCCTCA CTATCACTTGGTCGA TGCCA---------- --------------- ---------------   2393
```

Figure 11 Continued

```
        2881        2895 2896                                   2910 2911                              2925 2926                              2940 2941                              2955 2956                              2970
Fad3A   ACCAAAGACGTCAGG AGCAATACCGATCCA CTTAGTGGAAAGTTT GGTGGCAAGGATTAA GAAAGATCATTACGT CAGTGACACTGGTGA   2938
Fad3C   --------------- --------------- --------------- --------------- --------------- ---------------   2393

2971        2985 2986                                   3000 3001                              3015 3016                              3030 3031                              3045 3046                              3060
Fad3A   TATTGTCTTCTACGA GACAGATCCAGATCT CTACGTTTATGCTTC TGACAAATCCAAATC AATTAA                           3004 (SEQ ID NO: 6)
Fad3C   --------------- --------------- --------------- --------------- ------                           2393 (SEQ ID NO: 67)
```

PLANT FATTY ACID DESATURASES AND ALLELES THEREFOR

CROSS REFERENCE TO RELATED APPLICATIONS

This is a continuation of International Application No. PCT/CA00/01141, filed Sep. 29, 2000, which claims a right of priority from Canadian Application No. 2,284,246, filed Oct. 1, 1999. Both applications are incorporated herein in their entirety.

FIELD OF THE INVENTION

The invention is in the field of plant biology, involving compositions and methods related to fatty acid metabolism in plants. Aspects of the invention include genes and enzymes involved in fatty acid metabolism in plants, as well as plants and plant parts having the genes and expressing the enzymes, and methods for making the plants and plant parts using the genes (including recombinant genetic engineering methods and classical plant breeding methods using markers of the invention).

BACKGROUND OF THE INVENTION

Fatty acids are acyl lipids that are found in a variety of plant tissues, including the triacylglycerols in oil bodies of seeds and fruits, as well as the glycolipids and phospholipids in leaves, roots or shoots. Fatty acids include saturated and unsaturated monocarboxylic acids with unbranched even-numbered carbon chains, such as the unsaturated fatty acids: oleic (18:1, i.e. a C18 chain with a double bond in position 1), linoleic (18:2) and linolenic (18:3) acid.

Significant efforts have been made to manipulate the fatty acid profile of plants, particularly oil-seed varieties such as canola that are used for the large-scale production of commercial fats and oils (see for example U.S. Pat. No. 5,625,130 issued to Grant et al. 29 Apr. 1997; U.S. Pat. No. 5,668,299 issued to DeBonte et al. 16 Sep. 1997; U.S. Pat. No. 5,767,338 issued to Fan 16 Jun. 1998; U.S. Pat. No. 5,777,201 issued to Poutre et al. 7 Jul. 1998; U.S. Pat. No. 5,840,946 issued to Wong et al. 24 Nov. 1998; and U.S. Pat. No. 5,850,026 issued to DeBonte et al. 15 Dec. 1998).

A reduction in the linolenic acid content of plant oils may be desirable for some applications. Low linolenic acid cultivars of B. napus have for example been developed from the cultivar Oro (Röbbelen and Nitsch, 1975, L. Z PflanzenzÜchtg 75:93), by mutagenesis including the low linolenic acid cultivars Stellar (Scarth et al., 1988, Can J Plant Sci 68:509) and Apollo (Scarth et al., 1994, Can J Plant Sci 75:203). The Apollo line has been used to identify molecular markers associated with low linolenic acid loci in a double haploid population derived from a cross between the Apollo line (low linolenic) and a high linolenic line (YN90-1016), using random amplification of polymorphic DNAs and bulk segregant analysis (Somers et al., 1998, Theoretical and Applied Genetics 96(6/7):897). The rapeseed fad3 gene, one of 13 markers identified by Somers et al., supra, was mapped near the locus controlling 14% of the variation in linolenic acid content, confirming a link between the fad3 gene and a low linolenic acid phenotype (Jourdren et al., 1996, Theoretical and Applied Genetics 93:512).

The product of the Fad3 gene is a fatty acid desaturase known variously as delta-15 fatty acid desaturase, linoleic acid desaturase, omega-3 fatty acid desaturase, Fad3 or 15-DES (Arondel et al., 1992, Science 258:1353; Yadav et al., 1993, Plant Physiol. 103:467; WO 93/11245; and WO 98/56239 published 17 Dec. 1998), hereinafter called Fad3. Fad 3 is involved in the enzymatic conversion of linoleic acid to alpha-linolenic acid. In WO 98/56239, DeBonte et al. disclose mutant Fad3 genes, and identify regions of the Fad3 enzyme that are said to contain conserved amino acid motifs which may be mutated to alter fatty acid metabolism in a plant (see Tables 5 and 6 therein). The genomic regions identified by DeBonte et al. generally coincide with the first two of three 'Histidine Box' motifs that have been imputed to have a role in the functional activity of the Fad3 enzyme.

SUMMARY OF THE INVENTION

It has unexpectedly been discovered that plant fatty acid metabolism may be altered by mutations in the Fad3 enzyme, particularly by amino acid substitutions in regions of the protein outside of the regions taught to be functionally important in WO 98/56239. In one aspect, the invention accordingly provides new variants of the Fad3 enzyme, comprising non-conserved amino acid substitutions, as well as nucleic acid sequences encoding such peptides. It is disclosed herein that plants having the Fad3 alleles of the invention exhibit a low linolenic acid phenotype. Accordingly, other aspects of the invention include transgenic plants and plant parts. As used herein, 'plant parts' includes plant cells, seeds, pollen bearing the nucleic acids of the invention or expressing the Fad3 enzymes of the invention or having the Fad3 coding sequences of the invention. Vectors capable of transforming plant cells are provided, comprising the nucleic acids of the invention, including Fad3 coding sequences. Corresponding methods are provided for obtaining the transgenic plants of the invention. Methods are provided for using the plants of the invention, including selected plants and transgenic plants, to obtain plant products. As used herein, "plant products" includes anything derived from a plant of the invention, including plant parts such as seeds, meals, fats or oils, including such plant products having altered linolenic acid concentrations. Amplification primers for identifying the Fad3 alleles of the invention are provided, together with methods of obtaining plants using the Fad3 alleles of the invention as markers.

Marker assisted plant breeding programs are provided by the invention, wherein the Fad3 alleles of the invention, such as Fad3A and Fad3C, may be identified in plant lines subjected to selective breeding.

BRIEF DESCRIPTION OF THE DRAWINGS

FIG. 1 is a listing of the amino acid sequence of the Fad3A protein from the Apollo cultivar (SEQ ID NO: 1), showing positions of amino acid substitutions in accordance with various aspects of the invention, at positions 213, 275 and 347. One of the prior-art-identified histidine box sequences, HDCGH, is also boxed for reference.

FIG. 2 is a pairwise alignment of the Apollo Fad3A ("ApolloA") and partial Fad3C ("ApolloC") sequences with the derived Brassica napus omega-3 fatty acid desaturase amino acid sequence which is GenBank accession number L22962 (SEQ ID NO:2), showing: Identities=369/380 (97%), Positives=372/380 (97%), Gaps=3/380, using the BLASTp program. In the Consensus sequence, two regions identified as functionally important in WO 98/56239 appear in boxes. A putative 'histidine box' within the first of these regions, identified in the prior art relating to Fad3 enzymes, is also boxed in the ApolloA and L22962 sequences.

FIG. 3 a pairwise alignment of the Apollo Fad3A sequence and the derived *Brassica napus* omega-3 fatty acid desaturase amino acid sequence which is GenBank accession number L01418 (SEQ ID NO:3), showing: Identities=359/383 (93%), Positives=368/383 (95%), Gaps=3/383 (0%), using the BLASTp program.

FIG. 4 is a pairwise alignment of the Apollo Fad3A sequence and the derived *Arabidopsis thaliana* omega-3 fatty acid desaturase amino acid sequence which is GenBank accession numbers D17579 and D26508 (SEQ ID NO:4), showing: Identities=347/386 (89%), Positives=361/386 (92%), Gaps=6/386 (1%), using the BLASTp program. Position 98 in the sequence is also highlighted, to provide a reference point with respect to the sequence shown in FIG. 5 which begins at residue 98.

FIG. 5 is a partial pairwise alignment of the Apollo Fad3A and Fad3C sequences and the derived YN90-1016 Fad3 sequence (SEQ ID NO:5).

FIG. 6 is a partial pairwise alignment of the Apollo Fad3A sequence and the derived N89-53 Fad3 sequence (SEQ ID NO:6).

FIG. 7 shows an Apollo Fad3A cDNA sequence (SEQ ID NO:7) and a partial Fad3C cDNA sequence, aligned.

FIG. 8 is the Apollo Fad3A genomic DNA sequence (SEQ ID NO:8).

FIG. 9 is a multiple protein sequence alignment, carried out using BLASTP software, comparing the Apollo Fad3A sequence (SEQ ID NO:1) to a variety of known plant delta 15 fatty acid desaturase protein sequences (SEQ ID NO:9 to SEQ ID NO:42).

FIG. 10 is a comparison of the partial genomic pFad3A (Apollo) and partial genomic pFad3Y (YN90-1016) sequences, discussed in the Examples, with a consensus sequence shown between them. The pFad3A sequence is the top sequence, and begins at nucleotide 954 of the Apollo Fad3A genomic DNA sequence of FIG. 8.

FIG. 11 is a sequence alignment performed using the CLUSTALW program, showing the alignment betweeen a genomic Fad3A sequence (SEQ ID NO:8) and a partial genomic Fad3C sequence.

DETAILED DESCRIPTION OF THE INVENTION

In one aspect, the invention provides recombinant nucleic acids encoding a plant fatty acid desaturase. By recombinant, it is meant herein that a nucleic acid is not a naturally occurring sequence, or it is a sequence that is made by an artificial combination of two otherwise separated segments of nucleic acid sequence. Such combinations of sequences may be achieved by a wide variety of genetic engineering techniques, such as mutagenesis and site-specific-recombination of one or more nucleotides (Beetham et al., 1999, *Proc. Natl. Acad. Sci.* USA 96:8774; Zhu et al., 1999, *Proc. Natl. Acad. Sci.* USA 96:87768). By fatty acid desaturase, it is meant herein that a protein exhibits activity manifested as the introduction of a double bond in the biosynthesis of a fatty acid. For example, Fad3 enzymes are defined by the activity of introducing the third double bond in the biosynthesis of 16:3 or 18:3 fatty acids.

In various aspects of the invention, the nucleic acid sequence of the invention may encode an amino acid substitution in the desaturase. By substitution, it is meant that the amino acid sequence is other than it would have been but for the recombination of the nucleic acid encoding the protein. The amino acid substitution may for example be at a position selected from the group consisting of amino acid positions corresponding to amino acid positions 213, 217, 224, 275, 281 and 347 of Apollo Fad3A (SEQ ID NO: 1). By 'corresponding to', in comparison to the Apollo Fad3A (or Fad3C) sequence, it is meant that the positions are aligned when the sequences being compared are optimally aligned, for example using the BLASTP algorithm, with gaps permitted, and allowing for conservative substitutions, as discussed further herein.

In alternative embodiments, amino acid substitutions in the desaturase may be made in particular motifs. For example, substitutions may be made within motifs, such as the motif STTCWSIM (SEQ ID NO: 58) centered on a position corresponding to position 213 of Apollo Fad3A; the motif STTCWSIMLATLVYLSFL (SEQ ID NO: 59) corresponding to positions 210 to 227 of Apollo Fad3A; the motif SYLRGGL (SEQ ID NO: 60) centered on a position corresponding to position 275 of Apollo Fad3A; the motif SXXXDHYVSD (SEQ ID NO: 61) (in which X represents any amino acid) beginning at a position corresponding to position 347 of Apollo Fad3A; a position in the motif STTCWSIMLAT (SEQ ID NO: 62) corresponding to positions 210 to 220 of Apollo Fad3A; and, a position in the motif SYLRGGLTTIDRD (SEQ ID NO: 63) corresponding to positions 272 to 284 of Apollo Fad3A.

It is well known in the art that some modifications and changes can be made in the structure of a polypeptide without substantially altering the biological function of that peptide, to obtain a biologically equivalent polypeptide. As used herein, the term "conserved amino acid substitutions" refers to the substitution of one amino acid for another at a given location in the peptide, where the substitution can be made without any appreciable loss or gain of function, to obtain a biologically equivalent polypeptide. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing. Conversely, as used herein, the term "non-conserved amino acid substitutions" refers to the substitution of one amino acid for another at a given location in the peptide, where the substitution causes an appreciable loss or gain of function of the peptide, to obtain a polypeptide that is not biologically equivalent.

In some embodiments, conserved amino acid substitutions may be made where an amino acid residue is substituted for another having a similar hydrophilicity value (e.g., within a value of plus or minus 2.0), where the following hydrophilicity values are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4). Non-conserved amino acid substitutions may be made were the hydrophilicity value of the residues is significantly different, e.g. differing by more than 2.0. For example, on this basis, the following amino acid substitutions for the wild type Cys (−1.0) at a position corresponding to amino acid 213 in Apollo Fad3A would be non-conserved substitutions: Trp (−3.4), Arg (+3.0); Lys (+3.0); Asp (+3.0); Glu (+3.0). Similarly the following amino acid substitutions for the wild type Arg (+3.0) at a position corresponding to amino acid 275 in Apollo Fad3A would be non-conserved substitutions: Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3);

Phe (−2.5); and Trp (−3.4). Similarly the following amino acid substitutions for the wild type Ser (+0.3) at a position corresponding to amino acid 347 in Apollo Fad3A would be non-conserved substitutions: Arg (+3.0); Lys (+3.0); Asp (+3.0); Glu (+3.0); Leu (−1.8); Ile (−1.8); Tyr (−2.3); Phe (−2.5); and Trp (−3.4).

In alternative embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). Non-conserved amino acid substitutions may be made were the hydropathic index of the residues is significantly different, e.g. differing by more than 2.0. For example, on this basis, the following amino acid substitutions for the wild type Cys (+2.5) at a position corresponding to amino acid 213 in Apollo Fad3A would be non-conserved substitutions: Ile (+4.5); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). Similarly the following amino acid substitutions for the wild type Arg (−4.5) at a position corresponding to amino acid 275 in Apollo Fad3A would be non-conserved substitutions: Ile (+4.5); Val (+4.2); Leu (+3.8); Phe (+2.8); Cys (+2.5); Met (+1.9); Ala (+1.8); Gly (−0.4); Thr (−0.7 ); Ser (−0.8); Trp (−0.9); Tyr (−1.3); Pro (−1.6). Similarly the following amino acid substitutions for the wild type Ser (−0.8) at a position corresponding to amino acid 347 in Apollo Fad3A would be non-conserved substitutions: Ile (+4.5); Val (+4.2); Leu (+3.8); Phe (+2.8); Cys (+2.5); Met (+1.9); Ala (+1.8); His (−3.2); Glu (−3.5); Gln (−3.5); Asp (−3.5); Asn (−3.5); Lys (−3.9); and Arg (−4.5). Similarly, the the following amino acid substitutions for the wild type Met (+1.9) at a position corresponding to amino acid 217 in Apollo Fad3A would be non-conserved substitutions: Ile (+4.5); Val (+4.2); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). Similarly, the the following amino acid substitutions for the wild type Leu (+3.8) at a position corresponding to amino acid 224 in Apollo Fad3A would be non-conserved substitutions: Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr. Non-conserved amino acid substitutions may be made were the residues do not fall into the same class, for example substitution of a basic amino acid for a neutral or non-polar amino acid.

In alternative aspects of the invention, mutant plant fatty acid desaturases, such as Fad3 enzymes, are provided that have amino acid substitutions corresponding to the substitutions found in the Apollo Fad3A or Fad3C proteins: Ala substituted in position 213, or Cys substituted in position 275, or Arg substituted in position 347, or Val substituted in position 217, or Pro substituted in position 224, or Val substituted in position 281. In alternative embodiments, amino acid substitutions may be made at these positions that are at least as non-conserved as the substitutions found in Apollo Fad3A or Fad3C. For example, the substitution of Ala for Cys at position 213 of Apollo Fad3A constitutes a change on the foregoing hydrophilicity scale of −1.0 to −0.5, i.e. a difference of 0.5. Substitutions of similar magnitude of change would comprise substituting any one of the following amino acids for Cys (−1.0): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Val (−1.5); Leu (−1.8); Ile (−1.8); Tyr (−2.3); Phe (−2.5); and Trp (−3.4). Similarly, the substitution of Arg for Ser at position 347 of Apollo Fad3A constitutes a change on the foregoing hydrophilicity scale of +3.0 to +0.3, i.e. a difference of 2.7. Substitutions of similar magnitude of change would comprise substituting any one of the following amino acids for Ser (+0.3): Phe (−2.5); and Trp (−3.4).

In alternative embodiments, using amino acid substitutions based on the foregoing hydropathic index scale, the substitution of Ala for Cys at position 213 of Apollo Fad3A constitutes a change on the foregoing hydrophilicity scale of +2.5 to +1.8, i.e. a difference of 0.7. Substitutions of similar magnitude of change would comprise substituting any one of the following amino acids for Cys (+2.5): Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5); Ile (+4.5); Val (+4.2); Leu (+3.8). Similarly, the substitution of Cys for Arg at position 275 of Apollo Fad3A constitutes a change on the foregoing hydropathic index of −4.5 to +2.5, i.e. a difference of 7.0. Substitutions of similar magnitude of change would comprise substituting any one of the following amino acids for Arg (−4.5): Ile (+4.5); Val (+4.2); Leu (+3.8); Phe (+2.8). Similarly, the substitution of Arg for Ser at position 347 of Apollo Fad3A constitutes a change on the foregoing hydropathic index of −0.8 to −4.5, i.e. a difference of 3.7. Substitutions of similar magnitude of change would comprise substituting any one of the following amino acids for Ser (−0.8): Ile (+4.5); Val (+4.2); Leu (+3.8).

One aspect of the invention is the recognition of functionally important sequence motifs in plant delta 15 fatty acid desaturases, particularly the motifs in the conserved regions that surround the amino acid substitutions in the Apollo Fad3 proteins: including the motif STTCWSIM (SEQ ID NO: 58) centered on position 213; the motif SYLRGGL (SEQ ID NO: 60) centered on position 275; and the motif SXXXDHYVSD (SEQ ID NO: 61) beginning at position 347. Non-conservative amino acid substitutions within these motifs of plant delta 15 fatty acid desaturases are an aspect of the present invention. Plant delta 15 fatty acid desaturases having such non-conserved substitutions may be useful in transgenic plants of the invention to alter fatty acid metabolism, particularly the fatty acid composition of seed oils.

In various aspects, the invention provides isolated nucleic acid and protein sequences. By isolated, it is meant that the isolated substance has been substantially separated or purified away from other biological components with which it would other wise be associated, for example in vivo. The term 'isolated' therefore includes substances purified by standard purification methods, as well as substances prepared by recombinant expression in a host, as well as chemically synthesized substances.

The invention provides vectors comprising nucleic acids of the invention. A vector is a nucleic acid molecule that may be introduced into a host cell, to produce a transformed host cell. A vector may include nucleic acid sequences that permit it to replicate in the host cell, such as an origin of replication. A vector may also include one or more selectable marker genes and other genetic elements known in the art. A transformed cell is a cell into which has been introduced a nucleic acid molecule by molecular biology techniques. As used herein, the term transformation encompasses all such techniques by which a nucleic acid molecule might be introduced into a host cell, including transformation with *Agrobacterium* vectors, transfection with viral vectors, transformation with plasmid vectors and introduction of naked DNA by electroporation, lipofection and particle gun acceleration.

In one aspect the invention provides amplification primers or probes that may be used to identify Fad3 nucleic acid sequences of the invention, such as the Apollo Fad3A or Fad3C nucleic acid sequences, from other nucleic acid sequences. As used herein, the term "Apollo Fad3 nucleic acid sequences", means the naturally occurring nucleic acid sequences, and portions thereof, encoding the Apollo Fad3 enzyme, including Fad3A and Fad3C. For example, primers or probes may be synthesized that are complimentary to portions of the Apollo microsomal Fad3A or Fad3C alleles that differ from the sequence of the Fad3 allele reported by Yadav et al. 1993, Plant Physiology 103:467. An example of such a primer is described in Example 1, wherein one of the selected primers is shown to be capable of distinguishing plants having high linolenic acid content from plants having low linolenic acid content. Such primers or probes may comprise 5 or more contiguous residues complimentary to a Fad3 nucleic acid sequence of the invention, such as Fad3A or Fad3C. In some embodiments, the isolated nucleic acid probe or primer may be capable of hybridizing to a characteristic portion of the recombinant nucleic acid (i.e. a part of the recombinant sequence which differs from other sequences, such as wild type sequences), under selective hybridization conditions. Selective hybridization of this sort may be used to identify a Fad3 nucleic acid sequence of the invention.

In one aspect, the invention provides amplification primers that may be used to incorporate a sequence polymorphism into an amplified nucleic acid sequence, such that a novel restriction site is produced. For example, primers may be synthesized that are substantially complementary to portions of an allele of interest, but differ from the sequence by one or more point mutations that introduce a restriction enzyme cleavage site (Michaels et al., 1998, *The Plant Journal* 14(3): 381–385, and Neff et al., 1998, *The Plant Journal* 14(3): 387–392; both of which are incorporated herein by reference). Primers such as those described in Example 1, may be adapted to produce by amplification a nucleic acid that contains a restriction enzyme site that is unique to an allele. The restriction site may be cleaved by a restriction endonuclease to provide sequence information from allele-specific polymorphisms.

One aspect of the invention comprises a method of selecting plants, such as *Brassica napus* seedlings, having a low linolenic acid content by utilizing PCR primers to selectively amplify a desired Fad3 allele. This method may be used, for example, to ensure that selected progeny carry a desired allele conferring a low linolenic acid oil phenotype. In accordance with an embodiment of the method, seedlings of a first segregating backcross population, may be subjected to PCR analysis to detect the mutant Fad3 nucleic acid, and the selected plants backcrossed again to a recurrent parental line. The backcrossing and PCR analysis of the first seedling population may, for example, proceed through at least two more cycles to create a third segregating backcross seedling population, which may be self-pollinated to create a third seedling population. The third seedling population may be subjected to PCR analysis for the mutant Fad3 nucleic acid, and homozygotes may be selected for further pedigree breeding, such as breeding of an elite, low linolenic acid content strain.

In various embodiments, the invention comprises plants expressing the desaturases of the invention. In some embodiments, such plants will exhibit altered fatty acid content in one or more tissues. These aspects of the invention relate to all higher plants, including monocots and dicots, such as species from the genera *Fragaria, Lotus, Medicago, Onobrychis, Triforium, Trigonelia, Vigna, Citrus, Linum. Geranium, Manihot, Caucus, Arabidopsis, Brassica, Raphanus, Sinapis, Atropa, Capsicum, Hyoscyamus, Lycopersicon, Nicotiana, Solanum, Petunia, Digitalis, Majorana, Cichorium, Helianthus, Lactuca, Bromus, Asparagus, Antirrhinum, Heterocatlis, Nemesia, Pelargonium, Panicum, Penniserum, Ranunculus, Senecio, Salpiglossis, Cucarnis, Browallia, Glycine, Lolium, Zea, Triticum, Sorghum*, and *Datura*. Such plants may include maize, wheat, rice, barley, soybean, beans, rapeseed, canola, alfalfa, flax, sunflower, cotton, clover, lettuce, tomato, cucurbits, potato, carrot, radish, pea, lentils, cabbage, broccoli, brussel sprouts, peppers, apple, pear, peach, apricot, carnations and roses. More specifically, in alternative embodiments, plants for which the invention may be used in modifying fatty acid content include oil crops of the Cruciferae family: canola, rapeseed (*Brassica* spp.), crambe (*Crambe* spp.), honesty (*Lunaria* spp.) lesquerella (*Lesquerella* spp.), and others; the Compositae family: sunflower (*Helianthus* spp.), safflower (*Carthamus* spp.), niger (*Guizotia* spp.) and others; the Palmae family: palm (*Elaeis* spp.), coconut (*Cocos* spp.) and others; the Leguminosae family: peanut (*Arachis* spp.), soybean (*Glycine* spp.) and others; and plants of other families such as maize (*Zea* spp.), cotton (*Gossypium* spp.), jojoba (*Simonasia* spp.), flax (*Linum* spp.), sesame (*Sesamum* spp.), castor bean (*Ricinus* spp.), olive (*Olea* spp.), poppy (*Papaver* spp.), spurge (*Euphorbia*, spp.), meadow foam (*Limnanthes* spp.), mustard (*Sinapis* spp.) and cuphea (*Cuphea* spp.).

In some aspects of the invention, nucleic acids encoding novel Fad3 proteins may be introduced into plants by transformation, and expression of such nucleic acids may be mediated by promoters to which such coding sequences are operably linked. One aspect of the invention comprises plants transformed with nucleic acid sequences encoding the fatty acid desaturases of the invention. Transformation may for example be carried out as described in WO 94/11516, which is hereby incorporated by reference. In the context of the present invention, "promoter" means a sequence sufficient to direct transcription of a gene when the promoter is operably linked to the gene. The promoter is accordingly the portion of a gene containing DNA sequences that provide for the binding of RNA polymerase and initiation of transcription. Promoter sequences are commonly, but not universally, located in the 5' non-coding regions of a gene. A promoter and a gene are "operably linked" when such sequences are functionally connected so as to permit gene expression mediated by the promoter. The term "operably linked" accordingly indicates that DNA segments are arranged so that they function in concert for their intended purposes, such as initiating transcription in the promoter to proceed through the coding segment of a gene to a terminator portion of the gene. Gene expression may occur in some instances when appropriate molecules (such as transcriptional activator proteins) are bound to the promoter. Expression is the process of conversion of the information of a coding sequence of a gene into mRNA by transcription and subsequently into polypeptide (protein) by translation, as a result of which the protein is said to be expressed. As the term is used herein, a gene or nucleic acid is "expressible" if it is capable of expression under appropriate conditions in a particular host cell.

For the present invention, promoters may be used that provide for preferential gene expression within a specific organ or tissue, or during a specific period of development. For example, promoters may be used that are specific for embryogenesis (U.S. Pat. No. 5,723,765 issued 3 Mar. 1998 to Oliver et al.). Such promoters may, in some instances, be obtained from genomic clones of cDNAs. Depending upon the application of the present invention, those skilled in this art may choose a promoter for use in the invention which provides a desired expression pattern. Promoters may be identified from genes which have a differential pattern of expression in a specific tissue by screening a tissue of interest, for example, using methods described in U.S. Pat. No. 4,943,674 and European Patent Application EP-A 0255378.

Various aspects of the present invention encompass nucleic acid or amino acid sequences that are homologous to other sequences. As the term is used herein, an amino acid or nucleic acid sequence is "homologous" to another sequence if the two sequences are substantially identical and the functional activity of the sequences is conserved (for example, both sequences function as or encode a Fad3; as used herein, sequence conservation or identity does not infer evolutionary relatedness). Nucleic acid sequences may also be homologous if they encode substantially identical amino acid sequences, even if the nucleic acid sequences are not themselves substantially identical, for example as a result of the degeneracy of the genetic code.

Two amino acid or nucleic acid sequences are considered substantially identical if, when optimally aligned, they share at least about 70% sequence identity. In alternative embodiments, sequence identity may for example be at least 75%, at least 90% or at least 95%. Optimal alignment of sequences for comparisons of identity may be conducted using a variety of algorithms, such as the local homology algorithm of Smith and Waterman, 1981, *Adv. Appl. Math* 2:482, the homology alignment algorithm of Needleman and Wunsch, 1970, *J. Mol. Biol.*, 48:443, the search for similarity method of Pearson and Lipman, 1988, *Proc. Natl. Acad Sci.* USA 85:2444, and the computerized implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol* 215:403–410 (using the published default settings). Software for performing BLAST analysis may be available through the National Center for Biotechnology Information (through the internet at the NCBI website nobi.nlm.nih-.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold. Initial neighborhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci.* USA 89: 10915–10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially identical is that the two sequences hybridize to each other under moderately stringent, or preferably stringent, conditions. Hybridisation to filter-bound sequences under moderately stringent conditions may, for example, be performed in 0.5 M NaHPO$_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO$_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y.). Generally, stringent conditions are selected to be about 5° C. lower than the thermal melting point for the specific sequence at a defined ionic strength and pH.

An alternative indication that two amino acid sequences are substantially identical is that one peptide is specifically immunologically reactive with antibodies that are also specifically immunoreactive against the other peptide. Antibodies are specifically immunoreactive to a peptide if the antibodies bind preferentially to the peptide and do not bind in a significant amount to other proteins present in the sample, so that the preferential binding of the antibody to the peptide is detectable in an immunoassay and distinguishable from non-specific binding to other peptides. Specific immunoreactivity of antibodies to peptides may be assessed using a variety of immunoassay formats, such as solid-phase ELISA immunoassays for selecting monoclonal antibodies specifically immunoreactive with a protein (see Harlow and Lane (1988) *Antibodies, A Laboratory Manual*, Cold Spring Harbor Publications, New York).

As used herein to describe nucleic acid or amino acid sequences the term "heterologous" refers to molecules or portions of molecules, such as DNA sequences, that are artificially introduced into a particular host cell. Heterologous DNA sequences may for example be introduced into a host cell by transformation. Such heterologous molecules may include sequences derived from the host cell. Heterologous DNA sequences may become integrated into the host cell genome, either as a result of the original transformation of the host cells, or as the result of subsequent recombination events.

In accordance with various aspects of the invention, plant cells may be transformed with heterologous nucleic acids. In this context, "heterologous" denotes any nucleic acid that is introduced by transformation. Transformation techniques that may be employed include plant cell membrane disruption by electroporation, microinjection and polyethylene glycol based transformation (such as are disclosed in Paszkowski et al. *EMBO J* 3:2717 (1984); Fromm et al., *Proc. Natl. Acad. Sci.* USA 82:5824 (1985); Rogers et al., *Methods Enzymol.* 118:627 (1986); and in U.S. Pat. Nos. 4,684,611; 4,801,540; 4,743,548 and 5,231,019), biolistic transformation such as DNA particle bombardment (for example as disclosed in Klein, et al., *Nature* 327: 70 (1987); Gordon-Kamm, et al. "The Plant Cell" 2:603 (1990); and in U.S. Pat. Nos. 4,945,050; 5,015,580; 5,149,655 and 5,466,587); *Agrobacterium*-mediated transformation methods (such as those disclosed in Horsch et al. *Science* 233: 496 (1984); Fraley et al., *Proc. Nat'l Acad. Sci.* USA 80:4803 (1983); and U.S. Pat. Nos. 4,940,838 and 5,464,763).

Transformed plant cells may be cultured to regenerate whole plants having the transformed genotype and displaying a desired phenotype, as for example modified by the expression of a heterologous Fad3 during growth or development. A variety of plant culture techniques may be used to regenerate whole plants, such as are described in Gamborg and Phillips, "Plant Cell, Tissue and Organ Culture, Fundamental Methods", Springer Berlin, 1995); Evans et al. "Protoplasts Isolation and Culture", Handbook of Plant Cell Culture, Macmillian Publishing Company, New York, 1983; or Binding, "Regeneration of Plants, Plant Protoplasts", CRC Press, Boca Raton, 1985; or in Klee et al., *Ann. Rev. of Plant Phys.* 38:467 (1987).

Standard techniques may be used for plant transformation, such as transformation of *Arabidopsis*. For example, wild type (WT) *A. thaliana* seeds of ecotype "Columbia" may be planted in 4" pots containing soil and plants grown in a controlled growth chamber or greenhouse. The vacuum infiltration method of in planta transformation (Bechtold et al., 1993) may be used to transform *A. thaliana* plants with overnight culture of *A. tumefaciens* strain GV3101 bearing both the helper nopoline plasmid and the binary construct containing the described chimeric gene. pMP90 is a disarmed Ti plasmid with intact vir region acting in trans, gentamycin and kanamycin selection markers as described in Koncz and Schell (1986). Following infiltration, plants may be grown to maturity and seeds (T1) collected from each pod individually. Seeds may be surface-sterilized and screened on selective medium containing 50 mg/L kanamycin with or without 200–300 mg/L timentin. After about four weeks on selection medium, the non-transformed seedlings will generally die. The transformed seedlings may be transferred to soil in pots. Leaf DNA may be isolated (Edwards et al., 1991) and analyzed by PCR for the presence of the DNA insertion. Genomic DNA may also be isolated and used in Southern hybridization (Southern, 1975) to determine the copy number of the inserted sequence in a given transformant. To determine the segregation, T2 seeds may be collected from T1 plants.

Alternative embodiments of the invention may make use of techniques for transformation of Brassica. Such as transformation of *B. napus* cv. Westar and *B. carinala* cv. Dodolla by co-cultivation of cotyledonary petioles or hypocotyl explants with *A. tumefaciens* bearing the plasmids described herein. Transformation of *B. napus* plants may, for example, be performed according to the method of Moloney et al., 1989, *Plant Cell Rep* 8: 238. Modifications of that method may include the introduction of a 7-day explant-recovery period following co-cultivation, on MS medium with the hormone benzyladenine (BA), and the antibiotic timentin for the elimination of *Agrobacterium*. Transformation of *B. carinata* plants may be performed according to the method by Babic et al., 1998, *Plant Cell Rep* 17: 183. Cotyledonary petiole explants may be dipped in suspension of *Agrobacterium* bearing the desired constructs and placed on 7-cm filter paper (Whatman no. 1) on top of the regeneration medium for 2 days. After co-cultivation, explants may be transferred onto the selection medium containing 50 mg/L kanamycin. Regenerated green shoots may first be transferred to a medium to allow elongation and then to a rooting medium all containing 50 mg/L kanamycin. Putative transformants with roots (T0) may be transferred to soil. Genomic DNA may be isolated from developing leaves for PCR and Southern analyses. Seeds (T1) from transgenic plants may then be harvested. Transgenic plants may be observed and characterized for alteration of traits, particularly fatty acid content, and more particularly fatty acid content of seed oils.

EXAMPLE 1

Isolation of Apollo Fad3 Sequences

Cloning and sequence analysis of the Fad3A gene is described below, the Fad3C gene from Apollo was cloned and characterized in a similar manner.

PCR primers described in a publication by Jourdren et al. (1996) were used to amplify the microsomal delta-15 fatty acid desaturase coding sequences (Fad3) from the following *B. napus* accessions: low linolenic acid variety Apollo (Scarth et al. 1994) and normal linolenic acid breeding lines YN90-1016 and N89-53 (Agriculture and Agri-Food Canada). The PCR reaction conditions used are described in Somers et al., 1998, *Theor. Appl. Genet.* 96: 897. The primer sequences were degenerate and named FAD3L and FAD3R (see Table 1). An amplified DNA fragment was cloned from each accession into pGEM (Promega Corp, Madison Wis., USA) and each of the clones (pFad3A, from Apollo; pFAD3Y, from YN90-1016; and pFad3N89 from N89-53) was sequenced using the di-deoxy terminator cycle sequencing technique. The initial clones containing the Fad3 coding sequence were lacking the 3' and 5' coding sequences. The 3' end of the genomic sequence from Apollo was PCR amplified using a primer (A047F, Table 1) designed from the pFad3A clone and a primer (A047R, Table 1) derived from the terminus of the genebank sequence L01418, a *B. napus* microsomal Fad3 gene. The 5' end of the genomic sequence from Apollo was PCR amplified using a primer (A046F, Table 1) designed from the pFad3A clone and a primer (A046R, Table 1) derived from the terminus of the genebank sequence L01418. The Fad3 genomic DNA sequences were then aligned with genebank sequence L01418 (cDNA) and based on this alignment, the Apollo, YN90-1016 and N89-53 Fad3 coding and non-coding sequences were distinguished, and the coding frame determined.

The three *B. napus* Fad3 coding sequences were converted to amino acid sequences using Lasergene, DNA STAR software and the protein sequences were aligned with the protein sequence derived from L01418. Differences at the protein sequence level between pFad3A and L01418, pFad3Y, pFad3N89 correlated to differences in the DNA coding sequence.

An alignment of the genomic DNA sequences in pFad3A, pFad3Y and pFad3N89 revealed several sequence differences within intron regions. PCR primers were derived from the pFad3A intron sequences and included the observed sequence polymorphisms (Table 1). DNA was extracted from many other oilseed accessions and these are described in Table 2.

TABLE 1

PCR primer sequences derived from the sequence of pFad3A

| Primer name | Sequence (5'-3') | SEQ ID NO's |
|---|---|---|
| A006R | AAG AGT GGC CAA CAT GAT CG | 43 |
| A007F | ATT CTT AGC ATC TGC CTC G | 44 |
| A027F | CCC CTT CTG AAT ACT GCG GT | 45 |
| A028F | TTC CGG TAA TCC CCC TCT CA | 46 |
| A029R | ACT GTA GTC ATC CCC AAA CAA AT | 47 |
| A036F | GCA TCA AAA TCT TTA GCA TCG AA | 48 |
| A037F | GGT GCA TGT TAG CAA ACA GTA AT | 49 |
| A046F | CAT TTC ACT CAG AGC CCA CAC | 50 |
| A046R | GAC CAA CGC CAG TAT TCA GA | 51 |
| A047F | ATT ACG GGA TCT TCA ACA ACC A | 52 |
| A047R | TAA AAA CAA CCA GAA ATA AGT AAA | 53 |
| A048 | CTA TCA ATA GTT GTT AAT CCT CCA CA | 54 |
| A050 | TTG GAC GAC CAC TTG TCA GAT T | 55 |
| FAD3L | GTG GAC ATG GGA GTT TYT CNG A | 56 |
| FAD3R | TGG CAT CGA CCA ART GRT ART G | 57 |

Figure 10:
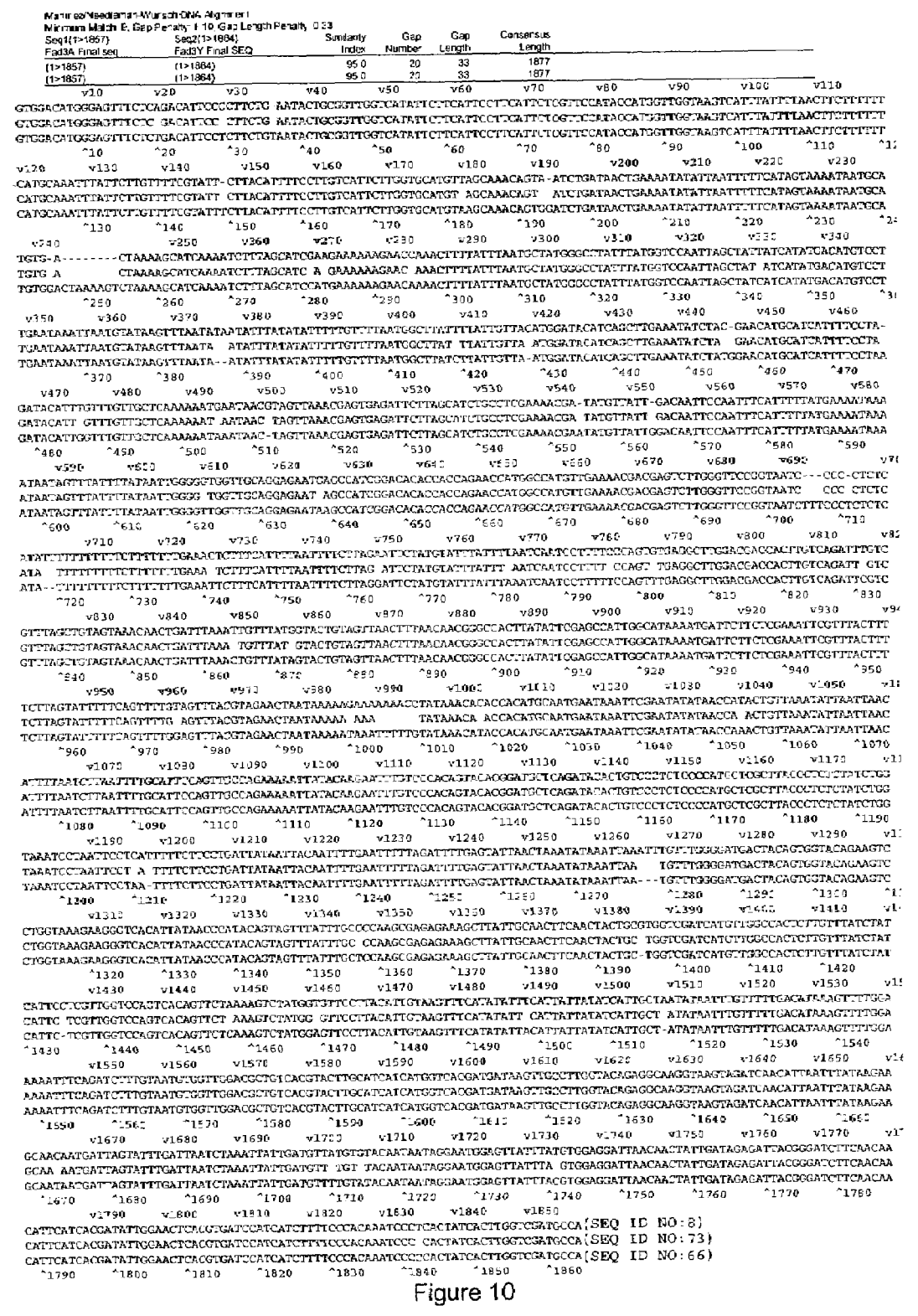

The pFad3A genomic DNA sequence is 3007 bp (FIG. 8) and includes the entire coding sequence. The pFad3A and pFad3Y (1864 bp) sequences were aligned and there were several sequence polymorphisms observed throughout the sequences (FIG. 10). A number of polymorphisms are further exemplified herein, centered at nucleotides 191, 270, 693 and 1267 of pFad3A as shown in FIG. 10.

PCR primers that included sequence polymorphisms observed in the Apollo Fad3 coding sequences were designed from the pFad3A sequence (primers A028F, A029R, A036F, A037F shown in Table 1). These primers were paired with different conserved PCR primers (designated A006R, A007F and A027F in Table 1) to demonstrate the ability to selectively amplify the Apollo Fad3 allele over other alleles, particularly wild-type alleles such as the YN90-1016 Fad3 allele. A DNA fragment of the predicted size was amplified from the Apollo DNA template in each case and was not amplified from the YN90-1016 DNA template. Therefore, the sequence polymorphisms observed in the Apollo Fad3 gene may be used to selectively amplify and detect the mutant Fad3 allele from Apollo. Similar sequence alignments of the Apollo Fad3 allele to other crucifer oilseed Fad3 alleles may be routinely used to identify sequence polymorphisms that may be used as a basis for the selective amplification of the Apollo Fad3 allele.

The alignment of pFad3A, pFad3Y and pFad3N89 with the Fad3 Genebank sequence L01418 showed the position of introns and exons within pFad3A, pFad3Y and pFad3N89. The intron sequences were edited out to identify the coding sequence of pFad3A (852 bp in length) to be aligned with the coding sequence of pFad3Y (657 bp in length), showing a number of nucleotide polymorphisms (FIG. 10).

Both the pFad3A and pFad3Y coding sequences were converted to amino acid sequences and aligned (FIG. 5). A non-conserved change (mutation) in the amino acid sequence between these protein sequences was identified at amino acid 275 of the Apollo Fad3 sequence (Apollo, cysteine; YN90-1016, arginine). FIG. 9 shows the extent to which this mutation distinguishes the Apollo Fad3 enzyme from a very wide variety of other known delta-15 fatty acid desaturases. Similarly, FIG. 9 shows a number of other amino acid substitutions in the Apollo Fad3 sequence compared to other delta-15 fatty acid desaturases.

Identifying DNA sequence differences and primers.

The mutation at amino acid 275 (cysteine) is due to a single base pair mutation, shown boxed in FIG. 7 (cDNA) at nucleotide 823, boxed in FIG. 8 at nucleotide 2685 and at corresponding nucleotide 1734 of the pFad3A DNA sequence of FIG. 10 (the pFad3A sequence of FIG. 10 begins at nucleotide 954 of FIG. 8). The wild type L01418, YN90-1016 and N89-53 Fad3 alleles all included a CGT (arginine) codon and the mutant Apollo Fad3 allele includes a TGT (cysteine) codon (FIG. 9).

A PCR primer (A048, Table 1) was designed to include the DNA sequence polymorphism at a nucleotide corresponding to nucleotide 1734 of pFad3A (FIG. 10) where the final nucleotide in the 3' end of the primer included an 'A' (Adenine) nucleotide to selectively PCR amplify the mutant Apollo Fad3 allele over corresponding wildtype Fad3 alleles.

Specificity of selective amplification of Apollo microsomal Fad3A allele.

The mutant microsomal Fad3 alleles of Apollo are thought to be derived from a low linolenic acid mutant line from Germany, designated 'M11' (Röbbelen G, Nitsch A, 1975, *L. Z PflanzenzÜchtg* 75:93). Amplification products indicative of the Apollo Fad3A allele were obtained using primers A048 and A050 (Table 1). A collection of genotypes were tested, as listed in table 2, for the presence of the C to T nucleotide polymorphism of the Apollo Fad3A allele. PCR amplification from an Apollo DNA template was also assayed as a control. Apart from Apollo, the only other genotypes showing the presence of the amplification product from the Apollo Fad3A gene included TO97-3414, S86-69 and Stellar. Stellar is the first spring canola quality *B. napus* variety developed carrying low linolenic acid and was derived from crosses with M11 (low linolenic acid) (Scarth et al. 1988). Accession S86-69 is a low linolenic acid *B. napus* line selected from the variety Apollo. TO97-3414 is a (BC3F4) *B. juncea* accession derived from interspecific crosses of *B. juncea* with S86-69 and selection for low linolenic acid. Therefore, all of the accessions showing amplification of the mutant Apollo Fad3A allele are related to Apollo, in the sense that they are all descended from *B. napus* line M11 (by "descended from" it is meant that a plant is derived from another by methods of classical plant breeding, including crossing parent plant lines or self crossing of parent plants, but this does not include methods of genetic engineering in which nucleic acid sequences are recombined to produce new strains). Such PCR tests may be highly specific, and may be used in one aspect of the invention as a selective amplification assay for the presence of the Apollo Fad3A or Fad3C alleles in a wide variety of genetic backgrounds.

TABLE 2

Crucifer oilseed species/accessions tested for the presence of the Fad3A allele using primers A048 and A050.

| Species | [1]Type | Accession | [2]Linolenic acid content |
|---|---|---|---|
| B. juncea | Spring/breeding | J90-2741 | High |
| B. juncea | Spring/breeding | J90-4253 | High |
| B. juncea | Spring/breeding | J90-223 | High |
| B. juncea | Spring/breeding | TO97-3422-1 | High |
| B. juncea | Spring/breeding | TO97-3421-1 | High |
| B. juncea | Spring/breeding | TO97-3414 | Low |
| B. juncea | Spring/breeding | TO97-3400 | High |
| B. napus | Spring/breeding | DH13830 | High |
| B. napus | Spring/breeding | DH13619 | High |
| B. napus | Spring/breeding | 9592 | High |
| B. napus | Spring/canola | Range | High |
| B. napus | Spring/canola | Dunkeld | High |
| B. napus | Spring/breeding | N89-17 | High |
| B. napus | Spring/breeding | YN90-1016 | High |
| B. napus | Spring/breeding | 264-663 | High |
| B. napus | Spring/breeding | 1269 | High |
| B. napus | Spring/breeding | 1526 | High |
| B. napus | Spring/breeding | S86-69 | Low |
| B. rapa | Spring/canola | Horizon | High |
| B. rapa | Spring/canola | Mavrick | High |
| B. rapa | Spring/canola | Reward | High |
| B. rapa | Spring/canola | Tobin | High |
| B. rapa | Spring/rape | Bronowski | High |
| B. rapa | Spring/rape | Cresor | High |
| B. rapa | Spring/rape | Midas | High |
| B. rapa | Spring/rape | Oro | High |
| B. napus | Spring/canola | AC Elect | High |
| B. napus | Spring/canola | AC Excel | High |
| B. napus | Spring/canola | AC H102 | High |
| B. napus | Spring/canola | Alto | High |
| B. napus | Spring/canola | Cyclone | High |
| B. napus | Spring/canola | Delta | High |
| B. napus | Spring/canola | Garrison | High |
| B. napus | Spring/canola | Global | High |
| B. napus | Spring/canola | Hyola 417 | High |
| B. napus | Spring/canola | Karat | High |
| B. napus | Spring/canola | Legacy | High |
| B. napus | Spring/canola | Legend | High |
| B. napus | Spring/canola | Polo | High |
| B. napus | Spring/canola | Profit | High |
| B. napus | Spring/canola | Regent | High |
| B. napus | Spring/canola | Shiralee | High |
| B. napus | Spring/canola | Stellar | Low |
| B. napus | Spring/canola | Topas | High |
| B. napus | Spring/canola | Tower | High |
| B. napus | Spring/canola | Tribute | High |
| B. napus | Spring/canola | Westar | High |
| B. napus | Winter/canola | Cascade | High |
| B. napus | Winter/canola | Ceres | High |
| B. napus | Winter/canola | Glacier | High |
| B. napus | Winter/canola | Mar | High |
| B. napus | Winter/canola | Rubin | High |
| B. napus | Winter/canola | Samourai | High |
| B. napus | Winter/canola | Tandem | High |
| B. napus | Winter/canola | Tapidor | High |
| B. napus | Winter/rape | Marcus | High |
| B. napus | Winter/rape | Jet Neuf | High |
| B. juncea | oriental | AC Vulcan | High |
| B. juncea | oriental | Forge | High |
| B. juncea | Brown | Scimitar | High |
| S. alba | Spring/canola | WD96-2-3 | High |
| S. alba | Mustard | Emergo | High |
| B. rapa | Spring/breeding | 7001 | High |
| B. rapa | Spring/breeding | 6909 | High |
| B. rapa | Spring/breeding | 6810 | High |
| B. rapa | Spring/breeding | 6794 | High |

[1]Winter and Spring represent the growth habit; canola indicates low in erucic acid and low in glucosinolate content, rape indicates high erucic acid content, breeding indicates unregistered lines.
[2]Low = <4% C18:3, High = >8% C18:3.

EXAMPLE 2

FIG. 9 shows a protein sequence alignment between the Apollo Fad3A protein and a wide variety of other Fad3 sequences, identified by database accession number, and more particularly described below. The alignment was produced using the BLASTP software available from the National Centre for Biotechnology Information (NCBI, Bethesda, Md., U.S.A.) through the internet at the NCBI website ncbi.hlm.nih.gov/BLAST/. A description of how to use this software, including how to optimally align sequences is available on the internet at the NCBI website cnbi.nlm.nih.gov/BLAST/blast/_help.html. In summary form, the database sequences are as follows, with the 'Expect' value of the match with the Apollo Fad3A sequence, as calculated by the BLAST algorithm:

TABLE 3

Fad3 Sequences Compared[2] to Apollo Fad3

| Accession | Expect[1] |
|---|---|
| sp|P46311|FD31_BRANA OMEGA-3 FATTY ACID DESATURASE, ENDOPLA . . . | 0.0 |
| sp|P48624|FD32_BRANA OMEGA-3 FATTY ACID DESATURASE, ENDOPLA . . . | 0.0 |
| sp|P48623|FD3E_ARATH OMEGA-3 FATTY ACID DESATURASE, ENDOPLA . . . | 0.0 |
| gi|3133289 (AF020204) omega-3 desaturase [Pelargonium x hor . . . | e-171 |
| sp|P32291|FD3E_PHAAU OMEGA-3 FATTY ACID DESATURASE, ENDOPLA . . . | e-168 |
| gi|4091113 (AF047172) omega-3 fatty acid desaturase [Vernic . . . | e-168 |
| sp|P48622|FD3D_ARATH TEMPERATURE-SENSITIVE OMEGA-3 FATTY AC . . . | e-167 |
| gb|AAD15744| (AF047039) omega-3 fatty acid desaturase [Peri . . . | e-166 |
| sp|P48619|FD3C_RICCO OMEGA-3 FATTY ACID DESATURASE, CHLOROP . . . | e-165 |
| gi|1754795 (U59477) omega-3 fatty acid desaturase [Perilla . . . | e-164 |
| sp|P48620|FD3C_SESIN OMEGA-3 FATTY ACID DESATURASE, CHLOROP . . . | e-164 |
| sp|P46310|FD3C_ARATH OMEGA-3 FATTY ACID DESATURASE, CHLOROP . . . | e-164 |
| dbj|BAA11475| (D79979) omega-3 fatty acid desaturase [Nicot . . . | e-163 |
| sp|P48626|FD3E_TOBAC OMEGA-3 FATTY ACID DESATURASE, ENDOPLA . . . | e-163 |

TABLE 3-continued

Fad3 Sequences Compared[2] to Apollo Fad3

| Accession | Expect[1] |
|---|---|
| gi\|4240385 (AF061027) omega-3 fatty acid desaturase precurs . . . | e-162 |
| gi\|1786066 (U75745) omega-3 fatty acid desaturase [Petrosel . . . | e-162 |
| sp\|P48625\|FD3E_SOYBN OMEGA-3 FATTY ACID DESATURASE, ENDOPLA . . . | e-162 |
| sp\|P48618\|FD3C_BRANA OMEGA-3 FATTY ACID DESATURASE, CHLOROP . . . | e-162 |
| dbj\|BAA22440\| (D63953) fatty acid desaturase [Zea mays] >gl . . . | e-162 |
| sp\|P48621\|FD3C_SOYBN OMEGA-3 FATTY ACID DESATURASE, CHLOROP . . . | e-161 |
| dbj\|BAA22441\| (D63954) fatty acid desaturase [Zea mays] | e-160 |
| emb\|CAA07638\| (AJ007739) w-3 desaturase [Solanum tuberosum] | e-160 |
| gi\|699590 (U17065) delta-15 lineoyl desaturase [Limnanthes . . . | e-155 |
| dbj\|BAA07785.1\| (D43698) plastid omega-3 fatty acid desatur . . . | e-154 |
| dbj\|BAA28358\| (D84678) omega-3 fatty acid desaturase [Triti . . . | e-154 |
| dbj\|BAA11397\| (D78506) w-3 fatty acid desaturase [Oryza sat . . . | e-147 |
| gi\|408490 (L22963) omega-3 fatty acid desaturase [Brassica . . . | e-145 |
| dbj\|BAA22439\| (D65952) fatty acid desaturase [Zea mays] | e-113 |
| dbj\|BAA11396\| (D78505) w-3 fatty acid desaturase [Oryza sat . . . | e-110 |
| gi\|2197199 (U36389) omega-3 desaturase [Synechococcus PCC7002] | e-102 |
| gb\|AAD41582.1\|AF056572_1 (AF056572) unknown [Brassica rapa] . . . | e-102 |
| pir\|\|S52650 desaturase delta 15—Synechocystis sp. (strain . . . | 6e-96 |
| gb\|AAD41581.1\|AF056571_1 (AF056571) unknown [Brassica olera . . . | 6e-80 |
| gb\|AAD41580.1\|AF056570_1 (AF056570) unknown [Brassica napus] | 2e-79 |

[1]Some "E" values shown as exponents, e.g. 'e-171 = 1 × $10^{-171}$
[2]The database used a basis for the BLASTP search was Non-redundant GenBank CDS (translations + PDB + SwissProt + SPupdate + PIR), Posted date: Sep. 14, 1999 3:12 PM (number of letters in database: 126,047,814; number of sequences in database: 411,698), using the following parameters:
Lambda   K     H
0.324   0.140 0.461
Gapped
Lambda   K     H
0.270   0.0470 0.230
Matrix: BLOSUM62
Gap Penalties: Existence: 11, Extension: 1
Number of Hits to DB: 106686529
Number of Sequences: 411698
Number of extensions: 4746913
Number of successful extensions: 13626
Number of sequences better than 10.0: 129
Number of HSP's better than 10.0 without gapping: 102
Number of HSP's successfully gapped in prelim test: 27
Number of HSP's that attempted gapping in prelim test: 13347
Number of HSP's gapped (non-prelim): 139
length of query: 380
length of database: 126,047,814
effective HSP length: 48
effective length of query: 332
effective length of database: 106286310
effective search space: 35287054920
effective search space used: 35287054920
T: 11
A: 40
X1: 15 (7.0 bits)
X2: 38 (14.8 bits)
X3: 64 (24.9 bits)
S1: 40 (21.5 bits)
S2: 71 (32.1 bits)

Further particulars of the non-Apollo Fad3 sequences included in FIG. 9 are as follows:

P46311 (Brassica napus)

| | |
|---|---|
| LOCUS | FD31_BRANA    377 aa          PLN       Feb. 1, 1996 |
| DEFINITION | OMEGA-3 FATTY ACID DESATURASE, ENDOPLASMIC RETICULUM (VERSION 1). |
| ACCESSION | P46311 |
| PID | g1169600 |
| VERSION | P46311 GI:1169600 |

```
DESOURCE    swissprot: locus FD31_BRANA, accession P46311;
            class: standard.
            created: Nov. 1, 1995.
            sequence updated: Nov. 1, 1995.
            annotation updated: Feb. 1, 1996.
            xrefs: gi: 408491, gi: 408492
KEYWORDS    OXIDOREDUCTASE; FATTY ACID BIOSYNTHESIS; ENDOPLASMIC
            RETICULUM; TRANSMEMBRANE.
SOURCE      rape.
ORGANISM    Brassica napus
            Eukaryotae; Viridiplantae; Charophyta/Embryophyta group;
            Embryophyta; Tracheophyta; seed plants; Magnoliophyta;
            eudicotyledons; Rosidae; Capparales; Brassicaceae; Brassica.
REFERENCE   1 (residues 1 to 377)
AUTHORS     YADAV, N. S., WIERZBICKI, A., AEGERTER, M., CASTER, C. S., PEREZ-
            GRAU, L., KIMNEY, A. J., HITZ, W. D., BOOTH, J. R. JR., SCHWEIGER, B.,
            STECCA, K. L., ALLEN, S. M., BLACKWELL, M.,
            REITER, R. S., CARLSON, T. J., RUSSELL, S. H., FELDMANN, K. A.,
            PIERCE, J. and BROWSE, J.
TITLE       Cloning of higher plant omega-3 fatty acid desaturases
JOURNAL     Plant Physiol. 103 (2), 467–476 (1993)
MEDLINE     94302147
REMARK      SEQUENCE FROM N.A.
            TISSUE = SEED
COMMENT     (FUNCTION) ER (MICROSOMAL) OMEGA-3 FATTY ACID DESATURASE
            INTRODUCES THE THIRD DOUBLEBOND IN THE BIOSYNTHESIS OF 18:3
            FATTY ACIDS, IMPORTANT CONSTITUENTS OF PLANT MEMBRANES. IT IS
            THOUGHT TO USE CYTOCHROME B5 AS AN ELECTRON DONOR AND TO ACT
            ON FATTY ACIDS ESTERIFIED TO PHOSPHATIDYLCHOLINE AND,
            POSSIBLY, OTHER PHOSPHOLIPIDS.
            [PATHWAY] POLYUNSATURATED FATTY ACID BIOSYNTHESIS.
            [SUBCELLULAR LOCATION] ENDOPLASMIC RETICULUM. [DOMAIN] THE
            HISTIDINE BOX DOMAINS MAY CONTAIN THE ACTIVE SITE AND/OR BE
            INVOLVED IN METAL ION BINDING.
            [SIMILARITY] TO OTHER PLANT OMEGA-3 FATTY ACID DESATURASES.
FEATURES    Location/Qualifiers
source      1 . . . 377
            /organism="Brassica napus"
            /db_xref="taxon:3708"
            1 . . . 377
Protein     1 . . . 377
            /product="OMEGA-3 FATTY ACID DESATURASE, ENDOPLASMIC
            RETICULUM"
            /EC_number="1.14.99.—"
Region      54 . . . 73
            /region_name="Transmembrane region"
Region      92 . . . 96
            /note="HISTIDINE BOX 1."
            /region_name="Domain"
Region      128 . . . 132
            /note="HISTIDINE BOX 2."
            /region_name="Domain"
Region      203 . . . 226
            /region_name="Transmembrane region"
Region      233 . . . 251
            /region_name="Transmembrane region"
Region      295 . . . 299
            /note="HISTIDINE BOX 3."
            /region_name="Domain"
ORIGIN (SEQ ID NO:9)
mvvamdqrsn angderfdps aqppfkigdi raaipkhcwv ksplrsmsyv ardifavval avaavyfdsw ffwplywaaq gtlfwaifvl ghdcghgsfs dipllntavg hilhsfilvp yhgwrishrt hhqnhghven deswvplpek lyknlshstr mlrytvplpm layplylwyr spgkegshyn pysslfapse rkliatsttc wsimlatlvy lsflvgpvtv lkvygvpyii fvmwldavty lhhhghddkl pwyrgkewsy lrgglttidr dygifnnihh digthvihhl fpqiphyhlv datksakhvl gryyrepkts gaipihlves lvasikkdhy vsdtgdivfy etdpdlyvya sdkskin
```

-continued

P48624 (*Brassica napus*)

```
LOCUS       FD32_BRANA       383 aa                      PLN       Feb. 1, 1996
DEFINITION  OMEGA-3 FATTY ACID DESATURASE, ENDOPLASMIC RETICULUM (VERSION 2).
ACCESSION   P48624
PID         g1345967
VERSION     P48624 GI:1345967
DBSOURCE    swissprot: locus FD32_BRANA, accession P48624;
            class: standard.
            created: Feb. 1, 1996.
            sequence updated: Feb. 1, 1996.
            annotation updated: Feb. 1, 1996.
            xrefs: gi: 167147, gi: 167148
KEYWORDS    OXIDOREDUCTASE; FATTY ACID BIOSYNTHESIS; ENDOPLASMIC
            RETICULUM; TRANEMEMBRANE.
SOURCE      rape.
ORGANISM    Brassica napus
            Eukaryotae; Viridiplantae; Charophyta/Embryophyta group;
            Embryophyta; Tracheophyta; seed plants; Magnoliophyta;
            eudicotyledons; Rosidae; Capparales; Brassicaceae; Brassica.
REFERENCE   1 (residues 1 to 383)
AUTHORS     Arondel, V., Lemieux, B., Hwang, I., Gibson, S., Goodmnan, H. M. and
            Somerville, C. R.
TITLE       Map-based cloning of a gene controlling omega-3 fatty acid
            desaturation in Arabidopsis
JOURNAL     Science 258 (5086), 1353-1355 (1992)
MEDLINE     93088059
REMARK      SEQUENCE FROM N.A.
COMMENT     [FUNCTION] ER (MICROSOMAL) OMEGA-3 FATTY ACID DESATURASE
            INTRODUCES THE THIRD DOUBLEBOND IN THE BIOSYNTHESIS OF 18:3
            FATTY ACIDS, IMPORTANT CONSTITUENTS OF PLANT MEMBRANES. IT IS
            THOUGHT TO USE CYTOCHROME B5 AS AN ELECTRON DONOR AND TO ACT
            ON FATTY ACIDS ESTERIFIED TO PHOSPHATIDYLCHOLINE AND,
            POSSIBLY, OTHER PHOSPHOLIPIDS.
            [PATHWAY] POLYUNSATURATED FATTY ACID BIOSYNTHESIS.
            [SUBCELLULAR LOCATION] ENDOPLASMIC RETICULUM. [DOMAIN] THE
            HISTIDINE BOX DOMAINS MAY CONTAIN THE ACTIVE SITE
            AND/OR BE INVOLVED IN METAL ION BINDING.
            [SIMILARITY] TO OTHER PLANT OMEGA-3 FATTY ACID DESATURASES.
FEATURES    Location/Qualifiers
source      1 . . . 383
            /organism="Brassica napus"
            /db_xref="taxon:3708"
            1 . . . 383
Protein     1 . . . 383
            /product="OMEGA-3 FATTY ACID DESATURASE, ENDOPLASMIC
            RETICULUM"
            /EC_number="1.14.99.-"
Region      53 . . . 73
            /region_name="Transmembrane region"
Region      98 . . . 102
            /note="HISTIDINE BOX 1."
            /region_name="Domain"
Region      134 . . . 138
            /note="HISTIDINE BOX 2."
            /region_name="Domain"
Region      210 . . . 230
            /region_name="Transmembrane region"
Region      234 . . . 254
            /region_name="Transmembrane region"
Region      301 . . . 305
            /note="HISTIDINE BOX 3."
            /region_name="Domain"
ORIGIN (SEQ ID NO:10)
mvvamdqrsn vngdsgarke egfdpsaqpp fkigdiraai pkhcwvkspl rsmsyvtrdi favaalamaa vyfdswflwp lywvaqgtlf waifvlghdc ghgsfsdipl lnsvvghilh sfilvpyhgw rishrthhqn hghvendesw vplpeklykn lphstrmlry tvplpmlayp iylwyrspgk egshfnpyss lfapserkli atsttcwsim latlvylsfl vdpvtvlkvy gvpyiifvmw ldavtylhhh ghdeklpwyr gkewsylrgg lttidrdygi fnnihhdigt hvihhlfpqi phyhlvdatr aakhvlgryy repktsgaip ihlveslvas ikkdhyvsdt gdivfyetdp dlyvyasdks kin
```

-continued

P48623 (thale cress, *Arabidopsis thaliana*)

```
Score = 753 bits (1922), Expect = 0.0
Identities = 348/386 90%), Positives = 362/386(93%), Gaps = 6/386(1%)
LOCUS       FD3E_ARATH      386 aa              PLN       Oct. 1, 1996
DEFINITION  OMEGA-3 FATTY ACID DESATURASE, ENDOPLASMIC RETICULUM.
ACCESSION   P48623
PID         g1345973
VERSION     P48623 GI:1345973
DBSOURCE    swissprot: locus FD3E_ARATH, accession P48623;
            class: standard.
            created: Feb. 1, 1996.
            sequence updated: Feb. 1, 1996.
            annotation updated: Oct. 1, 1996.
            xrefs: gi: 408482, gi: 408483, gi: 1030693, gi: 471091, gi:
            511907, gi: 1197795
KEYWORDS    OXIDOREDUCTASE; FATTY ACID BIOSYNTHESIS; ENDOPLASMIC
            RETICULUM; TRANSMEMBRANE.
SOURCE      thale cress.
ORGANISM    Arabidopsis thaliana
            Eukaryotae; Viridiplantae; Charophyta/Embryophyta group;
            Embryophyta; Tracheophyta; seed plants; Magnoliophyta;
            eudicotyledons; Rosidae; Capparales; Brassicaceae;
            Arabidopsis.
REFERENCE   1 (residues 1 to 386)
AUTHORS     YADAV, N. S., WIERZBICKI, A., AEGERTER, M., CASTER, C. S., PEREZ-
            GRAU, L., KINNEY, A. J., HITZ, W. D., BOOTH, J. R. JR.,
            SCHWEIGER, B., STECCA, K. L., ALLEN, S. M., BLACKWELL, M.,
            REITER, R. S., CARLSON, T. J., RUSSELL, S. H., FELDMANN, K. A.,
            PIERCE, J. and BROWSE, J.
TITLE       Cloning of higher plant omega-3 fatty acid desaturases
JOURNAL     Plant Physiol. 103 (2), 467–476 (1993)
MEDLINE     94302147
REMARK      SEQUENCE FROM N.A.
            STRAIN=CV. COLUMBIA; TISSUE=SEEDLING
REFERENCE   2 (residues 1 to 386)
AUTHORS     WATAHIKI, M. C. and YAMAMOTO, K. T.
TITLE       Direct Submission
JOURNAL     Submitted (Sep. ??, 1993) TO EMBL/GENBANK/DDBJ DATA BANKS
REMARK      SEQUENCE FROM N.A.
            STRAIN=CV. COLUMBIA; TISSUE=HYPOCOTYL
REFERENCE   3 (residues 1 to 386)
AUTHORS     Nishiuchi, T., Nishimura, M., Arondel, V. and Iba, K.
TITLE       Genomic nucleotide sequence of a gene encoding a microsomal
            omega-3 fatty acid desaturase from Arabidopsis thaliana
JOURNAL     Plant Physiol. 105 (2), 767–768 (1994)
MEDLINE     94345020
REMARK      SEQUENCE FROM N.A.
            STRAIN=CV. COLUMBIA
COMMENT     [FUNCTION] MICROSOMAL (ER) OMEGA-3 FATTY ACID DESATURASE
            INTRODUCES THE THIRD DOUBLEBOND IN THE BIOSYNTHESIS OF 18:3
            FATTY ACIDS, IMPORTANT CONSTITUENTS OF PLANT MEMBRANES. IT IS
            THOUGHT TO USE CYTOCHROME B5 AS AN ELECTRON DONOR AND TO ACT
            ON FATTY ACIDS ESTERIFIED TO PHOSPHATIDYLCHOLINE AND,
            POSSIBLY, OTHER PHOSPHOLIPIDS.
            [PATHWAY] POLYUNSATURATED FATTY ACID BIOSYNTHESIS.
            [SUBCELLULAR LOCATION] ENDOPLASMIC RETICULUM.
            [TISSUE SPECIFICITY] ABUNDANT IN LEAVES AND SEEDLINGS. BARELY
            DETECTABLE IN ROOT TISSUE. [DOMAIN] THE HISTIDINE BOX DOMAINS
            MAY CONTAIN THE ACTIVE SITE AND/OR BE INVOLVED IN METAL ION
            BINDING.
            [SIMILARITY] TO OTHER PLANT OMEGA-3 FATTY ACID DESATURASES.
FEATURES    Location/Qualifiers
source      1 . . . 386
            /organism="Arabidopsis thaliana"
            /db_xref="taxon:3702"
            1 . . . 386
Protein     1 . . . 386
            /product="OMEGA-3 FATTY ACID DESATURASE, ENDOPLASMIC
            RETICULUM"
            /EC_number="1.14.99.-"
Region      63 . . . 83
            /region_name="Transmembrane region"
Region      101 . . . 105
            /note="HISTIDINE BOX 1."
            /region_name="Domain"
Region      137 . . . 141
            /note="HISTIDINE BOX 2."
            /region_name="Domain"
```

-continued

```
Region          220 . . . 240
                /region_name="Transmembrane region"
Region          242 . . . 262
                /region_name="Transmembrane region"
Region          304 . . . 308
                /note="HISTIDINE BOX 3."
                /region_name="Domain"
ORIGIN (SEQ ID NO:11)
mvvamdqrtn vngdpgagdr kkeerfdpsa qppfkigdir aaipkhcwvk splrsmsyvv rdiiavaala iaavyvdswf lwplywaaqg tlfwaifvlg hdcghgsfsd ipllnsvvgh ilhsfilvpy hgwrishrth hqnhghvend eswvplperv ykklphstrm lrytvplpml ayplylcyrs pgkegshfnp ysslfapser kliatsttcw simfvslial sfvfgplavl kvygvpyiif vmwldavtyl hhhghdeklp wyrgkewsyl rgglttidrd ygifnnihhd igthvihhlf pqiphyhlvd atkaakhvlg ryyrepktsg aipihlvesl vasikkdhyv sdtgdivfye tdpdlyvyas dkskin
```

3133289 (*Pelargonium x hortorum*)

```
LOCUS           AAC16443         407 aa            PLN         May 15, 1998
DEFINITION      omega-3 desaturase.
ACCESSION       AAC16443
PID             g3133289
VERSION         AAC16443.1 GI:3133289
DBSOURCE        accession AF020204.1
KEYWORDS        .
SOURCE          Pelargonium x hortorum.
ORGANISM        Pelargonium x hortorum
                Eukaryota; Viridiplantae; Streptophyta; Embryophyta;
                Tracheophyta; euphyllophytes; Spermatophyta; Magnoliophyta;
                eudicotyledons; core eudicots; Rosidae; Geraniales;
                Geraniaceae; Pelargonium.
REFERENCE       1 (residues 1 to 407)
  AUTHORS       Schultz, D. J., Mumma, R. O., Cox-Foster. D., Craig, R. and
                Medford, J. I.
  TITLE         Geranium omega-3 desaturase
  JOURNAL       Unpublished
REFERENCE       2 (residues 1 to 407)
  AUTHORS       Schultz, D. J., Mumma, R. O., Cox-Foster, D., Craig, R. and
                Medford, J. I.
  TITLE         Direct Submission
  JOURNAL       Submitted (Aug. 19, 1997) Botany, MSU, 166 Plant Biology
                Building, East Lansing, MI 48824, USA
COMMENT         Method: conceptual translation supplied by author.
FEATURES        Location/Qualifiers
source          1 . . . 407
                /organism="Pelargonium x hortorum"
                /db_xref="taxon:4031"
Protein         <1 . . . 407
                /product="omega-3 desaturase"
CDS             1 . . . 407
                /gene="pxh-15"
                /coded_by="AF020204.1:<1 . . . 1226"
ORIGIN (SEQ ID NO:12)
sdfdp sapppfrlge iraaipqhcw vkspwrsmsy vvrdivvvfa lavaafrlds wlvwpiywav qgtmfwaifv lghdcghgsf sdshilnsvm ghilhssilv pyhgwrishk thhsnhghve ndeswvplte ktyksldvst rllrftipfp vfaypfylww rspgkkgshf npysdlfaps errdvltsti swsimvalla glscvfglvp mlklyggpyw ifvmwldtvt ylhhhghddh klpwyrgkew sylrgglttv drdyglfnni hhdigthvih hlfpqiphyh lveatraakp vlgkyyrepk rsgpfpyhli dnlvksiked hyvsdtgdiv fyetdpeqfk sdpkkl
```

―continued

| P32291 (mung bean, *Vigna radiata*) |
|---|

```
Score = 591 bits (1507), Expect = e-168
Identities = 259/359 (72%), Positives = 303/359 (84%)
LOCUS       FD3E_PHAAU      380 aa              PLN        Feb. 1, 1996
DEFINITION  OMEGA-3 FATTY ACID DESATURASE, ENDOPLASMIC RETICULUM
            (INDOLE-3-ACETIC ACID INDUCED PROTEIN ARG1).
ACCESSION   P32291
PID         g416638
VERSION     P32291 GI:416638
DBSOURCE    swissprot: locus FD3E_PHAAU, accession P32291;
            class: standard.
            created: Oct. 1, 1993.
            sequence updated: Oct. 1, 1993.
            annotation updated: Feb. 1, 1996.
            xrefs: gi: 287561, gi: 287562
KEYWORDS    OXIDOREDUCTASE; FATTY ACID BIOSYNTHESIS; ENDOPLASMIC
            RETICULUM; TRANSMEMBRANE.
SOURCE      mung bean.
ORGANISM    Vigna radiata
            Eukaryotae; Viridiplantae; Charophyta/Embryophyta group;
            Embryophyta; Tracheophyta; seed plants; Magnoliophyta;
            eudicotyledons; Rosidae; Fabales; Fabaceae; Papilionoideae;
            Vigna.
REFERENCE   1 (residues 1 to 380)
AUTHORS     YAMAMOTO, K. T., MORI, H. and IMASEKI, H.
JOURNAL     PLANT CELL PHYSIOL. 33, 13-20 (1992)
REMARK      SEQUENCE FROM N.A.
            TISSUE=HYPOCOTYL
COMMENT     [FUNCTION] MICROSOMAL (ER) OMEGA-3 FATTY ACID DESATURASE
            INTRODUCES THE THIRD DOUBLEBOND IN THE BIOSYNTHESIS OF 18:3
            FATTY ACIDS, IMPORTANT CONSTITUENTS OF PLANT MENBRANES. IT IS
            THOUGHT TO USE CYTOCHROME B5 AS AN ELECTRON DONOR AND TO ACT
            ON FATTY ACIDS ESTERIFIED TO PHOSPHATIDYLCHOLINE AND,
            POSSIBLY, OTHER PHOSPHOLIPIDS.
            [PATHWAY] POLYUNSATURATED FATTY ACID BIOSYNTHESIS.
            [SUBCELLULAR LOCATION] ENDOPLASMIC RETICULUM. INDUCTION] BY
            AUXIN, ETHYLENE AND WOUNDING. [DOMAIN] THE HISTIDINE BOX
            DOMAINS MAY CONTAIN THE ACTIVE SITE AND/OR BE INVOLVED IN
            METAL ION BINDING. [SIMILARITY] TO OTHER PLANT OMEGA-3 FATTY
            ACID DESATURASES.
FEATURES    Location/Qualifiers
source      1 . . . 380
            /organism="Vigna radiata"
            /db_xref="taxon:3916"
            1 . . . 380
Protein     1 . . . 380
            /product="OMEGA-3 FATTY ACID DESATURASE, ENDOPLASMIC
            RETICULUM"
            /EC_number="1.14.99.—"
Region      59 . . . 78
            /region_name="Transmembrane region"
Region      97 . . . 101
            /note="HISTIDINE BOX 1."
            /region_name="Domain"
Region      133 . . . 137
            /note="HISTIDINE BOX 2."
            /region_name="Domain"
Region      208 . . . 231
            /region_name="Transmembrane region"
Region      238 . . . 256
            /region_name="Transmembrane region"
Region      300 . . . 304
            /note="HISTIDINE BOX 3."
            /region_name="Domain"
ORIGIN (SEQ ID NO:13)
fdpgapppf kiadiraaip khcwekstlr slsyvlrdvl vvtalaasai sfnswffwpl ywpaqgtmfw alfvlghdcg hgsfsnsskl nsfvghilhs lilvpyngwr ishrthhqnh ghvekdeswv pltekvyknl ddmtrmlrys fpfpifaypf ylwnrspgke gshfnpysnl fspgerkgvv tstlcwgivl svllylslti gpifmlklyg vpylifvmwl dfvtylhhhg ythklpwyrg qewsylrggl ttvdrdygwi nnvhhdigth vihhlfpqip hyhlveatks aksvlgkyyr epqksgplpf hllkyllqsi sqdhfvsdtg divyyqtdpk lhqdswtkak
```

-continued

4091113 (*Vernicia fordii*)

```
Score = 590 bits (1504), Expect = e-168
Identities = 265/377 (70%), Positives = 305/377 (80%), Gaps = 7/377 (1%)
LOCUS       AAC98967       387 aa             PLN       Jan. 1, 1999
DEFINITION  omega-3 fatty acid desaturase.
ACCESSION   AAC98967
PID         g4091113
VERSION     AAC98967.1 GI:4091113
DBSOURCE    locus AF047172 accession AF047172.1
KEYWORDS    .
SOURCE      Vernicia fordii.
ORGANISM    Vernicia fordii
            Eukaryota; Viridiplantae; Streptophyta; Embryophyta;
            Tracheophyta; euphyllophytes; Spermatophyta; Magnoliophyta;
            eudicotyledons; core eudicots; Rosidae; eurosids I;
            Malpighiales; Euphorbiaceae; Vernicia.
REFERENCE   1 (residues 1 to 387)
AUTHORS     Tang, F., Dyer, J. M., Lax, A. R., Shih, D. S., Chapital, D. C. and
            Pepperman, A. B.
TITLE       Nucleotide sequence of a cDNA clone for endoplasmic reticular
            Fatty acid desaturase from Aleurites fordii seeds
JOURNAL     Unpublished
REFERENCE   2 (residues 1 to 387)
AUTHORS     Tang, F.
TITLE       Direct Submission
JOURNAL     Submitted (Feb. 6, 1998) Southern Regional Research Center,
            USDA-ARS, 1100 Robert E. Lee Blvd., New Orleans, LA 70179,
USA
COMMENT     Method: conceptual translation supplied by author.
FEATURES    Location/Qualifiers
source      1 . . . 387
            /organism="Vernicia fordii"
            /variety="L-2"
            /db_xref="taxon:73154"
            /dev_stage="seed"
Protein     1 . . . 387
            /product="omega-3 fatty acid desaturase"
CDS         1 . . . 387
            /gene="Fad3"
            /coded_by="AF047172.1:39 . . . 1202"
ORIGIN (SEQ ID NO:14)
ngvngfha keeeeeedfd lsnpppfnig qiraaipkhc wvknpwrslt yvfrdvvvvf alaaaafyfn swlfwplywf aqgtmfwaif vlghdcghgs fsnnsslnnv vghllhssil vpyhgwrish rthhqnhgnv ekdeswvplp ekiykemdls trilrysvpl pmfalpfylw wrspgkegsh fnpnsdffap herkavltsn fcfsimalll lyscfvfgpv qvlkfygipy lvfvmwldfv tymhhhghee klpwyrgkew sylrgglqtv drdygwinni hhdigthvih hlfpqiphyh lieatkaakp vlgkyyrepk ksgpfpfhlf snlvrsmsed hyvsdigdiv fyqtdpdiyk vdkskln
```

P48622 (*Arabidopsis thaliana*)

```
LOCUS       FD3D_ARATH     435 aa             PLN       Feb. 1, 1996
DEFINITION  TEMPERATURE-SENSITIVE OMEGA-3 FATTY ACID DESATURASE,
            CHLOROPLAST PRECURSOR.
ACCESSION   P48622
PID         g1345972
VERSION     P48622 GI:1345972
DBSOURCE    swissprot: locus FD3D_ARATH, accession P48622;
            class: standard.
            created: Feb. 1, 1996.
            sequence updated: Feb. 1, 1996.
            annotation updated: Feb. 1, 1996.
            xrefs: gi: 516044, gi: 516045, gi: 497218, gi: 497219, gi:
            1030694, gi: 471093
KEYWORDS    OXIDOREDUCTASE; FATTY ACID BIOSYNTHESIS; CHLOROPLAST;
            MEMBRANE; TRANSIT PEPTIDE.
SOURCE      thale cress.
ORGANISM    Arabidopsis thaliana Eukaryotae; Viridiplantae;
            Charophyta/Embryophyta group; Embryophyta; Tracheophyta; seed
            plants; Magnoliophyta; eudicetyledons; Rosidae; Capparales;
            Brassicaceae; Arabidopsis.
REFERENCE   1 (residues 1 to 435)
```

| | |
|---|---|
| AUTHORS | Gibson, S., Arondel, V., Iba, K. and Somerville, C. |
| TITLE | Cloning of a temperature-regulated gene encoding a chloroplast omega-3 desaturase from *Arabidopsis thaliana* |
| JOURNAL | Plant Physiol. 106 (4), 1615–1621 (1994) |
| MEDLINE | 95148742 |
| REMARK | SEQUENCE FROM N.A. STRAIN=CV. COLUMBIA; TISSUE=AERIAL PARTS |
| REFERENCE | 2 (residues 1 to 435) |
| AUTHORS | WATAHIKI, M. C. and YAMAMOTO, K. T. |
| TITLE | Direct Submission |
| JOURNAL | Submitted (Sep. ??, 1993) TO EMBL/GENBANK/DDBJ DATA BANKS |
| REMARK | SEQUENCE FROM N.A. STRAIN=CV. COLUMBIA; TISSUE=HYPOCOTYL |
| COMMENT | [FUNCTION] CHLOROPLAST OMEGA-3 FATTY ACID DESATURASE INTRODUCES THE THIRD DOUBLEBOND IN THE BIOSYNTHESIS OF 16:3 AND 18:3 FATTY ACIDS, IMPORTANT CONSTITUENTS OF PLANT MEMBRANES. IT IS THOUGHT TO USE FERREDOXIN AS AN ELECTRON DONOR AND TO ACT ON FATTY ACIDS ESTERIFIED TO GALACTOLIPIDS, SULFOLIPIDS AND PHOSPHATIDYLGLYCEROL. [PATHWAY] POLYUNSATURATED FATTY ACID BIOSYNTHESIS. [SUBCELLULAR LOCATION] CHLOROPLAST, MEMBRANE-BOUND (PROBABLE). [INDUCTION] BY LOW TEMPERATURES. [DOMAIN] THE HISTIDINE BOX DOMAINS MAY CONTAIN THE ACTIVE SITE AND/OR BE INVOLVED IN METAL ION BINDING. [SIMILARITY] TO OTHER PLANT OMEGA-3 FATTY ACID DESATURASES. |
| FEATURES | Location/Qualifiers |
| source | 1 . . . 435 /organism="*Arabidopsis thaliana*" /db_xref="taxon:3702" |
| Protein | 1 . . . 435 /product="TEMPERATURE-1 . . . 435 SENSITIVE OMEGA-3 FATTY ACID DESATURASE, CHLOROPLAST PRECURSOR" /EC_number="1.14.99.—" |
| Region | 1 . . . (2.435) /region_name="Transit peptide" /note="CHLOROPLAST." |
| Region | (1.434) . . . 435 /region_name="Mature chain" /note="TEMPERATURE-SENSITIVE OMEGA-3 FATTY ACID DESATURASE, CHLOROPLAST." |
| Region | 156 . . . 160 /region_name="Domain" /note="HISTIDINE BOX 1." |
| Region | 192 . . . 196 /region_name="Domain" /note="HISTIDINE BOX 2." |
| Region | 359 . . . 363 /region_name="Domain" /note="HISTIDINE BOX 3." |

ORIGIN (SEQ ID NO:15)
r fdpgapppfn ladiraaipk hcwvknpwms msyvvrdvai vfglaavaay fnnwllwply wfaqgtmfwa lfvlghdcgh gsfsndprln svaghllhss ilvpyhgwri shrthhqnhg hvendeswhp lpesiyknle kttqmfrftl pfpmlaypfy lwnrspgkqg shyhpdsdlf lpkekkdvlt stacwtamaa llvclnfvmg piqinlklygi pywifvmwld fvtylhhgh edklpwyrgk ewsylrgglt tldrdygwin nihhdigthv ihhlfpqiph yhlveateaa kpvlgkyyre pknsgplplh llgsliksmk qdhfvsdtgd vvyyeadpkl

AAD15744 (*Perilla frutescens*)

| | |
|---|---|
| LOCUS | AAD15744 391 aa PLN Mar. 3, 1999 |
| DEFINITION | omega-3 fatty acid desaturase. |
| ACCESSION | AAD15744 |
| PID | g4321399 |
| VERSION | AAD15744.1 GI:4321399 |
| DBSOURCE | locus AF047039 accession AF047039.1 |
| KEYWORDS | . |
| SOURCE | *Perilla frutescens.* |
| ORGANISM | *Perilla frutescens* Eukaryota; Viridiplantae; Streptophyta; Embryophyta; Tracheophyta; euphyllophytes; Spermatophyta; Magnoliophyta; eudicotyledons; core eudicots; Asteridae; euasterids I; Lamiales; Lamiaceae; Perilla. |
| REFERENCE | 1 (residues 1 to 391) |

-continued

```
AUTHORS     Chung, C. -H., Kim, J. -L., Lee, Y. -C. and Choi, Y. -L.
TITLE       Molecular cloning and characterization of a omega-3 cDNA from
            perilla seed
JOURNAL     Unpublished
REFERENCE   2 (residues 1 to 391)
AUTHORS     Chung, C. -H., Kim, J. -L., Lee, Y. -C. and Choi, Y. -L.
TITLE       Direct Submission
JOURNAL     Submitted (Feb. 7, 1998) Biotechnology, Dong-A University,
            840, Ha-Dan-Dong, Sa-Ha-Gu, Pusan 604-714, South Korea
COMMENT     Method: conceptual translation.
FEATURES    Location/Qualifiers
source      1 . . . 391
            /organism="Perilla frutescens"
            /cultivar="Suwon-8"
            /db_xref="taxon:48386"
            /dev_stage="seed"
Protein     1 . . . 391
            /product="omega-3 fatty acid desaturase"
CDS         1 . . . 391
            /gene="FAD3"
            /coded_by="AF047039.1:156 . . . 1331"
ORIGIN (SEQ ID NO:16)
gk raadkfdpaa pppfkiadir aaipahcwvk npwrslsyvv wdvaavfall aaavyinswa fwpvywiaqg tmfwalfvlg hdcghgsfsd nttlnnvvgh vlhssilvpy hgwrishrth hqnhghvekd eswvplpenl ykkldfstkf lrykipfpmf ayplylwyrs pgktgshfnp ysdlfkpner glivtstmcw aamgvfllya stivgpnmmf klygvpylif vmwldtvtyl hhhgydkklp wyrskewsyl rggltvdqd ygffnkihhd igthvihhlf pqiphyhlve atreakrvlg nyyreprksg pvplhlipal lkslgrdhyv sdngdivyyq tddelf I
```

P48619 (Ricinus communis)

```
LOCUS       FD3C_RICCO    460 aa              PLN       Dec. 15, 1998
DEFINITION  OMEGA-3 FATTY ACID DESATURASE, CHLOROPLAST PRECURSOR.
ACCESSION   P48619
PID         g1345969
VERSION     P48619 GI:1345969
DBSOURCE    swissprot: locus FD3C_RICCO, accession P48619;
            class: standard.
            created: Feb. 1, 1996.
            sequence updated: Feb. 1, 1996.
            annotation updated: Dec. 15, 1998.
            xrefs: gi: 414731, gi: 414732
            xrefs (non-sequence databases): PFAM PF00487
KEYWORDS    OXIDOREDUCTASE; FATTY ACID BIOSYNTHESIS; CHLOROPLAST;
            MEMBRANE; TRANSIT PEPTIDE.
SOURCE      castor bean.
ORGANISM    Ricinus communis
            Eukaryota; Viridiplantae; Charophyta/Embryophyta group;
            Embryophyta; Tracheophyta; euphyllophytes; Spermatophyta;
            Magnoliophyta; eudicotyledons; Rosidae; Euphorbiales;
            Euphorbiaceae; Ricinus.
REFERENCE   1 (residues 1 to 460)
AUTHORS     van de Loo, F. J. and Somerville, C.
TITLE       Plasmid omega-3 fatty acid desaturase cDNA from Ricinus
            communis
JOURNAL     Plant Physiol. 105 (1), 443-444 (1994)
MEDLINE     94302177
REMARK      SEQUENCE FROM N.A.
            STRAIN=CV. BAKER 296; TISSUE=SEED
            [FUNCTION] CHLOROPLAST OMEGA-3 FATTY ACID DESATURASE
            INTRODUCES THE THIRD DOUBLEBOND IN THE BIOSYNTHESIS OF 16:3
            AND 18:3 FATTY ACIDS, IMPORTANT CONSTITUENTS OF PLANT
            MEMBRANES. IT IS THOUGHT TO USE FERREDOXIN AS AN ELECTRON
            DONOR AND TO ACT ON FATTY ACIDS ESTERIFIED TO GALACTOLIPIDS,
            SULFOLIPIDS AND PHOSPHATIDYLGLYCEROL.
            [PATHWAY] POLYUNSATURATED FATTY ACID BIOSYNTHESIS.
            [SUBCELLULAR LOCATION] CHLOROPLAST, MEMBRANE-BOUND
            (PROBABLE). [DOMAIN] THE HISTIDINE BOX DOMAINS MAY CONTAIN
            THE ACTIVE SITE AND/OR BE INVOLVED IN METAL ION BINDING.
            [SIMILARITY] TO OTHER PLANT OMEGA-3 FATTY ACID DESATURASES.
```

```
FEATURES         Location/Qualifiers
source           1 . . . 460
                 /organism="Ricinus communis"
                 /db_xref="taxon:3988"
                 1 . . . 460
Protein          1 . . . 460
                 /product="OMEGA-3 FATTY ACID DESATURASE, CHLOROPLAST
                 PRECURSOR"
                 /EC_number="1.14.99.—"
Region           1 . . . (2.460)
                 /note="CHLOROPLAST."
                 /region_name="Transit peptide"
Region           (1.459) . . . 460
                 /note="OMEGA-3 FATTY ACID DESATURASE, CHLOROPLAST."
                 /region_name="Mature chain"
Region           177 . . . 181
                 /note="HISTIDINE BOX 1."
                 /region_name="Domain"
Region           213 . . . 217
                 /note="HISTIDINE BOX 2."
                 /region_name="Domain"
Region           380 . . . 384
                 /note="HISTIDINE BOX 3."
                 /region_name="Domain"
ORIGIN (SEQ ID NO:17)
ereefng  ivnvdegkge  ffdagapppf  tladiraaip  khcwvknpwr  smsyvlrdvv  vvfglaavaa yfnnwvawpl  ywfcqgtmfw  alfvlghdcg  hgsfsnnpkl  nsvvghllhs  silvpyhgwr ishrthhqnh  ghvendeswh  plsekifksl  dnvtktlrfs  lpfpmlaypf  ylwsrspgkk gshfhpdsgl  fvpkerkdii  tstacwtama  allvylnfsm  gpvqmlklyg  ipywifvnwl dfvtylhhhg  hedklpwyrg  kawsylrggl  ttldrdygwi  nnihhdigth  vihhlfpqip hyhlveatea  akpvmgkyyr  epkksgplpl  hllgslvrsm  kedhyvsdtg  dvvyyqkdpk lsgiggekte
```

1754795 (*Perilla frutescens*)

```
LOCUS       AAB39387       438 aa                    PLN       Dec. 28, 1996
DEFINITION  omega-3 fatty acid desaturase.
ACCESSION   AAB39387
PID         g1754795
VERSION     AAB39387.1  GI:1754795
DBSOURCE    locus PFU59477 accession U59477.1
KEYWORDS    .
SOURCE      Perilla frutescens.
ORGANISM    Perilla frutescens
            Eukaryota; Viridiplantae; Streptophyta; Embryophyta;
            Tracheophyta; euphyllophytes; Spermatophyta; Magnoliophyta;
            eudicotyledons; core eudicots; Asteridae; euasterids I;
            Lamiales; Lamiaceae; Perilla.
REFERENCE   1 (residues 1 to 438)
AUTHORS     Lee, S. -K., Kim, K. -H., Kim, Y. -M. and Hwang, Y. -S.
TITLE       Cloning of plant omega-3 fatty acid desaturase gene from
            Perilla frutescens
JOURNAL     Unpublished
REFERENCE   2 (residues 1 to 438)
AUTHORS     Lee, S. -K.
TITLE       Direct Submission
JOURNAL     Submitted (May 30, 1996) Biochemistry, National Agricultural
            Science and Technology Institute, 249 Seodundong, Suwon 441-
            707, Republic of Korea
FEATURES         Location/Qualifiers
source           1 . . . 438
                 /organism="Perilla frutescens"
                 /strain="Okdong"
                 /db_xref="taxon:48386"
                 /clone="Pfrfad7"
                 /dev_stage="seedling"
Protein          1 . . . 438
                 /product="omega-3 fatty acid desaturase"
CDS              1 . . . 438
                 /coded_by="U59477.1:222 . . . 1538"
```

```
ORIGIN (SEQ ID NO:18)
eergsv ivngvdefdp gapppfklsd iraaipkhcw vkdpwrsmsy vvrdvvvvfg laaaaayfnn wavwpiywfa qstmfwalfv lqhdcghgsf sndpklnsva ghllhssilv pyhgwrishr thhqnhghve ndeswhpipe kiyrtldfat kklrftlpfp mlaypfylwg rspgkkgshf hpdsdlfvpn erkdvitstv cwtamvaila glsfvmgpvq llklygipyi gfvawldlvt ylhhhghdek lpwyrgkews ylrgglttld rdygwinnih hdigthvihh lfpqiphyhl ieataaakpv lgkyykepkk sgpfpfyllg vlqksmkkdh yvsdtgdivy yqtdpe
```

P48620 (sesame, *Sesamum indicum*)

```
LOCUS       FD3C_SESIN      447 aa                  PLN       Dec. 15, 1998
DEFINITION  OMEGA-3 FATTY ACID DESATURASE, CHLOROPLAST PRECURSOR.
ACCESSION   P48620
PID         g1345970
VERSION     P48620 GI:1345970
DBSOURCE    swissprot: locus FD3C_SESIN, accession P48620;
            class: standard.
            created: Feb. 1, 1996.
            sequence updated: Feb. 1, 1996.
            annotation updated: Dec. 15, 1998.
            xrefs: gi: 870783, gi: 870784
            xrefs (non-sequence databases): PFAM PF00487
KEYWORDS    OXIDOREDUCTASE; FATTY ACID BIOSYNTHESIS; CHLOROPLAST;
            MEMBRANE; TRANSIT PEPTIDE.
SOURCE      sesame.
ORGANISM    Sesamum indicum
            Eukaryota; Viridiplantae; Charophyta/Embryophyta group;
            Embryophyta; Tracheophyta; euphyllophytes; Spermatophyta;
            Magnoliophyta; eudicotyledons; Asteridae; Gentiananae;
            Lamiales; Pedaliaceae; Sesamum.
REFERENCE   1 (residues 1 to 447)
AUTHORS     SHOJI, K.
TITLE       Direct Submission
JOURNAL     Submitted (Apr. ??, 1995) TO EMBL/GENBANK/DDBJ DATA BANKS
REMARK      SEQUENCE FROM N.A.
            STRAIN=CV. 4294; TISSUE=COTYLEDON
            [FUNCTION] CHLOROPLAST OMEGA-3 FATTY ACID DESATURASE
            INTRODUCES THE THIRD DOUBLEBOND IN THE BIOSYNTHESIS OF 16:3
            AND 18:3 FATTY ACIDS, IMPORTANT CONSTITUENTS OF PLANT
            MEMBRANES. IT IS THOUGHT TO USE FERREDOXIN AS AN ELECTRON
            DONOR AND TO ACT ON FATTY ACIDS ESTERIFIED TO GALACTOLIPIDS,
            SULFOLIPIDS AND PHOSPHATIDYLGLYCEROL.
            [PATHWAY] POLYUNSATURATED FATTY ACID BIOSYNTHESIS.
            [SUBCELLULAR LOCATION] CHLOROPLAST, MEMBRANE-BOUND
            (PROBABLE). [DOMAIN] THE HISTIDINE BOX DOMAINS MAY CONTAIN
            THE ACTIVE SITE AND/OR BE INVOLVED IN METAL ION BINDING.
            [SIMILARITY] TO OTHER PLANT OMEGA-3 FATTY ACID DESATURASES.
FEATURES    Location/Qualifiers
source      1 . . . 447
            /organism="Sesamum indicum"
            /db_xref="taxon:4182"
            1 . . . 447
Protein     1 . . . 447
            /product="OMEGA-3 FATTY ACID DESATURASE, CHLOROPLAST
            PRECURSOR"
            /EC_number="1.14.99.—"
Region      1 . . . (2.447)
            /note="CHLOROPLAST."
            /region_name="Transit peptide"
Region      (1.446) . . . 447
            /note="OMEGA-3 FATTY ACID DESATURASE, CHLOROPLAST."
            /region_name="Mature chain"
Region      167 . . . 171
            /note="HISTIDINE BOX 1."
            /region_name="Domain"
Region      203 . . . 207
            /note="HISTIDINE BOX 2."
            /region_name="Domain"
Region      370 . . . 374
            /note="HISTIDINE BOX 3."
            /region_name="Domain"
```

```
ORIGIN (SEQ ID NO:19)
e efdpgapppf klsdireaip khcwvkdpwr smgyvvrdva vvfglaavaa yfnnwvvwpl ywfaqstmfw alfvlghdcg hgsfsndpkl nsvvghilhs silvpyhgwr ishrthhqnh ghvendeswh plsekiyknl dtatkklrft lpfpllaypi ylwsrspgkq gshfhpdsdl fvpnekkdvi tstvcwtaml allvglsfvi gpvqllklyg ipylgnvmwl dlvtylhhhg hedklpwyrg kewsylrggl ttldrdygwi nnihhdigth vihhlfpqip hyhlieatea akpvlgkyyr epkksaplpf hllgdltrsl krdhyvsdvg dvvyyqtdpq l
```

P46310 (*Arabidopsis thaliana*)

```
LOCUS       FD3C_ARATH      446 aa              PLN        Feb. 1, 1996
DEFINITION  OMEGA-3 FATTY ACID DESATURASE, CHLOROPLAST PRECURSOR.
ACCESSION   P46310
PID         g1169599
VERSION     P46310 GI:1169599
DBSOURCE    swissprot: locus FD3C_ARATH, accession P46310;
            class: standard.
            created: Nov. 1, 1995.
            sequence updated: Nov. 1, 1995.
            annotation updated: Feb. 1, 1996.
            xrefs: gi: 408480, gi: 408481, gi: 461160, gi: 541653, gi:
            809491, gi: 468434
KEYWORDS    OXIDOREDUCTASE; FATTY ACID BIOSYNTHESIS; CHLOROPLAST;
            MEMBRANE; TRANSIT PEPTIDE.
SOURCE      thale cress.
ORGANISM    Chloroplast Arabidopsis thaliana
            Eukaryotae; Viridiplantae; Charophyta/Embryophyta group;
            Embryophyta; Tracheophyta; seed plants; Magnoliophyta;
            eudicotyledons; Rosidae; Capparales; Brassicaceae;
            Arabidopsis.
REFERENCE   1 (residues 1 to 446)
AUTHORS     YADAV, N. S., WIERZBICKI, A., AEGERTER, M., CASTER, C. S., PEREZ-
            GRAU, L., KINNEY, A. J., HITZ, W. D., BOOTH, J. R. JR.,
            SCHWEIGER, B., STECCA, K. L., ALLEN, S. M., BLACKWELL, M.,
            REITER, R. S., CARLSON, T. J., RUSSELL, S. H., FELDMANN, K. A.,
            PIERCE, J. and BROWSE, J.
TITLE       Cloning of higher plant omega-3 fatty acid desaturases
JOURNAL     Plant Physiol. 103 (2), 467-476 (1993)
MEDLINE     94302147
REMARK      SEQUENCE FROM N.A.
            STRAIN=CV. COLUMBIA; TISSUE=HYPOCOTYL
REFERENCE   2 (residues 1 to 446)
AUTHORS     Iba, K., Gibson, S., Nishiuchi, T., Fuse, T., Nishimura, M.,
            Arondel, V., Hugly, S. and Somerville, C.
TITLE       A gene encoding a chloroplast omega-3 fatty acid desaturase
            complements alterations in fatty acid desaturation and
            chloroplast copy number of the fad7 mutant of Arabidopsis
            thaliana
JOURNAL     J. Biol. Chain. 268 (32), 24099-24105 (1993)
MEDLINE     94043239
REMARK      SEQUENCE FROM N.A.
            STRAIN=CV. COLUMBIA; TISSUE=AERIAL PARTS
REFERENCE   3 (residues 1 to 446)
AUTHORS     WATAHIKI, M. and YAMAMOTO, K.
TITLE       Direct Submission
JOURNAL     Submitted (Nov. ??, 1993) TO EMBL/GENBANK/DDBJ DATA BANKS
REMARK      SEQUENCE FROM N.A.
            STRAIN=CV. COLUMBIA; TISSUE=HYPOCOTYL
COMMENT     [FUNCTION] CHLOROPLAST OMEGA-3 FATTY ACID DESATURASE
            INTRODUCES THE THIRD DOUBLEBOND IN THE BIOSYNTHESIS OF 16:3
            AND 18:3 FATTY ACIDS, IMPORTANT CONSTITUENTS OF PLANT
            MEMBRANES. IT IS THOUGHT TO USE FERREDOXIN AS AN ELECTRON
            DONOR AND TO ACT ON FATTY ACIDS ESTERIFIED TO GALACTOLIPIDS,
            SULFOLIPIDS AND PHOSPHATIDYLGLYCEROL.
            [PATHWAY] POLYUNSATURATED FATTY ACID BIOSYNTHESIS.
            [SUBCELLULAR LOCATION] CHLOROPLAST, MEMBRANE-BOUND
            (PROBABLE). [TISSUE SPECIFICITY] MOST ABUNDANT IN LEAVES AND
            SEEDLINGS. [DOMAIN] THE HISTIDINE BOX DOMAINS MAY CONTAIN THE
            ACTIVE SITE AND/OR BE INVOLVED IN METAL ION BINDING.
            [SIMILARITY] TO OTHER PLANT OMEGA-3 FATTY ACID DESATURASES.
```

```
FEATURES         Location/Qualifiers
source           1 . . . 446
                 /organism="Arabidopsis thaliana"
                 /chloroplast
                 /db_xref="taxon:3702"
                 1 . . . 446
Protein          1 . . . 446
                 /product="OMEGA-3 FATTY ACID DESATURASE, CHLOROPLAST
                 PRECURSOR"
                 /EC_number="1.14.99.—"
Region           1 . . . (2.446)
                 /note="CHLOROPLAST."
                 /region_name="Transit peptide"
Region           (1.445) . . . 446
                 /note="OMEGA-3 FATTY ACID DESATURASE, CHLOROPLAST."
                 /region_name="Mature chain"
Region           163 . . . 167
                 /note="HISTIDINE BOX 1."
                 /region_name="Domain"
Region           199 . . . 203
                 /note="HISTIDINE BOX 2."
                 /region_name="Domain"
Region           366 . . . 370
                 /note="HISTIDINE BOX 3."
                 /region_name="Domain"
ORIGIN (SEQ ID NO:20)
eespi eednkqrfdp gapppfnlad iraaipkhcw vknpwkslsy vvrdvaivfa laagaaylnn wivwplywla qgtmfwalfv lghdcghgsf sndpklnsvv ghllhssilv pyhgwrishr thhqnhghve ndeswhpmse kiyntldkpt rffrttlplv mlaypfylwa rspgkkgshy hpdsdlflpk erkdvltsta cwtamaallv clnftigpiq mklygipyw invmwldfvt ylhhhghedk lpwyrgkews ylrggltttld rdyglinnih hdigthvihh lfpqiphyhl veateaakpv lgkyyrepdk sgplplhlle ilaksikedh yvsdegevvy ykadpnly
```

BAA11475 (*Nicotiana tabacum*)

```
LOCUS       BAA11475         441 aa          PLN       Feb. 5, 1999
DEFINITION  omega-3 fatty acid desaturase.
ACCESSION   BAA11475
PID         g1694625
VERSION     BAA11475.1  GI:1694625
DBSOURCE    locus D79979 accession D79979.1
KEYWORDS
SOURCE      common tobacco.
ORGANISM    Nicotiana tabacum
            Eukaryota; Viridiplantae; Streptophyta; Embryophyta;
            Tracheophyta; euphyllophytes; Spermatophyta; Magnoliophyta;
            eudicotyledons; Asteridae; Solananae; Solanales; Solanaceae;
            Nicotiana.
REFERENCE   1 (residues 1 to 441)
AUTHORS     Hamada, T.
TITLE       Direct Submission
JOURNAL     Submitted (Dec. 12, 1995) to the DDBJ/EMBL/GenBank
            databases. Tatsurou Ramada, Faculty of Science, Kyushu
            University, Department of Biology; 6-10-1 Hakozaki, Higashi-
            ku, Fukuoka, Fukuoka 812, Japan
            (Tel:092-641-1101(ex.4414), Fax:092-632-2741)
REFERENCE   2 (residues 1 to 441)
AUTHORS     Hamada, T.
JOURNAL     Unpublished (1995)
REFERENCE   3 (residues 1 to 441)
AUTHORS     Hamada, T., Nishiuchi, T., Kodama, H., Nishimura, M. and Iba. K.
TITLE       cDNA cloning of a wounding-inducible gene encoding a plastid
            omega-3 fatty acid desaturase from tobacco
JOURNAL     Plant Cell Physiol. 37 (5), 606–611 (1996)
MEDLINE     96416425
FEATURES    Location/Qualifiers
source      1 . . . 441
            /organism="Nicotiana tabacum"
            /db_xref="taxon:4097"
            /clone="lambda H 1"
            /clone_lib="lambda gt11"
```

-continued

```
Protein        1 . . . 441
               /product="omega-3 fatty acid desaturase"
CDS            1 . . . 441
               /gene="NtFAD7"
               /coded_by="D79979.1:28 . . . 1353"
ORIGIN (SEQ ID NO:21)
eeesertn nsggeffdpg apppfklsdi kaaipkhcwv knpwksmsyv vrdvaivfgl aaaaayfnnw vvwplywfaq stmfwalfvl ghdcghgsfs nnhklnsvvg hilhssilvp yhgwrishrt hhqnhghven deswhpipek iynsldlatk klrftlpfpl laypfylwsr spgkkgshfd pnsdlfvpse kkdvmtstlc wtamaallvg lsfvmgpfqv lklygipywg fvmwldlvty lhhhghddkl pwyrgeewsy lrgglttldr dygwinnihh digthvihhl fpqiphyhlv eateaakpvl gkyykepkks gplpfyllgv liksmkqdhy vsdtqdivyy rtdpqlsgfq k
```

P48626 (Nicotiana tabacum)

```
LOCUS       FD3E_TOBAC     379 aa              PLN       Oct. 1, 1996
DEFINITION  OMEGA-3 FATTY ACID DESATURASE, ENDOPLASMIC RETICULUM.
ACCESSION   P48626
PID         g1345975
VERSION     P48626 GI:1345975
DBSOURCE    swissprot: locus FD3E_TOBAC, accession P48626;
            class: standard.
            created: Feb. 1, 1996.
            sequence updated: Feb. 1, 1996.
            annotation updated: Oct. 1, 1996.
            xrefs: gi: 1311480, gi: 599592
KEYWORDS    OXIDOREOUCTASE; FATTY ACID BIOSYNTHESIS; ENDOPLASMIC
            RETICULUM; TRANSMEMBRANE.
SOURCE      common tobacco.
ORGANISM    Nicotiana tabacum
            Eukaryotae; Viridiplantae; Charophyta/Embryophyta group;
            Embryophyta; Tracheophyta; seed plants; Magnoliophyta;
            eudicotyledons; Asteridae; Solananae; Solanales; Solanaceae;
            Nicotiana.
REFERENCE   1 (residues 1 to 379)
AUTHORS     Hamada, T., Kodama, H., Nishimura, M. and Iba, K.
TITLE       Cloning of a cDNA encoding tobacco omega-3 fatty acid
            desaturase
JOURNAL     Gene 147 (2), 293–294 (1994)
MEDLINE     95011632
REMARK      SEQUENCE FROM N.A.
            STRAIN=CV. SR1; TISSUE=LEAF
COMMENT     [FUNCTION] ER (MICROSOMAL) OMEGA-3 FATTY ACID DESATURASE
            INTRODUCES THE THIRD DOUBLEBOND IN THE BIOSYNTHESIS OF 18:3
            FATTY ACIDS, IMPORTANT CONSTITUENTS OF PLANT MEMBRANES. IT IS
            THOUGHT TO USE CYTOCHROME B5 AS AN ELECTRON DONOR AND TO ACT
            ON FATTY ACIDS ESTERIFIED TO PHOSPHATIDYLCHOLINE AND,
            POSSIBLY, OTHER PHOSPHOLIPIDS.
            [PATHWAY] POLYUNSATURATED FATTY ACID BIOSYNTHESIS.
            [SUBCELLULAR LOCATION] ENDOPLASMIC RETICULUM. [DOMAIN] THE
            HISTIDINE BOX DOMAINS MAY CONTAIN THE ACTIVE SITE
            AND/OR BE INVOLVED IN METAL ION BINDING. [SIMILARITY] TO
            OTHER PLANT OMEGA-3 FATTY ACID DESATURASES.
FEATURES    Location/Qualifiers
source      1 . . . 379
            /organism="=Nicotiana tabacum"
            /db_xref="taxon:4097"
            1 . . . 379
Protein     1 . . . 379
            /product="OMEGA-3 FATTY ACID DESATURASE, ENDOPLASMIC
            RETICULUM"
            /EC_number="1.14.99.—"
Region      52 . . . 72
            /region_name="Transmembrane region"
Region      97 . . . 101
            /note="HISTIDINE BOX 1."
            /region_name="Domain"
Region      133 . . . 137
            /note="HISTIDINE BOX 2."
            / region_name="Domain"
Region      213 . . . 233
            /region_name="Transmembrane region"
```

```
Region          236 . . . 256
                /region_name="Transmembrane region"
Region          300 . . . 304
                /note="HISTIDINE BOX 3."
                /region_name="Domain"
ORIGIN (SEQ ID NO; 22)
fdpsapppf rlaeirnvip khcwvkdplr slsyvvrdvi fvatligiai hldswlfypl ywaiqgtmfw aifvlghdcg hgsfsdsqll nnvvghilhs ailvpyhgwr ishkthhqnh gnvetdeswv pmpeklynkv gystkflryk ipfpllaypm ylmkrspgks gshfnpysdl fqpherkyvv tstlcwtvma alllylctaf gslqmfkiyg apylifvmwl dfvtylhhhg yekklpwyrg kewsylrggl ttvdrdyglf nnihhdigth vihhlfpqip hyhlreatka akpvlgkyyr epkksgpipf hlvkdltrsm kqdhyvsdsg eivfyqtdph if
```

AAD13527 (*Vernicia fordii*)

```
LOCUS           AAD13527         437 aa              PLN        Feb. 8, 1999
DEFINITION      omega-3 fatty acid desaturase precursor.
ACCESSION       AAD13527
PID             g4240385
VERSION         AAD13527.1 GI:4240385
DBSOURCE        locus AF061027 accession AF061027.1
KEYWORDS        .
SOURCE          Vernicia fordii.
ORGANISM        Vernicia fordii
                Eukaryota; Viridiplantae; Streptophyta; Embryophyta;
                Tracheophyta; euphyllophytes; Spermatophyta; Magnoliophyta;
                eudicotyledons; core eudicots; Rosidae; eurosids I;
                Malpighiales; Euphorbiaceae; Vernicia.
REFERENCE       1 (residues 1 to 437)
AUTHORS         Tang, F., Dyer, J. M., Lax, A. R., Shih, D. S., Chapital. D. C. and
                Pepperman, A. B.
TITLE           Nucleotide sequence of a cDNA clone for omega-3 fatty acid
                desaturase (Accession No. AF061027) from Aleurites fordii
                seeds (PGR99-009)
JOURNAL         Plant Physiol. 119, 364 (1999)
REFERENCE       2 (residues 1 to 437)
AUTHORS         Tang, F., Dyer, J. M., Lax, A. R., Shih, D. S. and Pepperman, A. B.
TITLE           Direct Submission
JOURNAL         Submitted (Apr. 21, 1998) Southern Regional Research Center,
                USDA-ARS, 1100 Robert E. Lee Blvd., New Orleans, LA 70124,
                USA
COMMENT         Method: conceptual translation.
FEATURES        Location/Qualifiers
source          1 . . . 437
                /organism="Vernicia fordii"
                /db_xref="taxon:73154"
                /tissue_type="seeds"
Protein         <1 . . . 437
                /product="omega-3 fatty acid desaturase precursor"
CDS             1 . . . 437
                /coded_by="AF061027.1:<1 . . . 1316"
ORIGIN (SEQ ID NO:23)
ereegin gvigiegeet efdpgapppf klsdireaip khcwvkdpwr smsyvvrdva vvfglaaaaa ylnnwivwpl ywaaqgtmfw alfvlghdcg hgsfshnpkl nsvvghllhs silvpyhgwr ishrthhqnh ghvendeswq plsekifrsl dymtrtlrft vpspmlaypf ylwnrspgkt gshfhpdsdl fgpnerkdvi tstvcwtama allvglslvm gpiqllklyg mpywifvmwl dfvtylhhhg heeklpwyrg newsylrggl ttgrdygwi nnihhdigth vihhffpqip hyhlidatea skpvlgkyyr epdksgplsf hligylirsl kkdhyvsdtg dvvyyqtdpq 1
```

-continued

AAB72241 (*Petroselinum crispum*)

```
LOCUS       AAB72241         438 aa                  PLN       Oct. 8, 1997
DEFINITION  omega-3 fatty acid desaturase.
ACCESSION   AAB72241
PID         g1786066
VERSION     AAB72241.1  GI:1786066
DBSOURCE    locus PCU75745 accession U75745.1
KEYWORDS    .
SOURCE      parsley.
ORGANISM    Petroselinum crispum
            Eukaryota; Viridiplantae; Streptophyta; Embryophyta;
            Tracheophyta; euphyllophytes; Spermacophyta; Magnoliophyta;
            eudicotyledons; core eudicots; Asteridae; euasterids II;
            Apiales; Apiaceae; Petroselinum.
REFERENCE   1 (residues 1 to 438)
AUTHORS     Kirsch, C., Takamiya-Wik, M., Reinold, S., Hahlbrock, K. and
            Somssich, I. E.
TITLE       Rapid, transient, and highly localized induction of
            plastidial omega-3 fatty acid desaturase mRNA at fungal
            infection sites in Petroselinum crispum
JOURNAL     Proc. Natl. Acad. Sci. U.S.A. 94 (5), 2079–2084 (1997)
MEDLINE     97203190
REFERENCE   2 (residues 1 to 438)
AUTHORS     Somssich, I. E. and Kirsch, C.
TITLE       Direct Submission
JOURNAL     Submitted (Oct. 23, 1996) Biochemistry, Max-Planck-Institut f.
            Zuchtungsforschung, Carl-von-Linne-Weg 10, Koln, NRW 50829,
            Germany
COMMENT     Method: conceptual translation supplied by author.
FEATURES    Location/Qualifiers
source      1 . . . 438
            /organism="Petroselinum crispum"
            /db_xref="taxon:4043"
            /cell_type="cultured parsley cells"
            /clone="15-1 and 25-2"
            /note="derived from two overlapping partial cDNAs"
Protein     1 . . . 438
            /product="omega-3 fatty acid desaturase"
CDS         1 . . . 438
            /coded_by="U75745.1:96 . . . 1412"
            /note="complements the Arabidopsis fad7/8 fatty acid
            double mutant"
ORIGIN (SEQ ID NO:24)
e enefdpgaap pfklsdvraa ipkhcwvkdp vrsmsyvlrd vlivfglava asfvnnwavw plywiaqgtm fwalfvlghd cghgsfsnda klnsvvghil hssilvpyhg wrishrthhq nhghvendes whplseklfn slddltrkfr ftlpfpmlay pfylwgrspg kkgshydpss dlfvpnerkd vitstvcwta maallvglnf vmgpvkmlml ygipywifvm wldfvtylhh hghddklpwy rgkewsylrg glttldrdyg winnihhdig thvvhhlfpq iphyhlieat eaakpvfgky yrepkksgpv pfhllatlwk sfkkdhfvsd tgdvvyyqah pe
```

P48625 (*Glycine max*)

```
LOCUS       FD3E_SOYBN       380 aa                  PLN       Oct. 1, 1996
DEFINITION  OMEGA-3 FATTY ACID DESATURASE, ENDOPLASMIC RETICULUM.
ACCESSION   P48625
PID         g1345974
VERSION     P48625  GI:1345974
DBSOURCE    swissprot: locus FD3E_SOYBN, accession P48625;
            class: standard.
            created: Feb. 1, 1996.
            sequence updated: Feb. 1, 1996.
            annotation updated: Oct. 1, 1996.
            xrefs: gi: 408793, gi: 408794, gi: 541946
KEYWORDS    OXIDOREDUCTASE; FATTY ACID BIOSYNTHESIS; ENDOPLASMIC
            RETICULUM; TRANSMEMBRANE.
SOURCE      soybean.
ORGANISM    Glycine max
            Eukaryotae; Viridiplantae; Charophyta/Embryophyta group;
            Embryophyta; Tracheophyta; seed plants; Magnoliophyta;
            eudicotyledons; Rosidae; Fabales; Fabaceae; Papilionoideae;
            Glycine.
```

```
REFERENCE   1 (residues 1 to 380)
AUTHORS     YADAV, N. S., WIERZBICKI, A., AEGERTER, M., CASTER, C. S., PEREZ-
            GRAU, L., KINNEY, A. J., HITZ, W. D., BOOTH, J. R. JR.,
            SCHWEIGER, B., STECCA, K. L., ALLEN, S. M., BLACKWELL, M.,
            REITER, R. S., CARLSON, T. J., RUSSELL, S. H., FELDMANN, K. A.,
            PIERCE, J. and BROWSE, J.
TITLE       Cloning of higher plant omega-3 fatty acid desaturases
JOURNAL     Plant Physiol. 103 (2), 467-476 (1993)
MEDLINE     94302147
REMARK      SEQUENCE FROM N.A.
            TISSUE=SEED
COMMENT     [FUNCTION] MICROSOMAL (ER) OMEGA-3 FATTY ACID DESATURASE
            INTRODUCES THE THIRD DOUBLEBOND IN THE BIOSYNTHESIS OF 18:3
            FATTY ACIDS, IMPORTANT CONSTITUENTS OF PLANT MEMBRANES. IT IS
            THOUGHT TO USE CYTOCHROME B5 AS AN ELECTRON DONOR AND TO ACT
            ON FATTY ACIDS ESTERIFIED TO PHOSPHATIDYLCHOLINE AND,
            POSSIBLY, OTHER PHOSPHOLIPIDS.
            [PATHWAY] POLYUNSATURATED FATTY ACID BIOSYNTHESIS.
            [SUBCELLULAR LOCATION] ENDOPLASMIC RETICULUM. [DOMAIN] THE
            HISTIDINE BOX DOMAINS MAY CONTAIN THE ACTIVE SITE
            AND/OR BE INVOLVED IN METAL ION BINDING. [SIMILARITY] TO
            OTHER PLANT OMEGA-3 FATTY ACID DESATURASES.
FEATURES    Location/Qualifiers
source      1 . . . 380
            /organism="Glycine max"
            /db_xref="taxon:3847"
            1 . . . 380
Protein     1 . . . 380
            /product="OMEGA-3 FATTY ACID DESATURASE, ENDOPLASMIC
            RETICULUM"
            /EC_number="1.14.99.-"
Region      55 . . . 75
            /region_name="Transmembrane region"
Region      100 . . . 104
            /note="HISTIDINE BOX 1."
            /region_name="Domain"
Region      136 . . . 140
            /note="HISTIDINE BOX 2."
            /region_name="Domain"
Region      212 . . . 232
            /region_name="Transmembrane region"
Region      236 . . . 256
            /region_name="Transmembrane region"
Region      303 . . . 307
            /note="HISTIDINE BOX 3."
            /region_name="Domain"
ORIGIN (SEQ ID NO:25)
fdpsap ppfkiaeira sipkhcwvkn pwrslsyvlr dvlviaalva aaihfdnwll wliycpiqgt mfwalfvlgh dcghgsfsds pllnslvghi lhssilvpyh gwrishrthh qnhghiekde swvpltekiy knldsmtrli rftvpfplfv ypiylfsrsp gkegshfnpy snlfppserk giaistlcwa tmfslliyls fitspllvlk lygipywifv mwldfvtylh hhghhqklpw yrgkewsylr gglttvdrdy gwiynihhdi gthvihhlfp qiphyhlvea tqaakpvlgd yyrepersap lpfhlikyli qsmrqdhfvs dtgdvvyyqt dslllhsqrd
```

P48618 (*Brassica napus*)

```
LOCUS       FD3C_BRANA       404 aa                  PLN      Feb. 1, 1996
DEFINITION  OMEGA-3 FATTY ACID DESATURASE, CHLOROPLAST PRECURSOR.
ACCESSION   P48618
PID         g1345968
VERSION     P48618 GI:1345968
DBSOURCE    swissprot: locus FD3C_BRANA, accession P48618;
            class: standard.
            created: Feb. 1, 1996.
            sequence updated: Feb. 1, 1996.
            annotation updated: Feb. 1, 1996.
            xrefs: gi: 408489, gi: 408490, gi: 541916
KEYWORDS    OXIDOREDUCTASE; FATTY ACID BIOSYNTHESIS; CHLOROPLAST;
            MEMBRANE; TRANSIT PEPTIDE.
SOURCE      rape.
ORGANISM    Brassica napus
            Eukaryotae; Viridiplantae; Charophyta/Embryophyta group;
            Embryophyta; Tracheophyta; seed plants; Magnoliophyta;
            eudicotyledons; Rosidae; Capparales; Brassicaceae; Brassica.
```

```
REFERENCE   1 (residues 1 to 404)
AUTHORS     YADAV, N. S., WIERZBICKI, A., AEGERTER, M., CASTER, C. S., PEREZ-
            GRAU, L., KINNEY, A. J., HITZ, W. D., BOOTH, J. R. JR.,
            SCHWEIGER, B., STECCA, K. L., ALLEN, S. M., BLACKWELL, M.,
            REITER, R. S., CARLSON, T. J., RUSSELL, S. H., FELDMANN, K. A.,
            PIERCE, J. and BROWSE, J.
TITLE       Cloning of higher plant omega-3 fatty acid desaturases
JOURNAL     Plant Physiol. 103 (2), 467-476 (1993)
MEDLINE     94302147
REMARK      SEQUENCE FROM N.A.
            TISSUE=SEED
COMMENT     [FUNCTION] CHLOROPLAST OMEGA-3 FATTY ACID DESATURASE
            INTRODUCES THE THIRD DOUBLEBOND IN THE BIOSYNTHESIS OF 16:3 AND 18:3
            FATTY ACIDS, IMPORTANT CONSTITUENTS OF PLANT MEMBRANES. IT IS
            THOUGHT TO USE FERREDOXIN AS AN ELECTRON DONOR AND TO ACT ON
            FATTY ACIDS ESTERIFIED TO GALACTOLIPIDS, SULFOLIPIDS AND
            PHOSPHATIDYLGLYCEROL.
            [PATHWAY] POLYUNSATURATED FATTY ACID BIOSYNTHESIS.
            [SUBCELLULAR LOCATION] CHLOROPLAST, MEMBRANE-BOUND
            (PROBABLE). [DOMAIN] THE HISTIDINE BOX DOMAINS MAY CONTAIN
            THE ACTIVE SITE AND/OR BE INVOLVED IN METAL ION BINDING.
            [SIMILARITY] TO OTHER PLANT OMEGA-3 FATTY ACID DESATURASES.
FEATURES    Location/Qualifiers
source      1 . . . 404
            /organism="Brassica napus"
            /db_xref="taxon:3708"
            1 . . . 404
Protein     <1 . . . 404
            /product="OMEGA-3 FATTY ACID DESATURASE, CHLOROPLAST
            PRECURSOR"
            /EC_number="1.14.99.-"
Region      <1 . . . (2.404)
            /note="CHLOROPLAST."
            /region_name="Transit peptide"
Region      (1.403) . . . 404
            /note="OMEGA-3 FATTY ACID DESATURASE, CHLOROPLAST."
            /region_name="Mature chain"
Region      121 . . . 125
            /note="HISTIDINE BOX 1."
            /region_name="Domain"
Region      157 . . . 161
            /note="HISTIDINE BOX 2."
            /region_name="Domain"
Region      324 . . . 323
            /note=="HISTIDINE BOX 3."
            /region_name="Domain"
ORIGIN (SEQ ID NO:26)
ieee pktqrfdpga pppfnladir aaipkhcwvk npwksmsyvv relaivfala agaaylnnwl vwplywiaqg tmfwalfvlg hdcghgsfsn dprlnsvvgh llhssilvpy hgwrishrth hqnhghvend eswhpmseki yksldkptrf frftlplvml aypfylwars pgkkgshyhp dsdlflpker ndvltstacw tamavllvcl nfvmgpmqml klyvipywin vmwldfvtyl hhhghedklp wyrgkewsyl rgglttldrd yglinnihhd igthvihhlf pqiphyhlve ateaakpvlg kyyrepdksg plplhllgil aksikedhfv sdegdvvyye adpnly
```

BAA22440 (Zea mays)

```
LOCUS       BAA22440        398 aa              PLN         Mar. 4, 1998
DEFINITION  fatty acid desaturase.
ACCESSION   BAA22440
PID         g2446996
VERSION     BAA22440.1 GI:2446996
DBSOURCE    locus D63953 accession D63953.1
KEYWORDS    .
SOURCE      Zea mays.
ORGANISM    Zea mays
            Eukaryota; Viridiplantae; Streptophyta; Embryophyta;
            Tracheophyta; euphyllophytes; Spermatophyta; Magnoliophyta;
            Liliopsida; Poales; Poaceae; Zea.
```

```
                                  -continued
REFERENCE   1 (residues 1 to 398)
AUTHORS     Kusano, T.
TITLE       Direct Submission
JOURNAL     Submitted (Aug. 30, 1995) to the DDBJ/EMBL/GenBank databases.
            Tomonobu Kusano, Akita Prefectural College of Agriculture,
            Biotechnology Institute; 2-2 Minami, Ohgatamura, Minamiakita-
            gun, Akita 010-04, Japan (E-mail:kusano@air.akita-u.ac.jp,
            Tel:0185-45-2026(ex.403), Fax:0185-45-2678)
REFERENCE   2 (sites)
AUTHORS     Berberich, T., Harada, M., Sugawara, K., Kodama, H., Iba, K. and
            Kusano, T.
TITLE       Two maize genes encoding omega-3 fatty acid desaturase and
            their differential expression to temperature
JOURNAL     Plant Mol. Biol. 36 (2), 297-306 (1998)
MEDLINE     98145435
COMMENT     Sequence updated (Apr. 11, 1996) by: Tomonobu Kusano.
FEATURES    Location/Qualifiers
source      1 . . . 398
            /organism="Zea mays"
            /strain="honey bantum"
            /db_xref="taxon:4577"
Protein     1 . . . 398
            /product="fatty acid desaturase"
CDS         1 . . . 398
            /gene="FAD8"
            /coded_by="D63953.1:<1 . . . 1198"
ORIGIN (SEQ ID NO:27)
veedkr ssplgegdeh vaasgaaqge fdpgapppfg laeiraaipk hcwvkdpwrs mayvlrdvvv vlglaaaaar ldswlvwply waaqqtmfwa lfvlghdcgh gsfsnnpkln svvghilhss ilvpyhqwri shrthhqnhg hvekdeswhp lperlyksld fmtrklrftm pfpllafply lfarspgksg shfnpssdlf qpnekkdiit staswlamvg vlagltflmg pvamlklygv pyfvfvawld mvtylhhhgh edklpwyrgq ewsylrgglt tldrdyglin nihhdigthv ihhlfpqiph yhlieateaa kpvlgkyyke pkksgplpwh lfgvlaqslk qdhyvsdtgd vvyyqtd P48621 (Glycine max)

LOCUS       FD3C_SOYBN    453 aa              PLN         Dec. 15, 1998
DEFINITION  OMEGA-3 FATTY ACID DESATURASE, CHLOROPLAST PRECURSOR.
ACCESSION   P48621
PID         g1345971
VERSION     P48621 GI:1345971
DBSOURCE    swissprot: locus FD3C_SOYBN, accession P48621;
            class: standard.
            created: Feb. 1, 1996.
            sequence updated: Feb. 1, 1996.
            annotation updated: Dec. 15, 1998.
            xrefs: gi: 408791, gi: 408792, gi: 541947
            xrefs (non-sequence databases): PFAM PF00487
KEYWORDS    OXIDOREDUCTASE; FATTY ACID BIOSYNTHESIS; CHLOROPLAST;
            MEMBRANE; TRANSIT PEPTIDE.
SOURCE      soybean.
ORGANISM    Glycine max
            Eukaryota; Viridiplantae; Charophyta/Embryophyta group;
            Embryophyta; Tracheophyta; euphyllophytes; Spermatophyta;
            Magnoliophyta; eudicotyledons; Rosidae; Fabales; Fabaceae;
            Papilionoideae; Glycine.
REFERENCE   1 (residues 1 to 453)
AUTHORS     YADAV, N. S., WIERZBICKI, A., AEGERTER, M., CASTER, C. S., PEREZ-
            GRAU, L., KINNEY, A. J., HITZ, W. D., BOOTH, J. R. JR.,
            SCHWEIGER, B., STECCA, K. L., ALLEN, S. M., BLACKWELL, M.,
            REITER, R. S., CARLSON, T. J., RUSSELL, S. H., FELDMANN, K. A.,
            PIERCE, J. and BROWSE J.
TITLE       Cloning of higher plant omega-3 fatty acid desaturases
JOURNAL     Plant Physiol. 103 (2), 467-476 (1993)
MEDLINE     94302147
REMARK      SEQUENCE FROM N.A.
            TISSUE=SEED
```

```
COMMENT      [FUNCTION] CHLOROPLAST OMEGA-3 FATTY ACID DESATURASE
             INTRODUCES THE THIRD DOUBLEBOND IN THE BIOSYNTHESIS OF 16:3
             AND 18:3 FATTY ACIDS, IMPORTANT CONSTITUENTS OF PLANT
             MEMBRANES. IT IS THOUGHT TO USE FERREDOXIN AS AN ELECTRON
             DONOR AND TO ACT ON FATTY ACIDS ESTERIFIED TO GALACTOLIPIDS,
             SULFOLIPIDS AND PHOSPHATIDYLGLYCEROL.
             [PATHWAY] POLYUNSATURATED FATTY ACID BIOSYNTHESIS.
             [SUBCELLULAR LOCATION] CHLOROPLAST, MEMBRANE-BOUND
             (PROBABLE). [DOMAIN] THE HISTIDINE BOX DOMAINS MAY CONTAIN
             THE ACTIVE SITE AND/OR BE INVOLVED IN METAL ION BINDING.
             [SIMILARITY] TO OTHER PLANT OMEGA-3 FATTY ACID DESATURASES.
FEATURES     Location/Qualifiers
source       1 . . . 453
             /organism="Glycine max"
             /db_xref="taxon:3847"
             1 . . . 453
Protein      1 . . . 453
             /product="OMEGA-3 FATTY ACID DESATURASE, CHLOROPLAST
             PRECURSOR"
             /EC_number="1.14.99.-"
Region       1 . . . (2.453)
             /region_name="Transit peptide"
             /note="CHLOROPLAST."
Region       (1.452) . . . 453
             /region_name="Mature chain"
             /note="OMEGA-3 FATTY ACID DESATURASE, CHLOROPLAST."
Region       171 . . . 175
             /region_name="Domain"
             /note="HISTIDINE BOX 1."
Region       207 . . . 211
             /region_name="Domain"
             /note="HISTIDINE BOX 2."
Region       374 . . . 378.
             /region_name="Domain"
             /note="HISTIDINE BOX 3."
ORIGIN (SEQ ID NO:28)
svd ltngtngveh eklpefdpga pppfnladir aaipkhcwvk dpwrsmsyvv rdviavfgla aaaaylnnwl vwplywaaqg tmfwalfvlg hdcghgsfsn nsklnsvvgh llhssilvpy hgwrishrth hqhhghaend eswhplpekl frsldtvtrm lrftapfpll afpvylfsrs pgktgshfdp ssdlfvpner kdvitstacw aamlgllvgl gfvmgpiqll klygvpyvif vmwldlvtyl hhhghedklp wyrgkewsyl rgglttldrd ygwinnihhd igthvihhlf pqiphyhlve ateaakpvfg kyyrepkksa aplpfhlige iirsfktdhf vsdtgdvvyy qtd BAA22441 (Zea mays)

LOCUS        BAA22441       443 aa              PLN         Mar. 4, 1998
DEFINITION   fatty acid desaturase.
ACCESSION    BAA22441
PID          g2446998
VERSION      BAA22441.1  GI:2446998
DBSOURCE     locus D63954 accession D63954.1
KEYWORDS     .
SOURCE       Zea mays.
ORGANISM     Zea mays Eukaryota; Viridiplantae; Streptophyta; Embryophyta;
             Tracheophyta; euphyllophytes; Spermatophyta; Magnoliophyta;
             Liliopsida; Poales; Poaceae; Zea.
REFERENCE    1 (residues 1 to 443)
AUTHORS      Kusano, T.
TITLE        Direct Submission
JOURNAL      Submitted (Aug. 30, 1995) to the DDBJ/EMBL/GenBank
             databases. Tomonobu Kusano, Akita Prefectural College of
             Agriculture, Biotechnology Institute; 2-2 Minami, Ohgatamura,
             Minamiakita-
             gun, Akita 010-04, Japan (E-mail:kusano@air.akita-u.ac.jp,
             Tel:0185-45-2026(ex.403), Fax:0185-45-2678)
REFERENCE    2 (sites)
AUTHORS      Berberich, T., Harada, M., Sugawara, K., Kodama, H., Iba, K. and
             Kusano, T.
TITLE        Two maize genes encoding omega-3 fatty acid desaturase and
             their differential expression to temperature
```

```
JOURNAL      Plant Mol. Biol. 36 (2), 297-306 (1998)
MEDLINE      98145435
FEATURES     Location/Qualifiers
source       1 . . . 443
             /organism="Zea mays"
             /strain=="honey bantum"
             /db_xref="taxon:4577"
Protein      1 . . . 443
             /product="fatty acid desaturase"
CDS          1 . . . 443
             /gene="FAD7"
             /coded_by="join(D63954.1:2178 . . . 2665, D63954.1:2775 . . . 2
             864,
             D63954.1:2944 . . . 3010, D63954.1:3113 . . . 3205,
             D63954.1:3323 . . . 3508, D63954.1:3615 . . . 3695,
             D63954.1:4259 . . . 4396, D63954.1:4492 . . . 4680)"
ORIGIN (SEQ ID NO:29)
ga  aaggefdpga pppfglaeir aaipkhcwvk dpwrsmsyvl rdvavvlgla aaaarldswl vwplywaaqg tmfwalfvlg hdcghgsfsn npklnsvvgh ilhssilvpy hgwrishrth hgnhghvekd eswhplperl yksldfmtrk lrftmpfpll afplylfars pgksgshfnp gsdlfqptek ndiitstasw lamvgvlagl tflmgpvpml klygvpylvf vawldmvtyl hhhghedklp wyrgkewsyl rgglttldrd ygwinnihhd igthvihhlf pqiphyhlie ateaakpvlg kyykepknsg alpwhlfrvl aqslkgdhyv shtgdvvyyq ae
```

CAA07638 (*Solanum tuberosum*)

```
LOCUS        CAA07638          431 aa            PLN       Sep. 4, 1998
DEFINITION   w-3 desaturase.
ACCESSION    CAA07638
PID          g3550663
VERSION      CAA07638.1  GI:3550663
DBSOURCE     embl locus STU007739, accession AJ007739.1
KEYWORDS     .
SOURCE       potato.
ORGANISM     Solanum tuberosum
             Eukaryota; Viridiplantae; Streptophyta; Embryophyta;
             Tracheophyta; euphyllophytes; Spermatophyta; Magnoliophyta;
             eudicotyledons; Asteridae; Solananae; Solanales; Solanaceae;
             Solanum; Potatoe; section Petota.
REFERENCE    1 (residues 1 to 431)
AUTHORS      Leon, J.
TITLE        Direct Submission
JOURNAL      Submitted (Aug. 20, 1998) Leon J., Genetica
             Molecular de PLantas, Centro Nacional de Biotecnologia
             (CSIC), Campus de Cantoblanco Ctra. Colmenar Viejo Km 15,500,
             Madrid 28049, SPAIN
REFERENCE    2 (residues 1 to 431)
AUTHORS      Martin, M.
JOURNAL      Unpublished
FEATURES     Location/Qualifiers
source       1 . . . 431
             /organism="Solanum tuberosum"
             /cultivar="Desiree"
             /db_xref="taxon:4113"
Protein      1 . . . 431
             /product="w-3 desaturase"
CDS          1 . . . 431
             /db_xref="SPTREMBL:O82068"
             /coded_by="AJ007739.1:1 . . . 1296"
ORIGIN (SEQ ID NO:30)
eeeqt tnngdefdpg asppfklsdi kaaipkhcwv knpwtsmsyv vrdvaivfql aaaaayfnnw lvwplywfaq stmfwalfvl ghdcghgsfs nnhnlnsvag hilhssilvp yhgwrishrt hhqnhghven deswhplsek lynsldditk kfrftlpfpl laypfylwgr spgkkgshfd pssdlfvase kkdvitstvc wtamaallvg lsfvmgplqv lklygipywg fvmwldivty lhhhghedkv pwyrgeewsy lrgglttldr dygwinnihh digthvihhl fpqiphyhlv eateaakpvl gkyykepkks gplpfyllgy liksmkedhf vsdtgnvvyy qtdpnly
```

-continued

AAA86690 (*Limnanthes douglasii*)

```
LOCUS       AAA86690        436 aa            PLN       Nov. 21, 1995
DEFINITION  delta-15 lineoyl desaturase.
ACCESSION   AAA86690
PID         g699390
VERSION     AAA86690.1 GI:699390
DBSOURCE    locus LDU17063 accession U17063.1
KEY WORDS
SOURCE      Douglas's meadowfoam.
ORGANISM    Limnanthes douglasii
            Eukaryota; Viridiplantae; Streptophyta; Embryophyta;
            Tracheophyta; euphyllophytes; Spermatophyta; Magnoliophyta;
            eudicotyledons; core eudicots; Rosidae; eurosids II;
            Brassicales; Limnanthaceae; Limnanthes.
REFERENCE   1 (residues 1 to 436)
AUTHORS     Bhella, R. S. and MacKenzie, S. L.
TITLE       Nucleotide sequence of a cDNA from Limnanthes douglasii L.
            Encoding a delta-15 linoleic acid desaturase
JOURNAL     Plant Physiol. 108 (2), 861 (1995)
MEDLINE     95334518
REFERENCE   2 (residues 1 to 436)
AUTHORS     MacKenzie, S. L.
TITLE       Direct Submission
JOURNAL     Submitted (Nov. 9, 1994) Samuel L. MacKenzie, Plant
            Biotechnology Institute, National Research Council of Canada,
            110 Gymnasium Place, Saskatoon, SK S7N 0W9, Canada
COMMENT     Method: conceptual translation.
FEATURES    Location/Qualifiers
source      1 . . . 436
            /organism="Limnanthes douglasii"
            /db_xref="taxon:28973"
            /dev_stage="seed, storage deposition stage"
Protein     1 . . . 438
            /product="delta-15 lineoyl desaturase"
CDS         1 . . . 436
            /function="linoleic acid desaturation"
            /coded_by="U17063.1:56 . . . 1366"
            /note="omega-3-fatty acid desaturase"
ORIGIN (SEQ ID NO:31)
sapfqiastt peeedevaef dpgspppfkl adiraaipkh cwvknqwrsm syvvrdvviv lglaaaavaa nswavwplyw vaqgtmfwal fvlghdcghg sfsnnhklns vvghllhssi lvpyhgwrir hrthhqnhgh vendeswhpm seklfrsldk ialtfrfkap fpmlaypfyl werspgktgs hyhpdsdlfv psekkdvits ticwttmvgl liglsfvmgp iqilklyvvp ywifvmwldf vtyldhhghe dklpwyrgee wsylrggltt ldrdyglinn ihhdigthvi hhlfpqiphy hlveatqaak pifgkyykep akskplpfhl idvllkslkr dhfvpdtgdi vyyqsdpq
```

BAA07785 (*Triticum aestivum*)

```
LOCUS       BAA07785        380 aa            PLN       Jun. 18, 1999
DEFINITION  plastid omega-3 fatty acid desaturase.
ACCESSION   BAA07785
PID         g1694615
VERSION     BAA07785.1 GI:1694615
DBSOURCE    locus D43688 accession D43688.1
KEYWORDS    .
SOURCE      bread wheat.
ORGANISM    Triticum aestivum
            Eukaryota; Viridiplantae; Streptophyta; Embryophyta;
            Tracheophyta; euphyllophytes; Spermatophyta; Magnoliophyta;
            Liliopsida; Poales; Poaceae; Triticum
REFERENCE   1 (sites)
AUTHORS     Horiguchi, G., Iwakawa, H., Kodama, H., Kawakami, N., Nishimura, M.
            And Iba, K.
TITLE       Expression of a gene for plastid omega-3 fatty acid
            desaturase and changes in lipid and fatty acid compositions
            in light- and dark-grown wheat leaves
```

```
                            -continued
JOURNAL      Physiol. Plantarurn 96, 275-283 (1996)
REFERENCE    2 (residues 1 to 380)
AUTHORS      Iwakawa, H.
TITLE        Direct Submission
JOURNAL      Submitted (Dec. 3, 1994) to the DDBJ/EMBL/GenBank
             databases. Hirotaka Iwakawa, Kyushu University, Facul.
             Science, Dept. Biology, Lab. Plant Physiology; 6-10-1
             Hakozaki, Higashi-ku,
             Fukuoka, Fukuoka 812, Japan (E-mail: koibascb@mbox.nc.kyushu-
             u.ac.jp, Tel:092-641-1101(ex.4414), Fax:092-632-2741)
FEATURES     Location/Qualifiers
source       1 . . . 380
             /organism="Triticum aestivum"
             /strain="cv. Chihoku"
             /db_xref="taxon:4565"
             /clone_lib="lambda-gt11"
             /tissue_type="leaf"
Protein      1 . . . 380
             /product="plastid omega-3 fatty acid desaturase"
CDS          1 . . . 380
             /gene="TaFAD7"
             /coded_by="D43688.1:<1 . . . 1143"
ORIGIN (SEQ ID NO:32)
fdpgapp pfgladiraa ipkhcwvkdh wssmgyvvrd vvvvlalaat aarldswlaw pvywaaqgtm fwalfvlghd cghgsfsnna klnsvvghil hssilvpynq wrishrthhq nhghvendes whplpeklyr sldsstrklr falpfpmlay pfylwsrspg ksgshfhpss dlfqpnekkd iltsttcwla maglllagltv vmgplqilkl yavpywifvm wldfvtylhh hghndklpwy rgkawsiytg glttldrdyg wlnnihhdig thvihhllpq iphyhlveat eaatvlgkyy repdksgpfp fhlfgalars mksdhyvsdt gdiiyyqtdp k BAA28358 (Triticum aestivum)

LOCUS        BAA28358       383 aa             PLN         May 30, 1998
DEFINITION   omega-3 fatty acid desaturase.
ACCESSION    BAA28358
PID          g3157460
VERSION      BAA28358.1 GI:3157460
DBSOURCE     locus D84678 accession D84678.1
KEYWORDS     .
SOURCE       Triticum aestivum.
ORGANISM     Triticum aestivun
             Eukaryota; Viridiplantae; Streptophyta; Embryophyta;
             Tracheophyta; euphyllophytes; Spermatophyta; Magnoliophyta;
             Liliopsida; Poales; Poaceae; Triticum.
REFERENCE    1 (residues 1 to 383)
AUTHORS      Horiguchi, G.
TITLE        Direct Submission
JOURNAL      Submitted (May 1, 1996) to the DDBJ/EMBL/GenBank databases.
             Gorou Horiguchi, Kyushu University, Faculty of Science,
             Department of Biology; 6-10-1 Hakozaki, Fukuoka, Fukuoka 812-
             8581, Japan (E-mail:ghoriscb@mbox.nc.kyushu-u.ac.jp, Tel:092-
             642-2621, Fax:092-642-2621)
REFERENCE    2 (sites)
AUTHORS      Horiguchi, G., Kawakami, N., Kusumi, K., Kodama, H. and Iba, K.
TITLE        Developmental regulation of genes for microsome and plastid
             omega-3 fatty acid desaturases in wheat (Triticum aestivum
             L.)
JOURNAL      Plant Cell Physiol. 39, 540-544 (1998)
FEATURES     Location/Qualifiers
source       1 . . . 383
             /organism="Triticum aestivum"
             /cultivar="Chihoku"
             /db_xref="taxon:4565"
             /clone="pWFD3"
             /clone_lib="lambda MOSE lox"
             /tissue_type="leaf and root"
Protein      1 . . . 383
             /product="omega-3 fatty acid desaturase"
CDS          1 . . . 383
             /gene="TaFAD3"
             /coded_by="D84678.1:132 . . . 1283"
```

```
ORIGIN (SEQ ID NO:33)
fdaakppp frigdvraav pahcwpqepp aslsyvardv avvaalaaaa wradswalwp lywavqgtmf walfvlghdc ghgsfsdsgt lnsvvghllh tfilvpyngw rishrthhqn hghidrdesw hpitekvyqk leprtktlrf svpfpllafp vylwyrspgk egshfnpssd lftpkerrdv iisttcwftm ialligmacv fglvpvlkly gvpyivnvmw ldlvtylhhh ghqdlpwyrg eewsylrggl ttvdrdygwi nnihhdigth vihhlfpqip hyhlveatka arpvlgryyr epeksgplpm hlitvllksl rvdhfvsdvg dvvfyqtdps l
```

BAA11397 (Oryza sativa)

```
LOCUS       BAA11397       381 aa              PLN       Feb. 5, 1999
DEFINITION  w-3 fatty acid desaturase.
ACCESSION   BAA11397
PID         g1777376
VERSION     BAA11397.1  GI:1777376
DBSOURCE    locus RICP181X2 accession D78506.1
KEYWORDS    .
SOURCE      Oryza sativa.
ORGANISM    Oryza sativa
            Eukaryota; Viridiplantae; Streptophyta; Embryophyta;
            Tracheophyta; euphyllophytes; Spermatophyte; Magnoliophyta;
            Liliopsida;
            Poales; Poaceae; Oryza.
REFERENCE   1 (residues 1 to 381)
AUTHORS     Akagi, H.
TITLE       Direct Submission
JOURNAL     Submitted (Nov. 27, 1995) to the DDBJ/EMBL/GenBank
            databases. Hiromori Akaqi, Life Science Institute, Mitsui
            Toatsu Chemicals Inc., Plant Biotechnology; Togo 1144,
            Mobara, Chiba 297, Japan
            (E-mail:tnirasaw@niguts.nig.ac.jp, Tel:0475-25-6729,
            Fax:0475-25-6553)
REFERENCE   2 (residues 1 to 381)
AUTHORS     Akagi, H.
TITLE       Nucleotide sequence of a w-3 fatty acid desaturase gene of
            rice
JOURNAL     Unpublished (1996)
REFERENCE   3 (sites)
AUTHORS     Kodama, H., Akagi, H., Kusumi, K., Fujimura, T. and Iba, K.
TITLE       Structure, chromosomal location and expression of a rice gene
            encoding the microsome omega-3 fatty acid desaturase
JOURNAL     Plant Mol. Biol. 33 (3), 493–502 (1997)
MEDLINE     97201483
FEATURES    Location/Qualifiers
source      1 . . . 381
            /organism="Oryza sativa"
            /strain="IR36"
            /db_xref="taxon:4530"
            /clone="pl8-1X2"
Protein     1 . . . 381
            /product="w-3 fatty acid desaturase"
CDS         1 . . . 381
            /coded_by="join(D78506.1:674 . . . 975, D78506.1:1069 . . . 115
            8, D78506.1:1613 . . . 1679, D78506.1:2499 . . . 2582,
            D78506.1:2741 . . . 2926, D78506.1:3030 . . . 3107,
            D78506.1:3662 . . . 3799, D78506.1:3917 . . . 4117)"
ORIGIN (SEQ ID NO:34)
sedarlf fdaakpppfr igdvraaipv hcwrktplrs lsyvardlli vaalfaaaas sidlawawaw plywarqgtm vwalfvlghd cghgsfsdsa mlnnvvghll hsfilvpyhg wrfshrthhq nhghierdes whpiteklyw qletrtkklr ftlpftllaf pwyrspgktg shflpssdlf spkeksdviv sttcwcimis llvalacvfg pvpvlmlygv pylvfvmwld lvtylhhhgh ndlpwyrgee wsylrggltt vdrdygwinn ihhdigthvi hhlfpqiphy hlveatkaar pvlgryyrep eksgplplhl fgvllrtlrv dhfvsdvgdv vyyqtdhsl
```

-continued

AAB61352 (*Synechococcus* PCC7002)

```
LOCUS       AAB61352       350 aa            BCT       Jun. 17, 1997
DEFINITION  omega-3 desaturase.
ACCESSION   AAB61352
PID         g2197199
VERSION     AAB61352.1  GI:2197199
DBSOURCE    locus SPU36389 accession U36389.1
KEYWORDS    .
SOURCE      Synechococcus PCC7002.
ORGANISM    Synechococcus PCC7002
            Bacteria; Cyanobacteria; Chroococcales; Synechococcus.
REFERENCE   1 (residues 1 to 350)
AUTHORS     Sakamoto, T. and Bryant, D. A.
TITLE       Temperature-regulated mRNA accumulation and stabilization for
            Fatty acid desaturase genes in the cyanobacterium
            Synechococcus sp. strain PCC 7002
JOURNAL     Mol. Microbiol. 23 (6), 1281–1292 (1997)
MEDLINE     97260123
REFERENCE   2 (residues 1 to 350)
AUTHORS     Sakamoto, T.
TITLE       Direct Submission
JOURNAL     Submitted (Sep. 14, 1995) Toshio Sakamoto, Biochemistry and
            Molecular Biology, The Pennsylvania State University, S-232
            Frear Bldg., University Park, PA 16802, USA
FEATURES    Location/Qualifiers
source      1 . . . 350
            /organism="Synechococcus PCC7002"
            /db_xref="taxon:32049"
Protein     1 . . . 350
            /function="desaturarion of fatty acids at omega-3
            position"
            /product="omega-3 desaturase"
CDS         1 . . . 350
            /gene="desB"
            /coded_by="U36389.1:747 . . . 1799"
            /transl_table=11
ORIGIN (SEQ ID NO:35)
pf tlkdvkaaip dycfqpsvfr slayffldig iiaglyaiaa yldswffypi fwfaqgtmfw alfvvghdcg hgsfsrskfl ndlighlsht pilvpfhgwr ishrthhsnt gnidtdeswy pipeskydqm gfaeklvrfy apliaypiyl fkrspgrgpg shfspksplf kpaerndiil staaiiamvg flgwftvqfg llafvkfyfv pyvifviwld lvtylhhtea dipwyrgddw yylkgalsti drdygifnei hhnigthvah hifhtiphyh lkdateaikp llgdyyrvsh apiwrsffrs qkachyiadq gshlyyq
```

S52650 (*Synechocystis* sp.)

```
LOCUS       S52650         359 aa            BCT       Mar. 13, 1997
DEFINITION  desaturase delta 15 - Synechocystis sp. (strain PCC6803)
ACCESSION   S52650
PID         g2126522
VERSION     S52650  GI:2126522
DBSOURCE    pir: locus S52650;
            summary: #length 359 #molecular-weight 41919 #checksum 9162;
            genetic: #start_codon GTG;
            PIR dates: Oct. 28, 1996 #sequence revision Mar. 13, 1997
            #text_change Mar. 13, 1997.
KEYWORDS
SOURCE      Synechocystis sp.
ORGANISM    Synechocystis sp.
            Eubacteria; Cyanobacteria; Chroococcales; Synechocystis.
REFERENCE   1 (residues 1 to 359)
AUTHORS     Sakamoto, T., Los, D. A., Higashi, S., Wada, H., Nishida, I.,
            Ohmori, M. and Murata, N.
TITLE       Cloning of omega 3 desaturase from cyanobacteria and its use
            in altering the degree of membrane-lipid unsaturation
JOURNAL     Plant Mol. Biol. 26 (1), 249–263 (1994)
MEDLINE     95035996
FEATURES    Location/Qualifiers
source      1 . . . 359
            /organism="Synechocystis sp."
            /db_xref="taxon:1143"
Protein     1 . . . 359
            /product="desaturase delta 15"
```

-continued

ORIGIN (SEQ ID NO:36)
pftlqelrna ipadcfepsv vrslgyffid vgliagfyal aayldswffy pifwliqgtl fwslfvvghd cghgsfsksk tlnnwighls htpilvpyhg wrishrthha ntgnidtdes wypvsegkyn qmawyekllr fylpliaypi ylfrrspnrq gshfmpgspl frpgekaavl tstfalaafv gflgfltwqf gwifllkfyv apylvfvvwl dlvtflhhte dnipwyrgdd wyflkgalst idrdygfinp ihhdigthva hhifsnmphy klrrateaik pilgeyyrys depiwqaffk sywachfvpn qgsgvyyqs

AAA61774 (Chloroplast *Brassica napus*)

```
LOCUS       AAA61774       329 aa            PLN       Jan. 31, 1995
DEFINITION  omega-3 fatty acid desaturase.
ACCESSION   AAA61774
PID         g408490
VERSION     AAA61774.1  GI:408490
DBSOURCE    locus BNACPFADD accession L22963.1
KEYWORDS    .
SOURCE      rape.
ORGANISM    Chloroplast Brassica napus
            Eukaryota; Viridiplantae; Streptophyta; Embryophyta;
            Tracheophyta; euphyllophytes; Spermatophyta; Magnoliophyta;
            eudicotyledons; core eudicots; Rosidae; eurosids II;
            Brassicales; Brassicaceae; Brassica.
REFERENCE   1 (residues 1 to 329)
AUTHORS     Yadav, N. S., Wierzbicki, A., Aegerter, M., Caster, C. S., Perez-
            Grau, L., Kinney, A. J., Hitz, W. D., Booth, J. R. Jr.,
            Schweiger, B., Stecca, K. L.
TITLE       Cloning of higher plant omega-3 fatty acid desaturases
JOURNAL     Plant Physiol. 103 (2), 467-476 (1993)
MEDLINE     94302147
COMMENT     Method: conceptual translation.
FEATURES    Location/Qualifiers
source      1 . . . 329
            /organism="Brassica napus"
            /chloroplast
            /db_xref="taxon:3708"
            /tissue_type="seed"
Protein     1 . . . 329
            /product="omega-3 fatty acid desaturase"
CDS         1 . . . 329
            /gene="Fadd"
            /coded_by="L22963.1:226 . . . 1215"
```
ORIGIN (SEQ ID NO:37)
msyvvrelai vfalaagaay lnnwlvwply wiaqgtmfwa lfvlghdcgh gsfsndprln svvghllhss ilvpyhgwri shrthhqnhg hvendeswhp msekiyksld kptrffrftl plvmlaypfy lwarspgkkg shyhpdsdlf lpkerndvlt stacwtamav llvclnfvmg pmqmlklyvi pywinvmwld fvtylhhhgh edklpwyrgk ewsylrgglt tldrdyglin nihhdigthv ihhlfpqiph yhlveateaa kpvlgkyyre pdksgplplh llgilaksik edhfvsdegd vvyyeadpnl y

BAA22439 (*Zea mays*)

```
LOCUS       BAA22439       262 aa            PLN       Mar. 4, 1998
DEFINITION  fatty acid desaturase.
ACCESSION   BAA22439
PID         g2446994
VERSION     BAA22439.1  GI:2446994
DBSOURCE    locus D63952 accession D63952.1
KEYWORDS    .
SOURCE      Zea mays.
ORGANISM    Zea mays
            Eukaryota; Viridiplantae; Streptophyta; Embryophyta;
            Tracheophyta; euphyllophytes; Spermatophyta; Magnoliophyta;
            Liliopsida; Poales; Poaceae; Zea.
```

```
REFERENCE   1 (residues 1 to 262)
AUTHORS     Kusano, T.
TITLE       Direct Submission
JOURNAL     Submitted (Aug. 30, 1995) to the DDBJ/EMBL/GenBank databases.
            Tomonobu Kusano, Akita Prefectural College of Agriculture,
            Biotechnology Institute; 2-2 Minami, Ohgatamura, Minamiakita-
            gun, Akita 010-04, Japan (E-mail:kusano@air.akita-u.ac.jp,
            Tel:0185-45-2026(ex.403), Fax:0185-45-2678)
REFERENCE   2 (sites)
AUTHORS     Berberich, T., Harada, M., Sugawara, K., Kodama, H., Iba, K. and
            Kusano, T.
TITLE       Two maize genes encoding omega-3 fatty acid desaturase and
            their differential expression to temperature
JOURNAL     Plant Mol. Biol. 36 (2), 297-306 (1998)
MEDLINE     98145435
FEATURES    Location/Qualifiers
source      1 . . . 262
            /organism="Zea mays"
            /strain="honey bantum"
            /db_xref="taxon:4577"
Protein     1 . . . 262
            /product="fatty acid desaturase"
CDS         1 . . . 262
            /gene="FAD7"
            /coded_by="D63952.1:<1 . . . 791"
ORIGIN (SEQ ID NO:38)
lhssilvpyh gwrishrthh qnhghvekde swhplperly ksldfmtrkl rftmptplla fplylfarsp gksgshfnpg sdlfqptekn diitstaswl amvgvlaglt flmgpvpmlk lygvpylvfv awldmvtylh hhghedklpw yrgkewsylr ggltttldrdy gwinnihhdi gthvihhlfp qiphyhliea teaakpvlgk yykepknsga lpwhlfrvla qslkqdhyvs htgdvvyyqa e
```

BAA11396 (*Oryza sativa*)

```
LOCUS       BAA11396        269 aa          PLN        Feb. 5, 1999
DEFINITION  w-3 fatty acid desaturase.
ACCESSION   BAA11396
PID         g1785856
VERSION     BAA11396.1 GI:1765856
DBSOURCE    locus RICPA11 accession D78505.1
KEYWORDS
SOURCE      Oryza sativa.
ORGANISM    Oryza sativa
            Eukaryota; Viridiplantae; Streptophyta; Embryophyta;
            Tracheophyta; euphyllophytes; Spermatophyta; Magnoliophyta;
            Liliopsida; Poales; Poaceae; Oryza.
REFERENCE   1 (residues 1 to 269)
AUTHORS     Akagi, H.
TITLE       Direct Submission
JOURNAL     Submitted (Nov. 27, 1995) to the DDBJ/EMBL/GenBank databases.
            Hiromori Akagi, Life Science Institute, Mitsui Toatsu Chemicals
            Inc., Plant Biothechnology; Togo 1144, Mobara, Chiba 297, Japan
            (E-mail:tnirasaw@niguts.nig.ac.jp, Tel:0475-25-6729,
            Fax:0475-25-6553)
REFERENCE   2 (residues 1 to 269)
AUTHORS     Akagi, H.
TITLE       Partial nucleotide sequence of a w-3 fatty acid desaturase
            cDNA Of rice
JOURNAL     Unpublished (1996)
REFERENCE   3 (sites)
AUTHORS     Kodama, H., Akagi, H., Kusumi, I., Fujimura, T. and Iba, K.
TITLE       Structure, chromosomal location and expression of a rice gene
            encoding the microsome omega-3 fatty acid desaturase
JOURNAL     Plant Mel. Biol. 33 (3), 493-502 (1997)
MEDLINE     97201483
COMMENT     Sequence updated (Jan. 20, 1997) by: Hiromori Akagi.
FEATURES    Location/Qualifiers
source      1 . . . 269
            /organism="Oryza sativa"
            /strain="Nipponbare"
            /db_xref="taxon:4530"
Protein     1 . . . 269
            /product="w-3 fatty acid desaturase"
CDS         1 . . . 269
            /coded_by="D78505.1:<1 . . . 810"
```

-continued

```
ORIGIN (SEQ ID NO:39)
nnvvghllhs filvpyhgwr fshrthhqnh ghierdeswh piteklywql etrtkklrft lpftllafpw yrspgktgsh flpssdlfsp keksdvivst tcwcimisll valacvfqpv pvlmlygvpy lvfvmwldlv tylhhhghnd lpwyrgeews ylrgglttvd rdygwinnih hdigthvihh lfpqiphyhl veatkaarpv lgryyrepek sgplplhlfg vllrtlrvdh fvsdvgdvvy yqtdhsl
```

AAD41582 (*Brassica rapa*)

```
LOCUS       AF056572_1      172 aa              PLN       Jul. 1, 1999
DEFINITION  unknown.
ACCESSION   AAD41582
PID         g5305314
VERSION     AAD41582.1  GI:5305314
DBSOURCE    locus AF056572 accession AF056572.1
KEYWORDS    .
SOURCE      Brassica rapa.
ORGANISM    Brassica rapa
            Eukaryoca; Viridiplantae; Streptophyta; Embryophyta;
            Tracheophyta; euphyllophytes; Spermatophyta; Magnoliophyta;
            eudicotyledons; core eudicots; Rosidae; eurosids II;
            Brassicales; Brassicaceae; Brassica.
REFERENCE   1 (residues 1 to 172)
AUTHORS     Brunel, D., Froger, N. and Pelletier, G.
TITLE       Development of amplified consensus genetic markers (A.C.G.M.)
            in Brassica napus from Arabidopsis thaliana sequences of
            known biological function
JOURNAL     Unpublished
REFERENCE   2 (residues 1 to 172)
AUTHORS     Brunel, D., Froger, N. and Pelletier, G.
TITLE       Direct Submission
JOURNAL     Submitted (Apr. 1, 1998) Station de Genetique et
            d'Amelioration des Plantes, INRA, Route de St Cyr, Versailles
            78026, France
COMMENT     Method: conceptual translation.
FEATURES    Location/Qualifiers
source      1 . . . 172
            /organism="Brassica rapa"
            /cultivar=R500"
            /db_xref="taxon:3711"
Protein     <1 . . . >172
            /product="unknown"
CDS         1 . . . 172
            /gene="FAD31"
            /note="similar to Arabidopsis thaliana FAD3"
            /coded_by="join(AF056572.1:<1 . . . 26, AF056572.1:557 . . . 62
            3, AF056572.1:1221 . . . 1406,
            AF056572.1:1484 . . . 1564, AF056572.1:1652 . . . >1714)"
ORIGIN (SEQ ID NO:40)
filvpyhgwr ishrthhqnh ghvendeswv plpeklyknl shstrmlryt vplpmlaypl ylwyrspgke gshynpyssl fapserklia tsttcwsiml atlvylsflv gpvtvlkvyg vpyiifvmwl davtylhhhg hddklpwyrg kewsylrggl ttidrdygif nn
```

AAD41581 (*Brassica oleracea*)

```
LOCUS       AF056571_1      141 aa              PLN       Jul. 1, 1999
DEFINITION  unknown.
ACCESSION   AAD41581
PID         g5305312
VERSION     AAD41581.1  GI:5305312
DBSOURCE    locus AF056571 accession AF056571.1
KEYWORDS    .
SOURCE      Brassica oleracea.
ORGANISM    Brassica oleracea
            Eukaryota; Viridiplantae; Streptophyta; Embryophyta;
            Tracheophyta; euphyllophytes; Spermatophyta; Magnoliophyta;
            eudicotyledons; core eudicots; Rosidae; eurosids II;
            Brassicales; Brassicaceae; Brassica.
REFERENCE   1 (residues 1 to 141)
AUTHORS     Brunel, D., Froger, N. and Pelletier, G.
TITLE       Development of amplified consensus genetic markers (A.C.G.M.)
            in Brassica napus from Arabidopsis thaliana sequences of
            known biological function
```

-continued

```
JOURNAL       Unpublished
REFERENCE     2  (residues 1 to 141)
AUTHORS       Brunel, D., Froger, N. and Pelletier, G.
TITLE         Direct Submission
JOURNAL       Submitted (Apr. 1, 1998) Station de Genetique et
              d'Amelioration des Plantes, INRA, Route de St Cyr, Versailles
              78026, France
COMMENT       Method: conceptual translation.
FEATURES      Location/Qualifiers
source        1 . . . 141
              /organism="Brassica oleracea"
              /cultivar="Rapide Cycling"
              /db_xref="taxon:3712"
Protein       <1 . . . >141
              /product="unknown"
CDS           1 . . . 141
              /partial
              /gene="FAD31"
              /note="similar to Arabidopsis thaliana FAD3"
              coded_by="join(AF056571.1:<235 . . . 327, AF056571.
              1:436 . . . 621, AF056571.1:699 . . . 779,
              AF056571.1:865 . . . >927)"
ORIGIN (SEQ ID NO:41)
lpeklyknls hstrmlrytv plpmlayply lwyrspgkeg shynpysslf apserkliat sttcwsivla tlvylsflvg pvtvlkvygv pyiifvmwld avtylhhhgh ddklpwyrgk 121 ewsylrgglt tvdrdygifn n
```

AAD41580 (Brassica napus)

```
LOCUS         AF056570_1     141 aa             PLN       Jul. 1, 1999
DEFINITION    unknown.
ACCESSION     AAD41580
PID           g5305310
VERSION       AAD41580.1  GI:5305310
DBSOURCE      locus AF056570 accession AF056570.1
KEYWORDS      .
SOURCE        rape.
ORGANISM      Brassica napus
              Eukaryota; Viridiplantae; Streptophyta; Embryophyta;
              Tracheophyta; euphyllophytes; Spermatophyta; Magnoliophyta;
              eudicotyledons; core eudicots; Rosidae; eurosids II;
              Brassicales; Brassicaceae; Brassica.
REFERENCE     1 (residues 1 to 141)
AUTHORS       Brunel, D., Froger, N. and Pelletier, G.
TITLE         Development of amplified consensus genetic markers (A.C.G.M.)
              I in Brassica napus from Arabidopsis thaliana sequences of
              known biological function
JOURNAL       Unpublished
REFERENCE     2 (residues 1 to 141)
AUTHORS       Brunel, D., Froger, N. and Pelletier, G.
TITLE         Direct Submission
JOURNAL       Submitted (Apr. 1, 1998) Station de Genetique et
              d'Amelioration des Plantes, INRA, Route de St Cyr,
              Versailles 78026, France
COMMENT       Method: conceptual translation.
FEATURES      Location/Qualifiers
source        1 . . . 141
              /organism="Brassica napus"
              /cultivar="Darmor"
              /db_xref="taxon:3708"
Protein       <1 . . . >141
              /product="unknown"
CDS           1 . . . 141
              /partial
              /gene="FAD32"
              /note="similar to Arabidopsis thaliana FAD3"
              /coded_by="join(AF056570.1:<107 . . . 199, AF056570.1:308.
              .493,
              AF056570.1:572 . . . 652, AF056570.1:738 . . . >800)"
ORIGIN (SEQ ID NO:42)
lpeklyknls hstrmlrytv plpmlayply lwyrspgkeg shynpysslf apserkliat sttcwsivla slvylsflvg pvtvlkvygv pyiifvmwld avtylhhhgh ddklpwyrgk ewsylrgglt tvdrdygifn n
```

EXAMPLE 3

Cloning of the Fad3A gene by PCR from the 'A' genome of *B. napus* Apollo also amplified fragments of the 'C' genome which represent a second FAD3 gene, designated Fad3C herein, from the 'C' genome of the low linolenic acid *B. napus* variety Apollo. Sequence polymorphisms in the Fad3C sequence have been identified that facilitate mapping the Fad3C gene. A partial genomic DNA sequence of Fad3C is shown in FIG. 11, a partial cDNA sequence of Fad3C is shown in FIG. 7 and a partial amino acid seqence of Fad3C is shown in FIG. 2.

CONCLUSION

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. All documents referred to herein are hereby incorporated by reference, although no admission is made that any such documents constitute prior art. In the claims, the word "comprising" is used as an open-ended term, substantially equivalent to the phrase "including, but not limited to".

---

What is claimed is:

1. A recombinant nucleic acid encoding a plant fatty acid desaturase, wherein the nucleic acid sequence encodes an amino acid substitution in the motif SYLRGGL (SEQ ID NO: 60) in the desaturase at the position corresponding to position 275 of Apollo Fad3 (SEQ ID NO: 1) and wherein the substitution is the replacement of the arginine residue with an amino acid selected from the group consisting of Ile, Val, Leu, Cys, and Phe.

2. The recombinant nucleic acid of claim 1, wherein the substitution is the replacement of the arginine residue with a cysteine.

3. The recombinant nucleic acid of claim 1, wherein the nucleic acid is capable of altering the fatty acid composition of a plant.

4. An isolated vector comprising the nucleic acid of claim 1.

5. A method of modifying a plant comprising transforming the plant with a recombinant nucleic acid encoding a plant fatty acid desaturase, wherein the nucleic acid sequence encodes an amino acid substitution in the motif SYLRGGL (SEQ ID NO: 60) in the desaturase at the position corresponding to amino acid 275 of Apollo Fad3A (SEQ ID NO: 1), and wherein the substitution is the replacement of the arginine residue with an amino acid selected from the group consisting of Ile, Val, Leu, Cys, and Phe.

6. The method of claim 5, wherein the plant is selected from the group consisting of Cruciferae family: canola, rapeseed (*Brassica* spp.), crambe (*Crambe* spp.), honesty (*Lunaria* spp.) lesquerella (*Lesquerella* spp.); the Compositae family: sunflower (*Helianthus* spp.), safflower (*Carthamus* spp.), niger (*Guizotia* spp.); the Palmae family: palm (*Elaeis* spp.), coconut (*Cocos* spp.), the Leguminosae family: peanut (*Arachis* spp.), soybean (*Glycine* spp.); and plants of other families such as maize (*Zea* spp.), cotton (*Gossypium* spp.), jojoba (*Simmondsia* spp.), flax (*Linum* spp.), sesame (*Sesamum* spp.), castor bean (*Ricinus* spp.), olive (*Olea* spp.), poppy (*Papaver* spp.), spurge (*Euphorbia*, spp.), meadow foam (*Limnanthes* spp.), mustard (Sinapis spp.) and cuphea (*Cuphea* spp.).

7. The method of claim 5, wherein the plant is selected from the group consisting of members of the Cruciferae family, including canola, rapeseed (*Brassica* spp.), crambe (*Crambe* spp.), honesty (*Lunaria* spp.) and lesquerella (*Lesquerella* spp.).

8. The method of claim 5, wherein the plant is a *Brassica*.

9. The method of claim 5, wherein the plant is canola.

10. A plant, or a part of the plant, comprising the recombinant nucleic acid of claim 1.

11. The plant or part of the plant of claim 10, wherein the plant is selected from the group consisting of Cruciferae family: canola, rapeseed (*Brassica* spp.), crambe (*Crambe* spp.), honesty (*Lunaria* spp.) lesquerella (*Lesquerella* spp.); the Compositae family: sunflower (*Helianthus* spp.), safflower (*Carthamus* spp.), niger (*Guizotia* spp.); the Palmae family: palm (*Elaeis* spp.), coconut (*Cocos* spp.); the Leguminosae family: peanut (*Arachis* spp.), soybean (*Glycine* spp.); and plants of other families such as maize (*Zea* spp.), cotton (*Gossypium* spp.), jojoba (*Simmondsia* spp.), flax (*Linum* spp.), sesame (*Sesamum* spp.), castor bean (*Ricinus* spp.), olive (*Olea* spp.), poppy (*Papaver* spp.), spurge (*Euphorbia*, spp.), meadow foam (*Limnanthes* spp.), mustard (*Sinapis* spp.) and cuphea (*Cuphea* spp.).

12. The plant or part of the plant of claim 10, wherein the plant is selected from the group consisting of members of the Cruciferae family, including canola, rapeseed (*Brassica* spp.), crambe (*Crambe* spp.), honesty (*Lunaria* spp.) and lesquerella (*Lesquerella* spp.).

13. The plant or part of the plant of claim 10, wherein the plant is a *Brassica*.

14. The plant or part of the plant of claim 10, wherein the plant is canola.

15. A method of plant selection comprising:
   a) obtaining a progeny plant by transformation of a parent plant with the nucleic acid of claim 1, crossing parent plant lines or self crossing of the parent plant; and,
   b) identifying progeny plants that comprise said nucleic acid.

16. The method of claim 15, wherein the progeny plant is selected from the group consisting of Cruciferae family: canola, rapeseed (*Brassica* spp.), crambe (*Crambe* spp.), honesty (*Lunaria* spp.) lesquerella (*Lesquerella* spp.); the Compositae family: sunflower (*Helianthus* spp.), safflower (*Carthamus* spp.), niger (*Guizotia* spp.); the Pa/mae family: palm (*Elaeis* spp.), coconut (*Cocos* spp.); the Leguminosae family: peanut (*Arachis* spp.), soybean (*Glycine* spp.); and plants of other families such as maize (*Zea* spp.), cotton (*Gossypium* spp.), jojoba (*Simmondsia* spp.), flax (*Linum* spp.), sesame (*Sesamum* spp.), castor bean (*Ricinus* spp.), olive (*Olea* spp.), poppy (*Papaver* spp.), spurge (*Euphorbia*, spp.), meadow foam (*Limnanthes* spp.), mustard (*Sinapis* spp.) and cuphea (*Cuphea* spp.).

17. The method of claim 15, wherein the progeny plant is selected from the group consisting of members of the Cruciferae family, including canola, rapeseed (*Brassica* spp.), crambe (*Crambe* spp.), honesty (*Lunaria* spp.) and lesquerella (*Lesquerella* spp.).

18. The method of claim 15, wherein the progeny plant is a *Brassica*.

19. The method of claim 15, wherein the progeny plant is canola.

20. A method of plant selection comprising:
   a) obtaining a progeny plant by (i) transformation of a parent plant with a nucleic acid that encodes an amino acid substitution in the motif SYLRGGL (SEQ ID NO: 60) in the desaturase at the position corresponding to amino acid 275 of Apollo Fad3A (SEQ ID NO: 1); and wherein the substitution is the replacement of an arginine residue with an amino acid selected from the group consisting of Ile, Val, Leu, Cys, and Phe, (ii) crossing parent plant lines or (iii) self crossing of the parent plant; and,
   b) identifying in the progeny plants said nucleic acid.

21. The method of claim 20, wherein the progeny plant is selected from the group consisting of Cruciferae family: canola, rapeseed (*Brassica* spp.), crambe (*Crambe* spp.), honesty (*Lunaria* spp.) lesquerella (*Lesquerella* spp.); the Compositae family: sunflower (*Helianthus* spp.), safflower (*Carthamus* spp.), niger (*Guizotia* spp.); the Palmae family: palm (*Elaeis* spp.), coconut (*Cocos* spp.); the Leguminosae family: peanut (*Arachis* spp.), soybean (*Glycine* spp.), and plants of other families such as maize (*Zea* spp.), cotton (*Gossypium* spp.), jojoba (*Simmondsia* spp.), flax (*Linum* spp.), sesame (*Sesamum* spp.), castor bean (*Ricinus* spp.), olive (*Olea* spp.), poppy (*Papaver* spp.), spurge (*Euphorbia*, spp.), meadow foam (*Limnanthes* spp.), mustard (*Sinapis* spp.) and cuphea (*Cuphea* spp.).

22. The method of claim 20, wherein the progeny plant is selected from the group consisting of members of the Cruciferae family, including canola, rapeseed (*Brassica* spp.), crambe (*Crambe* spp.), honesty (*Lunaria* spp.) and lesquerella (*Lesquerella* spp.).

23. The method of claim 20, wherein the progeny plant is a *Brassica*.

24. The method of claim 20, wherein the progeny plant is a canola.

25. The progeny plant or a part of the progeny plant produced by the method of claim 20.

26. The method of claim 5 wherein the substitution is the replacement of the arginine residue with an isoleucine.

27. The method of claim 5 wherein the substitution is the replacement of the arginine residue with a valine.

28. The method of claim 5 wherein the substitution is the replacement of the arginine residue with leucine.

29. The method of claim 5 wherein the substitution is the replacement of the arginine residue with cysteine.

30. The method of claim 5 wherein the substitution is the replacement of the arginine residue with phenylalanine.

31. The method of claim 20 wherein the substitution is the replacement of the arginine residue with isoleucine.

32. The method of claim 20 wherein the substitution is the replacement of the arginine residue with valine.

33. The method of claim 20 wherein the substitution is the replacement of the arginine residue with leucine.

34. The method of claim 20 wherein the substitution is the replacement of the arginine residue with cysteine.

35. The method of claim 20 wherein the substitution is the replacement of the arginine residue with phenylalanine.

* * * * *

SEQUENCE LISTING

```
<160> NUMBER OF SEQ ID NOS: 73

<210> SEQ ID NO 1
<211> LENGTH: 380
<212> TYPE: PRT
<213> ORGANISM: Brassica napus
<220> FEATURE:
<221> NAME/KEY: SITE
<222> LOCATION: (95)..(99)
<223> OTHER INFORMATION: Histadine  box sequence
<220> FEATURE:
<221> NAME/KEY: SITE
<222> LOCATION: (213)..(213)
<223> OTHER INFORMATION: Position of amino acid substitution in
      accordance with various aspects of the invention
<220> FEATURE:
<221> NAME/KEY: SITE
<222> LOCATION: (275)..(275)
<223> OTHER INFORMATION: Position of amino acid substitution in
      accordance with various aspects of the invention
<220> FEATURE:
<221> NAME/KEY: SITE
<222> LOCATION: (347)..(347)
<223> OTHER INFORMATION: Position of amino acid substitution in
      accordance with various aspects of the invention

<400> SEQUENCE: 1

Met Val Val Ala Met Asp Gln Arg Ser Asn Val Asn Gly Asp Ser Lys
1               5                   10                  15

Asp Glu Arg Phe Asp Pro Ser Ala Gln Pro Pro Phe Lys Ile Gly Asp
            20                  25                  30

Ile Arg Ala Ala Ile Pro Lys His Cys Trp Val Lys Ser Pro Leu Arg
        35                  40                  45

Ser Met Ser Tyr Val Ala Arg Asp Ile Phe Ser Val Val Ala Leu Ala
    50                  55                  60

Val Ala Ala Val Tyr Phe Asp Ser Trp Phe Phe Trp Pro Leu Tyr Trp
65                  70                  75                  80

Ala Ala Gln Gly Thr Leu Phe Trp Ala Ile Phe Val Leu Gly His Asp
                85                  90                  95

Cys Gly His Gly Ser Phe Ser Asp Ile Pro Leu Leu Asn Thr Ala Val
            100                 105                 110

Gly His Ile Leu His Ser Phe Ile Leu Val Pro Tyr His Gly Trp Arg
        115                 120                 125

Met Ser His Arg Thr His His Gln Asn His Gly His Val Glu Asn Asp
    130                 135                 140

Glu Ser Trp Val Pro Leu Pro Glu Lys Leu Tyr Lys Asn Leu Ser His
145                 150                 155                 160
```

```
Ser Thr Arg Met Leu Arg Tyr Thr Val Pro Leu Pro Met Leu Ala Tyr
            165                 170                 175

Pro Leu Tyr Leu Trp Tyr Arg Ser Pro Gly Lys Glu Gly Ser His Tyr
            180                 185                 190

Asn Pro Tyr Ser Ser Leu Phe Ala Pro Ser Glu Arg Lys Leu Ile Ala
            195                 200                 205

Thr Ser Thr Thr Ala Trp Ser Ile Met Leu Ala Thr Leu Val Tyr Leu
            210                 215                 220

Ser Phe Leu Val Gly Pro Val Thr Val Leu Lys Val Tyr Gly Val Pro
225                 230                 235                 240

Tyr Ile Ile Phe Val Met Trp Leu Asp Ala Val Thr Tyr Leu His His
                245                 250                 255

His Gly His Asp Asp Lys Leu Pro Trp Tyr Arg Gly Lys Glu Trp Ser
            260                 265                 270

Tyr Leu Cys Gly Gly Leu Thr Thr Ile Asp Arg Asp Tyr Gly Ile Phe
            275                 280                 285

Asn Asn Ile His His Asp Ile Gly Thr His Val Ile His His Leu Phe
            290                 295                 300

Pro Gln Ile Pro His Tyr His Leu Val Asp Ala Thr Lys Ala Ala Lys
305                 310                 315                 320

His Val Leu Gly Arg Tyr Tyr Arg Glu Pro Lys Thr Ser Gly Ala Ile
                325                 330                 335

Pro Ile His Leu Val Glu Ser Leu Val Ala Arg Ile Lys Lys Asp His
            340                 345                 350

Tyr Val Ser Asp Thr Gly Asp Ile Val Phe Tyr Glu Thr Asp Pro Asp
            355                 360                 365

Leu Tyr Val Tyr Ala Ser Asp Lys Ser Lys Ile Asn
            370                 375
```

<210> SEQ ID NO 2
<211> LENGTH: 377
<212> TYPE: PRT
<213> ORGANISM: Brassica napus
<220> FEATURE:
<221> NAME/KEY: SITE
<222> LOCATION: (92)..(96)
<223> OTHER INFORMATION: Putatitve 'Histadine Box'
<300> PUBLICATION INFORMATION:
<308> DATABASE ACCESSION NUMBER: GenBank/L22962
<309> DATABASE ENTRY DATE: 1995-01-31

<400> SEQUENCE: 2

```
Met Val Val Ala Met Asp Gln Arg Ser Asn Ala Asn Gly Asp Glu Arg
1               5                   10                  15

Phe Asp Pro Ser Ala Gln Pro Pro Phe Lys Ile Gly Asp Ile Arg Ala
            20                  25                  30

Ala Ile Pro Lys His Cys Trp Val Lys Ser Pro Leu Arg Ser Met Ser
            35                  40                  45

Tyr Val Ala Arg Asp Ile Phe Ala Val Ala Leu Ala Val Ala Ala
            50                  55                  60

Val Tyr Phe Asp Ser Trp Phe Trp Pro Leu Tyr Trp Ala Ala Gln
65                  70                  75                  80

Gly Thr Leu Phe Trp Ala Ile Phe Val Leu Gly His Asp Cys Gly His
                85                  90                  95

Gly Ser Phe Ser Asp Ile Pro Leu Leu Asn Thr Ala Val Gly His Ile
            100                 105                 110
```

```
Leu His Ser Phe Ile Leu Val Pro Tyr His Gly Trp Arg Ile Ser His
        115                 120                 125

Arg Thr His His Gln Asn His Gly His Val Glu Asn Asp Glu Ser Trp
    130                 135                 140

Val Pro Leu Pro Glu Lys Leu Tyr Lys Asn Leu Ser His Ser Thr Arg
145                 150                 155                 160

Met Leu Arg Tyr Thr Val Pro Leu Pro Met Leu Ala Tyr Pro Leu Tyr
                165                 170                 175

Leu Trp Tyr Arg Ser Pro Gly Lys Glu Gly Ser His Tyr Asn Pro Tyr
            180                 185                 190

Ser Ser Leu Phe Ala Pro Ser Glu Arg Lys Leu Ile Ala Thr Ser Thr
        195                 200                 205

Thr Cys Trp Ser Ile Met Leu Ala Thr Leu Val Tyr Leu Ser Phe Leu
    210                 215                 220

Val Gly Pro Val Thr Val Leu Lys Val Tyr Gly Val Pro Tyr Ile Ile
225                 230                 235                 240

Phe Val Met Trp Leu Asp Ala Val Thr Tyr Leu His His His Gly His
                245                 250                 255

Asp Asp Lys Leu Pro Trp Tyr Arg Gly Lys Glu Trp Ser Tyr Leu Arg
            260                 265                 270

Gly Gly Leu Thr Thr Ile Asp Arg Asp Tyr Gly Ile Phe Asn Asn Ile
        275                 280                 285

His His Asp Ile Gly Thr His Val Ile His His Leu Phe Pro Gln Ile
    290                 295                 300

Pro His Tyr His Leu Val Asp Ala Thr Lys Ser Ala Lys His Val Leu
305                 310                 315                 320

Gly Arg Tyr Tyr Arg Glu Pro Lys Thr Ser Gly Ala Ile Pro Ile His
                325                 330                 335

Leu Val Glu Ser Leu Val Ala Ser Ile Lys Lys Asp His Tyr Val Ser
            340                 345                 350

Asp Thr Gly Asp Ile Val Phe Tyr Glu Thr Asp Pro Asp Leu Tyr Val
        355                 360                 365

Tyr Ala Ser Asp Lys Ser Lys Ile Asn
        370                 375

<210> SEQ ID NO 3
<211> LENGTH: 383
<212> TYPE: PRT
<213> ORGANISM: Brassica napus
<300> PUBLICATION INFORMATION:
<308> DATABASE ACCESSION NUMBER: GenBank/L01418
<309> DATABASE ENTRY DATE: 1993-04-27

<400> SEQUENCE: 3

Met Val Val Ala Met Asp Gln Arg Ser Asn Val Asn Gly Asp Ser Gly
1               5                   10                  15

Ala Arg Lys Glu Glu Gly Phe Asp Pro Ser Ala Gln Pro Pro Phe Lys
            20                  25                  30

Ile Gly Asp Ile Arg Ala Ala Ile Pro Lys His Cys Trp Val Lys Ser
        35                  40                  45

Pro Leu Arg Ser Met Ser Tyr Val Thr Arg Asp Ile Phe Ala Val Ala
    50                  55                  60

Ala Leu Ala Met Ala Ala Val Tyr Phe Asp Ser Trp Phe Leu Trp Pro
65                  70                  75                  80

Leu Tyr Trp Val Ala Gln Gly Thr Leu Phe Trp Ala Ile Phe Val Leu
                85                  90                  95
```

```
Gly His Asp Cys Gly His Gly Ser Phe Ser Asp Ile Pro Leu Leu Asn
            100                 105                 110

Ser Val Val Gly His Ile Leu His Ser Phe Ile Leu Val Pro Tyr His
        115                 120                 125

Gly Trp Arg Ile Ser His Arg Thr His His Gln Asn His Gly His Val
130                 135                 140

Glu Asn Asp Glu Ser Trp Val Pro Leu Pro Glu Lys Leu Tyr Lys Asn
145                 150                 155                 160

Leu Pro His Ser Thr Arg Met Leu Arg Tyr Thr Val Pro Leu Pro Met
                165                 170                 175

Leu Ala Tyr Pro Ile Tyr Leu Trp Tyr Arg Ser Pro Gly Lys Glu Gly
            180                 185                 190

Ser His Phe Asn Pro Tyr Ser Ser Leu Phe Ala Pro Ser Glu Arg Lys
        195                 200                 205

Leu Ile Ala Thr Ser Thr Thr Cys Trp Ser Ile Met Leu Ala Thr Leu
    210                 215                 220

Val Tyr Leu Ser Phe Leu Val Asp Pro Val Thr Val Leu Lys Val Tyr
225                 230                 235                 240

Gly Val Pro Tyr Ile Ile Phe Val Met Trp Leu Asp Ala Val Thr Tyr
                245                 250                 255

Leu His His His Gly His Asp Glu Lys Leu Pro Trp Tyr Arg Gly Lys
            260                 265                 270

Glu Trp Ser Tyr Leu Arg Gly Gly Leu Thr Thr Ile Asp Arg Asp Tyr
        275                 280                 285

Gly Ile Phe Asn Asn Ile His His Asp Ile Gly Thr His Val Ile His
    290                 295                 300

His Leu Phe Pro Gln Ile Pro His Tyr His Leu Val Asp Ala Thr Arg
305                 310                 315                 320

Ala Ala Lys His Val Leu Gly Arg Tyr Tyr Arg Glu Pro Lys Thr Ser
                325                 330                 335

Gly Ala Ile Pro Ile His Leu Val Glu Ser Leu Val Ala Ser Ile Lys
            340                 345                 350

Lys Asp His Tyr Val Ser Asp Thr Gly Asp Ile Val Phe Tyr Glu Thr
        355                 360                 365

Asp Pro Asp Leu Tyr Val Tyr Ala Ser Asp Lys Ser Lys Ile Asn
    370                 375                 380

<210> SEQ ID NO 4
<211> LENGTH: 386
<212> TYPE: PRT
<213> ORGANISM: Arabidopsis thaliana
<300> PUBLICATION INFORMATION:
<308> DATABASE ACCESSION NUMBER: GenBank/D17579
<309> DATABASE ENTRY DATE: 1999-02-04

<400> SEQUENCE: 4

Met Val Val Ala Met Asp Gln Arg Thr Asn Val Asn Gly Asp Pro Gly
1               5                   10                  15

Ala Gly Asp Arg Lys Lys Glu Glu Arg Phe Asp Pro Ser Ala Gln Pro
            20                  25                  30

Pro Phe Lys Ile Gly Asp Ile Arg Ala Ala Ile Pro Lys His Cys Trp
        35                  40                  45

Val Lys Ser Pro Leu Arg Ser Met Ser Tyr Val Val Arg Asp Ile Ile
    50                  55                  60

Ala Val Ala Ala Leu Ala Ile Ala Ala Val Tyr Val Asp Ser Trp Phe
65                  70                  75                  80
```

```
Leu Trp Pro Leu Tyr Trp Ala Ala Gln Gly Thr Leu Phe Trp Ala Ile
                85                  90                  95

Phe Val Leu Gly His Asp Cys Gly His Gly Ser Phe Ser Asp Ile Pro
            100                 105                 110

Leu Leu Asn Ser Val Val Gly His Ile Leu His Ser Phe Ile Leu Val
            115                 120                 125

Pro Tyr His Gly Trp Arg Ile Ser His Arg Thr His His Gln Asn His
        130                 135                 140

Gly His Val Glu Asn Asp Glu Ser Trp Val Pro Leu Pro Glu Arg Val
145                 150                 155                 160

Tyr Lys Lys Leu Pro His Ser Thr Arg Met Leu Arg Tyr Thr Val Pro
                165                 170                 175

Leu Pro Met Leu Ala Tyr Pro Leu Tyr Leu Cys Tyr Arg Ser Pro Gly
            180                 185                 190

Lys Glu Gly Ser His Phe Asn Pro Tyr Ser Ser Leu Phe Ala Pro Ser
        195                 200                 205

Glu Arg Lys Leu Ile Ala Thr Ser Thr Thr Cys Trp Ser Ile Met Phe
210                 215                 220

Val Ser Leu Ile Ala Leu Ser Phe Val Phe Gly Pro Leu Ala Val Leu
225                 230                 235                 240

Lys Val Tyr Gly Val Pro Tyr Ile Ile Phe Val Met Trp Leu Asp Ala
                245                 250                 255

Val Thr Tyr Leu His His His Gly His Asp Glu Lys Leu Pro Trp Tyr
            260                 265                 270

Arg Gly Lys Glu Trp Ser Tyr Leu Arg Gly Gly Leu Thr Thr Ile Asp
        275                 280                 285

Arg Asp Tyr Gly Ile Phe Asn Asn Ile His His Asp Ile Gly Thr His
290                 295                 300

Val Ile His His Leu Phe Pro Gln Ile Pro His Tyr His Leu Val Asp
305                 310                 315                 320

Ala Thr Lys Ala Ala Lys His Val Leu Gly Arg Tyr Tyr Arg Glu Pro
                325                 330                 335

Lys Thr Ser Gly Ala Ile Pro Ile His Leu Val Glu Ser Leu Val Ala
            340                 345                 350

Ser Ile Lys Lys Asp His Tyr Val Ser Asp Thr Gly Asp Ile Val Phe
        355                 360                 365

Tyr Glu Thr Asp Pro Asp Leu Tyr Val Tyr Ala Ser Asp Lys Ser Lys
370                 375                 380

Ile Asn
385

<210> SEQ ID NO 5
<211> LENGTH: 283
<212> TYPE: PRT
<213> ORGANISM: Brassica napus

<400> SEQUENCE: 5

Gly His Gly Ser Phe Ser Asp Ile Pro Leu Leu Asn Thr Ala Val Gly
1               5                   10                  15

His Ile Leu His Ser Phe Ile Leu Val Pro Tyr His Gly Trp Arg Ile
            20                  25                  30

Ser His Arg Thr His His Gln Asn His Gly His Val Glu Asn Asp Glu
        35                  40                  45

Ser Trp Val Pro Leu Pro Glu Lys Leu Tyr Lys Asn Leu Ser His Ser
50                  55                  60
```

```
Thr Arg Met Leu Arg Tyr Thr Val Pro Leu Pro Met Leu Ala Tyr Pro
 65                  70                  75                  80

Leu Tyr Leu Trp Tyr Arg Ser Pro Gly Lys Glu Gly Ser His Tyr Asn
             85                  90                  95

Pro Tyr Ser Ser Leu Phe Ala Pro Ser Glu Arg Lys Leu Ile Ala Thr
            100                 105                 110

Ser Thr Thr Ala Trp Ser Ile Met Leu Ala Thr Leu Val Tyr Leu Ser
            115                 120                 125

Phe Leu Val Gly Pro Val Thr Val Leu Lys Val Tyr Gly Val Pro Tyr
        130                 135                 140

Ile Ile Phe Val Met Trp Leu Asp Ala Val Thr Tyr Leu His His His
145                 150                 155                 160

Gly His Asp Asp Lys Leu Pro Trp Tyr Arg Gly Lys Glu Trp Ser Tyr
                165                 170                 175

Leu Arg Gly Gly Leu Thr Thr Ile Asp Arg Asp Tyr Gly Ile Phe Asn
            180                 185                 190

Asn Ile His His Asp Ile Gly Thr His Val Ile His His Leu Phe Pro
        195                 200                 205

Gln Ile Pro His Tyr His Leu Val Asp Ala Thr Lys Ala Ala Lys His
    210                 215                 220

Val Leu Gly Arg Tyr Tyr Arg Glu Pro Lys Thr Ser Gly Ala Ile Pro
225                 230                 235                 240

Ile His Leu Val Glu Ser Leu Val Ala Ser Ile Lys Lys Asp His Tyr
                245                 250                 255

Val Ser Asp Thr Gly Asp Ile Val Phe Tyr Glu Thr Asp Pro Asp Leu
            260                 265                 270

Tyr Val Tyr Ala Ser Asp Lys Ser Lys Ile Asn
        275                 280

<210> SEQ ID NO 6
<211> LENGTH: 217
<212> TYPE: PRT
<213> ORGANISM: Brassica napus

<400> SEQUENCE: 6

Gly His Gly Ser Phe Ser Asp Ile Pro Leu Leu Asn Thr Ala Val Gly
  1               5                  10                  15

His Ile Leu His Ser Phe Ile Leu Val Pro Tyr His Gly Trp Arg Ile
             20                  25                  30

Ser His Arg Thr His His Gln Asn His Gly His Val Glu Asn Asp Glu
         35                  40                  45

Ser Trp Val Pro Leu Pro Glu Lys Leu Tyr Lys Asn Leu Ser His Ser
     50                  55                  60

Thr Arg Met Leu Arg Tyr Thr Val Pro Leu Pro Met Leu Asp Tyr Pro
 65                  70                  75                  80

Leu Tyr Leu Trp Tyr Arg Ser Pro Gly Lys Glu Gly Ser His Tyr Asn
             85                  90                  95

Thr Tyr Ser Ser Leu Phe Ala Pro Ser Glu Arg Lys Leu Ile Ala Thr
            100                 105                 110

Ser Thr Thr Cys Trp Ser Ile Met Leu Ala Thr Leu Val Tyr Leu Ser
            115                 120                 125

Phe Leu Val Asp Pro Val Thr Val Leu Lys Val Tyr Gly Val Pro Tyr
        130                 135                 140

Ile Ile Phe Val Met Trp Leu Asp Ala Val Thr Tyr Leu His His His
145                 150                 155                 160
```

```
Gly His Asp Glu Lys Leu Pro Tyr Arg Gly Lys Glu Trp Ser Tyr Leu
            165                 170                 175

Arg Gly Gly Leu Thr Thr Ile Asp Arg Asp Tyr Gly Ile Phe Asn Asn
        180                 185                 190

Ile His His Asp Ile Gly Thr His Val Ile His Leu Phe Pro Gln
        195                 200                 205

Ile Pro His Tyr His Leu Val Asp Ala
    210                 215

<210> SEQ ID NO 7
<211> LENGTH: 1142
<212> TYPE: DNA
<213> ORGANISM: Brassica napus

<400> SEQUENCE: 7
atggttgtcg ctatggacca gcgtagcaat gtgaacggag attccaagga cgaaaggttt      60
gatccgagcg cacaaccacc gtttaagatc ggagatataa gggctgcgat tcctaagcat     120
tgttgggtca agagtccttt gagatccatg agctacgtcg cgagagacat tttctccgtc     180
gtggctctgg ccgtcgccgc cgtgtatttt gatagctggt tcttctggcc tctttattgg     240
gccgcccaag ggaccctttt ctgggccatc ttcgtactcg ccacgactg tggacatggg      300 agtttctcag acattcccct tctgaatact gcggttggtc atattcttca ttccttcatt     360
ctcgttccat accatggttg agaatgagc catcggacac accaccagaa ccatggccat      420
gttgaaaacg acgagtcttg ggttccgttg ccagaaaaat tatacaagaa tttgtcccac     480
agtacacgga tgctcagata cactgtccct ctccccatgc tcgcttaccc tctctatctg     540
tggtacagaa gtcctggtaa agaagggtca cattataacc catacagtag tttatttgcc     600
ccaagcgaga gaaagcttat tgcaacttca actactgcgt ggtcgatcat gttggccact     660
cttgtttatc tatcattcct cgttggtcca gtcacagttc taaaagtcta tggtgttcct     720
tacattatct ttgtaatgtg gttggacgct gtcacgtact gcatcatca tggtcacgat      780 gataagttgc cttggtacag aggcaaggaa tggagttatt tatgtggagg attaacaact     840
attgatagag attacgggat cttcaacaac attcatcacg atattggaac tcacgtgatc     900
catcatcttt tcccacaaat ccctcactat cacttggtcg atgccacgaa agcagctaaa     960
catgtgttgg aagatacta cagagaacca aagacgtcag gagcaatacc gatccactta    1020
gtggaaagtt tggtggcaag gattaagaaa gatcattacg tcagtgacac tggtgatatt    1080
gtcttctacg agacagatcc agatctctac gtttatgctt ctgacaaatc caaatcaatt    1140
aa                                                                   1142

<210> SEQ ID NO 8
<211> LENGTH: 3004
<212> TYPE: DNA
<213> ORGANISM: Brassica napus

<400> SEQUENCE: 8
catttcactc agagcccaca cagttttaga gagagagaaa catccctcaa agctctctct      60
ttctccggcg atggttgtcg ctatggacca gcgtagcaat gtgaacggag attccaagga    120
cgaaaggttt gatccgagcg cacaaccacc gtttaagatc ggagatataa gggctgcgat    180
tcctaagcat tgttgggtca agagtccttt gagatccatg agctacgtcg cgagagacat    240
tttctccgtc gtggctctgg ccgtcgccgc cgtgtatttt gatagctggt tcttctggcc    300
tctttattgg gccgcccaag ggaccctttt ctgggccatc ttcgtactcg ccacgactg     360
```

-continued

```
gtaatttaat tttcaattta ttttttcttc aacttcttaa ttttgatatg tttatatgtt      420
tttttcgttt tttgcatcgt ctttgatttc ttgaacgcac gttcgatatg agattttcac      480
tgacttcaag atttgattct cttcaggttt actttaaaaa aaaaaaaaat tattatgttc      540
acccaaattg gcctatttta aaagcaaaag gggatctaag attttaatt cttctctttt       600 tcagtcgtaa cactgctaac tttttttttt tgatcaaatc gtaacactca taagtcctaa      660
ctaaacatct ttttctttcc tataattatt gttggttccg cattttatgg atctacgttt     720
gaaagtttca ataaaacaca ttttattgtt tgaaagtaac aatataatta ctgtatattg      780
attcatttaa ttattgtgtg ttgttccaat ctactttcga aatatagtca tgtgacacgt      840
catattctat ttttgttacc ttgttggaac gtttgaattg agtaaagttt aattaacatt      900
gtgcaataaa tgataaacat gtttatgatg taaaattcaa tttgaataat acagtggaca      960
tgggagttct cagacattcc cttctgaata ctgcggttgg tcatattctt cattccttca     1020
ttctcgttcc ataccatggt tggtaagtca tttattttaa cttcttttttt catgcaaatt     1080 tattcttgtt ttcgtattct tacattttcc ttgtcattct tggtgcatgt tagcaaacag     1140
tattctgata actgaaaata tattaatttt tcatagtaaa ataatgcatg tgactaaaag     1200
catcaaaatc tttagcatcg aagaaaaaag aaccaaactt ttatttaatg ctatgggcct     1260
atttatggtc caattagcta ttatcatatg acatgtcctt gaataaatta atgtataagt     1320
ttaatataat atttatatat ttttgtttta atggcttatt ttattgttac atggatacat     1380
cagcttgaaa tatctacgaa catgcatcat tttcctagat acatttgttt gttgctcaaa     1440
aaatgaataa cgtagttaaa cgagtgagat tcttagcatc tgcctcgaaa acgatatgtt     1500
attgacaatt ccaatttcat ttttatgaaa ataaaataat agtttatttt ataattgggg     1560
gtggttgcag gagaatgagc catcggacac accaccagaa ccatggccat gttgaaaacg     1620
acgagtcttg ggttccggta atccccctct catattttt tttttctttt tttgaaactc      1680 tttcattttta atttcttag aattctatgt atttattta atcaatcctt tcccagtgt      1740 gaggcttgga cgaccacttg tcagatttgt cgtttagctg tagtaaacaa ctgatttaaa     1800
ttgtttatgg tactgtagtt aactttaaca acgggccact tatattcgag ccattggcat     1860
aaaatgattc ttctcgaaat tcgtttactt ttcttagtat ttttcagttt tgtagttttac    1920 gtagaactaa taaaagaaa aaaacctata acacaccac atgcaatgaa taaattcgaa       1980
tatataacca tactgttaaa tattaattaa cattttaatc ttaattttgc attccagttg     2040
ccagaaaaat tatacaagaa tttgtcccac agtacacgga tgctcagata cactgtccct     2100
ctccccatgc tcgcttaccc tctctatctg gtaaatccta attcctcatt tttcttcctg    2160
attataatta caatttgaa tttttagatt ttgagtatta actaaatata aattaaatttt     2220 gtttgggat gactacagtg gtacagaagt cctggtaaag aagggtcaca ttataaccca     2280
tacagtagtt tatttgcccc aagcgagaga aagcttattg caacttcaac tactgcgtgg    2340
tcgatcatgt tggccactct tgtttatcta tcattcctcg ttggtccagt cacagttcta    2400
aaagtctatg tgttcctta cattgtaagt ttcatatatt tcattattat atcattgcta    2460
atataatttg ttttttgacat aaagttttgg aaaaatttca gatctttgta atgtggttgg   2520
acgctgtcac gtacttgcat catcatggtc acgatgataa gttgccttgg tacagaggca    2580
aggtaagtag atcaacatta atttataaga agcaacaatg attagtatttt gattaatcta   2640 aattattgat gttatgtgta caataatagg aatggagtta tttatgtgga ggattaacaa    2700
ctattgatag agattacggg atcttcaaca acattcatca cgatattgga actcacgtga    2760
```

-continued

| | |
|---|---|
| tccatcatct tttcccacaa atccctcact atcacttggt cgatgccacg aaagcagcta | 2820 |
| aacatgtgtt gggaagatac tacagagaac caaagacgtc aggagcaata ccgatccact | 2880 |
| tagtggaaag tttggtggca aggattaaga aagatcatta cgtcagtgac actggtgata | 2940 |
| ttgtcttcta cgagacagat ccagatctct acgtttatgc ttctgacaaa tccaaatcaa | 3000 |
| ttaa | 3004 |

<210> SEQ ID NO 9
<211> LENGTH: 377
<212> TYPE: PRT
<213> ORGANISM: Brassica napus
<300> PUBLICATION INFORMATION:
<308> DATABASE ACCESSION NUMBER: GenBank/P46311
<309> DATABASE ENTRY DATE: 1996-02-01
<313> RELEVANT RESIDUES: (1)..(377)

<400> SEQUENCE: 9

Met Val Val Ala Met Asp Gln Arg Ser Asn Ala Asn Gly Asp Glu Arg
1               5                   10                  15

Phe Asp Pro Ser Ala Gln Pro Pro Phe Lys Ile Gly Asp Ile Arg Ala
            20                  25                  30

Ala Ile Pro Lys His Cys Trp Val Lys Ser Pro Leu Arg Ser Met Ser
        35                  40                  45

Tyr Val Ala Arg Asp Ile Phe Ala Val Ala Leu Ala Val Ala Ala
    50                  55                  60

Val Tyr Phe Asp Ser Trp Phe Phe Trp Pro Leu Tyr Trp Ala Ala Gln
65                  70                  75                  80

Gly Thr Leu Phe Trp Ala Ile Phe Val Leu Gly His Asp Cys Gly His
                85                  90                  95

Gly Ser Phe Ser Asp Ile Pro Leu Leu Asn Thr Ala Val Gly His Ile
            100                 105                 110

Leu His Ser Phe Ile Leu Val Pro Tyr His Gly Trp Arg Ile Ser His
        115                 120                 125

Arg Thr His His Gln Asn His Gly His Val Glu Asn Asp Glu Ser Trp
    130                 135                 140

Val Pro Leu Pro Glu Lys Leu Tyr Lys Asn Leu Ser His Ser Thr Arg
145                 150                 155                 160

Met Leu Arg Tyr Thr Val Pro Leu Pro Met Leu Ala Tyr Pro Leu Tyr
                165                 170                 175

Leu Trp Tyr Arg Ser Pro Gly Lys Glu Gly Ser His Tyr Asn Pro Tyr
            180                 185                 190

Ser Ser Leu Phe Ala Pro Ser Glu Arg Lys Leu Ile Ala Thr Ser Thr
        195                 200                 205

Thr Cys Trp Ser Ile Met Leu Ala Thr Leu Val Tyr Leu Ser Phe Leu
    210                 215                 220

Val Gly Pro Val Thr Val Leu Lys Val Tyr Gly Val Pro Tyr Ile Ile
225                 230                 235                 240

Phe Val Met Trp Leu Asp Ala Val Thr Tyr Leu His His His Gly His
                245                 250                 255

Asp Asp Lys Leu Pro Trp Tyr Arg Gly Lys Glu Trp Ser Tyr Leu Arg
            260                 265                 270

Gly Gly Leu Thr Thr Ile Asp Arg Asp Tyr Gly Ile Phe Asn Asn Ile
        275                 280                 285

His His Asp Ile Gly Thr His Val Ile His His Leu Phe Pro Gln Ile
    290                 295                 300

```
Pro His Tyr His Leu Val Asp Ala Thr Lys Ser Ala Lys His Val Leu
305                 310                 315                 320

Gly Arg Tyr Tyr Arg Glu Pro Lys Thr Ser Gly Ala Ile Pro Ile His
            325                 330                 335

Leu Val Glu Ser Leu Val Ala Ser Ile Lys Lys Asp His Tyr Val Ser
            340                 345                 350

Asp Thr Gly Asp Ile Val Phe Tyr Glu Thr Asp Pro Asp Leu Tyr Val
            355                 360                 365

Tyr Ala Ser Asp Lys Ser Lys Ile Asn
            370                 375

<210> SEQ ID NO 10
<211> LENGTH: 383
<212> TYPE: PRT
<213> ORGANISM: Brassica napus
<300> PUBLICATION INFORMATION:
<308> DATABASE ACCESSION NUMBER: GenBank/P48624
<309> DATABASE ENTRY DATE: 1996-02-01
<313> RELEVANT RESIDUES: (1)..(383)

<400> SEQUENCE: 10

Met Val Val Ala Met Asp Gln Arg Ser Asn Val Asn Gly Asp Ser Gly
1               5                   10                  15

Ala Arg Lys Glu Glu Gly Phe Asp Pro Ser Ala Gln Pro Pro Phe Lys
            20                  25                  30

Ile Gly Asp Ile Arg Ala Ala Ile Pro Lys His Cys Trp Val Lys Ser
            35                  40                  45

Pro Leu Arg Ser Met Ser Tyr Val Thr Arg Asp Ile Phe Ala Val Ala
        50                  55                  60

Ala Leu Ala Met Ala Ala Val Tyr Phe Asp Ser Trp Phe Leu Trp Pro
65                  70                  75                  80

Leu Tyr Trp Val Ala Gln Gly Thr Leu Phe Trp Ala Ile Phe Val Leu
                85                  90                  95

Gly His Asp Cys Gly His Gly Ser Phe Ser Asp Ile Pro Leu Leu Asn
            100                 105                 110

Ser Val Val Gly His Ile Leu His Ser Phe Ile Leu Val Pro Tyr His
            115                 120                 125

Gly Trp Arg Ile Ser His Arg Thr His His Gln Asn His Gly His Val
130                 135                 140

Glu Asn Asp Glu Ser Trp Val Pro Leu Pro Glu Lys Leu Tyr Lys Asn
145                 150                 155                 160

Leu Pro His Ser Thr Arg Met Leu Arg Tyr Thr Val Pro Leu Pro Met
                165                 170                 175

Leu Ala Tyr Pro Ile Tyr Leu Trp Tyr Arg Ser Pro Gly Lys Glu Gly
            180                 185                 190

Ser His Phe Asn Pro Tyr Ser Ser Leu Phe Ala Pro Ser Glu Arg Lys
            195                 200                 205

Leu Ile Ala Thr Ser Thr Thr Cys Trp Ser Ile Met Leu Ala Thr Leu
210                 215                 220

Val Tyr Leu Ser Phe Leu Val Asp Pro Val Thr Val Leu Lys Val Tyr
225                 230                 235                 240

Gly Val Pro Tyr Ile Ile Phe Val Met Trp Leu Asp Ala Val Thr Tyr
                245                 250                 255

Leu His His His Gly His Asp Glu Lys Leu Pro Trp Tyr Arg Gly Lys
            260                 265                 270
```

```
Glu Trp Ser Tyr Leu Arg Gly Leu Thr Thr Ile Asp Arg Asp Tyr
            275                 280                 285

Gly Ile Phe Asn Asn Ile His His Asp Ile Gly Thr His Val Ile His
        290                 295                 300

His Leu Phe Pro Gln Ile Pro His Tyr His Leu Val Asp Ala Thr Arg
305                 310                 315                 320

Ala Ala Lys His Val Leu Gly Arg Tyr Tyr Arg Glu Pro Lys Thr Ser
                325                 330                 335

Gly Ala Ile Pro Ile His Leu Val Glu Ser Leu Val Ala Ser Ile Lys
                340                 345                 350

Lys Asp His Tyr Val Ser Asp Thr Gly Asp Ile Val Phe Tyr Glu Thr
            355                 360                 365

Asp Pro Asp Leu Tyr Val Tyr Ala Ser Asp Lys Ser Lys Ile Asn
370                 375                 380
```

<210> SEQ ID NO 11
<211> LENGTH: 386
<212> TYPE: PRT
<213> ORGANISM: Arabidopsis thaliana
<300> PUBLICATION INFORMATION:
<308> DATABASE ACCESSION NUMBER: GenBank/P48623
<309> DATABASE ENTRY DATE: 1996-10-01
<313> RELEVANT RESIDUES: (1)..(386)

<400> SEQUENCE: 11

```
Met Val Val Ala Met Asp Gln Arg Thr Asn Val Asn Gly Asp Pro Gly
1               5                   10                  15

Ala Gly Asp Arg Lys Lys Glu Glu Arg Phe Asp Pro Ser Ala Gln Pro
                20                  25                  30

Pro Phe Lys Ile Gly Asp Ile Arg Ala Ala Ile Pro Lys His Cys Trp
            35                  40                  45

Val Lys Ser Pro Leu Arg Ser Met Ser Tyr Val Val Arg Asp Ile Ile
50                  55                  60

Ala Val Ala Ala Leu Ala Ile Ala Ala Val Tyr Val Asp Ser Trp Phe
65                  70                  75                  80

Leu Trp Pro Leu Tyr Trp Ala Ala Gln Gly Thr Leu Phe Trp Ala Ile
                85                  90                  95

Phe Val Leu Gly His Asp Cys Gly His Gly Ser Phe Ser Asp Ile Pro
            100                 105                 110

Leu Leu Asn Ser Val Val Gly His Ile Leu His Ser Phe Ile Leu Val
            115                 120                 125

Pro Tyr His Gly Trp Arg Ile Ser His Arg Thr His His Gln Asn His
            130                 135                 140

Gly His Val Glu Asn Asp Glu Ser Trp Val Pro Leu Pro Glu Arg Val
145                 150                 155                 160

Tyr Lys Lys Leu Pro His Ser Thr Arg Met Leu Arg Tyr Thr Val Pro
                165                 170                 175

Leu Pro Met Leu Ala Tyr Pro Leu Tyr Leu Cys Tyr Arg Ser Pro Gly
            180                 185                 190

Lys Glu Gly Ser His Phe Asn Pro Tyr Ser Ser Leu Phe Ala Pro Ser
            195                 200                 205

Glu Arg Lys Leu Ile Ala Thr Ser Thr Thr Cys Trp Ser Ile Met Phe
210                 215                 220

Val Ser Leu Ile Ala Leu Ser Phe Val Phe Gly Pro Leu Ala Val Leu
225                 230                 235                 240
```

```
Lys Val Tyr Gly Val Pro Tyr Ile Ile Phe Val Met Trp Leu Asp Ala
                245                 250                 255

Val Thr Tyr Leu His His His Gly His Asp Glu Lys Leu Pro Trp Tyr
            260                 265                 270

Arg Gly Lys Glu Trp Ser Tyr Leu Arg Gly Gly Leu Thr Thr Ile Asp
            275                 280                 285

Arg Asp Tyr Gly Ile Phe Asn Asn Ile His His Asp Ile Gly Thr His
            290                 295                 300

Val Ile His His Leu Phe Pro Gln Ile Pro Tyr His Leu Val Asp
305                 310                 315                 320

Ala Thr Lys Ala Ala Lys His Val Leu Gly Arg Tyr Tyr Arg Glu Pro
                325                 330                 335

Lys Thr Ser Gly Ala Ile Pro Ile His Leu Val Glu Ser Leu Val Ala
            340                 345                 350

Ser Ile Lys Lys Asp His Tyr Val Ser Asp Thr Gly Asp Ile Val Phe
            355                 360                 365

Tyr Glu Thr Asp Pro Asp Leu Tyr Val Tyr Ala Ser Asp Lys Ser Lys
            370                 375                 380

Ile Asn
385

<210> SEQ ID NO 12
<211> LENGTH: 361
<212> TYPE: PRT
<213> ORGANISM: Pelargonium x hortorum
<300> PUBLICATION INFORMATION:
<308> DATABASE ACCESSION NUMBER: GenBank/AAC16443
<309> DATABASE ENTRY DATE: 1998-05-15
<313> RELEVANT RESIDUES: (46)..(406)

<400> SEQUENCE: 12

Ser Asp Phe Asp Pro Ser Ala Pro Pro Phe Arg Leu Gly Glu Ile
1               5                   10                  15

Arg Ala Ala Ile Pro Gln His Cys Trp Val Lys Ser Pro Trp Arg Ser
            20                  25                  30

Met Ser Tyr Val Val Arg Asp Ile Val Val Phe Ala Leu Ala Val
            35                  40                  45

Ala Ala Phe Arg Leu Asp Ser Trp Leu Val Trp Pro Ile Tyr Trp Ala
50                  55                  60

Val Gln Gly Thr Met Phe Trp Ala Ile Phe Val Leu Gly His Asp Cys
65                  70                  75                  80

Gly His Gly Ser Phe Ser Asp Ser His Ile Leu Asn Ser Val Met Gly
                85                  90                  95

His Ile Leu His Ser Ser Ile Leu Val Pro Tyr His Gly Trp Arg Ile
            100                 105                 110

Ser His Lys Thr His His Ser Asn His Gly His Val Glu Asn Asp Glu
            115                 120                 125

Ser Trp Val Pro Leu Thr Glu Lys Thr Tyr Lys Ser Leu Asp Val Ser
            130                 135                 140

Thr Arg Leu Leu Arg Phe Thr Ile Pro Phe Pro Val Phe Ala Tyr Pro
145                 150                 155                 160

Phe Tyr Leu Trp Trp Arg Ser Pro Gly Lys Lys Gly Ser His Phe Asn
                165                 170                 175

Pro Tyr Ser Asp Leu Phe Ala Pro Ser Glu Arg Arg Asp Val Leu Thr
            180                 185                 190
```

```
Ser Thr Ile Ser Trp Ser Ile Met Val Ala Leu Leu Ala Gly Leu Ser
        195                 200                 205

Cys Val Phe Gly Leu Val Pro Met Leu Lys Leu Tyr Gly Gly Pro Tyr
    210                 215                 220

Trp Ile Phe Val Met Trp Leu Asp Thr Val Thr Tyr Leu His His His
225                 230                 235                 240

Gly His Asp Asp His Lys Leu Pro Trp Tyr Arg Gly Lys Glu Trp Ser
                245                 250                 255

Tyr Leu Arg Gly Gly Leu Thr Thr Val Asp Arg Asp Tyr Gly Leu Phe
            260                 265                 270

Asn Asn Ile His His Asp Ile Gly Thr His Val Ile His His Leu Phe
        275                 280                 285

Pro Gln Ile Pro His Tyr His Leu Val Glu Ala Thr Arg Ala Ala Lys
    290                 295                 300

Pro Val Leu Gly Lys Tyr Tyr Arg Glu Pro Lys Arg Ser Gly Pro Phe
305                 310                 315                 320

Pro Tyr His Leu Ile Asp Asn Leu Val Lys Ser Ile Lys Glu Asp His
                325                 330                 335

Tyr Val Ser Asp Thr Gly Asp Ile Val Phe Tyr Glu Thr Asp Pro Glu
            340                 345                 350

Gln Phe Lys Ser Asp Pro Lys Lys Leu
        355                 360

<210> SEQ ID NO 13
<211> LENGTH: 359
<212> TYPE: PRT
<213> ORGANISM: Vigna radiata var. radiata
<300> PUBLICATION INFORMATION:
<308> DATABASE ACCESSION NUMBER: GenBank/P32291
<309> DATABASE ENTRY DATE: 1996-02-01
<313> RELEVANT RESIDUES: (22)..(380)

<400> SEQUENCE: 13

Phe Asp Pro Gly Ala Pro Pro Phe Lys Ile Ala Asp Ile Arg Ala
1               5                   10                  15

Ala Ile Pro Lys His Cys Trp Glu Lys Ser Thr Leu Arg Ser Leu Ser
            20                  25                  30

Tyr Val Leu Arg Asp Val Leu Val Thr Ala Leu Ala Ala Ser Ala
            35                  40                  45

Ile Ser Phe Asn Ser Trp Phe Trp Pro Leu Tyr Trp Pro Ala Gln
    50                  55                  60

Gly Thr Met Phe Trp Ala Leu Phe Val Leu Gly His Asp Cys Gly His
65                  70                  75                  80

Gly Ser Phe Ser Asn Ser Ser Lys Leu Asn Ser Phe Val Gly His Ile
                85                  90                  95

Leu His Ser Leu Ile Leu Val Pro Tyr Asn Gly Trp Arg Ile Ser His
            100                 105                 110

Arg Thr His His Gln Asn His Gly His Val Glu Lys Asp Glu Ser Trp
        115                 120                 125

Val Pro Leu Thr Glu Lys Val Tyr Lys Asn Leu Asp Asp Met Thr Arg
    130                 135                 140

Met Leu Arg Tyr Ser Phe Pro Phe Pro Ile Phe Ala Tyr Pro Phe Tyr
145                 150                 155                 160

Leu Trp Asn Arg Ser Pro Gly Lys Glu Gly Ser His Phe Asn Pro Tyr
                165                 170                 175
```

```
Ser Asn Leu Phe Ser Pro Gly Glu Arg Lys Gly Val Val Thr Ser Thr
            180                 185                 190

Leu Cys Trp Gly Ile Val Leu Ser Val Leu Tyr Leu Ser Leu Thr
        195                 200                 205

Ile Gly Pro Ile Phe Met Leu Lys Leu Tyr Gly Val Pro Tyr Leu Ile
    210                 215                 220

Phe Val Met Trp Leu Asp Phe Val Thr Tyr Leu His His Gly Tyr
225                 230                 235                 240

Thr His Lys Leu Pro Trp Tyr Arg Gly Gln Glu Trp Ser Tyr Leu Arg
                245                 250                 255

Gly Gly Leu Thr Thr Val Asp Arg Asp Tyr Gly Trp Ile Asn Asn Val
            260                 265                 270

His His Asp Ile Gly Thr His Val Ile His His Leu Phe Pro Gln Ile
        275                 280                 285

Pro His Tyr His Leu Val Glu Ala Thr Lys Ser Ala Lys Ser Val Leu
    290                 295                 300

Gly Lys Tyr Tyr Arg Glu Pro Gln Lys Ser Gly Pro Leu Pro Phe His
305                 310                 315                 320

Leu Leu Lys Tyr Leu Leu Gln Ser Ile Ser Gln Asp His Phe Val Ser
                325                 330                 335

Asp Thr Gly Asp Ile Val Tyr Tyr Gln Thr Asp Pro Lys Leu His Gln
            340                 345                 350

Asp Ser Trp Thr Lys Ser Lys
        355

<210> SEQ ID NO 14
<211> LENGTH: 375
<212> TYPE: PRT
<213> ORGANISM: Vernicia fordii
<300> PUBLICATION INFORMATION:
<308> DATABASE ACCESSION NUMBER: GenBank/AAC98967
<309> DATABASE ENTRY DATE: 1999-01-01
<313> RELEVANT RESIDUES: (13)..(387)

<400> SEQUENCE: 14

Asn Gly Val Asn Gly Phe His Ala Lys Glu Glu Glu Glu Glu Glu Asp
1               5                   10                  15

Phe Asp Leu Ser Asn Pro Pro Phe Asn Ile Gly Gln Ile Arg Ala
            20                  25                  30

Ala Ile Pro Lys His Cys Trp Val Lys Asn Pro Trp Arg Ser Leu Thr
        35                  40                  45

Tyr Val Phe Arg Asp Val Val Val Phe Ala Leu Ala Ala Ala Ala
    50                  55                  60

Phe Tyr Phe Asn Ser Trp Leu Phe Trp Pro Leu Tyr Trp Phe Ala Gln
65                  70                  75                  80

Gly Thr Met Phe Trp Ala Ile Phe Val Leu Gly His Asp Cys Gly His
            85                  90                  95

Gly Ser Phe Ser Asn Asn Ser Ser Leu Asn Asn Val Val Gly His Leu
        100                 105                 110

Leu His Ser Ser Ile Leu Val Pro Tyr His Gly Trp Arg Ile Ser His
    115                 120                 125

Arg Thr His His Gln Asn His Gly Asn Val Glu Lys Asp Glu Ser Trp
130                 135                 140

Val Pro Leu Pro Glu Lys Ile Tyr Lys Glu Met Asp Leu Ser Thr Arg
145                 150                 155                 160
```

-continued

```
Ile Leu Arg Tyr Ser Val Pro Leu Pro Met Phe Ala Leu Pro Phe Tyr
            165                 170                 175

Leu Trp Trp Arg Ser Pro Gly Lys Glu Gly Ser His Phe Asn Pro Asn
        180                 185                 190

Ser Asp Phe Phe Ala Pro His Glu Arg Lys Ala Val Leu Thr Ser Asn
        195                 200                 205

Phe Cys Phe Ser Ile Met Ala Leu Leu Leu Tyr Ser Cys Phe Val
210                 215                 220

Phe Gly Pro Val Gln Val Leu Lys Phe Tyr Gly Ile Pro Tyr Leu Val
225                 230                 235                 240

Phe Val Met Trp Leu Asp Phe Val Thr Tyr Met His His Gly His
                245                 250                 255

Glu Glu Lys Leu Pro Trp Tyr Arg Gly Lys Glu Trp Ser Tyr Leu Arg
            260                 265                 270

Gly Gly Leu Gln Thr Val Asp Arg Asp Tyr Gly Trp Ile Asn Asn Ile
        275                 280                 285

His His Asp Ile Gly Thr His Val Ile His His Leu Phe Pro Gln Ile
290                 295                 300

Pro His Tyr His Leu Ile Glu Ala Thr Lys Ala Ala Lys Pro Val Leu
305                 310                 315                 320

Gly Lys Tyr Tyr Arg Glu Pro Lys Lys Ser Gly Pro Phe Pro Phe His
            325                 330                 335

Leu Phe Ser Asn Leu Val Arg Ser Met Ser Glu Asp His Tyr Val Ser
            340                 345                 350

Asp Ile Gly Asp Ile Val Phe Tyr Gln Thr Asp Pro Asp Ile Tyr Lys
            355                 360                 365

Val Asp Lys Ser Lys Leu Asn
            370                 375
```

<210> SEQ ID NO 15
<211> LENGTH: 351
<212> TYPE: PRT
<213> ORGANISM: Arabidopsis thaliana
<300> PUBLICATION INFORMATION:
<308> DATABASE ACCESSION NUMBER: GenBank/P48622
<309> DATABASE ENTRY DATE: 1996-02-01
<313> RELEVANT RESIDUES: (80)..(429)

<400> SEQUENCE: 15

```
Arg Phe Asp Pro Gly Ala Pro Pro Phe Asn Leu Ala Asp Ile Arg
1               5                   10                  15

Ala Ala Ile Pro Lys His Cys Trp Val Lys Asn Pro Trp Met Ser Met
            20                  25                  30

Ser Tyr Val Val Arg Asp Val Ala Ile Val Phe Gly Leu Ala Ala Val
        35                  40                  45

Ala Ala Tyr Phe Asn Asn Trp Leu Leu Trp Pro Leu Tyr Trp Phe Ala
    50                  55                  60

Gln Gly Thr Met Phe Trp Ala Leu Phe Val Leu Gly His Asp Cys Gly
65              70                  75                  80

His Gly Ser Phe Ser Asn Asp Pro Arg Leu Asn Ser Val Ala Gly His
            85                  90                  95

Leu Leu His Ser Ser Ile Leu Val Pro Tyr His Gly Trp Arg Ile Ser
        100                 105                 110

His Arg Thr His His Gln Asn His Gly His Val Glu Asn Asp Glu Ser
    115                 120                 125
```

```
Trp His Pro Leu Pro Glu Ser Ile Tyr Lys Asn Leu Glu Lys Thr Thr
        130                 135                 140

Gln Met Phe Arg Phe Thr Leu Pro Phe Pro Met Leu Ala Tyr Pro Phe
145                 150                 155                 160

Tyr Leu Trp Asn Arg Ser Pro Gly Lys Gln Gly Ser His Tyr His Pro
                165                 170                 175

Asp Ser Asp Leu Phe Leu Pro Lys Glu Lys Asp Val Leu Thr Ser
            180                 185                 190

Thr Ala Cys Trp Thr Ala Met Ala Ala Leu Leu Val Cys Leu Asn Phe
            195                 200                 205

Val Met Gly Pro Ile Gln Met Leu Lys Leu Tyr Gly Ile Pro Tyr Trp
210                 215                 220

Ile Phe Val Met Trp Leu Asp Phe Val Thr Tyr Leu His His Gly
225                 230                 235                 240

His Glu Asp Lys Leu Pro Trp Tyr Arg Gly Lys Glu Trp Ser Tyr Leu
                245                 250                 255

Arg Gly Gly Leu Thr Thr Leu Asp Arg Asp Tyr Gly Trp Ile Asn Asn
            260                 265                 270

Ile His His Asp Ile Gly Thr His Val Ile His Leu Phe Pro Gln
275                 280                 285

Ile Pro His Tyr His Leu Val Glu Ala Thr Glu Ala Lys Pro Val
290                 295                 300

Leu Gly Lys Tyr Tyr Arg Glu Pro Lys Asn Ser Gly Pro Leu Pro Leu
305                 310                 315                 320

His Leu Leu Gly Ser Leu Ile Lys Ser Met Lys Gln Asp His Phe Val
                325                 330                 335

Ser Asp Thr Gly Asp Val Val Tyr Glu Ala Asp Pro Lys Leu
            340                 345                 350

<210> SEQ ID NO 16
<211> LENGTH: 358
<212> TYPE: PRT
<213> ORGANISM: Perilla frutescens
<300> PUBLICATION INFORMATION:
<308> DATABASE ACCESSION NUMBER: GenBank/AAD15744
<309> DATABASE ENTRY DATE: 1999-03-03
<313> RELEVANT RESIDUES: (29)..(386)

<400> SEQUENCE: 16

Gly Lys Arg Ala Ala Asp Lys Phe Asp Pro Ala Ala Pro Pro Pro Phe
1               5                   10                  15

Lys Ile Ala Asp Ile Arg Ala Ala Ile Pro Ala His Cys Trp Val Lys
            20                  25                  30

Asn Pro Trp Arg Ser Leu Ser Tyr Val Val Trp Asp Val Ala Ala Val
            35                  40                  45

Phe Ala Leu Leu Ala Ala Val Tyr Ile Asn Ser Trp Ala Phe Trp
    50                  55                  60

Pro Val Tyr Trp Ile Ala Gln Gly Thr Met Phe Trp Ala Leu Phe Val
65                  70                  75                  80

Leu Gly His Asp Cys Gly His Gly Ser Phe Ser Asp Asn Thr Leu
                85                  90                  95

Asn Asn Val Val Gly His Val Leu His Ser Ser Ile Leu Val Pro Tyr
            100                 105                 110

His Gly Trp Arg Ile Ser His Arg Thr His Gln Asn His Gly His
            115                 120                 125
```

```
Val Glu Lys Asp Glu Ser Trp Val Pro Leu Pro Glu Asn Leu Tyr Lys
    130                 135                 140

Lys Leu Asp Phe Ser Thr Lys Phe Leu Arg Tyr Lys Ile Pro Phe Pro
145                 150                 155                 160

Met Phe Ala Tyr Pro Leu Tyr Leu Trp Tyr Arg Ser Pro Gly Lys Thr
                165                 170                 175

Gly Ser His Phe Asn Pro Tyr Ser Asp Leu Phe Lys Pro Asn Glu Arg
            180                 185                 190

Gly Leu Ile Val Thr Ser Thr Met Cys Trp Ala Ala Met Gly Val Phe
        195                 200                 205

Leu Leu Tyr Ala Ser Thr Ile Val Gly Pro Asn Met Met Phe Lys Leu
    210                 215                 220

Tyr Gly Val Pro Tyr Leu Ile Phe Val Met Trp Leu Asp Thr Val Thr
225                 230                 235                 240

Tyr Leu His His Gly Tyr Asp Lys Lys Leu Pro Trp Tyr Arg Ser
                245                 250                 255

Lys Glu Trp Ser Tyr Leu Arg Gly Gly Leu Thr Thr Val Asp Gln Asp
                260                 265                 270

Tyr Gly Phe Phe Asn Lys Ile His His Asp Ile Gly Thr His Val Ile
            275                 280                 285

His His Leu Phe Pro Gln Ile Pro His Tyr His Leu Val Glu Ala Thr
    290                 295                 300

Arg Glu Ala Lys Arg Val Leu Gly Asn Tyr Tyr Arg Glu Pro Arg Lys
305                 310                 315                 320

Ser Gly Pro Val Pro Leu His Leu Ile Pro Ala Leu Leu Lys Ser Leu
                325                 330                 335

Gly Arg Asp His Tyr Val Ser Asp Asn Gly Asp Ile Val Tyr Tyr Gln
            340                 345                 350

Thr Asp Asp Glu Leu Phe
        355

<210> SEQ ID NO 17
<211> LENGTH: 377
<212> TYPE: PRT
<213> ORGANISM: Ricinus communis
<300> PUBLICATION INFORMATION:
<308> DATABASE ACCESSION NUMBER: GenBank/P48619
<309> DATABASE ENTRY DATE: 1998-12-15
<313> RELEVANT RESIDUES: (84)..(460)

<400> SEQUENCE: 17

Glu Arg Glu Glu Phe Asn Gly Ile Val Asn Val Asp Glu Gly Lys Gly
1               5                   10                  15

Glu Phe Phe Asp Ala Gly Ala Pro Pro Phe Thr Leu Ala Asp Ile
            20                  25                  30

Arg Ala Ala Ile Pro Lys His Cys Trp Val Lys Asn Pro Trp Arg Ser
        35                  40                  45

Met Ser Tyr Val Leu Arg Asp Val Val Val Phe Gly Leu Ala Ala
    50                  55                  60

Val Ala Ala Tyr Phe Asn Asn Trp Val Ala Trp Pro Leu Tyr Trp Phe
65                  70                  75                  80

Cys Gln Gly Thr Met Phe Trp Ala Leu Phe Val Leu Gly His Asp Cys
                85                  90                  95

Gly His Gly Ser Phe Ser Asn Asn Pro Lys Leu Asn Ser Val Val Gly
            100                 105                 110
```

-continued

```
His Leu Leu His Ser Ser Ile Leu Val Pro Tyr His Gly Trp Arg Ile
            115                 120                 125

Ser His Arg Thr His His Gln Asn His Gly His Val Glu Asn Asp Glu
        130                 135                 140

Ser Trp His Pro Leu Ser Glu Lys Ile Phe Lys Ser Leu Asp Asn Val
145                 150                 155                 160

Thr Lys Thr Leu Arg Phe Ser Leu Pro Phe Pro Met Leu Ala Tyr Pro
                165                 170                 175

Phe Tyr Leu Trp Ser Arg Ser Pro Gly Lys Lys Gly Ser His Phe His
            180                 185                 190

Pro Asp Ser Gly Leu Phe Val Pro Lys Glu Arg Lys Asp Ile Ile Thr
        195                 200                 205

Ser Thr Ala Cys Trp Thr Ala Met Ala Ala Leu Leu Val Tyr Leu Asn
210                 215                 220

Phe Ser Met Gly Pro Val Gln Met Leu Lys Leu Tyr Gly Ile Pro Tyr
225                 230                 235                 240

Trp Ile Phe Val Met Trp Leu Asp Phe Val Thr Tyr Leu His His His
                245                 250                 255

Gly His Glu Asp Lys Leu Pro Trp Tyr Arg Gly Lys Ala Trp Ser Tyr
            260                 265                 270

Leu Arg Gly Gly Leu Thr Thr Leu Asp Arg Asp Tyr Gly Trp Ile Asn
        275                 280                 285

Asn Ile His His Asp Ile Gly Thr His Val Ile His His Leu Phe Pro
290                 295                 300

Gln Ile Pro His Tyr His Leu Val Glu Ala Thr Glu Ala Ala Lys Pro
305                 310                 315                 320

Val Met Gly Lys Tyr Tyr Arg Glu Pro Lys Lys Ser Gly Pro Leu Pro
                325                 330                 335

Leu His Leu Leu Gly Ser Leu Val Arg Ser Met Lys Glu Asp His Tyr
            340                 345                 350

Val Ser Asp Thr Gly Asp Val Val Tyr Tyr Gln Lys Asp Pro Lys Leu
        355                 360                 365

Ser Gly Ile Gly Gly Glu Lys Thr Glu
    370                 375

<210> SEQ ID NO 18
<211> LENGTH: 362
<212> TYPE: PRT
<213> ORGANISM: Perilla frutescens
<300> PUBLICATION INFORMATION:
<308> DATABASE ACCESSION NUMBER: GenBank/AAB39387
<309> DATABASE ENTRY DATE: 1996-12-28
<313> RELEVANT RESIDUES: (75)..(436)

<400> SEQUENCE: 18

Glu Glu Arg Gly Ser Val Ile Val Asn Gly Val Asp Glu Phe Asp Pro
1               5                   10                  15

Gly Ala Pro Pro Pro Phe Lys Leu Ser Asp Ile Arg Ala Ala Ile Pro
            20                  25                  30

Lys His Cys Trp Val Lys Asp Pro Trp Arg Ser Met Ser Tyr Val Val
        35                  40                  45

Arg Asp Val Val Val Phe Gly Leu Ala Ala Ala Ala Tyr Phe
    50                  55                  60

Asn Asn Trp Ala Val Trp Pro Ile Tyr Trp Phe Ala Gln Ser Thr Met
65                  70                  75                  80
```

```
Phe Trp Ala Leu Phe Val Leu Gly His Asp Cys Gly His Gly Ser Phe
            85                  90                  95

Ser Asn Asp Pro Lys Leu Asn Ser Val Ala Gly His Leu Leu His Ser
           100                 105                 110

Ser Ile Leu Val Pro Tyr His Gly Trp Arg Ile Ser His Arg Thr His
           115                 120                 125

His Gln Asn His Gly His Val Glu Asn Asp Glu Ser Trp His Pro Ile
       130                 135                 140

Pro Glu Lys Ile Tyr Arg Thr Leu Asp Phe Ala Thr Lys Lys Leu Arg
145                 150                 155                 160

Phe Thr Leu Pro Phe Pro Met Leu Ala Tyr Pro Phe Tyr Leu Trp Gly
               165                 170                 175

Arg Ser Pro Gly Lys Lys Gly Ser His Phe His Pro Asp Ser Asp Leu
           180                 185                 190

Phe Val Pro Asn Glu Arg Lys Asp Val Ile Thr Ser Thr Val Cys Trp
       195                 200                 205

Thr Ala Met Val Ala Ile Leu Ala Gly Leu Ser Phe Val Met Gly Pro
210                 215                 220

Val Gln Leu Leu Lys Leu Tyr Gly Ile Pro Tyr Ile Gly Phe Val Ala
225                 230                 235                 240

Trp Leu Asp Leu Val Thr Tyr Leu His His Gly His Asp Glu Lys
               245                 250                 255

Leu Pro Trp Tyr Arg Gly Lys Glu Trp Ser Tyr Leu Arg Gly Gly Leu
               260                 265                 270

Thr Thr Leu Asp Arg Asp Tyr Gly Trp Ile Asn Asn Ile His His Asp
       275                 280                 285

Ile Gly Thr His Val Ile His His Leu Phe Pro Gln Ile Pro His Tyr
       290                 295                 300

His Leu Ile Glu Ala Thr Ala Ala Ala Lys Pro Val Leu Gly Lys Tyr
305                 310                 315                 320

Tyr Lys Glu Pro Lys Lys Ser Gly Pro Phe Pro Phe Tyr Leu Leu Gly
               325                 330                 335

Val Leu Gln Lys Ser Met Lys Lys Asp His Tyr Val Ser Asp Thr Gly
           340                 345                 350

Asp Ile Val Tyr Tyr Gln Thr Asp Pro Glu
       355                 360

<210> SEQ ID NO 19
<211> LENGTH: 352
<212> TYPE: PRT
<213> ORGANISM: Sesamum indicum
<300> PUBLICATION INFORMATION:
<308> DATABASE ACCESSION NUMBER: GenBank/P48620
<309> DATABASE ENTRY DATE: 1998-12-15
<313> RELEVANT RESIDUES: (90)..(441)

<400> SEQUENCE: 19

Glu Glu Phe Asp Pro Gly Ala Pro Pro Phe Lys Leu Ser Asp Ile
1               5                  10                  15

Arg Glu Ala Ile Pro Lys His Cys Trp Val Lys Asp Pro Trp Arg Ser
               20                  25                  30

Met Gly Tyr Val Val Arg Asp Val Ala Val Phe Gly Leu Ala Ala
           35                  40                  45

Val Ala Ala Tyr Phe Asn Asn Trp Val Val Trp Pro Leu Tyr Trp Phe
       50                  55                  60
```

Ala Gln Ser Thr Met Phe Trp Ala Leu Phe Val Leu Gly His Asp Cys
 65                  70                  75                  80

Gly His Gly Ser Phe Ser Asn Asp Pro Lys Leu Asn Ser Val Val Gly
             85                  90                  95

His Ile Leu His Ser Ser Ile Leu Val Pro Tyr His Gly Trp Arg Ile
        100                 105                 110

Ser His Arg Thr His His Gln Asn His Gly His Val Glu Asn Asp Glu
    115                 120                 125

Ser Trp His Pro Leu Ser Glu Lys Ile Tyr Lys Asn Leu Asp Thr Ala
130                 135                 140

Thr Lys Lys Leu Arg Phe Thr Leu Pro Phe Pro Leu Leu Ala Tyr Pro
145                 150                 155                 160

Ile Tyr Leu Trp Ser Arg Ser Pro Gly Lys Gln Gly Ser His Phe His
                165                 170                 175

Pro Asp Ser Asp Leu Phe Val Pro Asn Glu Lys Lys Asp Val Ile Thr
            180                 185                 190

Ser Thr Val Cys Trp Thr Ala Met Leu Ala Leu Leu Val Gly Leu Ser
        195                 200                 205

Phe Val Ile Gly Pro Val Gln Leu Leu Lys Leu Tyr Gly Ile Pro Tyr
    210                 215                 220

Leu Gly Asn Val Met Trp Leu Asp Leu Val Thr Tyr Leu His His His
225                 230                 235                 240

Gly His Glu Asp Lys Leu Pro Trp Tyr Arg Gly Lys Glu Trp Ser Tyr
                245                 250                 255

Leu Arg Gly Gly Leu Thr Thr Leu Asp Arg Asp Tyr Gly Trp Ile Asn
            260                 265                 270

Asn Ile His His Asp Ile Gly Thr His Val Ile His His Leu Phe Pro
        275                 280                 285

Gln Ile Pro His Tyr His Leu Ile Glu Ala Thr Glu Ala Ala Lys Pro
    290                 295                 300

Val Leu Gly Lys Tyr Tyr Arg Glu Pro Lys Lys Ser Ala Pro Leu Pro
305                 310                 315                 320

Phe His Leu Leu Gly Asp Leu Thr Arg Ser Leu Lys Arg Asp His Tyr
                325                 330                 335

Val Ser Asp Val Gly Asp Val Val Tyr Tyr Gln Thr Asp Pro Gln Leu
            340                 345                 350

<210> SEQ ID NO 20
<211> LENGTH: 363
<212> TYPE: PRT
<213> ORGANISM: Arabidopsis thaliana
<300> PUBLICATION INFORMATION:
<308> DATABASE ACCESSION NUMBER: GenBank/P46310
<309> DATABASE ENTRY DATE: 1996-02-01
<313> RELEVANT RESIDUES: (76)..(438)

<400> SEQUENCE: 20

Glu Glu Ser Pro Leu Glu Glu Asp Asn Lys Gln Arg Phe Asp Pro Gly
1               5                   10                  15

Ala Pro Pro Pro Phe Asn Leu Ala Asp Ile Arg Ala Ala Ile Pro Lys
            20                  25                  30

His Cys Trp Val Lys Asn Pro Trp Lys Ser Leu Ser Tyr Val Val Arg
        35                  40                  45

Asp Val Ala Ile Val Phe Ala Leu Ala Ala Gly Ala Ala Tyr Leu Asn
    50                  55                  60

-continued

```
Asn Trp Ile Val Trp Pro Leu Tyr Trp Leu Ala Gln Gly Thr Met Phe
 65                  70                  75                  80

Trp Ala Leu Phe Val Leu Gly His Asp Cys Gly His Gly Ser Phe Ser
                 85                  90                  95

Asn Asp Pro Lys Leu Asn Ser Val Val Gly His Leu Leu His Ser Ser
            100                 105                 110

Ile Leu Val Pro Tyr His Gly Trp Arg Ile Ser His Arg Thr His His
        115                 120                 125

Gln Asn His Gly His Val Glu Asn Asp Glu Ser Trp His Pro Met Ser
130                 135                 140

Glu Lys Ile Tyr Asn Thr Leu Asp Lys Pro Thr Arg Phe Phe Arg Phe
145                 150                 155                 160

Thr Leu Pro Leu Val Met Leu Ala Tyr Pro Phe Tyr Leu Trp Ala Arg
                165                 170                 175

Ser Pro Gly Lys Lys Gly Ser His Tyr His Pro Asp Ser Asp Leu Phe
            180                 185                 190

Leu Pro Lys Glu Arg Lys Asp Val Leu Thr Ser Thr Ala Cys Trp Thr
        195                 200                 205

Ala Met Ala Ala Leu Leu Val Cys Leu Asn Phe Thr Ile Gly Pro Ile
210                 215                 220

Gln Met Leu Lys Leu Tyr Gly Ile Pro Tyr Trp Ile Asn Val Met Trp
225                 230                 235                 240

Leu Asp Phe Val Thr Tyr Leu His His Gly His Glu Asp Lys Leu
                245                 250                 255

Pro Trp Tyr Arg Gly Lys Glu Trp Ser Tyr Leu Arg Gly Gly Leu Thr
            260                 265                 270

Thr Leu Asp Arg Asp Tyr Gly Leu Ile Asn Asn Ile His His Asp Ile
        275                 280                 285

Gly Thr His Val Ile His His Leu Phe Pro Gln Ile Pro His Tyr His
290                 295                 300

Leu Val Glu Ala Thr Glu Ala Ala Lys Pro Val Leu Gly Lys Tyr Tyr
305                 310                 315                 320

Arg Glu Pro Asp Lys Ser Gly Pro Leu Pro Leu His Leu Leu Glu Ile
                325                 330                 335

Leu Ala Lys Ser Ile Lys Glu Asp His Tyr Val Ser Asp Glu Gly Glu
            340                 345                 350

Val Val Tyr Tyr Lys Ala Asp Pro Asn Leu Tyr
        355                 360
```

<210> SEQ ID NO 21
<211> LENGTH: 369
<212> TYPE: PRT
<213> ORGANISM: Nicotiana tabacum
<300> PUBLICATION INFORMATION:
<308> DATABASE ACCESSION NUMBER: GenBank/BAA11475
<309> DATABASE ENTRY DATE: 1999-02-05
<313> RELEVANT RESIDUES: (73)..(441)

<400> SEQUENCE: 21

```
Glu Glu Glu Ser Glu Arg Thr Asn Asn Ser Gly Gly Glu Phe Phe Asp
  1               5                  10                  15

Pro Gly Ala Pro Pro Pro Phe Lys Leu Ser Asp Ile Lys Ala Ala Ile
                 20                  25                  30

Pro Lys His Cys Trp Val Lys Asn Pro Trp Lys Ser Met Ser Tyr Val
             35                  40                  45
```

```
Val Arg Asp Val Ala Ile Val Phe Gly Leu Ala Ala Ala Ala Tyr
 50                  55                  60

Phe Asn Asn Trp Val Val Trp Pro Leu Tyr Trp Phe Ala Gln Ser Thr
 65                  70                  75                  80

Met Phe Trp Ala Leu Phe Val Leu Gly His Asp Cys Gly His Gly Ser
                 85                  90                  95

Phe Ser Asn Asn His Lys Leu Asn Ser Val Val Gly His Ile Leu His
                100                 105                 110

Ser Ser Ile Leu Val Pro Tyr His Gly Trp Arg Ile Ser His Arg Thr
            115                 120                 125

His His Gln Asn His Gly His Val Glu Asn Asp Glu Ser Trp His Pro
130                 135                 140

Ile Pro Glu Lys Ile Tyr Asn Ser Leu Asp Leu Ala Thr Lys Lys Leu
145                 150                 155                 160

Arg Phe Thr Leu Pro Phe Pro Leu Leu Ala Tyr Pro Phe Tyr Leu Trp
                165                 170                 175

Ser Arg Ser Pro Gly Lys Lys Gly Ser His Phe Asp Pro Asn Ser Asp
            180                 185                 190

Leu Phe Val Pro Ser Glu Lys Lys Asp Val Met Thr Ser Thr Leu Cys
            195                 200                 205

Trp Thr Ala Met Ala Ala Leu Leu Val Gly Leu Ser Phe Val Met Gly
210                 215                 220

Pro Phe Gln Val Leu Lys Leu Tyr Gly Ile Pro Tyr Trp Gly Phe Val
225                 230                 235                 240

Met Trp Leu Asp Leu Val Thr Tyr Leu His His Gly His Asp Asp
                245                 250                 255

Lys Leu Pro Trp Tyr Arg Gly Glu Glu Trp Ser Tyr Leu Arg Gly Gly
            260                 265                 270

Leu Thr Thr Leu Asp Arg Asp Tyr Gly Trp Ile Asn Asn Ile His His
            275                 280                 285

Asp Ile Gly Thr His Val Ile His His Leu Phe Pro Gln Ile Pro His
290                 295                 300

Tyr His Leu Val Glu Ala Thr Glu Ala Ala Lys Pro Val Leu Gly Lys
305                 310                 315                 320

Tyr Tyr Lys Glu Pro Lys Lys Ser Gly Pro Leu Pro Phe Tyr Leu Leu
                325                 330                 335

Gly Val Leu Ile Lys Ser Met Lys Gln Asp His Tyr Val Ser Asp Thr
            340                 345                 350

Gly Asp Ile Val Tyr Tyr Arg Thr Asp Pro Gln Leu Ser Gly Phe Gln
            355                 360                 365

Lys

<210> SEQ ID NO 22
<211> LENGTH: 351
<212> TYPE: PRT
<213> ORGANISM: Nicotiana tabacum
<300> PUBLICATION INFORMATION:
<308> DATABASE ACCESSION NUMBER: GenBank/P48626
<309> DATABASE ENTRY DATE: 1996-10-01
<313> RELEVANT RESIDUES: (22)..(372)

<400> SEQUENCE: 22

Phe Asp Pro Ser Ala Pro Pro Phe Arg Leu Ala Glu Ile Arg Asn
 1               5                  10                  15

Val Ile Pro Lys His Cys Trp Val Lys Asp Pro Leu Arg Ser Leu Ser
                20                  25                  30
```

```
Tyr Val Val Arg Asp Val Ile Phe Val Ala Thr Leu Ile Gly Ile Ala
            35                  40                  45

Ile His Leu Asp Ser Trp Leu Phe Tyr Pro Leu Tyr Trp Ala Ile Gln
     50                  55                  60

Gly Thr Met Phe Trp Ala Ile Phe Val Leu Gly His Asp Cys Gly His
 65                  70                  75                  80

Gly Ser Phe Ser Asp Ser Gln Leu Leu Asn Asn Val Val Gly His Ile
                 85                  90                  95

Leu His Ser Ala Ile Leu Val Pro Tyr His Gly Trp Arg Ile Ser His
                100                 105                 110

Lys Thr His His Gln Asn His Gly Asn Val Glu Thr Asp Glu Ser Trp
            115                 120                 125

Val Pro Met Pro Glu Lys Leu Tyr Asn Lys Val Gly Tyr Ser Thr Lys
130                 135                 140

Phe Leu Arg Tyr Lys Ile Pro Phe Pro Leu Leu Ala Tyr Pro Met Tyr
145                 150                 155                 160

Leu Met Lys Arg Ser Pro Gly Lys Ser Gly Ser His Phe Asn Pro Tyr
                165                 170                 175

Ser Asp Leu Phe Gln Pro His Glu Arg Lys Tyr Val Val Thr Ser Thr
                180                 185                 190

Leu Cys Trp Thr Val Met Ala Ala Leu Leu Leu Tyr Leu Cys Thr Ala
            195                 200                 205

Phe Gly Ser Leu Gln Met Phe Lys Ile Tyr Gly Ala Pro Tyr Leu Ile
        210                 215                 220

Phe Val Met Trp Leu Asp Phe Val Thr Tyr Leu His His Gly Tyr
225                 230                 235                 240

Glu Lys Lys Leu Pro Trp Tyr Arg Gly Lys Glu Trp Ser Tyr Leu Arg
                245                 250                 255

Gly Gly Leu Thr Thr Val Asp Arg Asp Tyr Gly Leu Phe Asn Asn Ile
                260                 265                 270

His His Asp Ile Gly Thr His Val Ile His His Leu Phe Pro Gln Ile
            275                 280                 285

Pro His Tyr His Leu Arg Glu Ala Thr Lys Ala Ala Lys Pro Val Leu
        290                 295                 300

Gly Lys Tyr Tyr Arg Glu Pro Lys Lys Ser Gly Pro Ile Pro Phe His
305                 310                 315                 320

Leu Val Lys Asp Leu Thr Arg Ser Met Lys Gln Asp His Tyr Val Ser
                325                 330                 335

Asp Ser Gly Glu Ile Val Phe Tyr Gln Thr Asp Pro His Ile Phe
                340                 345                 350

<210> SEQ ID NO 23
<211> LENGTH: 368
<212> TYPE: PRT
<213> ORGANISM: Vernicia fordii
<300> PUBLICATION INFORMATION:
<308> DATABASE ACCESSION NUMBER: GenBank/AAD13527
<309> DATABASE ENTRY DATE: 1999-02-08
<313> RELEVANT RESIDUES: (64)..(431)

<400> SEQUENCE: 23

Glu Arg Glu Glu Gly Ile Asn Gly Val Ile Gly Ile Glu Gly Glu Glu
1               5                   10                  15

Thr Glu Phe Asp Pro Gly Ala Pro Pro Pro Phe Lys Leu Ser Asp Ile
            20                  25                  30
```

-continued

```
Arg Glu Ala Ile Pro Lys His Cys Trp Val Lys Asp Pro Trp Arg Ser
         35                  40                  45

Met Ser Tyr Val Val Arg Asp Val Ala Val Phe Gly Leu Ala Ala
 50                  55                  60

Ala Ala Ala Tyr Leu Asn Asn Trp Ile Val Trp Pro Leu Tyr Trp Ala
 65                  70                  75                  80

Ala Gln Gly Thr Met Phe Trp Ala Leu Phe Val Leu Gly His Asp Cys
                 85                  90                  95

Gly His Gly Ser Phe Ser His Asn Pro Lys Leu Asn Ser Val Val Gly
            100                 105                 110

His Leu Leu His Ser Ser Ile Leu Val Pro Tyr His Gly Trp Arg Ile
            115                 120                 125

Ser His Arg Thr His His Gln Asn His Gly His Val Glu Asn Asp Glu
130                 135                 140

Ser Trp Gln Pro Leu Ser Glu Lys Ile Phe Arg Ser Leu Asp Tyr Met
145                 150                 155                 160

Thr Arg Thr Leu Arg Phe Thr Val Pro Ser Pro Met Leu Ala Tyr Pro
                165                 170                 175

Phe Tyr Leu Trp Asn Arg Ser Pro Gly Lys Thr Gly Ser His Phe His
                180                 185                 190

Pro Asp Ser Asp Leu Phe Gly Pro Asn Glu Arg Lys Asp Val Ile Thr
            195                 200                 205

Ser Thr Val Cys Trp Thr Ala Met Ala Ala Leu Leu Val Gly Leu Ser
210                 215                 220

Leu Val Met Gly Pro Ile Gln Leu Leu Lys Leu Tyr Gly Met Pro Tyr
225                 230                 235                 240

Trp Ile Phe Val Met Trp Leu Asp Phe Val Thr Tyr Leu His His His
                245                 250                 255

Gly His Glu Glu Lys Leu Pro Trp Tyr Arg Gly Asn Glu Trp Ser Tyr
            260                 265                 270

Leu Arg Gly Gly Leu Thr Thr Leu Gly Arg Asp Tyr Gly Trp Ile Asn
            275                 280                 285

Asn Ile His His Asp Ile Gly Thr His Val Ile His His Phe Phe Pro
290                 295                 300

Gln Ile Pro His Tyr His Leu Ile Asp Ala Thr Glu Ala Ser Lys Pro
305                 310                 315                 320

Val Leu Gly Lys Tyr Tyr Arg Glu Pro Asp Lys Ser Gly Pro Leu Ser
                325                 330                 335

Phe His Leu Ile Gly Tyr Leu Ile Arg Ser Leu Lys Lys Asp His Tyr
                340                 345                 350

Val Ser Asp Thr Gly Asp Val Val Tyr Tyr Gln Thr Asp Pro Gln Leu
            355                 360                 365
```

<210> SEQ ID NO 24
<211> LENGTH: 353
<212> TYPE: PRT
<213> ORGANISM: Petroselinum crispum
<300> PUBLICATION INFORMATION:
<308> DATABASE ACCESSION NUMBER: GenBank/AAB72241
<309> DATABASE ENTRY DATE: 1997-10-08
<313> RELEVANT RESIDUES: (80)..(432)

<400> SEQUENCE: 24

```
Glu Glu Asn Glu Phe Asp Pro Gly Ala Ala Pro Pro Phe Lys Leu Ser
1               5                   10                  15
Asp Val Arg Ala Ala Ile Pro Lys His Cys Trp Val Lys Asp Pro Val
            20                  25                  30
Arg Ser Met Ser Tyr Val Leu Arg Asp Val Leu Ile Val Phe Gly Leu
        35                  40                  45
Ala Val Ala Ala Ser Phe Val Asn Asn Trp Ala Val Trp Pro Leu Tyr
    50                  55                  60
Trp Ile Ala Gln Gly Thr Met Phe Trp Ala Leu Phe Val Leu Gly His
65                  70                  75                  80
Asp Cys Gly His Gly Ser Phe Ser Asn Asp Ala Lys Leu Asn Ser Val
                85                  90                  95
Val Gly His Ile Leu His Ser Ser Ile Leu Val Pro Tyr His Gly Trp
            100                 105                 110
Arg Ile Ser His Arg Thr His His Gln Asn His Gly His Val Glu Asn
        115                 120                 125
Asp Glu Ser Trp His Pro Leu Ser Glu Lys Leu Phe Asn Ser Leu Asp
    130                 135                 140
Asp Leu Thr Arg Lys Phe Arg Phe Thr Leu Pro Phe Pro Met Leu Ala
145                 150                 155                 160
Tyr Pro Phe Tyr Leu Trp Gly Arg Ser Pro Gly Lys Lys Gly Ser His
                165                 170                 175
Tyr Asp Pro Ser Ser Asp Leu Phe Val Pro Asn Glu Arg Lys Asp Val
            180                 185                 190
Ile Thr Ser Thr Val Cys Trp Thr Ala Met Ala Ala Leu Leu Val Gly
        195                 200                 205
Leu Asn Phe Val Met Gly Pro Val Lys Met Leu Met Leu Tyr Gly Ile
    210                 215                 220
Pro Tyr Trp Ile Phe Val Met Trp Leu Asp Phe Val Thr Tyr Leu His
225                 230                 235                 240
His His Gly His Asp Asp Lys Leu Pro Trp Tyr Arg Gly Lys Glu Trp
                245                 250                 255
Ser Tyr Leu Arg Gly Gly Leu Thr Thr Leu Asp Arg Asp Tyr Gly Trp
            260                 265                 270
Ile Asn Asn Ile His His Asp Ile Gly Thr His Val His His Leu
        275                 280                 285
Phe Pro Gln Ile Pro His Tyr His Leu Ile Glu Ala Thr Glu Ala Ala
    290                 295                 300
Lys Pro Val Phe Gly Lys Tyr Arg Glu Pro Lys Lys Ser Gly Pro
305                 310                 315                 320
Val Pro Phe His Leu Leu Ala Thr Leu Trp Lys Ser Phe Lys Lys Asp
                325                 330                 335
His Phe Val Ser Asp Thr Gly Asp Val Val Tyr Tyr Gln Ala His Pro
            340                 345                 350
Glu
```

<210> SEQ ID NO 25
<211> LENGTH: 356
<212> TYPE: PRT
<213> ORGANISM: Glycine max
<300> PUBLICATION INFORMATION:
<308> DATABASE ACCESSION NUMBER: GenBank/P48625
<309> DATABASE ENTRY DATE: 1996-10-01
<313> RELEVANT RESIDUES: (25)..(380)

<400> SEQUENCE: 25

```
Phe Asp Pro Ser Ala Pro Pro Phe Lys Ile Ala Glu Ile Arg Ala
1               5                   10                  15
Ser Ile Pro Lys His Cys Trp Val Lys Asn Pro Trp Arg Ser Leu Ser
            20                  25                  30
Tyr Val Leu Arg Asp Val Leu Val Ile Ala Leu Val Ala Ala Ala
        35                  40                  45
Ile His Phe Asp Asn Trp Leu Leu Trp Leu Ile Tyr Cys Pro Ile Gln
    50                  55                  60
Gly Thr Met Phe Trp Ala Leu Phe Val Leu Gly His Asp Cys Gly His
65                  70                  75                  80
Gly Ser Phe Ser Asp Ser Pro Leu Leu Asn Ser Leu Val Gly His Ile
                85                  90                  95
Leu His Ser Ser Ile Leu Val Pro Tyr His Gly Trp Arg Ile Ser His
            100                 105                 110
Arg Thr His His Gln Asn His Gly His Ile Glu Lys Asp Glu Ser Trp
            115                 120                 125
Val Pro Leu Thr Glu Lys Ile Tyr Lys Asn Leu Asp Ser Met Thr Arg
130                 135                 140
Leu Ile Arg Phe Thr Val Pro Phe Pro Leu Phe Val Tyr Pro Ile Tyr
145                 150                 155                 160
Leu Phe Ser Arg Ser Pro Gly Lys Glu Gly Ser His Phe Asn Pro Tyr
                165                 170                 175
Ser Asn Leu Phe Pro Pro Ser Glu Arg Lys Gly Ile Ala Ile Ser Thr
            180                 185                 190
Leu Cys Trp Ala Thr Met Phe Ser Leu Leu Ile Tyr Leu Ser Phe Ile
            195                 200                 205
Thr Ser Pro Leu Leu Val Leu Lys Leu Tyr Gly Ile Pro Tyr Trp Ile
210                 215                 220
Phe Val Met Trp Leu Asp Phe Val Thr Tyr Leu His His Gly His
225                 230                 235                 240
His Gln Lys Leu Pro Trp Tyr Arg Gly Lys Glu Trp Ser Tyr Leu Arg
                245                 250                 255
Gly Gly Leu Thr Thr Val Asp Arg Asp Tyr Gly Trp Ile Tyr Asn Ile
            260                 265                 270
His His Asp Ile Gly Thr His Val Ile His His Leu Phe Pro Gln Ile
            275                 280                 285
Pro His Tyr His Leu Val Glu Ala Thr Gln Ala Ala Lys Pro Val Leu
290                 295                 300
Gly Asp Tyr Tyr Arg Glu Pro Glu Arg Ser Ala Pro Leu Pro Phe His
305                 310                 315                 320
Leu Ile Lys Tyr Leu Ile Gln Ser Met Arg Gln Asp His Phe Val Ser
                325                 330                 335
Asp Thr Gly Asp Val Val Tyr Tyr Gln Thr Asp Ser Leu Leu Leu His
            340                 345                 350
Ser Gln Arg Asp
        355
```

<210> SEQ ID NO 26
<211> LENGTH: 360
<212> TYPE: PRT
<213> ORGANISM: Brassica napus -continued <300> PUBLICATION INFORMATION:
<308> DATABASE ACCESSION NUMBER: GenBank/P48618
<309> DATABASE ENTRY DATE: 1996-02-01
<313> RELEVANT RESIDUES: (37)..(396)

<400> SEQUENCE: 26

```
Ile Glu Glu Pro Lys Thr Gln Arg Phe Asp Pro Gly Ala Pro Pro
1               5                   10                  15

Pro Phe Asn Leu Ala Asp Ile Arg Ala Ala Ile Pro Lys His Cys Trp
            20                  25                  30

Val Lys Asn Pro Trp Lys Ser Met Ser Tyr Val Val Arg Glu Leu Ala
            35                  40                  45

Ile Val Phe Ala Leu Ala Ala Gly Ala Ala Tyr Leu Asn Asn Trp Leu
    50                  55                  60

Val Trp Pro Leu Tyr Trp Ile Ala Gln Gly Thr Met Phe Trp Ala Leu
65                  70                  75                  80

Phe Val Leu Gly His Asp Cys Gly His Gly Ser Phe Ser Asn Asp Pro
                85                  90                  95

Arg Leu Asn Ser Val Val Gly His Leu Leu His Ser Ser Ile Leu Val
                100                 105                 110

Pro Tyr His Gly Trp Arg Ile Ser His Arg Thr His His Gln Asn His
            115                 120                 125

Gly His Val Glu Asn Asp Glu Ser Trp His Pro Met Ser Glu Lys Ile
    130                 135                 140

Tyr Lys Ser Leu Asp Lys Pro Thr Arg Phe Phe Arg Phe Thr Leu Pro
145                 150                 155                 160

Leu Val Met Leu Ala Tyr Pro Phe Tyr Leu Trp Ala Arg Ser Pro Gly
                165                 170                 175

Lys Lys Gly Ser His Tyr His Pro Asp Ser Asp Leu Phe Leu Pro Lys
            180                 185                 190

Glu Arg Asn Asp Val Leu Thr Ser Thr Ala Cys Trp Thr Ala Met Ala
    195                 200                 205

Val Leu Leu Val Cys Leu Asn Phe Val Met Gly Pro Met Gln Met Leu
210                 215                 220

Lys Leu Tyr Val Ile Pro Tyr Trp Ile Asn Val Met Trp Leu Asp Phe
225                 230                 235                 240

Val Thr Tyr Leu His His Gly His Glu Asp Lys Leu Pro Trp Tyr
                245                 250                 255

Arg Gly Lys Glu Trp Ser Tyr Leu Arg Gly Gly Leu Thr Thr Leu Asp
            260                 265                 270

Arg Asp Tyr Gly Leu Ile Asn Asn Ile His His Asp Ile Gly Thr His
    275                 280                 285

Val Ile His His Leu Phe Pro Gln Ile Pro His Tyr His Leu Val Glu
    290                 295                 300

Ala Thr Glu Ala Ala Lys Pro Val Leu Gly Lys Tyr Tyr Arg Glu Pro
305                 310                 315                 320

Asp Lys Ser Gly Pro Leu Pro Leu His Leu Leu Gly Ile Leu Ala Lys
                325                 330                 335

Ser Ile Lys Glu Asp His Phe Val Ser Asp Glu Gly Asp Val Val Tyr
                340                 345                 350

Tyr Glu Ala Asp Pro Asn Leu Tyr
            355                 360
```

```
<210> SEQ ID NO 27
<211> LENGTH: 373
<212> TYPE: PRT
<213> ORGANISM: Zea mays
<300> PUBLICATION INFORMATION:
<308> DATABASE ACCESSION NUMBER: GenBank/BAA22440
<309> DATABASE ENTRY DATE: 1998-03-04
<313> RELEVANT RESIDUES: (15)..(387)

<400> SEQUENCE: 27
```

Val Glu Glu Asp Lys Arg Ser Ser Pro Leu Gly Glu Gly Asp Glu His
1               5                   10                  15

Val Ala Ala Ser Gly Ala Ala Gly Gly Glu Phe Asp Pro Gly Ala Pro
            20                  25                  30

Pro Pro Phe Gly Leu Ala Glu Ile Arg Ala Ala Ile Pro Lys His Cys
            35                  40                  45

Trp Val Lys Asp Pro Trp Arg Ser Met Ala Tyr Val Leu Arg Asp Val
        50                  55                  60

Val Val Val Leu Gly Leu Ala Ala Ala Ala Arg Leu Asp Ser Trp
65                  70                  75                  80

Leu Val Trp Pro Leu Tyr Trp Ala Ala Gln Gly Thr Met Phe Trp Ala
                85                  90                  95

Leu Phe Val Leu Gly His Asp Cys Gly His Gly Ser Phe Ser Asn Asn
            100                 105                 110

Pro Lys Leu Asn Ser Val Val Gly His Ile Leu His Ser Ser Ile Leu
        115                 120                 125

Val Pro Tyr His Gly Trp Arg Ile Ser His Arg Thr His His Gln Asn
130                 135                 140

His Gly His Val Glu Lys Asp Glu Ser Trp His Pro Leu Pro Glu Arg
145                 150                 155                 160

Leu Tyr Lys Ser Leu Asp Phe Met Thr Arg Lys Leu Arg Phe Thr Met
                165                 170                 175

Pro Phe Pro Leu Leu Ala Phe Pro Leu Tyr Leu Phe Ala Arg Ser Pro
            180                 185                 190

Gly Lys Ser Gly Ser His Phe Asn Pro Ser Ser Asp Leu Phe Gln Pro
        195                 200                 205

Asn Glu Lys Lys Asp Ile Ile Thr Ser Thr Ala Ser Trp Leu Ala Met
210                 215                 220

Val Gly Val Leu Ala Gly Leu Thr Phe Leu Met Gly Pro Val Ala Met
225                 230                 235                 240

Leu Lys Leu Tyr Gly Val Pro Tyr Phe Val Phe Val Ala Trp Leu Asp
                245                 250                 255

Met Val Thr Tyr Leu His His His Gly His Glu Asp Lys Leu Pro Trp
            260                 265                 270

Tyr Arg Gly Gln Glu Trp Ser Tyr Leu Arg Gly Gly Leu Thr Thr Leu
        275                 280                 285

Asp Arg Asp Tyr Gly Leu Ile Asn Asn Ile His His Asp Ile Gly Thr
290                 295                 300

His Val Ile His His Leu Phe Pro Gln Ile Pro His Tyr His Leu Ile
305                 310                 315                 320

Glu Ala Thr Glu Ala Ala Lys Pro Val Leu Gly Lys Tyr Tyr Lys Glu
                325                 330                 335

Pro Lys Lys Ser Gly Pro Leu Pro Trp His Leu Phe Gly Val Leu Ala
            340                 345                 350

```
Gln Ser Leu Lys Gln Asp His Tyr Val Ser Asp Thr Gly Asp Val Val
            355                 360                 365

Tyr Tyr Gln Thr Asp
        370

<210> SEQ ID NO 28
<211> LENGTH: 366
<212> TYPE: PRT
<213> ORGANISM: Glycine max
<300> PUBLICATION INFORMATION:
<308> DATABASE ACCESSION NUMBER: GenBank/P48621
<309> DATABASE ENTRY DATE: 1998-12-15
<313> RELEVANT RESIDUES: (78)..(443)

<400> SEQUENCE: 28

Ser Val Asp Leu Thr Asn Gly Thr Asn Gly Val Glu His Glu Lys Leu
1               5                   10                  15

Pro Glu Phe Asp Pro Gly Ala Pro Pro Phe Asn Leu Ala Asp Ile
            20                  25                  30

Arg Ala Ala Ile Pro Lys His Cys Trp Val Lys Asp Pro Trp Arg Ser
            35                  40                  45

Met Ser Tyr Val Val Arg Asp Val Ile Ala Val Phe Gly Leu Ala Ala
    50                  55                  60

Ala Ala Ala Tyr Leu Asn Asn Trp Leu Val Trp Pro Leu Tyr Trp Ala
65                  70                  75                  80

Ala Gln Gly Thr Met Phe Trp Ala Leu Phe Val Leu Gly His Asp Cys
            85                  90                  95

Gly His Gly Ser Phe Ser Asn Asn Ser Lys Leu Asn Ser Val Val Gly
            100                 105                 110

His Leu Leu His Ser Ser Ile Leu Val Pro Tyr His Gly Trp Arg Ile
            115                 120                 125

Ser His Arg Thr His His Gln His His Gly His Ala Glu Asn Asp Glu
        130                 135                 140

Ser Trp His Pro Leu Pro Glu Lys Leu Phe Arg Ser Leu Asp Thr Val
145                 150                 155                 160

Thr Arg Met Leu Arg Phe Thr Ala Pro Phe Pro Leu Leu Ala Phe Pro
            165                 170                 175

Val Tyr Leu Phe Ser Arg Ser Pro Gly Lys Thr Gly Ser His Phe Asp
            180                 185                 190

Pro Ser Ser Asp Leu Phe Val Pro Asn Glu Arg Lys Asp Val Ile Thr
        195                 200                 205

Ser Thr Ala Cys Trp Ala Ala Met Leu Gly Leu Leu Val Gly Leu Gly
210                 215                 220

Phe Val Met Gly Pro Ile Gln Leu Leu Lys Leu Tyr Gly Val Pro Tyr
225                 230                 235                 240

Val Ile Phe Val Met Trp Leu Asp Leu Val Thr Tyr Leu His His His
            245                 250                 255

Gly His Glu Asp Lys Leu Pro Trp Tyr Arg Gly Lys Glu Trp Ser Tyr
            260                 265                 270

Leu Arg Gly Gly Leu Thr Thr Leu Asp Arg Asp Tyr Gly Trp Ile Asn
        275                 280                 285

Asn Ile His His Asp Ile Gly Thr His Val Ile His His Leu Phe Pro
        290                 295                 300

Gln Ile Pro His Tyr His Leu Val Glu Ala Thr Glu Ala Ala Lys Pro
305                 310                 315                 320
```

```
Val Phe Gly Lys Tyr Tyr Arg Glu Pro Lys Lys Ser Ala Ala Pro Leu
                325                 330                 335

Pro Phe His Leu Ile Gly Glu Ile Ile Arg Ser Phe Lys Thr Asp His
            340                 345                 350

Phe Val Ser Asp Thr Gly Asp Val Val Tyr Tyr Gln Thr Asp
            355                 360                 365

<210> SEQ ID NO 29
<211> LENGTH: 354
<212> TYPE: PRT
<213> ORGANISM: Zea mays
<300> PUBLICATION INFORMATION:
<308> DATABASE ACCESSION NUMBER: GenBank/BAA22441
<309> DATABASE ENTRY DATE: 1998-03-04
<313> RELEVANT RESIDUES: (79)..(432)

<400> SEQUENCE: 29

Gly Ala Ala Ala Gly Gly Glu Phe Asp Pro Gly Ala Pro Pro Pro Phe
1               5                   10                  15

Gly Leu Ala Glu Ile Arg Ala Ala Ile Pro Lys His Cys Trp Val Lys
            20                  25                  30

Asp Pro Trp Arg Ser Met Ser Tyr Val Leu Arg Asp Val Ala Val Val
            35                  40                  45

Leu Gly Leu Ala Ala Ala Ala Arg Leu Asp Ser Trp Leu Val Trp
50                  55                  60

Pro Leu Tyr Trp Ala Ala Gln Gly Thr Met Phe Trp Ala Leu Phe Val
65                  70                  75                  80

Leu Gly His Asp Cys Gly His Gly Ser Phe Ser Asn Asn Pro Lys Leu
            85                  90                  95

Asn Ser Val Val Gly His Ile Leu His Ser Ser Ile Leu Val Pro Tyr
            100                 105                 110

His Gly Trp Arg Ile Ser His Arg Thr His His Gln Asn His Gly His
            115                 120                 125

Val Glu Lys Asp Glu Ser Trp His Pro Leu Pro Glu Arg Leu Tyr Lys
130                 135                 140

Ser Leu Asp Phe Met Thr Arg Lys Leu Arg Phe Thr Met Pro Phe Pro
145                 150                 155                 160

Leu Leu Ala Phe Pro Leu Tyr Leu Phe Ala Arg Ser Pro Gly Lys Ser
            165                 170                 175

Gly Ser His Phe Asn Pro Gly Ser Asp Leu Phe Gln Pro Thr Glu Lys
            180                 185                 190

Asn Asp Ile Ile Thr Ser Thr Ala Ser Trp Leu Ala Met Val Gly Val
            195                 200                 205

Leu Ala Gly Leu Thr Phe Leu Met Gly Pro Val Pro Met Leu Lys Leu
210                 215                 220

Tyr Gly Val Pro Tyr Leu Val Phe Val Ala Trp Leu Asp Met Val Thr
225                 230                 235                 240

Tyr Leu His His His Gly His Glu Asp Lys Leu Pro Trp Tyr Arg Gly
            245                 250                 255

Lys Glu Trp Ser Tyr Leu Arg Gly Gly Leu Thr Thr Leu Asp Arg Asp
            260                 265                 270

Tyr Gly Trp Ile Asn Asn Ile His His Asp Ile Gly Thr His Val Ile
            275                 280                 285

His His Leu Phe Pro Gln Ile Pro His Tyr His Leu Ile Glu Ala Thr
290                 295                 300
```

```
Glu Ala Ala Lys Pro Val Leu Gly Lys Tyr Tyr Lys Glu Pro Lys Asn
305                 310                 315                 320

Ser Gly Ala Leu Pro Trp His Leu Phe Arg Val Leu Ala Gln Ser Leu
            325                 330                 335

Lys Gln Asp His Tyr Val Ser His Thr Gly Asp Val Val Tyr Tyr Gln
            340                 345                 350

Ala Glu

<210> SEQ ID NO 30
<211> LENGTH: 362
<212> TYPE: PRT
<213> ORGANISM: Solanum tuberosum
<300> PUBLICATION INFORMATION:
<308> DATABASE ACCESSION NUMBER: GenBank/CAA07638
<309> DATABASE ENTRY DATE: 1998-09-04
<313> RELEVANT RESIDUES: (66)..(427)

<400> SEQUENCE: 30

Glu Glu Glu Gln Thr Thr Asn Asn Gly Asp Glu Phe Asp Pro Gly Ala
1               5                   10                  15

Ser Pro Pro Phe Lys Leu Ser Asp Ile Lys Ala Ala Ile Pro Lys His
            20                  25                  30

Cys Trp Val Lys Asn Pro Trp Thr Ser Met Ser Tyr Val Val Arg Asp
            35                  40                  45

Val Ala Ile Val Phe Gly Leu Ala Ala Ala Ala Tyr Phe Asn Asn
        50                  55                  60

Trp Leu Val Trp Pro Leu Tyr Trp Phe Ala Gln Ser Thr Met Phe Trp
65                  70                  75                  80

Ala Leu Phe Val Leu Gly His Asp Cys Gly His Gly Ser Phe Ser Asn
                85                  90                  95

Asn His Asn Leu Asn Ser Val Ala Gly His Ile Leu His Ser Ser Ile
            100                 105                 110

Leu Val Pro Tyr His Gly Trp Arg Ile Ser His Arg Thr His His Gln
            115                 120                 125

Asn His Gly His Val Glu Asn Asp Glu Ser Trp His Pro Leu Ser Glu
130                 135                 140

Lys Leu Tyr Asn Ser Leu Asp Asp Ile Thr Lys Lys Phe Arg Phe Thr
145                 150                 155                 160

Leu Pro Phe Pro Leu Leu Ala Tyr Pro Phe Tyr Leu Trp Gly Arg Ser
                165                 170                 175

Pro Gly Lys Lys Gly Ser His Phe Asp Pro Ser Ser Asp Leu Phe Val
            180                 185                 190

Ala Ser Glu Lys Lys Asp Val Ile Thr Ser Thr Val Cys Trp Thr Ala
            195                 200                 205

Met Ala Ala Leu Leu Val Gly Leu Ser Phe Val Met Gly Pro Leu Gln
210                 215                 220

Val Leu Lys Leu Tyr Gly Ile Pro Tyr Trp Gly Phe Val Met Trp Leu
225                 230                 235                 240

Asp Ile Val Thr Tyr Leu His His His Gly His Glu Asp Lys Val Pro
                245                 250                 255

Trp Tyr Arg Gly Glu Glu Trp Ser Tyr Leu Arg Gly Gly Leu Thr Thr
            260                 265                 270

Leu Asp Arg Asp Tyr Gly Trp Ile Asn Asn Ile His His Asp Ile Gly
            275                 280                 285

Thr His Val Ile His His Leu Phe Pro Gln Ile Pro His Tyr His Leu
            290                 295                 300
```

```
Val Glu Ala Thr Glu Ala Ala Lys Pro Val Leu Gly Lys Tyr Tyr Lys
305                 310                 315                 320

Glu Pro Lys Lys Ser Gly Pro Leu Pro Phe Tyr Leu Leu Gly Tyr Leu
                325                 330                 335

Ile Lys Ser Met Lys Glu Asp His Phe Val Ser Asp Thr Gly Asn Val
                340                 345                 350

Val Tyr Tyr Gln Thr Asp Pro Asn Leu Tyr
            355                 360

<210> SEQ ID NO 31
<211> LENGTH: 369
<212> TYPE: PRT
<213> ORGANISM: Limnanthes douglasii
<300> PUBLICATION INFORMATION:
<308> DATABASE ACCESSION NUMBER: GenBank/AAA86690
<309> DATABASE ENTRY DATE: 1995-11-21
<313> RELEVANT RESIDUES: (60)..(428)

<400> SEQUENCE: 31

Val Ser Ala Pro Phe Gln Ile Ala Ser Thr Thr Pro Glu Glu Glu Asp
1               5                   10                  15

Glu Val Ala Glu Phe Asp Pro Gly Ser Pro Pro Phe Lys Leu Ala
            20                  25                  30

Asp Ile Arg Ala Ala Ile Pro Lys His Cys Trp Val Lys Asn Gln Trp
        35                  40                  45

Arg Ser Met Ser Tyr Val Val Arg Asp Val Val Ile Val Leu Gly Leu
    50                  55                  60

Ala Ala Ala Ala Val Ala Ala Asn Ser Trp Ala Val Trp Pro Leu Tyr
65                  70                  75                  80

Trp Val Ala Gln Gly Thr Met Phe Trp Ala Leu Phe Val Leu Gly His
                85                  90                  95

Asp Cys Gly His Gly Ser Phe Ser Asn Asn His Lys Leu Asn Ser Val
            100                 105                 110

Val Gly His Leu Leu His Ser Ser Ile Leu Val Pro Tyr His Gly Trp
        115                 120                 125

Arg Ile Arg His Arg Thr His His Gln Asn His Gly His Val Glu Asn
    130                 135                 140

Asp Glu Ser Trp His Pro Met Ser Glu Lys Leu Phe Arg Ser Leu Asp
145                 150                 155                 160

Lys Ile Ala Leu Thr Phe Arg Phe Lys Ala Pro Phe Pro Met Leu Ala
                165                 170                 175

Tyr Pro Phe Tyr Leu Trp Glu Arg Ser Pro Gly Lys Thr Gly Ser His
            180                 185                 190

Tyr His Pro Asp Ser Asp Leu Phe Val Pro Ser Glu Lys Lys Asp Val
        195                 200                 205

Ile Thr Ser Thr Ile Cys Trp Thr Thr Met Val Gly Leu Leu Ile Gly
    210                 215                 220

Leu Ser Phe Val Met Gly Pro Ile Gln Ile Leu Lys Leu Tyr Val Val
225                 230                 235                 240

Pro Tyr Trp Ile Phe Val Met Trp Leu Asp Phe Val Thr Tyr Leu Asp
                245                 250                 255

His His Gly His Glu Asp Lys Leu Pro Trp Tyr Arg Gly Glu Glu Trp
            260                 265                 270

Ser Tyr Leu Arg Gly Gly Leu Thr Thr Leu Asp Arg Asp Tyr Gly Leu
        275                 280                 285
```

```
Ile Asn Asn Ile His His Asp Ile Gly Thr His Val Ile His His Leu
    290                 295                 300

Phe Pro Gln Ile Pro His Tyr His Leu Val Glu Ala Thr Gln Ala Ala
305                 310                 315                 320

Lys Pro Ile Phe Gly Lys Tyr Lys Glu Pro Ala Lys Ser Lys Pro
                325                 330                 335

Leu Pro Phe His Leu Ile Asp Val Leu Leu Lys Ser Leu Lys Arg Asp
                340                 345                 350

His Phe Val Pro Asp Thr Gly Asp Ile Val Tyr Tyr Gln Ser Asp Pro
            355                 360                 365

Gln

<210> SEQ ID NO 32
<211> LENGTH: 348
<212> TYPE: PRT
<213> ORGANISM: Triticum aestivum
<300> PUBLICATION INFORMATION:
<308> DATABASE ACCESSION NUMBER: GenBank/BAA07785
<309> DATABASE ENTRY DATE: 1999-06-18
<313> RELEVANT RESIDUES: (24)..(371)

<400> SEQUENCE: 32

Phe Asp Pro Gly Ala Pro Pro Phe Gly Leu Ala Asp Ile Arg Ala
1               5                   10                  15

Ala Ile Pro Lys His Cys Trp Val Lys Asp Pro Trp Arg Ser Met Gly
                20                  25                  30

Tyr Val Val Arg Asp Val Val Val Leu Ala Leu Ala Ala Thr Ala
            35                  40                  45

Ala Arg Leu Asp Ser Trp Leu Ala Trp Pro Val Tyr Trp Ala Ala Gln
    50                  55                  60

Gly Thr Met Phe Trp Ala Leu Phe Val Leu Gly His Asp Cys Gly His
65                  70                  75                  80

Gly Ser Phe Ser Asn Asn Ala Lys Leu Asn Ser Val Val Gly His Ile
                85                  90                  95

Leu His Ser Ser Ile Leu Val Pro Tyr Asn Gly Trp Arg Ile Ser His
                100                 105                 110

Arg Thr His His Gln Asn His Gly His Val Glu Asn Asp Glu Ser Trp
            115                 120                 125

His Pro Leu Pro Glu Lys Leu Tyr Arg Ser Leu Asp Ser Ser Thr Arg
    130                 135                 140

Lys Leu Arg Phe Ala Leu Pro Phe Pro Met Leu Ala Tyr Pro Phe Tyr
145                 150                 155                 160

Leu Trp Ser Arg Ser Pro Gly Lys Ser Gly Ser His Phe His Pro Ser
                165                 170                 175

Ser Asp Leu Phe Gln Pro Asn Glu Lys Lys Asp Ile Leu Thr Ser Thr
                180                 185                 190

Thr Cys Trp Leu Ala Met Ala Gly Leu Leu Ala Gly Leu Thr Val Val
            195                 200                 205

Met Gly Pro Leu Gln Ile Leu Lys Leu Tyr Ala Val Pro Tyr Trp Ile
    210                 215                 220

Phe Val Met Trp Leu Asp Phe Val Thr Tyr Leu His His Gly His
225                 230                 235                 240

Asn Asp Lys Leu Pro Trp Tyr Arg Gly Lys Ala Trp Ser Ile Tyr Thr
                245                 250                 255

Gly Gly Leu Thr Thr Leu Asp Arg Asp Tyr Gly Trp Leu Asn Asn Ile
            260                 265                 270
```

```
His His Asp Ile Gly Thr His Val Ile His His Leu Leu Pro Gln Ile
        275                 280                 285

Pro His Tyr His Leu Val Glu Ala Thr Glu Ala Ala Thr Val Leu Gly
        290                 295                 300

Lys Tyr Tyr Arg Glu Pro Asp Lys Ser Gly Pro Phe Pro Phe His Leu
305                 310                 315                 320

Phe Gly Ala Leu Ala Arg Ser Met Lys Ser Asp His Tyr Val Ser Asp
                    325                 330                 335

Thr Gly Asp Ile Ile Tyr Tyr Gln Thr Asp Pro Lys
            340                 345

<210> SEQ ID NO 33
<211> LENGTH: 349
<212> TYPE: PRT
<213> ORGANISM: Triticum aestivum
<300> PUBLICATION INFORMATION:
<308> DATABASE ACCESSION NUMBER: GenBank/BAA28358
<309> DATABASE ENTRY DATE: 1998-05-30
<313> RELEVANT RESIDUES: (23)..(371)

<400> SEQUENCE: 33

Phe Asp Ala Ala Lys Pro Pro Phe Arg Ile Gly Asp Val Arg Ala
1               5                   10                  15

Ala Val Pro Ala His Cys Trp Pro Gln Glu Pro Ala Ser Leu Ser
                20                  25                  30

Tyr Val Ala Arg Asp Val Ala Val Ala Leu Ala Ala Ala Ala
                35                  40                  45

Trp Arg Ala Asp Ser Trp Ala Leu Trp Pro Leu Tyr Trp Ala Val Gln
    50                  55                  60

Gly Thr Met Phe Trp Ala Leu Phe Val Leu Gly His Asp Cys Gly His
65                  70                  75                  80

Gly Ser Phe Ser Asp Ser Gly Thr Leu Asn Ser Val Val Gly His Leu
                85                  90                  95

Leu His Thr Phe Ile Leu Val Pro Tyr Asn Gly Trp Arg Ile Ser His
                100                 105                 110

Arg Thr His His Gln Asn His Gly His Ile Asp Arg Asp Glu Ser Trp
        115                 120                 125

His Pro Ile Thr Glu Lys Val Tyr Gln Lys Leu Glu Pro Arg Thr Lys
    130                 135                 140

Thr Leu Arg Phe Ser Val Pro Phe Pro Leu Leu Ala Phe Pro Val Tyr
145                 150                 155                 160

Leu Trp Tyr Arg Ser Pro Gly Lys Glu Gly Ser His Phe Asn Pro Ser
                165                 170                 175

Ser Asp Leu Phe Thr Pro Lys Glu Arg Arg Asp Val Ile Ile Ser Thr
                180                 185                 190

Thr Cys Trp Phe Thr Met Ile Ala Leu Leu Ile Gly Met Ala Cys Val
            195                 200                 205

Phe Gly Leu Val Pro Val Leu Lys Leu Tyr Gly Val Pro Tyr Ile Val
    210                 215                 220

Asn Val Met Trp Leu Asp Leu Val Thr Tyr Leu His His Gly His
225                 230                 235                 240

Gln Asp Leu Pro Trp Tyr Arg Gly Glu Glu Trp Ser Tyr Leu Arg Gly
                245                 250                 255

Gly Leu Thr Thr Val Asp Arg Asp Tyr Gly Trp Ile Asn Asn Ile His
            260                 265                 270
```

```
His Asp Ile Gly Thr His Val Ile His His Leu Phe Pro Gln Ile Pro
        275                 280                 285
His Tyr His Leu Val Glu Ala Thr Lys Ala Ala Arg Pro Val Leu Gly
        290                 295                 300
Arg Tyr Tyr Arg Glu Pro Glu Lys Ser Gly Pro Leu Pro Met His Leu
305                 310                 315                 320
Ile Thr Val Leu Leu Lys Ser Leu Arg Val Asp His Phe Val Ser Asp
                325                 330                 335
Val Gly Asp Val Val Phe Tyr Gln Thr Asp Pro Ser Leu
                340                 345

<210> SEQ ID NO 34
<211> LENGTH: 356
<212> TYPE: PRT
<213> ORGANISM: Oryza sativa (indica cultivar-group)
<300> PUBLICATION INFORMATION:
<308> DATABASE ACCESSION NUMBER: GenBank/BAA11397
<309> DATABASE ENTRY DATE: 1999-02-05
<313> RELEVANT RESIDUES: (14)..(369)

<400> SEQUENCE: 34

Ser Glu Asp Ala Arg Leu Phe Phe Asp Ala Ala Lys Pro Pro Pro Phe
1               5                   10                  15
Arg Ile Gly Asp Val Arg Ala Ala Ile Pro Val His Cys Trp Arg Lys
                20                  25                  30
Thr Pro Leu Arg Ser Leu Ser Tyr Val Ala Arg Asp Leu Leu Ile Val
                35                  40                  45
Ala Ala Leu Phe Ala Ala Ala Ser Ser Ile Asp Leu Ala Trp Ala
        50                  55                  60
Trp Ala Trp Pro Leu Tyr Trp Ala Arg Gln Gly Thr Met Val Trp Ala
65                  70                  75                  80
Leu Phe Val Leu Gly His Asp Cys Gly His Gly Ser Phe Ser Asp Ser
                85                  90                  95
Ala Met Leu Asn Asn Val Val Gly His Leu Leu His Ser Phe Ile Leu
                100                 105                 110
Val Pro Tyr His Gly Trp Arg Phe Ser His Arg Thr His His Gln Asn
        115                 120                 125
His Gly His Ile Glu Arg Asp Glu Ser Trp His Pro Ile Thr Glu Lys
        130                 135                 140
Leu Tyr Trp Gln Leu Glu Thr Arg Thr Lys Lys Leu Arg Phe Thr Leu
145                 150                 155                 160
Pro Phe Thr Leu Leu Ala Phe Pro Trp Tyr Arg Ser Pro Gly Lys Thr
                165                 170                 175
Gly Ser His Phe Leu Pro Ser Ser Asp Leu Phe Ser Pro Lys Glu Lys
                180                 185                 190
Ser Asp Val Ile Val Ser Thr Thr Cys Trp Cys Ile Met Ile Ser Leu
        195                 200                 205
Leu Val Ala Leu Ala Cys Val Phe Gly Pro Val Pro Val Leu Met Leu
210                 215                 220
Tyr Gly Val Pro Tyr Leu Val Phe Val Met Trp Leu Asp Leu Val Thr
225                 230                 235                 240
Tyr Leu His His His Gly His Asn Asp Leu Pro Trp Tyr Arg Gly Glu
                245                 250                 255
Glu Trp Ser Tyr Leu Arg Gly Gly Leu Thr Thr Val Asp Arg Asp Tyr
                260                 265                 270
```

```
Gly Trp Ile Asn Asn Ile His His Asp Ile Gly Thr His Val Ile His
        275                 280                 285

His Leu Phe Pro Gln Ile Pro His Tyr His Leu Val Glu Ala Thr Lys
        290                 295                 300

Ala Ala Arg Pro Val Leu Gly Arg Tyr Tyr Arg Glu Pro Glu Lys Ser
305                 310                 315                 320

Gly Pro Leu Pro Leu His Leu Phe Gly Val Leu Leu Arg Thr Leu Arg
                325                 330                 335

Val Asp His Phe Val Ser Asp Val Gly Asp Val Val Tyr Tyr Gln Thr
                340                 345                 350

Asp His Ser Leu
        355

<210> SEQ ID NO 35
<211> LENGTH: 329
<212> TYPE: PRT
<213> ORGANISM: Synechococcus sp. PCC 7002
<300> PUBLICATION INFORMATION:
<308> DATABASE ACCESSION NUMBER: GenBank/AAB61352
<309> DATABASE ENTRY DATE: 1997-06-17
<313> RELEVANT RESIDUES: (19)..(347)

<400> SEQUENCE: 35

Pro Phe Thr Leu Lys Asp Val Lys Ala Ala Ile Pro Asp Tyr Cys Phe
1               5                   10                  15

Gln Pro Ser Val Phe Arg Ser Leu Ala Tyr Phe Phe Leu Asp Ile Gly
                20                  25                  30

Ile Ile Ala Gly Leu Tyr Ala Ile Ala Ala Tyr Leu Asp Ser Trp Phe
            35                  40                  45

Phe Tyr Pro Ile Phe Trp Phe Ala Gln Gly Thr Met Phe Trp Ala Leu
        50                  55                  60

Phe Val Val Gly His Asp Cys Gly His Gly Ser Phe Ser Arg Ser Lys
65                  70                  75                  80

Phe Leu Asn Asp Leu Ile Gly His Leu Ser His Thr Pro Ile Leu Val
                85                  90                  95

Pro Phe His Gly Trp Arg Ile Ser His Arg Thr His His Ser Asn Thr
                100                 105                 110

Gly Asn Ile Asp Thr Asp Glu Ser Trp Tyr Pro Ile Pro Glu Ser Lys
            115                 120                 125

Tyr Asp Gln Met Gly Phe Ala Glu Lys Leu Val Arg Phe Tyr Ala Pro
        130                 135                 140

Leu Ile Ala Tyr Pro Ile Tyr Leu Phe Lys Arg Ser Pro Gly Arg Gly
145                 150                 155                 160

Pro Gly Ser His Phe Ser Pro Lys Ser Pro Leu Phe Lys Pro Ala Glu
                165                 170                 175

Arg Asn Asp Ile Ile Leu Ser Thr Ala Ala Ile Ala Met Val Gly
            180                 185                 190

Phe Leu Gly Trp Phe Thr Val Gln Phe Gly Leu Leu Ala Phe Val Lys
        195                 200                 205

Phe Tyr Phe Val Pro Tyr Val Ile Phe Val Ile Trp Leu Asp Leu Val
        210                 215                 220

Thr Tyr Leu His His Thr Glu Ala Asp Ile Pro Trp Tyr Arg Gly Asp
225                 230                 235                 240

Asp Trp Tyr Tyr Leu Lys Gly Ala Leu Ser Thr Ile Asp Arg Asp Tyr
                245                 250                 255
```

```
Gly Ile Phe Asn Glu Ile His His Asn Ile Gly Thr His Val Ala His
            260                 265                 270

His Ile Phe His Thr Ile Pro His Tyr His Leu Lys Asp Ala Thr Glu
        275                 280                 285

Ala Ile Lys Pro Leu Leu Gly Asp Tyr Tyr Arg Val Ser His Ala Pro
    290                 295                 300

Ile Trp Arg Ser Phe Phe Arg Ser Gln Lys Ala Cys His Tyr Ile Ala
305                 310                 315                 320

Asp Gln Gly Ser His Leu Tyr Tyr Gln
                325

<210> SEQ ID NO 36
<211> LENGTH: 329
<212> TYPE: PRT
<213> ORGANISM: Synechocystis sp.
<300> PUBLICATION INFORMATION:
<308> DATABASE ACCESSION NUMBER: GenBank/S52650
<309> DATABASE ENTRY DATE: 1997-03-13
<313> RELEVANT RESIDUES: (21)..(349)

<400> SEQUENCE: 36

Pro Phe Thr Leu Gln Glu Leu Arg Asn Ala Ile Pro Ala Asp Cys Phe
1               5                   10                  15

Glu Pro Ser Val Val Arg Ser Leu Gly Tyr Phe Phe Leu Asp Val Gly
            20                  25                  30

Leu Ile Ala Gly Phe Tyr Ala Leu Ala Ala Tyr Leu Asp Ser Trp Phe
        35                  40                  45

Phe Tyr Pro Ile Phe Trp Leu Ile Gln Gly Thr Leu Phe Trp Ser Leu
    50                  55                  60

Phe Val Val Gly His Asp Cys Gly His Gly Ser Phe Ser Lys Ser Lys
65                  70                  75                  80

Thr Leu Asn Asn Trp Ile Gly His Leu Ser His Thr Pro Ile Leu Val
                85                  90                  95

Pro Tyr His Gly Trp Arg Ile Ser His Arg Thr His His Ala Asn Thr
            100                 105                 110

Gly Asn Ile Asp Thr Asp Glu Ser Trp Tyr Pro Val Ser Glu Gln Lys
        115                 120                 125

Tyr Asn Gln Met Ala Trp Tyr Glu Lys Leu Leu Arg Phe Tyr Leu Pro
    130                 135                 140

Leu Ile Ala Tyr Pro Ile Tyr Leu Phe Arg Arg Ser Pro Asn Arg Gln
145                 150                 155                 160

Gly Ser His Phe Met Pro Gly Ser Pro Leu Phe Arg Pro Gly Glu Lys
                165                 170                 175

Ala Ala Val Leu Thr Ser Thr Phe Ala Leu Ala Ala Phe Val Gly Phe
            180                 185                 190

Leu Gly Phe Leu Thr Trp Gln Phe Gly Trp Leu Phe Leu Leu Lys Phe
        195                 200                 205

Tyr Val Ala Pro Tyr Leu Val Phe Val Val Trp Leu Asp Leu Val Thr
    210                 215                 220

Phe Leu His His Thr Glu Asp Asn Ile Pro Trp Tyr Arg Gly Asp Asp
225                 230                 235                 240

Trp Tyr Phe Leu Lys Gly Ala Leu Ser Thr Ile Asp Arg Asp Tyr Gly
                245                 250                 255

Phe Ile Asn Pro Ile His His Asp Ile Gly Thr His Val Ala His His
            260                 265                 270
```

-continued

```
Ile Phe Ser Asn Met Pro His Tyr Lys Leu Arg Arg Ala Thr Glu Ala
            275                 280                 285

Ile Lys Pro Ile Leu Gly Glu Tyr Tyr Arg Tyr Ser Asp Glu Pro Ile
            290                 295                 300

Trp Gln Ala Phe Lys Ser Tyr Trp Ala Cys His Phe Val Pro Asn
305                 310                 315                 320

Gln Gly Ser Gly Val Tyr Tyr Gln Ser
                325
```

<210> SEQ ID NO 37
<211> LENGTH: 321
<212> TYPE: PRT
<213> ORGANISM: Chloroplast Brassica napus
<300> PUBLICATION INFORMATION:
<308> DATABASE ACCESSION NUMBER: GenBank/AAA61774
<309> DATABASE ENTRY DATE: 1995-01-31
<313> RELEVANT RESIDUES: (1)..(321)

<400> SEQUENCE: 37

```
Met Ser Tyr Val Val Arg Glu Leu Ala Ile Val Phe Ala Leu Ala Ala
1               5                   10                  15

Gly Ala Ala Tyr Leu Asn Asn Trp Leu Val Trp Pro Leu Tyr Trp Ile
            20                  25                  30

Ala Gln Gly Thr Met Phe Trp Ala Leu Phe Val Leu Gly His Asp Cys
            35                  40                  45

Gly His Gly Ser Phe Ser Asn Asp Pro Arg Leu Asn Ser Val Val Gly
        50                  55                  60

His Leu Leu His Ser Ser Ile Leu Val Pro Tyr His Gly Trp Arg Ile
65                  70                  75                  80

Ser His Arg Thr His His Gln Asn His Gly His Val Glu Asn Asp Glu
                85                  90                  95

Ser Trp His Pro Met Ser Glu Lys Ile Tyr Lys Ser Leu Asp Lys Pro
            100                 105                 110

Thr Arg Phe Phe Arg Phe Thr Leu Pro Leu Val Met Leu Ala Tyr Pro
            115                 120                 125

Phe Tyr Leu Trp Ala Arg Ser Pro Gly Lys Lys Gly Ser His Tyr His
        130                 135                 140

Pro Asp Ser Asp Leu Phe Leu Pro Lys Glu Arg Asn Asp Val Leu Thr
145                 150                 155                 160

Ser Thr Ala Cys Trp Thr Ala Met Ala Val Leu Leu Val Cys Leu Asn
                165                 170                 175

Phe Val Met Gly Pro Met Gln Met Leu Lys Leu Tyr Val Ile Pro Tyr
            180                 185                 190

Trp Ile Asn Val Met Trp Leu Asp Phe Val Thr Tyr Leu His His His
            195                 200                 205

Gly His Glu Asp Lys Leu Pro Trp Tyr Arg Gly Lys Glu Trp Ser Tyr
        210                 215                 220

Leu Arg Gly Gly Leu Thr Thr Leu Asp Arg Asp Tyr Gly Leu Ile Asn
225                 230                 235                 240

Asn Ile His His Asp Ile Gly Thr His Val Ile His His Leu Phe Pro
                245                 250                 255

Gln Ile Pro His Tyr His Leu Val Glu Ala Thr Glu Ala Ala Lys Pro
            260                 265                 270

Val Leu Gly Lys Tyr Tyr Arg Glu Pro Asp Lys Ser Gly Pro Leu Pro
            275                 280                 285
```

```
Leu His Leu Gly Ile Leu Ala Lys Ser Ile Lys Glu Asp His Phe
    290             295             300

Val Ser Asp Glu Gly Asp Val Val Tyr Tyr Glu Ala Asp Pro Asn Leu
305             310             315             320

Tyr
```

```
<210> SEQ ID NO 38
<211> LENGTH: 251
<212> TYPE: PRT
<213> ORGANISM: Zea mays
<300> PUBLICATION INFORMATION:
<308> DATABASE ACCESSION NUMBER: GenBank/BAA22439
<309> DATABASE ENTRY DATE: 1998-03-04
<313> RELEVANT RESIDUES: (1)..(251)

<400> SEQUENCE: 38

Leu His Ser Ser Ile Leu Val Pro Tyr His Gly Trp Arg Ile Ser His
1               5                   10                  15

Arg Thr His His Gln Asn His Gly His Val Glu Lys Asp Glu Ser Trp
                20                  25                  30

His Pro Leu Pro Glu Arg Leu Tyr Lys Ser Leu Asp Phe Met Thr Arg
            35                  40                  45

Lys Leu Arg Phe Thr Met Pro Phe Pro Leu Leu Ala Phe Pro Leu Tyr
    50                  55                  60

Leu Phe Ala Arg Ser Pro Gly Lys Ser Gly Ser His Phe Asn Pro Gly
65                  70                  75                  80

Ser Asp Leu Phe Gln Pro Thr Glu Lys Asn Asp Ile Ile Thr Ser Thr
                85                  90                  95

Ala Ser Trp Leu Ala Met Val Gly Val Leu Ala Gly Leu Thr Phe Leu
            100                 105                 110

Met Gly Pro Val Pro Met Leu Lys Leu Tyr Gly Val Pro Tyr Leu Val
    115                 120                 125

Phe Val Ala Trp Leu Asp Met Val Thr Tyr Leu His His Gly His
130                 135                 140

Glu Asp Lys Leu Pro Trp Tyr Arg Gly Lys Glu Trp Ser Tyr Leu Arg
145                 150                 155                 160

Gly Gly Leu Thr Thr Leu Asp Arg Asp Tyr Gly Trp Ile Asn Asn Ile
                165                 170                 175

His His Asp Ile Gly Thr His Val Ile His His Leu Phe Pro Gln Ile
            180                 185                 190

Pro His Tyr His Leu Ile Glu Ala Thr Glu Ala Ala Lys Pro Val Leu
    195                 200                 205

Gly Lys Tyr Tyr Lys Glu Pro Lys Asn Ser Gly Ala Leu Pro Trp His
    210                 215                 220

Leu Phe Arg Val Leu Ala Gln Ser Leu Lys Gln Asp His Tyr Val Ser
225                 230                 235                 240

His Thr Gly Asp Val Val Tyr Tyr Gln Ala Glu
                245                 250
```

```
<210> SEQ ID NO 39
<211> LENGTH: 257
<212> TYPE: PRT
<213> ORGANISM: Oryza sativa (japonica cultivar-group)
<300> PUBLICATION INFORMATION:
<308> DATABASE ACCESSION NUMBER: GenBank/BAA11396
<309> DATABASE ENTRY DATE: 1999-02-05
<313> RELEVANT RESIDUES: (1)..(257)
```

-continued

```
<400> SEQUENCE: 39

Asn Asn Val Val Gly His Leu His Ser Phe Ile Leu Val Pro Tyr
1               5                   10                  15

His Gly Trp Arg Phe Ser His Arg Thr His His Gln Asn His Gly His
            20                  25                  30

Ile Glu Arg Asp Glu Ser Trp His Pro Ile Thr Glu Lys Leu Tyr Trp
        35                  40                  45

Gln Leu Glu Thr Arg Thr Lys Lys Leu Arg Phe Thr Leu Pro Phe Thr
    50                  55                  60

Leu Leu Ala Phe Pro Trp Tyr Arg Ser Pro Gly Lys Thr Gly Ser His
65                  70                  75                  80

Phe Leu Pro Ser Ser Asp Leu Phe Ser Pro Lys Glu Lys Ser Asp Val
                85                  90                  95

Ile Val Ser Thr Thr Cys Trp Cys Ile Met Ile Ser Leu Leu Val Ala
            100                 105                 110

Leu Ala Cys Val Phe Gly Pro Val Pro Val Leu Met Leu Tyr Gly Val
        115                 120                 125

Pro Tyr Leu Val Phe Val Met Trp Leu Asp Leu Val Thr Tyr Leu His
    130                 135                 140

His His Gly His Asn Asp Leu Pro Trp Tyr Arg Gly Glu Glu Trp Ser
145                 150                 155                 160

Tyr Leu Arg Gly Gly Leu Thr Thr Val Asp Arg Asp Tyr Gly Trp Ile
                165                 170                 175

Asn Asn Ile His His Asp Ile Gly Thr His Val Ile His His Leu Phe
            180                 185                 190

Pro Gln Ile Pro His Tyr His Leu Val Glu Ala Thr Lys Ala Ala Arg
        195                 200                 205

Pro Val Leu Gly Arg Tyr Tyr Arg Glu Pro Glu Lys Ser Gly Pro Leu
    210                 215                 220

Pro Leu His Leu Phe Gly Val Leu Leu Arg Thr Leu Arg Val Asp His
225                 230                 235                 240

Phe Val Ser Asp Val Gly Asp Val Val Tyr Tyr Gln Thr Asp His Ser
                245                 250                 255

Leu

<210> SEQ ID NO 40
<211> LENGTH: 172
<212> TYPE: PRT
<213> ORGANISM: Brassica rapa
<300> PUBLICATION INFORMATION:
<308> DATABASE ACCESSION NUMBER: GenBank/AAD41582
<309> DATABASE ENTRY DATE: 1999-07-01
<313> RELEVANT RESIDUES: (1)..(172)

<400> SEQUENCE: 40

Phe Ile Leu Val Pro Tyr His Gly Trp Arg Ile Ser His Arg Thr His
1               5                   10                  15

His Gln Asn His Gly His Val Glu Asn Asp Glu Ser Trp Val Pro Leu
            20                  25                  30

Pro Glu Lys Leu Tyr Lys Asn Leu Ser His Ser Thr Arg Met Leu Arg
        35                  40                  45

Tyr Thr Val Pro Leu Pro Met Leu Ala Tyr Pro Leu Tyr Leu Trp Tyr
    50                  55                  60

Arg Ser Pro Gly Lys Glu Gly Ser His Tyr Asn Pro Tyr Ser Ser Leu
65                  70                  75                  80
```

```
Phe Ala Pro Ser Glu Arg Lys Leu Ile Ala Thr Ser Thr Thr Cys Trp
                85                  90                  95

Ser Ile Met Leu Ala Thr Leu Val Tyr Leu Ser Phe Leu Val Gly Pro
            100                 105                 110

Val Thr Val Leu Lys Val Tyr Gly Val Pro Tyr Ile Ile Phe Val Met
        115                 120                 125

Trp Leu Asp Ala Val Thr Tyr Leu His His His Gly His Asp Asp Lys
    130                 135                 140

Leu Pro Trp Tyr Arg Gly Lys Glu Trp Ser Tyr Leu Arg Gly Gly Leu
145                 150                 155                 160

Thr Thr Ile Asp Arg Asp Tyr Gly Ile Phe Asn Asn
                165                 170

<210> SEQ ID NO 41
<211> LENGTH: 141
<212> TYPE: PRT
<213> ORGANISM: Brassica oleracea
<300> PUBLICATION INFORMATION:
<308> DATABASE ACCESSION NUMBER: GenBank/AAD41581
<309> DATABASE ENTRY DATE: 1999-07-01
<313> RELEVANT RESIDUES: (1)..(141)

<400> SEQUENCE: 41

Leu Pro Glu Lys Leu Tyr Lys Asn Leu Ser His Ser Thr Arg Met Leu
1               5                   10                  15

Arg Tyr Thr Val Pro Leu Pro Met Leu Ala Tyr Pro Leu Tyr Leu Trp
            20                  25                  30

Tyr Arg Ser Pro Gly Lys Glu Gly Ser His Tyr Asn Pro Tyr Ser Ser
        35                  40                  45

Leu Phe Ala Pro Ser Glu Arg Lys Leu Ile Ala Thr Ser Thr Thr Cys
    50                  55                  60

Trp Ser Ile Val Leu Ala Thr Leu Val Tyr Leu Ser Phe Leu Val Gly
65                  70                  75                  80

Pro Val Thr Val Leu Lys Val Tyr Gly Val Pro Tyr Ile Ile Phe Val
                85                  90                  95

Met Trp Leu Asp Ala Val Thr Tyr Leu His His His Gly His Asp Asp
            100                 105                 110

Lys Leu Pro Trp Tyr Arg Gly Lys Glu Trp Ser Tyr Leu Arg Gly Gly
        115                 120                 125

Leu Thr Thr Val Asp Arg Asp Tyr Gly Ile Phe Asn Asn
    130                 135                 140

<210> SEQ ID NO 42
<211> LENGTH: 141
<212> TYPE: PRT
<213> ORGANISM: Brassica napus
<300> PUBLICATION INFORMATION:
<308> DATABASE ACCESSION NUMBER: GenBank/AAD41580
<309> DATABASE ENTRY DATE: 1999-07-01
<313> RELEVANT RESIDUES: (1)..(141)

<400> SEQUENCE: 42

Leu Pro Glu Lys Leu Tyr Lys Asn Leu Ser His Ser Thr Arg Met Leu
1               5                   10                  15

Arg Tyr Thr Val Pro Leu Pro Met Leu Ala Tyr Pro Leu Tyr Leu Trp
            20                  25                  30

Tyr Arg Ser Pro Gly Lys Glu Gly Ser His Tyr Asn Pro Tyr Ser Ser
        35                  40                  45
```

```
Leu Phe Ala Pro Ser Glu Arg Lys Leu Ile Ala Thr Ser Thr Thr Cys
    50                  55                  60

Trp Ser Ile Val Leu Ala Ser Leu Val Tyr Leu Ser Phe Leu Val Gly
65                  70                  75                  80

Pro Val Thr Val Leu Lys Val Tyr Gly Val Pro Tyr Ile Ile Phe Val
                85                  90                  95

Met Trp Leu Asp Ala Val Thr Tyr Leu His His Gly His Asp Asp
            100                 105                 110

Lys Leu Pro Trp Tyr Arg Gly Lys Glu Trp Ser Tyr Leu Arg Gly Gly
        115                 120                 125

Leu Thr Thr Val Asp Arg Asp Tyr Gly Ile Phe Asn Asn
    130                 135                 140

<210> SEQ ID NO 43
<211> LENGTH: 20
<212> TYPE: DNA
<213> ORGANISM: Artificial sequence
<220> FEATURE:
<223> OTHER INFORMATION: PCR primer sequence derived from the sequence
      of pFad3A

<400> SEQUENCE: 43
aagagtggcc aacatgatcg                                                 20

<210> SEQ ID NO 44
<211> LENGTH: 19
<212> TYPE: DNA
<213> ORGANISM: Artificial sequence
<220> FEATURE:
<223> OTHER INFORMATION: PCR primer sequence derived from the sequence
      of pFad3A

<400> SEQUENCE: 44
attcttagca tctgcctcg                                                  19

<210> SEQ ID NO 45
<211> LENGTH: 20
<212> TYPE: DNA
<213> ORGANISM: Artificial sequence
<220> FEATURE:
<223> OTHER INFORMATION: PCR primer sequence derived from the sequence
      of pFad3A

<400> SEQUENCE: 45
ccccttctga atactgcggt                                                 20

<210> SEQ ID NO 46
<211> LENGTH: 20
<212> TYPE: DNA
<213> ORGANISM: Artificial sequence
<220> FEATURE:
<223> OTHER INFORMATION: PCR primer sequence derived form the sequence
      of pFad3A

<400> SEQUENCE: 46
ttccggtaat cccctctca                                                  20

<210> SEQ ID NO 47
<211> LENGTH: 23
<212> TYPE: DNA
<213> ORGANISM: Artificial sequence
<220> FEATURE:
<223> OTHER INFORMATION: PCR primer sequence derived from the sequence
      of pFad3A
```

```
<400> SEQUENCE: 47
actgtagtca tccccaaaca aat                                            23

<210> SEQ ID NO 48
<211> LENGTH: 23
<212> TYPE: DNA
<213> ORGANISM: Artificial sequence
<220> FEATURE:
<223> OTHER INFORMATION: PCR primer sequence derived from the sequence
      of pFad3A

<400> SEQUENCE: 48
gcatcaaaat ctttagcatc gaa                                            23

<210> SEQ ID NO 49
<211> LENGTH: 23
<212> TYPE: DNA
<213> ORGANISM: Artificial sequence
<220> FEATURE:
<223> OTHER INFORMATION: PCR primer sequence derived from the sequence
      of pFad3A

<400> SEQUENCE: 49
ggtgcatgtt agcaaacagt aat                                            23

<210> SEQ ID NO 50
<211> LENGTH: 21
<212> TYPE: DNA
<213> ORGANISM: Artificial sequence
<220> FEATURE:
<223> OTHER INFORMATION: PCR primer sequence derived from the sequence
      of pFad3A

<400> SEQUENCE: 50
catttcactc agagcccaca c                                              21

<210> SEQ ID NO 51
<211> LENGTH: 20
<212> TYPE: DNA
<213> ORGANISM: Artificial sequence
<220> FEATURE:
<223> OTHER INFORMATION: PCR primer sequence derived from the sequence
      of pFad3A

<400> SEQUENCE: 51
gaccaacgcc agtattcaga                                                20

<210> SEQ ID NO 52
<211> LENGTH: 22
<212> TYPE: DNA
<213> ORGANISM: Artificial sequence
<220> FEATURE:
<223> OTHER INFORMATION: PCR primer sequence derived from the sequence
      of pFad3A

<400> SEQUENCE: 52
attacgggat cttcaacaac ca                                             22

<210> SEQ ID NO 53
<211> LENGTH: 24
<212> TYPE: DNA
<213> ORGANISM: Artificial sequence
<220> FEATURE:
<223> OTHER INFORMATION: PCR primer sequence derived from the sequence
      of pFad3A
```

```
<400> SEQUENCE: 53 taaaacaac cagaaataag taaa                                                    24

<210> SEQ ID NO 54
<211> LENGTH: 26
<212> TYPE: DNA
<213> ORGANISM: Artificial sequence
<220> FEATURE:
<223> OTHER INFORMATION: PCR primer sequence derived from the sequence
      of pFad3A

<400> SEQUENCE: 54
ctatcaatag ttgttaatcc tccaca                                                 26

<210> SEQ ID NO 55
<211> LENGTH: 22
<212> TYPE: DNA
<213> ORGANISM: Artificial sequence
<220> FEATURE:
<223> OTHER INFORMATION: PCR primer sequence derived from the sequence
      of pFad3A

<400> SEQUENCE: 55
ttggacgacc acttgtcaga tt                                                     22

<210> SEQ ID NO 56
<211> LENGTH: 22
<212> TYPE: DNA
<213> ORGANISM: Artificial sequence
<220> FEATURE:
<223> OTHER INFORMATION: PCR primer sequence derived from the sequence
      of pFad3A
<220> FEATURE:
<221> NAME/KEY: misc_feature
<222> LOCATION: (20)..(20)
<223> OTHER INFORMATION: n = any nucleic acd

<400> SEQUENCE: 56
gtggacatgg gagtttytcn ga                                                     22

<210> SEQ ID NO 57
<211> LENGTH: 22
<212> TYPE: DNA
<213> ORGANISM: Artificial sequence
<220> FEATURE:
<223> OTHER INFORMATION: PCR primer sequence derived from the sequence
      of pFad3A

<400> SEQUENCE: 57
tggcatcgac caartgrtar tg                                                     22

<210> SEQ ID NO 58
<211> LENGTH: 8
<212> TYPE: PRT
<213> ORGANISM: Brassica napus
<220> FEATURE:
<221> NAME/KEY: misc_feature
<222> LOCATION: (1)..(8)
<223> OTHER INFORMATION: motif for which substitutions may be made
      within centered on a position corresponding to position 213 of
      Apollo Fad3A

<400> SEQUENCE: 58

Ser Thr Thr Cys Trp Ser Ile Met
1               5
```

```
<210> SEQ ID NO 59
<211> LENGTH: 18
<212> TYPE: PRT
<213> ORGANISM: Brassica napus
<220> FEATURE:
<221> NAME/KEY: misc_feature
<222> LOCATION: (1)..(18)
<223> OTHER INFORMATION: motif for which substitutoins may be made
      within corresponding to positions 210 to 227 of Apollo Fad3A

<400> SEQUENCE: 59

Ser Thr Thr Cys Trp Ser Ile Met Leu Ala Thr Leu Val Tyr Leu Ser
1               5                   10                  15

Phe Leu

<210> SEQ ID NO 60
<211> LENGTH: 7
<212> TYPE: PRT
<213> ORGANISM: Brassica napus
<220> FEATURE:
<221> NAME/KEY: misc_feature
<222> LOCATION: (1)..(7)
<223> OTHER INFORMATION: motif for which substitutoins may be made
      within centered on a position corresponding to position 275 of
      Apollo Fad3A

<400> SEQUENCE: 60

Ser Tyr Leu Arg Gly Gly Leu
1               5

<210> SEQ ID NO 61
<211> LENGTH: 10
<212> TYPE: PRT
<213> ORGANISM: Brassica napus
<220> FEATURE:
<221> NAME/KEY: misc_feature
<222> LOCATION: (1)..(10)
<223> OTHER INFORMATION: motif for which substitutoins may be made
      within beginning at a position corresponding to position 347 of
      Apollo Fad3A
<220> FEATURE:
<221> NAME/KEY: SITE
<222> LOCATION: (2)..(2)
<223> OTHER INFORMATION: Xaa = any amino acid
<220> FEATURE:
<221> NAME/KEY: SITE
<222> LOCATION: (3)..(3)
<223> OTHER INFORMATION: Xaa = any amino acid
<220> FEATURE:
<221> NAME/KEY: SITE
<222> LOCATION: (4)..(4)
<223> OTHER INFORMATION: Xaa = any amino acid

<400> SEQUENCE: 61

Ser Xaa Xaa Xaa Asp His Tyr Val Ser Asp
1               5                   10

<210> SEQ ID NO 62
<211> LENGTH: 11
<212> TYPE: PRT
<213> ORGANISM: Brassica napus
<220> FEATURE:
<221> NAME/KEY: misc_feature
<222> LOCATION: (1)..(11)
<223> OTHER INFORMATION: motif for which substitutoins may be made
      within corresponding to positions 210 to 220 of Apollo Fad3A

<400> SEQUENCE: 62

Ser Thr Thr Cys Trp Ser Ile Met Leu Ala Thr
1               5                   10
```

-continued

```
<210> SEQ ID NO 63
<211> LENGTH: 13
<212> TYPE: PRT
<213> ORGANISM: Brassica napus
<220> FEATURE:
<221> NAME/KEY: misc_feature
<222> LOCATION: (1)..(13)
<223> OTHER INFORMATION: motif for which substitutoins may be made
      within corresponding to positions 272 to 284 of Apollo Fad3A

<400> SEQUENCE: 63

Ser Tyr Leu Arg Gly Gly Leu Thr Thr Ile Asp Arg Asp
1               5                   10

<210> SEQ ID NO 64
<211> LENGTH: 218
<212> TYPE: PRT
<213> ORGANISM: Brassica napus

<400> SEQUENCE: 64

Gly His Gly Ser Phe Ser Asp Ile Pro Leu Leu Asn Thr Ala Val Gly
1               5                   10                  15

His Ile Leu His Ser Phe Ile Leu Val Pro Tyr His Gly Trp Arg Ile
            20                  25                  30

Ser His Arg Thr His His Gln Asn His Gly His Val Glu Asn Asp Glu
        35                  40                  45

Ser Trp Val Pro Leu Pro Glu Lys Leu Tyr Lys Asn Leu Ser His Ser
    50                  55                  60

Thr Arg Met Leu Arg Tyr Thr Val Pro Leu Pro Met Leu Ala Tyr Pro
65                  70                  75                  80

Leu Tyr Leu Trp Tyr Arg Ser Pro Gly Lys Glu Gly Ser His Tyr Asn
                85                  90                  95

Pro Tyr Ser Ser Leu Phe Ala Pro Ser Glu Arg Lys Leu Ile Ala Thr
            100                 105                 110

Ser Thr Thr Cys Trp Ser Ile Val Leu Ala Thr Leu Val Tyr Pro Ser
        115                 120                 125

Phe Leu Val Gly Pro Val Thr Val Leu Lys Val Tyr Gly Val Pro Tyr
    130                 135                 140

Ile Ile Phe Val Met Trp Leu Asp Ala Val Thr Tyr Leu His His His
145                 150                 155                 160

Gly His Asp Asp Lys Leu Pro Trp Tyr Arg Gly Lys Glu Trp Ser Tyr
                165                 170                 175

Leu Arg Gly Gly Leu Thr Thr Val Asp Arg Asp Tyr Gly Ile Phe Asn
            180                 185                 190

Asn Ile His His Asp Ile Gly Thr His Val Ile His His Leu Phe Pro
        195                 200                 205

Gln Ile Pro His Tyr His Leu Val Asp Ala
    210                 215

<210> SEQ ID NO 65
<211> LENGTH: 655
<212> TYPE: DNA
<213> ORGANISM: Brassica napus

<400> SEQUENCE: 65
ggacatggga gttttcgga cattcctctt ctgaatactg cggttggtca tattcttcat      60
tccttcattc tcgttccata ccatggttgg agaataagcc atcggacaca ccaccagaac    120
catggccatg ttgaaaacga cgagtcttgg gttccgttgc cagaaaaatt atacaagaat    180
```

```
ttgtcccaca gtacacggat gctcagatac actgtccctc tccccatgct cgcttaccct        240
ctctatctgt ggtacagaag tcctggtaaa gaagggtcac attataaccc atacagtagt        300
ttatttgccc caagcgagag aaagcttatt gcaacttcaa ctacttgctg gtcgatcgtg        360
ttggccactc ttgtttatcc atcattcctc gttggtccgg tcacagttct aaaagtctat        420
ggtgttcctt acattatctt tgtaatgtgg ttggacgctg tcacgtactt gcatcatcat        480
ggtcacgatg ataagctgcc ttggtacaga ggcaaggaat ggagttattt acgtggagga        540
ttaacaactg ttgatagaga ttacgggatc ttcaacaaca ttcatcacga tattggaact        600
cacgtgatcc atcatctttt cccacaaatc cctcactatc acttggtcga tgcca            655

<210> SEQ ID NO 66
<211> LENGTH: 1864
<212> TYPE: DNA
<213> ORGANISM: Brassica napus

<400> SEQUENCE: 66
gtggacatgg gagtttctct gacattcctc ttctgtaata ctgcggttgg tcatattctt         60
cattccttca ttctcgttcc ataccatggt tggtaagtca tttatttaa  cttctttttt        120 catgcaaatt tattcttgtt ttcgtatttc ttacattttc cttgtcattc ttggtgcatg        180
taagcaaaca gtggatctga taactgaaaa tatattaatt tttcatagta aaataatgca        240
tgtggactaa aagtctaaaa gcatcaaaat ctttagcatc catgaaaaaa gaacaaaact        300
tttatttaat gctatgggcc tatttatggt ccaattagct atcatcatat gacatgtcct        360
tgaataaatt aatgtataag tttaataata tttatatatt tttgttttaa tggcttatct        420
tattgttaat ggatacatca gcttgaaata tctatggaac atgcatcatt tcctaagat        480 acattggttt gttgctcaaa aaataaataa ctagttaaac gagtgagatt cttagcatct        540
gcctcgaaaa cgaatatgtt attggacaat tccaatttca tttttatgaa aataaaataa        600
tagtttattt tataattggg gttggttgca ggagaataag ccatcggaca caccaccaga        660
accatggcca tgttgaaaac gacgagtctt gggttccggt aatctttccc tctctcatat        720 tttttttct ttttttgaaa ttcttttcatt ttaatttttct taggattcta tgtatttatt        780
taaatcaatc ctttttccag tttgaggctt ggacgaccac ttgtcagatt cgtcgtttag        840
ctgtagtaaa caactgattt aaactgttta tagtactgta gttaacttta acaacgggcc        900
acttatattc gagccattgg cataaaatga ttcttctcga aattcgttta ctttttcttag       960 tatttttcag ttttggagtt tacgtagaac taataaaaat aaattttgt ataaacatac        1020 cacatgcaat gaataaattc gaatatataa ccaaactgtt aaatattaat taacatttta       1080
atcttaattt tgcattccag ttgccagaaa aattatacaa gaatttgtcc cacagtacac       1140
ggatgctcag atacactgtc cctctcccca tgctcgctta ccctctctat ctggtaaatc       1200
ctaattccta attttcttcc tgattataat tacaattttg aatttttaga ttttgagtat       1260
taactaaata taaattaatg tttggggatg actacagtgg tacagaagtc ctggtaaaga       1320
agggtcacat tataacccat acagtagttt atttgctcca agcgagagaa agcttattgc       1380
aacttcaact actgctggtc gatcatgttg gccactcttg tttatctatc attctcgttg       1440
gtccagtcac agtctcaaa gtctatggag ttccttacat tgtaagtttc atatattaca       1500
ttattatatc attgctatat aatttgtttt tgacataaag ttttggaaaa atttcagatc       1560
tttgtaatgt ggttggacgc tgtcacgtac ttgcatcatc atggtcacga tgataagttg       1620
ccttggtaca gaggcaaggt aagtagatca acattaattt ataagaagca ataatgatta       1680
```

-continued

| | |
|---|---|
| gtatttgatt aatctaaatt attgatgttt tgtatacaat aataggaatg gagttattta | 1740 |
| cgtggaggat taacaactat tgatagagat tacgggatct tcaacaacat tcatcacgat | 1800 |
| attggaactc acgtgatcca tcatcttttc ccacaaatcc cccactatca cttggtcgat | 1860 |
| gcca | 1864 |

<210> SEQ ID NO 67
<211> LENGTH: 2393
<212> TYPE: DNA
<213> ORGANISM: Brassica napus

<400> SEQUENCE: 67

| | |
|---|---|
| gtggacatgg gagtttttcg gacattcctc ttctgaatac tgcggttggt catattcttc | 60 |
| attccttcat tctcgttcca taccatggtt ggtaagtcat ttatttaaac atcttttca | 120 |
| tgcaaattta ttctagtttt cgtatttctt acattttcct tgtcattctt ggtgcatgtt | 180 |
| agcaaactgt aatctgataa ctgaaaatat attaattttc catagtaaaa taatgcatgt | 240 |
| gactaaaagc atcaaaatct ttagcatcga agaaaaaaga accaaacttt tatttaatgc | 300 |
| tatgggccta tttatggtcc aattagctat tatcatatga catgtccttg aataaattaa | 360 |
| tgtagcttca tatgtgagtt taataatatt tatatatttt tgtttaatg gcttatttta | 420 |
| ttgttaaatg gatacatcag cttgaaatgt ctacgaacat gcatcatttc ctagatacac | 480 |
| ttgtttgttg ctcaaaaatg aataacttag ttaaacgagt gagcatgttc tatggggttt | 540 |
| cttagagcat gattattgag aagttcctag agtgaggttc ttaccggaat ataagaatct | 600 |
| atctcttaac ttttaactaa aaaaattaag aaccggcttt taaaactcgt atttaagaac | 660 |
| cgttttttag ttttttttagt taaaaatcaa gagacgagtt cttatattcc gctaagaact | 720 |
| ccaccctgag aacttctcaa taatcatgct cttagtgctc taagaagggt ccttaacaaa | 780 |
| atattaataa taagatatag tgtgggccca aaaaaaaaca aaaaaccggt tacaaaagtc | 840 |
| gcgaaagaag gatcgatttt ggtcttttac ttgtactgtt tgtggatccc actggtggtg | 900 |
| gtccgcgatt ggtttctttt ttaatttaat ttatttttt taatcggaga aaaaaaatta | 960 |
| agaaaccaaa aaacagtttt aatcatggcc tcatgttggg gttgagtttt atattctgat | 1020 |
| aagaatccca tcttaaaaac cccgttaaac atgctcttac catctgcttc gaaaatgata | 1080 |
| tgttattgac aattccaatt tcatttttat gaaaataaaa ttatagttta ttttataact | 1140 |
| gagggtggtt gcaggagaat aagccatcgg acacaccacc agaaccatgg ccatgttgaa | 1200 |
| aacgacgagt cttgggttcc ggtaatcttt ccctctctca tatttttttt tctttttttt | 1260 |
| tgaaattctt tcatttaat tttcttagga ttctatgtat ttattttaat caatccttt | 1320 |
| tccagtttga ggctaggacg accactagtc agatttgtcg tttagctgta gttaacaact | 1380 |
| gatttaaatt gttatagta ctgtagttaa ctttaacaac ggaccactta tattcgagcc | 1440 |
| attggcataa aatgattctt ctcgaaattc gtttactttt cttagtattt ttcaattttg | 1500 |
| gagcttacgt agaactaata aaagaaaac cttataaaca caccacatgc aatgaataaa | 1560 |
| ttcgaatata taaccatact gttaaatatt aatttacatt ttaatcttaa ttttgcattc | 1620 |
| cagttgccag aaaaattata caagaatttg tcccacagta cacggatgct cagatacact | 1680 |
| gtccctctcc ccatgctcgc ttaccctctc tatctggtaa atcctaattc ctaatttttc | 1740 |
| ttcctgacta taattacaat tttgaatttt tagattttga gtattaacta aatataaatt | 1800 |
| aaatttgttt ggggatgact acagtggtac agaagtcctg gtaaagaagg gtcacattat | 1860 |
| aacccataca gtagtttatt tgccccaagc gagagaaagc ttattgcaac ttcaactact | 1920 |

|               |               |               |               |      |
|---------------|---------------|---------------|---------------|------|
| tgctggtcga    | tcgtgttggc    | cactcttgtt    | tatccatcat    | tcctcgttgg tccggtcaca | 1980 |
| gttctaaaag    | tctatggtgt    | tccttacatt    | gtaagtttca    | tatatttctt tattatatca | 2040 |
| ttgctaatat    | aatttgtttt    | tgacataaaa    | gttttggaaa    | aatttcagat ctttgtaatg | 2100 |
| tggttggacg    | ctgtcacgta    | cttgcatcat    | catggtcacg    | atgataagct gccttggtac | 2160 |
| agaggcaaga    | taagtagatc    | aacattattt    | ataagaagca    | ataatgatta gtagttgaat | 2220 |
| aatctgaatt    | tttgatgttt    | ttgtacaata    | ataggaatgg    | agttatttac gtggaggatt | 2280 |
| aacaactgtt    | gatagagatt    | acgggatctt    | caacaacatt    | catcacgata ttggaactca | 2340 |
| cgtgatccat    | catcttttcc    | cacaaatccc    | tcactatcac    | ttggtcgatg cca | 2393 |

```
<210> SEQ ID NO 68
<211> LENGTH: 379
<212> TYPE: PRT
<213> ORGANISM: Artificial sequence
<220> FEATURE:
<223> OTHER INFORMATION: ApolloA/ApolloC/L22962 consensus sequence
<220> FEATURE:
<221> NAME/KEY: misc_feature
<222> LOCATION: (1)..(379)
<223> OTHER INFORMATION: Xaa = Any Amino Acid
<220> FEATURE:
<221> NAME/KEY: SITE
<222> LOCATION: (88)..(106)
<223> OTHER INFORMATION: putative 'histadine box'

<400> SEQUENCE: 68

Met Val Val Ala Met Asp Gln Arg Ser Asn Xaa Asn Gly Asp Xaa Xaa
1               5                   10                  15

Xaa Glu Arg Phe Asp Pro Ser Ala Gln Pro Pro Phe Lys Ile Gly Asp
                20                  25                  30

Ile Arg Ala Ala Ile Pro Lys His Cys Trp Val Lys Ser Pro Leu Arg
            35                  40                  45

Ser Met Ser Tyr Val Ala Arg Asp Ile Phe Xaa Val Ala Leu Ala Val
        50                  55                  60

Ala Ala Val Tyr Phe Asp Ser Trp Phe Phe Trp Pro Leu Tyr Trp Ala
65                  70                  75                  80

Ala Gln Gly Thr Leu Phe Trp Ala Ile Phe Val Leu Gly His Asp Cys
                85                  90                  95

Gly His Gly Ser Phe Ser Asp Ile Pro Leu Leu Asn Thr Ala Val Gly
            100                 105                 110

His Ile Leu His Ser Phe Ile Leu Val Pro Tyr His Gly Trp Arg Xaa
        115                 120                 125

Ser His Arg Thr His His Gln Asn His Gly His Val Glu Asn Asp Glu
    130                 135                 140

Ser Trp Val Pro Leu Pro Glu Lys Leu Tyr Lys Asn Leu Ser His Ser
145                 150                 155                 160

Thr Arg Met Leu Arg Tyr Thr Val Pro Leu Pro Met Leu Ala Tyr Pro
                165                 170                 175

Leu Tyr Leu Trp Tyr Arg Ser Pro Gly Lys Glu Gly Ser His Tyr Asn
            180                 185                 190

Pro Tyr Ser Ser Leu Phe Ala Pro Ser Glu Arg Lys Leu Ile Ala Thr
        195                 200                 205

Ser Thr Thr Xaa Trp Ser Ile Met Leu Ala Thr Leu Val Tyr Leu Ser
    210                 215                 220

Phe Leu Val Gly Pro Val Thr Val Leu Lys Val Tyr Gly Val Pro Tyr
225                 230                 235                 240
```

```
Ile Ile Phe Val Met Trp Leu Asp Ala Val Thr Tyr Leu His His His
                245                 250                 255

Gly His Asp Asp Lys Leu Pro Trp Tyr Arg Gly Lys Glu Trp Ser Tyr
                260                 265                 270

Leu Xaa Gly Gly Leu Thr Thr Ile Asp Arg Asp Tyr Gly Ile Phe Asn
                275                 280                 285

Asn Ile His His Asp Ile Gly Thr His Val Ile His His Leu Phe Pro
                290                 295                 300

Gln Ile Pro His Tyr His Leu Val Asp Ala Thr Lys Xaa Ala Lys His
305                 310                 315                 320

Val Leu Gly Arg Tyr Tyr Arg Glu Pro Lys Thr Ser Gly Ala Ile Pro
                325                 330                 335

Ile His Leu Val Glu Ser Leu Val Ala Xaa Ile Lys Lys Asp His Tyr
                340                 345                 350

Val Ser Asp Thr Gly Asp Ile Val Phe Tyr Glu Thr Asp Pro Asp Leu
                355                 360                 365

Tyr Val Tyr Ala Ser Asp Lys Ser Lys Ile Asn
                370                 375

<210> SEQ ID NO 69
<211> LENGTH: 382
<212> TYPE: PRT
<213> ORGANISM: Artificial sequence
<220> FEATURE:
<223> OTHER INFORMATION: Apollo Fad3A/L01418 consensus sequence
<220> FEATURE:
<221> NAME/KEY: misc_feature
<222> LOCATION: (1)..(382)
<223> OTHER INFORMATION: Xaa = Any Amino Acid

<400> SEQUENCE: 69

Met Val Val Ala Met Asp Gln Arg Ser Asn Val Asn Gly Asp Ser Xaa
1               5                   10                  15

Xaa Xaa Lys Xaa Glu Xaa Phe Asp Pro Ser Ala Gln Pro Pro Phe Lys
                20                  25                  30

Ile Gly Asp Ile Arg Ala Ala Ile Pro Lys His Cys Trp Val Lys Ser
                35                  40                  45

Pro Leu Arg Ser Met Ser Tyr Val Xaa Arg Asp Ile Phe Xaa Val Xaa
                50                  55                  60

Ala Leu Ala Xaa Ala Ala Val Tyr Phe Asp Ser Trp Phe Xaa Trp Pro
65                  70                  75                  80

Leu Tyr Trp Xaa Ala Gln Gly Thr Leu Phe Trp Ala Ile Phe Val Leu
                85                  90                  95

Gly His Asp Cys Gly His Gly Ser Phe Ser Asp Ile Pro Leu Leu Asn
                100                 105                 110

Xaa Xaa Val Gly His Ile Leu His Ser Phe Ile Leu Val Pro Tyr His
                115                 120                 125

Gly Trp Arg Xaa Ser His Arg Thr His His Gln Asn His Gly His Val
                130                 135                 140

Glu Asn Asp Glu Ser Trp Val Pro Leu Pro Glu Lys Leu Tyr Lys Asn
145                 150                 155                 160

Leu Xaa His Ser Thr Arg Met Leu Arg Tyr Thr Val Pro Leu Pro Met
                165                 170                 175

Leu Ala Tyr Pro Xaa Tyr Leu Trp Tyr Arg Ser Pro Gly Lys Glu Gly
                180                 185                 190

Ser His Asn Pro Tyr Ser Ser Leu Phe Ala Pro Ser Glu Arg Lys Leu
                195                 200                 205
```

```
Ile Ala Thr Ser Thr Thr Xaa Trp Ser Ile Met Leu Ala Thr Leu Val
    210                 215                 220

Tyr Leu Ser Phe Leu Val Xaa Pro Val Thr Val Leu Lys Val Tyr Gly
225                 230                 235                 240

Val Pro Tyr Ile Ile Phe Val Met Trp Leu Asp Ala Val Thr Tyr Leu
                245                 250                 255

His His His Gly His Asp Xaa Lys Leu Pro Trp Tyr Arg Gly Lys Glu
            260                 265                 270

Trp Ser Tyr Leu Xaa Gly Gly Leu Thr Thr Ile Asp Arg Asp Tyr Gly
        275                 280                 285

Ile Phe Asn Asn Ile His His Asp Ile Gly Thr His Val Ile His His
    290                 295                 300

Leu Phe Pro Gln Ile Pro His Tyr His Leu Val Asp Ala Thr Xaa Ala
305                 310                 315                 320

Ala Lys His Val Leu Gly Arg Tyr Tyr Arg Glu Pro Lys Thr Ser Gly
                325                 330                 335

Ala Ile Pro Ile His Leu Val Glu Ser Leu Val Ala Xaa Ile Lys Lys
                340                 345                 350

Asp His Tyr Val Ser Asp Thr Gly Asp Ile Val Phe Tyr Glu Thr Asp
            355                 360                 365

Pro Asp Leu Tyr Val Tyr Ala Ser Asp Lys Ser Lys Ile Asn
370                 375                 380

<210> SEQ ID NO 70
<211> LENGTH: 384
<212> TYPE: PRT
<213> ORGANISM: Artificial sequence
<220> FEATURE:
<223> OTHER INFORMATION: Apollo FAD3A/D17579 consensus sequence
<220> FEATURE:
<221> NAME/KEY: misc_feature
<222> LOCATION: (1)..(384)
<223> OTHER INFORMATION: Xaa = Any Amino Acid

<400> SEQUENCE: 70

Met Val Val Ala Met Asp Gln Arg Asn Val Asn Gly Asp Xaa Xaa Xaa
1               5                   10                  15

Xaa Xaa Xaa Xaa Lys Xaa Glu Arg Phe Asp Pro Ser Ala Gln Pro Pro
                20                  25                  30

Phe Lys Ile Gly Asp Ile Arg Ala Ala Ile Pro Lys His Cys Trp Val
                35                  40                  45

Lys Ser Pro Leu Arg Ser Met Ser Tyr Val Arg Asp Ile Xaa Xaa Val
50                  55                  60

Xaa Ala Leu Ala Xaa Ala Val Tyr Xaa Asp Ser Trp Phe Xaa Trp
65                  70                  75                  80

Pro Leu Tyr Trp Ala Ala Gln Gly Thr Leu Phe Trp Ala Ile Phe Val
                85                  90                  95

Leu Gly His Asp Cys Gly His Gly Ser Phe Ser Asp Ile Pro Leu Leu
                100                 105                 110

Asn Xaa Xaa Val Gly His Ile Leu His Ser Phe Ile Leu Val Pro Tyr
            115                 120                 125

His Gly Trp Arg Xaa Ser His Arg Thr His His Gln Asn His Gly His
            130                 135                 140

Val Glu Asn Asp Glu Ser Trp Val Pro Leu Pro Glu Xaa Xaa Tyr Lys
145                 150                 155                 160

Xaa Leu Xaa His Ser Thr Arg Met Leu Arg Tyr Thr Val Pro Leu Pro
                165                 170                 175
```

```
Met Leu Ala Tyr Pro Leu Tyr Leu Xaa Tyr Arg Ser Pro Gly Lys Glu
                180                 185                 190

Gly Ser His Xaa Asn Pro Tyr Ser Ser Leu Phe Ala Pro Ser Glu Arg
            195                 200                 205

Lys Leu Ile Ala Thr Ser Thr Xaa Trp Ser Ile Met Xaa Xaa Xaa
        210                 215                 220

Leu Xaa Xaa Leu Ser Phe Xaa Xaa Gly Pro Xaa Xaa Val Leu Lys Val
225                 230                 235                 240

Tyr Gly Val Pro Tyr Ile Ile Phe Val Met Trp Leu Asp Ala Val Thr
                245                 250                 255

Tyr Leu His His Gly His Asp Xaa Lys Leu Pro Trp Tyr Arg Gly
            260                 265                 270

Lys Glu Trp Ser Tyr Leu Xaa Gly Gly Leu Thr Thr Ile Asp Arg Asp
        275                 280                 285

Tyr Gly Ile Phe Asn Asn Ile His His Asp Ile Gly Thr His Val Ile
    290                 295                 300

His His Leu Phe Pro Gln Ile Pro His Tyr His Leu Val Asp Ala Thr
305                 310                 315                 320

Lys Ala Ala Lys His Val Leu Gly Arg Tyr Tyr Arg Glu Pro Lys Thr
                325                 330                 335

Ser Gly Ala Ile Pro Ile His Leu Val Glu Ser Leu Val Ala Xaa Ile
            340                 345                 350

Lys Lys Asp His Tyr Val Ser Asp Thr Gly Asp Ile Val Phe Tyr Glu
        355                 360                 365

Thr Asp Pro Asp Leu Tyr Val Tyr Ala Ser Asp Lys Ser Lys Ile Asn
    370                 375                 380

<210> SEQ ID NO 71
<211> LENGTH: 283
<212> TYPE: PRT
<213> ORGANISM: Artificial sequence
<220> FEATURE:
<223> OTHER INFORMATION: ApolloC/ApolloA/YN90-1016 consensus sequence
<220> FEATURE:
<221> NAME/KEY: misc_feature
<222> LOCATION: (1)..(283)
<223> OTHER INFORMATION: Xaa = Any Amino Acid

<400> SEQUENCE: 71

Gly His Gly Ser Phe Ser Asp Ile Pro Leu Leu Asn Thr Ala Val Gly
1               5                   10                  15

His Ile Leu His Ser Phe Ile Leu Val Pro Tyr His Gly Trp Arg Xaa
            20                  25                  30

Ser His Arg Thr His Gln Asn His Gly His Val Glu Asn Asp Glu
        35                  40                  45

Ser Trp Val Pro Leu Pro Glu Lys Leu Tyr Lys Asn Leu Ser His Ser
50                  55                  60

Thr Arg Met Leu Arg Tyr Thr Val Pro Leu Pro Met Leu Ala Tyr Pro
65                  70                  75                  80

Leu Tyr Leu Trp Tyr Arg Ser Pro Gly Lys Glu Gly Ser His Tyr Asn
                85                  90                  95

Pro Tyr Ser Ser Leu Phe Ala Pro Ser Glu Arg Lys Leu Ile Ala Thr
            100                 105                 110

Ser Thr Thr Xaa Trp Ser Ile Xaa Leu Ala Thr Leu Val Tyr Leu Ser
        115                 120                 125

Phe Leu Val Gly Pro Val Thr Val Leu Lys Val Tyr Gly Val Pro Tyr
130                 135                 140
```

```
Ile Ile Phe Val Met Trp Leu Asp Ala Val Thr Tyr Leu His His His
145                 150                 155                 160

Gly His Asp Asp Lys Leu Pro Trp Tyr Arg Gly Lys Glu Trp Ser Tyr
                165                 170                 175

Leu Xaa Gly Gly Leu Thr Thr Xaa Asp Arg Asp Tyr Gly Ile Phe Asn
            180                 185                 190

Asn Ile His His Asp Ile Gly Thr His Val Ile His His Leu Phe Pro
        195                 200                 205

Gln Ile Pro His Tyr His Leu Val Asp Ala Thr Lys Ala Ala Lys His
    210                 215                 220

Val Leu Gly Arg Tyr Tyr Arg Glu Pro Lys Thr Ser Gly Ala Ile Pro
225                 230                 235                 240

Ile His Leu Val Glu Ser Leu Val Ala Xaa Ile Lys Lys Asp His Tyr
                245                 250                 255

Val Ser Asp Thr Gly Asp Ile Val Phe Tyr Glu Thr Asp Pro Asp Leu
            260                 265                 270

Tyr Val Tyr Ala Ser Asp Lys Ser Lys Ile Asn
    275                 280

<210> SEQ ID NO 72
<211> LENGTH: 218
<212> TYPE: PRT
<213> ORGANISM: Artificial sequence
<220> FEATURE:
<223> OTHER INFORMATION: Apollo Fad3A/N89-53 consensus sequence
<220> FEATURE:
<221> NAME/KEY: misc_feature
<222> LOCATION: (1)..(218)
<223> OTHER INFORMATION: Xaa = Any Amino Acid

<400> SEQUENCE: 72

Gly His Gly Ser Phe Ser Asp Ile Pro Leu Leu Asn Thr Ala Val Gly
1               5                   10                  15

His Ile Leu His Ser Phe Ile Leu Val Pro Tyr His Gly Trp Arg Xaa
                20                  25                  30

Ser His Arg Thr His His Gln Asn His Gly His Val Glu Asn Asp Glu
            35                  40                  45

Ser Trp Val Pro Leu Pro Glu Lys Leu Tyr Lys Asn Leu Ser His Ser
    50                  55                  60

Thr Arg Met Leu Arg Tyr Thr Val Pro Leu Pro Met Leu Xaa Tyr Pro
65                  70                  75                  80

Leu Tyr Leu Trp Tyr Arg Ser Pro Gly Lys Glu Gly Ser His Tyr Asn
                85                  90                  95

Xaa Tyr Ser Ser Leu Phe Ala Pro Ser Glu Arg Lys Leu Ile Ala Thr
            100                 105                 110

Ser Thr Thr Xaa Trp Ser Ile Met Leu Ala Thr Leu Val Tyr Leu Ser
        115                 120                 125

Phe Leu Val Xaa Pro Val Thr Val Leu Lys Val Tyr Gly Val Pro Tyr
    130                 135                 140

Ile Ile Phe Val Met Trp Leu Asp Ala Val Thr Tyr Leu His His His
145                 150                 155                 160

Gly His Asp Xaa Lys Leu Pro Xaa Tyr Arg Gly Lys Glu Trp Ser Tyr
                165                 170                 175

Leu Xaa Gly Gly Leu Thr Thr Ile Asp Arg Asp Tyr Gly Ile Phe Asn
            180                 185                 190
```

```
Asn Ile His His Asp Ile Gly Thr His Val Ile His His Leu Phe Pro
        195                 200                 205

Gln Ile Pro His Tyr His Leu Val Asp Ala
        210                 215
```

<210> SEQ ID NO 73
<211> LENGTH: 1877
<212> TYPE: DNA
<213> ORGANISM: Artificial sequence
<220> FEATURE:
<223> OTHER INFORMATION: pFad3Y/pFad3A genomic consensus sequence
<220> FEATURE:
<221> NAME/KEY: misc_feature
<222> LOCATION: (1)..(1877)
<223> OTHER INFORMATION: n = any nucleic acid

<400> SEQUENCE: 73

| | | | | | |
|---|---|---|---|---|---|
| gtggacatgg | gagtttctcn | gacattccnc | ttctgnaata | ctgcggttgg | tcatattctt | 60 |
| cattccttca | ttctcgttcc | ataccatggt | tggtaagtca | tttattttaa | cttcttttt | 120 |
| catgcaaatt | tattcttgtt | ttcgtattnc | ttacattttc | cttgtcattc | ttggtgcatg | 180 |
| tnagcaaaca | gtnnatctga | taactgaaaa | tatattaatt | tttcatagta | aaataatgca | 240 |
| tgtgnannnn | nnnnctaaaa | gcatcaaaat | ctttagcatc | nangaaaaaa | gaacnaaact | 300 |
| tttatttaat | gctatgggcc | tatttatggt | ccaattagct | atnatcatat | gacatgtcct | 360 |
| tgaataaatt | aatgtataag | tttaatanna | tatttatata | tttttgtttt | aatggcttat | 420 |
| nttattgtta | natggataca | tcagcttgaa | atatctanng | aacatgcatc | attttcctan | 480 |
| gatacattng | tttgttgctc | aaaaaatnaa | taacntagtt | aaacgagtga | gattcttagc | 540 |
| atctgcctcg | aaaacganta | tgttattnga | caattccaat | ttcattttta | tgaaaataaa | 600 |
| ataatagttt | attttataat | tggggntggt | tgcaggagaa | tnagccatcg | acacaccac | 660 |
| cagaaccatg | gccatgttga | aaacgacgag | tcttgggttc | cggtaatcnn | ncccnctctc | 720 |
| atannttttt | ttttcttttt | tgaaantcct | ttcattttaa | ttttcttagn | attctatgta | 780 |
| tttatttnaa | tcaatcctt | tnccagtntg | aggcttggac | gaccacttgt | cagattngtc | 840 |
| gtttagctgt | agtaaacaac | tgatttaaan | tgtttatngt | actgtagtta | actttaacaa | 900 |
| cgggccactt | atattcgagc | cattggcata | aaatgattct | tctcgaaatt | cgtttacttt | 960 |
| tcttagtatt | tttcagtttt | gnagtttacg | tagaactaat | aaaaanaaan | nnnntataa | 1020 |
| acanaccaca | tgcaatgaat | aaattcgaat | atataaccan | actgttaaat | attaattaac | 1080 |
| attttaatct | taattttgca | ttccagttgc | cagaaaaatt | atacaagaat | ttgtcccaca | 1140 |
| gtacacggat | gctcagatac | actgtccctc | tccccatgct | cgcttaccct | ctctatctgg | 1200 |
| taaatcctaa | ttcctnantt | ttcttcctga | ttataattac | aattttgaat | ttttagattt | 1260 |
| tgagtattaa | ctaaatataa | attaannntg | tttggggatg | actacagtgg | tacagaagtc | 1320 |
| ctggtaaaga | agggtcacat | tataacccat | acagtagttt | atttgcncca | agcgagagaa | 1380 |
| agcttattgc | aacttcaact | actgcntggt | cgatcatgtt | ggccactctt | gtttatctat | 1440 |
| cattcntcgt | tggtccagtc | acagttctna | aagtctatgg | ngttccttac | attgtaagtt | 1500 |
| tcatatattn | cattattata | tcattgctna | tataatttgt | ttttgacata | aagttttgga | 1560 |
| aaaatttcag | atctttgtaa | tgtggttgga | cgctgtcacg | tacttgcatc | atcatggtca | 1620 |
| cgatgataag | ttgccttggt | acagaggcaa | ggtaagtaga | tcaacattaa | tttataagaa | 1680 |
| gcaanaatga | ttagtatttg | attaatctaa | attattgatg | ttntgtntac | aataataggaa | 1740 |

```
atggagttat ttangtggag gattaacaac tattgataga gattacggga tcttcaacaa    1800
cattcatcac gatattggaa ctcacgtgat ccatcatctt ttcccacaaa tcccncacta    1860
tcacttggtc gatgcca                                                   1877
```